United States Patent
Bibillo et al.

(10) Patent No.: US 11,739,307 B2
(45) Date of Patent: Aug. 29, 2023

(54) METHODS FOR PRODUCING MODIFIED REVERSE TRANSCRIPTASES

(71) Applicant: Bio-Rad Laboratories, Inc., Hercules, CA (US)

(72) Inventors: Arkadiusz Bibillo, Walnut Creek, CA (US); Pranav Patel, Pleasanton, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 0 days.

(21) Appl. No.: 17/055,801

(22) PCT Filed: May 16, 2019

(86) PCT No.: PCT/US2019/032701
§ 371 (c)(1),
(2) Date: Nov. 16, 2020

(87) PCT Pub. No.: WO2019/222523
PCT Pub. Date: Nov. 21, 2019

(65) Prior Publication Data
US 2021/0207109 A1 Jul. 8, 2021

Related U.S. Application Data

(60) Provisional application No. 62/779,371, filed on Dec. 13, 2018, provisional application No. 62/672,480, filed on May 16, 2018.

(51) Int. Cl.
*C12N 9/12* (2006.01)

(52) U.S. Cl.
CPC .... *C12N 9/1276* (2013.01); *C12Y 207/07049* (2013.01); *C07K 2319/20* (2013.01)

(58) Field of Classification Search
None
See application file for complete search history.

(56) References Cited

U.S. PATENT DOCUMENTS

| 2006/0281079 A1* | 12/2006 | Eickbush | C12N 9/1276 |
| | | | 435/6.13 |
| 2014/0363854 A1* | 12/2014 | Smith | C12N 9/1276 |
| | | | 435/91.51 |

OTHER PUBLICATIONS

Jamburuthugoda et al. Nucleic Acids Res. Jul. 2014;42(13):8405-15.Epub Jun. 23, 2014 (Year: 2014).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Thompson et al. Mob Genet Elements. May-Jun. 2011; 1(1): 29-37 (Year: 2011).*
Accession A0A0V0T7M5. Mar. 16, 2016 (Year: 2016).*

* cited by examiner

*Primary Examiner* — Christian L Fronda
(74) *Attorney, Agent, or Firm* — Withers Bergman, LLP; Thomas C. Meyers

(57) ABSTRACT

The present disclosure provides methods and systems for amplifying and analyzing nucleic acid samples. The present disclosure provides methods for preparing cDNA and/or DNA molecules ad cDNA and/or DNA libraries using modified reverse transcriptases.

15 Claims, 31 Drawing Sheets
Specification includes a Sequence Listing.

KTAGRRNDLHDDRTA
SAHKTSRQKRRAEYARVQELYKKCRSRAAAEVIDGACGGVGHSLEEMETYWRPILERVSD
APGPTPEALHALGRAEWHGGNRDYTQLWKPISVEEIKASRFDWRTSPGPDGIRSGQWRAV
PVHLKAEMFNAWMARGEIPEILRQCRTVFVPKVERPGGPGEYRPISIASIPLRHFHSILA
RRLLACCPPDARQRGFICADGTLENSAVLDAVLGDSRKKLRECHVAVLDFAKAFDTVSHE
ALVELLRLRGMPEQFCGYIAHLYDTASTTLAVNNEMSSPVKVGRGVRQGDPLSPILFNVV
MDLILASLPERVGYRLEMELVSALAYADDLVLLAGSKVGMQESISAVDCVGRQMGLRLNC
RKSAVLSMIPDGHRKKHHYLTERTFNIGGKPLRQVSCVERWRYLGVDFEASGCVTLEHSI
SSALNNISRAPLKPQQRLEILRAHLIPRFQHGFVLGNISDDRLRMLDVQIRKAVGQWLRL
PADVPKAYYHAAVQDGGLAIPSVRATIPDLIVRRFGGLDSSPWSVARAAAKSDKIRKKLR
WAWKQLRRFSRVDSTTQRPSVRLFWREHLHASVDGRELRESTRTPTSTKWIRERCAQITG
RDFVQFVHTHINALPSRIRGSRGRRGGGESSLTCRAGCKVRETTAHILQQCHRTHGGRIL
RHNKIVSFVAKAMEENKWTVELEPRLRTSVGLRKPDIIASRDGVGVIVDVQVVSGQRSLD
ELHREKRNKYGNHGELVELVAGRLGLPKAECVRATSCTISWRGVWSLTSYKELRSIIGLR
EPTLQIVPILALRGSHMNWTRFNQMTSVMGGGVG

FIG. 14

SUBSTITUTION: MOTIF-1

SUBSTITUTION: MOTIF 0

Q101 TO N, S
L102 TO V, I
W103 TO M, V
K104 TO R, S, D
P105 TO A
I106 TO L, V
S107 TO T, V
V108 TO N, L, S
E109 TO D, Q, L
E110 TO D
I111 TO V, M
K112 TO I, R
R115 TO K, H
F116 TO L, A
D117 TO C, S, E
R119 TO T, N
T120 TO S
S121 TO A
P122 TO A
G123 TO A
P124 TO L
D125 TO N, E
G126 TO S, K
I127 TO M, V
R128 TO T, K
S129 TO L, H
G130 TO K, S
Q131 TO D, R
W132 TO L, A

R133 TO N, Y, K
A134 TO L, M
V135 TO T, S
P136 TO S
V137 TO A, Q
H138 TO I, A
L139 TO A, M, V
K140 TO R, N, L
A141 TO DELETION
E142 TO S, K, D
M143 TO I, V
F144 TO L, Y
N145 TO D
A146 TO L, V
W147 TO F, L
M148 TO L, V
A149 TO L, F
R150 TO T, H, K
G151 TO R, E
E152 TO R, N, D
I153 TO V, C
P154 TO A
E155 TO K, P, Q, A, D
I156 TO E, R, V
L157 TO V, F
R158 TO K, L, K
Q159 TO L, M, H, N
C160 TO G, S, H
R161 TO K

FIG. 16

SUBSTITUTION: THUMB SUBUNIT

G403 TO D,S
G404 TO D,R,S
K405 TO Q,V,R
P406 TO V,Q,K
L407 TO V,M
R408 TO G,P,H,T,K
Q409 TO A,E,S
V410 TO M,L
S411 TO D,G,K
C412 TO L,H,A,R
V413 TO E,L,A,G
E414 TO G,H,Q,D
R415 TO T,E,Q,K
W416 TO Y,V,F
R417 TO K,H,T,G
Y418 TO F
L419 TO V, I
G420 TO A
V421 TO I, A, H
D422 TO R, W, N, T, P, E
F423 TO V, Y, I
E424 TO G, A, N, R, T, S, D
A425 TO S, H, G
S426 TO T, A, E
G427 TO A
C428 TO T, P, R, M
V429 TO C, I , E, A
T430 TO I, D, Q, R, H
S434 TO E, N
I435 TO V, L, M
S436 TO M, L, A, D, K

S437 TO P, G, A, D, T
A438 TO L, G, K, D, L
L439 TO I, V
N440 TO E, D, Q, K
N441 TO E, R, A, Q
I442 TO T, V
S443 TO T, K, Q
R444 TO A, C, S, Q, K
A445 TO G, S
P446 TO G
L447 TO I
K448 TO R
P449 TO L
Q450 TO E, H
Q451 TO E, H
R452 TO K
L453 TO V, M
E454 TO K, H, F, A, D
I455 TO L, M, A
L456 TO I
R457 TO C, G, N, K
A458 TO N, T, V, S
H459 TO Y, F, V
L460 TO F, V
H461 TO L, V
P462 TO G
R463 TO K, Q, G
F464 TO Y, S, A, H
Q465 TO T, Y
H466 TO Y, F
G467 TO N, I, K, A
F468 TO L, W

V469 TO T, A, S, L
L470 TO F, M, T
G471 TO S, T, A
N472 TO R, S, G

R477 TO L, M, D, K
L478 TO V, A
R479 TO N, K, C, L, W
M480 TO Q, K, T, R
L481 TO G, T, M
D482 TO N, E
V483 TO S, K, R, L
Q484 TO A, I, V, M
I485 TO T, V
R486 TO K, L
K487 TO A, T, Q, G, V, R
A488 TO H, T, Y, S
V489 TO I, G
G490 TO R, K
Q491 TO R, T, K

FIG. 17

SUBSTITUTION: THUMB SUBUNIT

W492 TO L
L493 TO C, I
R494 TO V, K, G, N, A, M
L495 TO V
P496 TO K
A497 TO D, K, H
D498 TO G, S, E
V499 TO I, T, M
P500 TO S, C
K501 TO N, L, R, V
A502 TO G, D
Y503 TO F, K,
Y504 TO F, L
H505 TO Y
A506 TO T, S
A507 TO D, P, S, K
V508 TO T, Y, A
Q509 TO K, R, S, G
D510 TO Q, S, A, E
G511 TO A
G512 TO A
L513 TO M, K
A514 TO G, S
I515 TO L, V
P516 TO Q, L
S517 TO R, A, Q, E
V518 TO Y, L, F
R519 TO Q, E, S, G, K

T521 TO R, F, I
I522 TO A, V, G, S
P523 TO L
D524 TO R, F, E, M
L525 TO C, M, N
I526 TO R, K, V
V527 TO A, K, F, L
R528 TO K, A, S, H, Q
R529 TO A, K
F530 TO W, M, L
G531 TO A, N, D, E
G532 TO K, R, A, N
L533 TO Y, M, I
D534 TO N, K, G, E, L
S535 TO T, D, K, R, A
S536 TO T, N, P, C
P537 TO E, Q, A
W538 TO Y, R, D
S539 TO E, D, Q
V540 TO M, A, T, Y
A541 TO L, V
R542 TO K, Q, A, E
A543 TO V, M, E, R
A544 TO V, L, C, I
A545 TO R, G, L, V
K546 TO F, S, E, R

*FIG. 18*

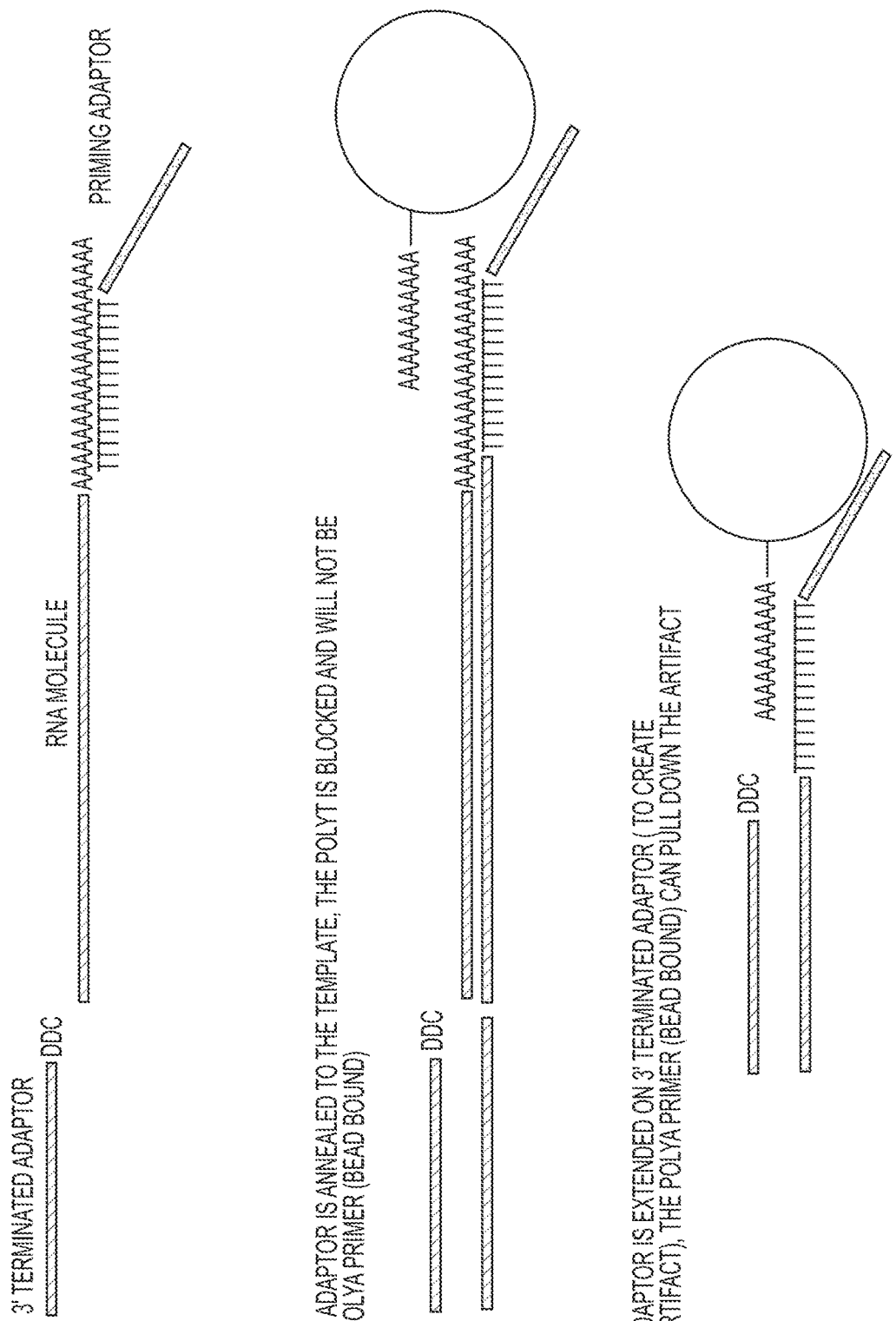

SEQUENCE LISTING

<160> NUMBER OF SEQ ID NOS: 67

<210> SEQ ID NO 1
<211> LENGTH: 805
<212> TYPE: PRT
<213> ORGANISM: Artificial Sequence
<220> FEATURE:
<223> OTHER INFORMATION: Synthesized

<400> SEQUENCE: 1

Cys Glu Pro Lys Arg His Gln Ser Pro Pro Pro Lys Lys Arg Thr
1               5                   10                  15

Thr Glu Glu Pro Lys Asn Arg Arg Gln Lys Ile Arg Ser Lys Tyr Ala
            20                  25                  30

Gln Met Gln Ser Leu Phe Lys Arg Asp Pro Lys Arg Val Ala Ala His
        35                  40                  45

Leu Ile Lys Asn Gln Pro Leu Cys Asn Val Ser Cys Pro Ile Asp Ala
    50                  55                  60

Ala Glu Ser Ala Leu Arg Gln Arg Leu Ser Gln Arg Pro Gly Val Asp
65                  70                  75                  80

Ala Ala Pro Phe Thr Ser Lys Cys Pro Gln Tyr Ser Lys Asn Ile Leu
                85                  90                  95

Asp Pro Ile Phe Pro Glu Glu Val Thr Leu His Leu Gln Lys Ile Lys
            100                 105                 110

Ile His Thr Leu Glu Gly Pro Asp Gly Ile Lys Val Ser His Leu Arg
        115                 120                 125

Ser Cys Asp Pro Asp Cys Arg Thr Thr Leu Ile Pro Lys Thr Asp Asp
    130                 135                 140

Pro His Pro Asp Ala Glu Asp Tyr Arg Pro Ile Thr Val Ala Ser Cys
145                 150                 155                 160

Leu Tyr Arg Leu Phe Ser Lys Val Val Thr Arg Arg Leu Glu Asp Ser
                165                 170                 175

Leu Ser Leu His Pro Arg Gln Lys Ala Phe Arg Ser Gly Thr Asp Gly
            180                 185                 190

Ala Phe Asp Asn Thr Ser Thr Leu Met Thr Val Ile Arg Glu Ala His
        195                 200                 205

Asn Cys Gly Glu Glu Leu Asn Ile Val Ser Ile Asp Leu Ala Lys Ala
    210                 215                 220

Phe Asp Asn Val Asn His Thr Ser Ile Thr Arg Ala Leu Arg Met His
225                 230                 235                 240

Gly Leu Asp Asp Ser Arg Thr Leu Ile Thr Gln Met Val Thr Gly
            245                 250                 255

Ser Ser Thr Ile Ile Lys Asp Gly Gly Ala Leu Ser Asn Arg Ile Glu
            260                 265                 270

Ile Asn Gln Gly Val Arg Gln Gly Asp Pro Ile Ser Pro Leu Leu Phe
            275                 280                 285

Asn Ala Val Met Asp Glu Leu Val Glu Arg Leu Gln Leu Thr Gly Glu
            290                 295                 300

Gly Phe Lys Leu Lys Gly Val Glu Val Thr Thr Leu Ala Phe Ala Asp
305                 310                 315                 320

Asp Val Thr Leu Ile Ser Arg Ser His Arg Gly Ile Glu Lys Leu Leu
                325                 330                 335

Ser Ile Thr Leu Asp Phe Leu Asn Glu Arg Gly Leu Lys Leu Asn Ile
                340                 345                 350

Asn Lys Cys Lys Gly Ile Arg Leu Val Arg Thr Pro Lys Thr Lys Ser
            355                 360                 365

Leu Val Glu Asp Thr Ser Lys Pro Phe Thr Val Pro Ser Tyr Gly Glu
            370                 375                 380

Glu Asn Gln His Ile Pro Met Val Pro Pro Gly Asp Leu Ile Lys Phe
385                 390                 395                 400

Leu Gly Val Asp Ile Thr Leu Asn Gly Lys Pro His Phe Asp Leu Ala
                405                 410                 415

Pro Leu Glu Cys Thr Leu Glu Arg Ile Arg Lys Ala Pro Leu Lys Pro
            420                 425                 430

Thr Gln Lys Leu Ala Thr Val Arg Asp Tyr Leu Ile Pro Ser Leu Glu
            435                 440                 445

Tyr Arg Leu Gly Val Pro Gly Ile Ser Arg Lys Ile Leu Glu Ser Val
450                 455                 460

Asp Gly Ala Ile Arg Ser Ala Val Lys Arg Phe Leu His Leu Pro Thr
465                 470                 475                 480

Thr Gly Met Asn Ser Met Phe Leu Ser Met Pro Ile Lys Lys Gly Gly
                485                 490                 495

Leu Gly Leu Arg Pro Leu Thr Thr Gln His Met Ala Arg Val Ala Val
            500                 505                 510

Gly Ala Asn Asn Met Met Thr Ser Met Asp Cys Leu Ser Arg Val Val
            515                 520                 525

Ala Asp Thr Thr Leu Arg Lys Pro Leu Leu Ser Ala Leu Glu His
530                 535                 540

Phe Ala Val Pro Ala Ala Thr Lys Ser Ala Ile Arg Glu Gly Lys Gln
545                 550                 555                 560

Asn Leu Leu Arg Glu Glu Ile Ala Gln Leu Ser Glu Thr Tyr His Gly
                565                 570                 575

Ser Cys Leu Pro Ser Phe Lys Lys Gly Ser Leu Val Asn Ser Trp Leu
            580                 585                 590

Arg Gly Thr Gly Gly Met Arg Ser Arg Asp Tyr Ile Thr Gly Leu Lys
            595                 600                 605

Leu Arg Phe Gly Val Ile Glu Thr Arg Ser Gln Lys Trp Lys Gly Arg
610                 615                 620

Thr Pro Gln Asn Pro Asp Ala Leu Leu Cys Arg His Cys Gly His Leu
625                 630                 635                 640

-continued

```
Ser Gly His Arg Glu Thr Ala Ala His Ile Ser Gln Lys Cys Pro Thr
                645                 650                 655

Thr Gln Ala Thr Ile Ile Gln Arg His Asn Lys Ile Val Asn Leu Val
            660                 665                 670

Gly Asp Arg Ala Lys Arg Glu Gly Phe Ala Val His Val Glu Pro Ala
        675                 680                 685

Ile Lys Ser Gly Asp Ala Val Tyr Lys Pro Asp Leu Val Leu Val Lys
    690                 695                 700

Asp Asp Thr Ala His Ile Leu Asp Val Ala Ala Pro Trp Glu Lys Gly
705                 710                 715                 720

Thr Thr Met His Glu Lys His Glu Arg Lys Ile Ser Lys Tyr Thr Val
                725                 730                 735

Leu Thr Glu Asp Val Lys Ala Leu Phe Asp Val Gln Thr Cys Thr Val
            740                 745                 750

Gly Ala Ile Ile Ile Gly Ala Ser Ser Ser Trp Cys Pro Ser Asn Asn
        755                 760                 765

Arg Ser Leu Lys Ala Cys Gly Leu His Met Pro Lys Lys Phe Lys Arg
    770                 775                 780

Leu Leu Cys Arg Val Ala Leu Glu Gly Thr Cys Lys Ile Phe Gln Asn
785                 790                 795                 800

Phe Phe Thr Leu Thr
                805

<210> SEQ ID NO 2
<211> LENGTH: 898
<212> TYPE: PRT
<213> ORGANISM: Artificial Sequence
<220> FEATURE:
<223> OTHER INFORMATION: Synthesized

<400> SEQUENCE: 2

Cys Glu Ser Lys Ser His Gln Pro Pro Pro Arg Lys Lys Arg Thr
1               5                   10                  15

Arg Glu Glu Pro Lys Asn Arg Arg Gln Lys Ile Arg Ser Lys Tyr Ala
            20                  25                  30

Gln Met Gln Thr Leu Phe Lys Arg Asp Pro Lys Arg Val Ala Ala His
        35                  40                  45

Leu Ile Arg Asn Gln Pro Leu Cys Asn Val Ser Cys Pro Ile Asp Ala
    50                  55                  60

Ala Glu Ser Ala Leu Arg Gln Arg Leu Ser Gln Arg Pro Gly Val Asp
65                  70                  75                  80

Ala Ala Pro Ile Thr Ser Lys Cys Pro Gln Asn Ser Lys Asn Ile Leu
                85                  90                  95

Asp Pro Ile Phe Pro Glu Glu Val Thr Leu His Leu Gln Lys Met Lys
            100                 105                 110

Ile His Thr Ser Ala Gly Pro Asp Gly Ile Lys Val Ser His Leu Arg
        115                 120                 125

Ser Cys Asp Pro Val Cys Leu Ala Lys Ala Phe Asn Leu Phe Leu Leu
    130                 135                 140

Ala Arg His Ile Pro Gln Gln Leu Lys Asp Cys Arg Thr Thr Leu Ile
145                 150                 155                 160

Pro Lys Thr Asp Asp Pro Arg Pro Asp Ala Glu Asp Tyr Arg Pro Ile
                165                 170                 175

Thr Val Ala Ser Cys Leu Tyr Arg Leu Phe Ser Lys Ile Val Thr Arg
            180                 185                 190
```

```
Arg Leu Glu Asp Ser Leu Ser Leu His Pro Arg Gln Lys Ala Phe Arg
            195                 200                 205

Ser Gly Thr Asp Gly Ala Phe Asp Asn Thr Ser Thr Leu Met Thr Val
210                 215                 220

Ile Arg Glu Ala His Asn Cys Gly Lys Glu Leu Asn Ile Val Ser Ile
225                 230                 235                 240

Asp Leu Ala Lys Ala Phe Asp Thr Val Asn His Thr Ser Ile Thr Arg
            245                 250                 255

Ala Leu Arg Met His Gly Leu Asp Glu Ser Arg Thr Leu Ile Thr
            260                 265                 270

Glu Met Val Thr Gly Ser Ser Thr Ile Ile Lys Gly Asp Gly Gly Ala
            275                 280                 285

Leu Ser Asn Arg Ile Glu Ile Asn Gln Gly Val Arg Gln Gly Asp Pro
290                 295                 300

Ile Ser Pro Leu Leu Phe Asn Ala Val Met Asp Glu Leu Val Glu Arg
305                 310                 315                 320

Leu Glu Arg Thr Gly Glu Gly Phe Lys Leu Lys Gly Val Glu Val Thr
            325                 330                 335

Thr Leu Ala Phe Ala Asp Asp Val Thr Leu Ile Ser Arg Ser His Arg
            340                 345                 350

Gly Met Glu Lys Leu Leu Ser Ile Thr Leu Asp Phe Leu Asn Glu Arg
            355                 360                 365

Gly Leu Gln Leu Asn Ile Asn Lys Cys Lys Gly Ile Arg Leu Val Arg
            370                 375                 380

Thr Pro Lys Thr Lys Ser Leu Val Glu Asp Thr Ser Lys Pro Phe Arg
385                 390                 395                 400

Val Pro Ser Phe Gly Glu Glu Asn Gln His Ile Pro Met Val Leu Pro
            405                 410                 415

Gly Asp Leu Ile Lys Phe Leu Gly Ile Asp Ile Thr Leu Asn Gly Lys
            420                 425                 430

Pro His Phe Asp Leu Ala Pro Leu Glu Asp Thr Leu Glu Arg Ile Arg
            435                 440                 445

Lys Ala Pro Leu Lys Pro Ala Gln Lys Leu Ala Thr Val Arg Asp Tyr
450                 455                 460

Leu Ile Pro Ser Leu Glu Tyr Arg Leu Gly Val Pro Gly Ile Ser Arg
465                 470                 475                 480

Lys Leu Leu Glu Ser Val Asp Gly Ala Ile Arg Leu Thr Val Lys Arg
            485                 490                 495

Phe Leu His Leu Pro Leu Thr Gly Met Asn Ser Met Phe Leu Ser Met
            500                 505                 510

Pro Val Lys Glu Gly Gly Leu Gly Leu Arg Ser Leu Ser Thr Gln His
            515                 520                 525

Ile Ala Arg Leu Ala Val Gly Thr Asn Ser Met Ser Ile Ser Thr Asp
            530                 535                 540

Thr Val Ser Arg Val Val Ala Asp Thr Thr Leu Arg Lys Pro Leu
545                 550                 555                 560

Leu Ser Ala Leu Glu His Phe Ala Val Pro Thr Ala Thr Lys Ser Ala
            565                 570                 575

Ile Arg Glu Gly Lys Arg Asn Leu Leu Arg Ala Glu Ile Ala Gln Leu
            580                 585                 590

Ser Glu Thr Tyr Gln Gly Ser Cys Leu Pro Ser Phe Lys His Gly Ser
            595                 600                 605

Leu Val Asn Thr Trp Leu Arg Gly Thr Ser Gly Met Arg Ser Arg Asp
```

```
                 610                 615                 620

Tyr Ile Thr Gly Leu Lys Leu Arg Phe Gly Val Ile Glu Thr Arg Ser
625                 630                 635                 640

Gln Lys Trp Arg Gly Arg Thr Pro Gln Asn Pro Asp Ala Leu Leu Cys
                645                 650                 655

Arg His Cys Gly His Ser Ser Gly Asn Arg Glu Thr Ala Ala His Val
                660                 665                 670

Ser Gln Lys Cys Leu Val Thr His Ala Leu Ile Val Gln Arg His Asn
                675                 680                 685

Lys Ile Val Arg Leu Val Gly Asp Arg Ala Lys Asp Glu Gly Phe Ala
690                 695                 700

Val His Val Glu Thr Ala Val Lys Ser Gly Glu Glu Val Tyr Lys Pro
705                 710                 715                 720

Asp Leu Ile Leu Ile Lys Ala Asp Thr Ala His Ile Ile Asp Val Ala
                725                 730                 735

Val Pro Trp Glu Lys Gly Thr Asn Met His Glu Lys His Glu Arg Lys
                740                 745                 750

Thr Asn Lys Tyr Ala Gln Leu Val Asp Asp Val Lys Ala Leu Phe Gly
                755                 760                 765

Val Gln Asn Cys Thr Val Gly Ala Leu Val Ile Gly Ala Arg Ser Ser
770                 775                 780

Trp Cys Thr Ser Asn Asp Gly Ser Leu Lys Ala Cys Gly Leu His Leu
785                 790                 795                 800

Pro Lys Lys Thr Asp Gly Glu Asp Leu Thr Thr Glu Ala Asp Asp Ser
                805                 810                 815

Asp Ala Glu Pro Trp Gln Lys Pro Glu His Ser Pro His Ala Lys
                820                 825                 830

Glu Asn Thr Glu Asp Arg Asn Thr Glu Glu Gln Ser Glu Pro Tyr Thr
                835                 840                 845

Thr Pro Gln Thr Leu Arg Thr Ser Glu Asn Pro Glu Ile Gln Arg Arg
                850                 855                 860

Arg Arg Leu His Arg Thr Thr Arg Arg Asp Cys Ala Arg Arg Thr
865                 870                 875                 880

Asp His Asn Trp Thr Pro Glu Arg Gly Thr Thr His Pro Gln Lys Gln
                885                 890                 895

Gly Pro

<210> SEQ ID NO 3
<211> LENGTH: 906
<212> TYPE: PRT
<213> ORGANISM: Artificial Sequence
<220> FEATURE:
<223> OTHER INFORMATION: Synthesized

<400> SEQUENCE: 3

Asn Cys Asp Gly Arg Asn Pro Pro Ala Pro Thr Asn Arg Arg Lys Arg
1               5                   10                  15

Leu Pro Pro Pro Ala Arg Asn Arg Ser Glu Arg Lys Arg Cys Asn Tyr
                20                  25                  30

Ala Ser Phe Gln Ser Leu Phe Lys Arg Asp Pro Lys Arg Ile Ala Ala
            35                  40                  45

His Leu Ile Lys Asn Gln Pro Leu Arg Asn Val Ser Cys Pro Ile Asp
        50                  55                  60

Val Ala Glu Ser Ala Leu Arg Gln Arg Leu Ser Gln Arg Pro Gly Ile
65                  70                  75                  80
```

```
Asp Ala Ala Pro Phe Lys Phe Lys Arg Pro Pro Asn Ser Glu Cys Ile
                 85                  90                  95

Leu Ser Pro Ile Ser Ala Asp Glu Val Thr Leu His Leu Lys Leu Met
            100                 105                 110

Ser Ala Glu Thr Ser Ala Gly Leu Asp Gly Val Gln Val Ser His Leu
        115                 120                 125

Arg Gln Cys Asp Pro Met Cys Leu Ala Lys Ala Phe Asn Cys Phe Leu
    130                 135                 140

Leu Ala Arg Tyr Ile Pro Pro Gln Leu Lys Asp Cys Arg Thr Thr Leu
145                 150                 155                 160

Ile Pro Lys Thr Asp Asn Pro Arg Pro Asp Ala Asp Tyr Arg Pro
                165                 170                 175

Ile Thr Ile Ala Ser Cys Ile Tyr Arg Leu Phe Ser Lys Ile Val Thr
            180                 185                 190

Arg Arg Leu Glu Asn Cys Ile Ser Leu His Pro Arg Gln Lys Ala Phe
        195                 200                 205

Arg Ser Gly Thr Asp Gly Ala Phe Asp Asn Ile Thr Thr Leu Thr Thr
    210                 215                 220

Ile Val Arg Asp Ala His Lys Ser Gly Lys Glu Leu Asn Ile Val Cys
225                 230                 235                 240

Val Asp Leu Ala Lys Ala Phe Asp Thr Val Asn His Ser Ser Ile Asp
                245                 250                 255

Arg Ala Leu Arg Met His Gly Leu Asp Ala Asn Ser Arg Ala Leu Ile
            260                 265                 270

Ala Gln Met Val Thr Gly Ser Thr Thr Val Ile Lys Gly Asp Gly Gly
        275                 280                 285

Val Leu Ser His Lys Ile Glu Ile Asn Gln Gly Val Arg Gln Gly Asp
    290                 295                 300

Pro Ile Ser Pro Leu Leu Phe Asn Ser Val Met Asp Glu Leu Ile Glu
305                 310                 315                 320

Arg Leu Glu Gln Ser Gly Val Gly Tyr Lys Ile Asn Asn Thr Glu Val
                325                 330                 335

Val Thr Leu Ala Phe Ala Asp Asp Val Thr Leu Val Ser Ser Ser His
            340                 345                 350

Arg Gly Met Glu Lys Leu Leu Ser Ile Thr His Asp Phe Ile Asn Glu
        355                 360                 365

Arg Gly Leu Lys Leu Asn Ile Arg Lys Cys Lys Gly Ile Arg Phe Val
    370                 375                 380

Arg Thr Pro Lys Thr Lys Ser Leu Val Gln Asp Thr Ser Lys Ala Phe
385                 390                 395                 400

Lys Val Arg Gly Ser Gly Glu Glu Ser Ser Cys Ile Pro Met Ala Gly
                405                 410                 415

Pro Gly Glu Phe Ile Lys Ile Leu Gly Val Pro Ile Ala Pro Asn Gly
            420                 425                 430

Lys Pro Ser Phe Asp Ile Asp Thr Leu Glu Gly Thr Leu Glu Arg Ile
        435                 440                 445

Arg Lys Ala Pro Leu Lys Pro Ala Gln Lys Leu Ala Ile Val Arg Asp
    450                 455                 460

Tyr Leu Ile Pro Ser Leu Glu Tyr Lys Leu Gly Val Pro Gly Val Gly
465                 470                 475                 480

Arg Arg Val Leu Asp Glu Val Asp Ala Ser Ile Arg Gln Thr Val Lys
                485                 490                 495
```

```
Arg Phe Leu His Leu Pro His Thr Gly Met Asn Ser Met Phe Leu Thr
                500                 505                 510
Met Pro Ile Lys Asp Gly Gly Leu Gly Leu Arg Ser Leu Arg Thr Gln
            515                 520                 525
His Leu Ala Arg Val Ala Val Gly Thr Asn Ser Met Met Ser Ser Ala
        530                 535                 540
Asp Pro Thr Ser His Thr Ile Ala Ser Met Pro Gln His Gln Lys Pro
545                 550                 555                 560
Leu His Ala Ala Leu Gln His Phe Ser Val Pro Ala Ala Thr Lys Asp
                565                 570                 575
Ala Leu Lys Lys Gly Lys Arg Gln Leu Leu Cys Ala Glu Ile Ala Glu
            580                 585                 590
Leu Thr Glu Thr Tyr Gln Gly Ser Cys Leu Pro Thr Phe Arg Lys Arg
        595                 600                 605
Pro Val Gly Asn Ser Trp Leu Ser Gly Leu Asn Gly Met Arg Ser Arg
    610                 615                 620
Asp Phe Ile Thr Gly Leu Lys Leu Arg Phe Gly Val Ile Glu Thr Arg
625                 630                 635                 640
Ser Gln Lys Trp Arg Gly Arg Thr Pro Gln Asn Pro Ala Val Leu Leu
                645                 650                 655
Cys Arg His Cys Gly His Ser Thr Gly Lys Arg Glu Thr Ala Ala His
            660                 665                 670
Ile Ser Gln Lys Cys Pro Gln Thr Lys Asn Leu Asn Ile Gln Arg His
        675                 680                 685
Asn Lys Ile Val His Leu Val Ala Glu His Ala Arg Arg Glu Gly Phe
    690                 695                 700
Thr Val His Val Glu His Ala Leu Lys Ser Asp Gly Gln Val Tyr Lys
705                 710                 715                 720
Pro Asp Leu Ile Leu Thr Lys Gly Asn Ala Ala His Val Leu Asp Val
                725                 730                 735
Ala Val Pro Trp Glu Thr Gly Thr Asp Met His Glu His His Glu Arg
            740                 745                 750
Lys Val Thr Lys Tyr Cys Met Ile Ser Asp Asp Val Lys Ala His Phe
        755                 760                 765
Gly Val Asp Ser Cys Thr Val Gly Ala Ile Val Val Gly Ala Arg Ser
    770                 775                 780
Ser Trp Cys Ala Ser Asn Lys Thr Thr Leu Lys Ala Cys Asn Thr His
785                 790                 795                 800
Phe Thr Lys Arg Phe Lys Arg Leu Leu Cys Arg Val Ala Leu Glu Gly
                805                 810                 815
Thr Cys Arg Pro Leu Leu Ser Ala Leu Glu His Phe Ala Val Pro Ala
            820                 825                 830
Ala Thr Lys Ser Ala Ile Arg Glu Asp Lys Gln Asn Leu Leu Arg Glu
        835                 840                 845
Glu Ile Gly Gln Leu Ser Glu Thr Tyr Arg Ser Ser Cys Leu Pro Ser
    850                 855                 860
Phe Lys Lys Ala Ser Leu Val Asn Ser Trp Leu Arg Gly Thr Ser Gly
865                 870                 875                 880
Met Arg Ser Arg Asp Tyr Ile Ala Gly Leu Lys Leu Arg Phe Gly Val
                885                 890                 895
Ile Lys Thr Arg Ser Gln Lys Trp Arg Gly
            900                 905
```

-continued

```
<210> SEQ ID NO 4
<211> LENGTH: 827
<212> TYPE: PRT
<213> ORGANISM: Artificial Sequence
<220> FEATURE:
<223> OTHER INFORMATION: Synthesized

<400> SEQUENCE: 4

Gly Ala Met Arg Pro Glu Glu Arg Gly Pro Lys Lys Gly Arg Lys
1               5                   10                  15

Lys Lys Lys Pro Glu Pro Ser Val Pro Leu Asn Ser Lys Gln Arg Lys
            20                  25                  30

Arg Met Ala Tyr Arg Lys Val Gln Gln Ala Tyr His Lys Asp Pro Lys
        35                  40                  45

Arg Val Val Ala His Leu Phe His Ser Gln Pro Leu Glu Asn Val Ser
    50                  55                  60

Cys Pro Val Glu Ser Gly Glu Lys Ala Leu Gln Ala Arg Leu Gly Lys
65                  70                  75                  80

Arg Pro Pro Ala Asp Arg Ala Pro Phe Leu Pro Lys Arg Ala Pro Leu
                85                  90                  95

Lys Asn His Leu Leu Ser Pro Ile Ser Ala Lys Glu Val Ser Glu His
            100                 105                 110

Leu Lys Gln Met Asn Leu Ala Ser Ala Ser Gly Pro Asp Gly Val Lys
        115                 120                 125

Val Ser His Leu Arg Asp Ile Gly Pro Gln Cys Leu Ser Lys Ile Phe
    130                 135                 140

Asn Thr Phe Leu Leu Glu Arg His Ile Pro Gln Val Leu Lys Asp Cys
145                 150                 155                 160

Arg Thr Thr Leu Ile Pro Lys Val Asp Asn Pro Arg Pro Asp Ala Glu
                165                 170                 175

Asp Phe Arg Pro Ile Thr Ile Gly Ser Cys Ile Tyr Arg Leu Phe Ser
            180                 185                 190

Lys Ile Val Thr Ser Arg Leu Ser Gln Leu Thr Pro Leu Asn Pro Arg
        195                 200                 205

Gln Lys Ala Phe Arg Ser Gly Thr Asp Gly Ala Phe Asp Asn Ile Thr
    210                 215                 220

Thr Val Ala Ser Leu Leu Lys Leu Ala Arg Lys Thr Gly Lys Glu Ile
225                 230                 235                 240

Asn Leu Ala Cys Ile Asp Leu Ala Lys Ala Phe Asp Thr Val Asn His
                245                 250                 255

Thr Ser Ile Thr Arg Ala Leu His Arg His Gly Val Asp Ser Ala Ser
            260                 265                 270

Ile Glu Leu Val Glu Ser Met Val Gly Glu Ala Thr Thr Val Ile Ile
        275                 280                 285

Asn Ser Asp Gly Thr Arg Ser Asn Val Ile Lys Phe Asn Arg Gly Val
    290                 295                 300

Arg Gln Gly Asp Pro Ile Ser Pro Leu Leu Phe Asn Leu Val Leu Asp
305                 310                 315                 320

Glu Leu Ile Asp Asn Leu Asp Gln Ala Arg Cys Gly Phe Ser Ile Thr
                325                 330                 335

Lys Glu Ile Gln Val Ser Cys Val Ala Phe Ala Asp Asp Ile Thr Leu
            340                 345                 350

Val Ser Gly Ser Arg Glu Gly Met Asn Asn Leu Leu Thr Ile Thr Arg
        355                 360                 365

Glu Phe Leu Gly Glu Arg Gly Leu Gly Ile Asn His Ser Lys Cys Lys
```

```
              370                 375                 380
Gly Ile Arg Phe Thr Lys Val Pro Lys Ser Lys Ser Leu Ile Ile Asp
385                 390                 395                 400

Thr Asn Pro Asn Cys Phe Leu Ile Arg Asn Gln Gln Gly Thr Pro Glu
                405                 410                 415

Pro Ile Pro Met Ala Lys Pro Gly Glu Pro Leu Lys Thr Leu Gly Ile
            420                 425                 430

Asn Leu Thr Leu Glu Gly Asn Pro Thr Phe Asn Tyr Pro Glu Leu Thr
        435                 440                 445

Arg Ile Leu Asn Thr Ile Lys His Ala Pro Leu Lys Pro His Gln Lys
    450                 455                 460

Val Gln Ile Ile Arg Asp His Leu Ile Pro Leu Leu Gln Tyr Lys Leu
465                 470                 475                 480

Gly Val Pro Thr Phe Tyr Arg Ala Thr Leu Asn Asn Ile Asp Lys Ser
                485                 490                 495

Ile Arg Leu Thr Val Lys Glu Ile Leu His Leu Pro Thr Thr Gly Leu
            500                 505                 510

His Asn Ser Tyr Leu Tyr Leu Pro Leu Lys Glu Gly Gly Leu Gly Leu
        515                 520                 525

Lys Arg Leu Ala Thr Gln Tyr Ala Ser Arg Val Gly Leu Gly Leu Ser
    530                 535                 540

Asn Met Ala Thr Ser Asp Asp Ala Val Ser Arg Ala Val Ala Gly Leu
545                 550                 555                 560

His Leu Ser Leu Met Asp Lys Ala Lys Asn Cys Leu Gly Leu Ser Glu
                565                 570                 575

Ile Ser Lys Glu Ala Ile Lys Lys Ala Lys Glu Lys Leu Val Gln Ala
            580                 585                 590

Glu Ile Arg Thr Leu Leu Gln Cys His Leu Gly Arg Ser His Ser Ser
        595                 600                 605

Phe Thr Asn Asp Thr Ile Ser Asn Ser Trp Met Arg Tyr Pro Thr Phe
    610                 615                 620

Leu Ser Ala Arg Asn Tyr Ile Met Gly Ile Lys Leu Arg Ala Gly Ile
625                 630                 635                 640

Ile Glu Thr Arg Ala Gln Lys Trp Arg Gly Arg Ser Pro Pro His Pro
                645                 650                 655

Thr Met Leu Leu Cys Arg His Cys Gly Ala Arg Ser Arg Thr Arg Glu
            660                 665                 670

Thr Asp Ile His Val Ser Gln Lys Cys Leu His Asn Lys Lys Leu Ile
        675                 680                 685

Leu Arg Arg His Asn Cys Val Val Ser Thr Leu Gly Arg Arg Ala Thr
    690                 695                 700

Gln Gln Gly Phe Ala Val Tyr Tyr Glu Pro Cys Ile Lys His Gly Glu
705                 710                 715                 720

Thr Val Leu Lys Pro Asp Leu Val Ile Ile Lys Gly Asp Thr Ala Thr
                725                 730                 735

Ile Ile Asp Val Ala Val Pro Trp Glu Gln Gly Thr Asn Leu Arg Glu
            740                 745                 750

His Asn Ser Arg Lys Ile Ser Lys Tyr Gln Cys Leu Glu Arg Glu Ala
        755                 760                 765

Ala Lys Tyr Phe Asn Val Lys Thr Val Lys Thr Gly Ser Leu Val Val
    770                 775                 780

Gly Ala Arg Gly Lys Trp Ser Ala Gly Asn Asp Ser Thr Leu Lys Ser
785                 790                 795                 800
```

Cys Gly Leu His Cys Ser Lys Arg Leu Lys Lys Leu Cys Thr Ile
            805                 810                 815

Ala Leu Glu Gly Thr Cys Ala Val Phe Lys His
            820                 825

<210> SEQ ID NO 5
<211> LENGTH: 813
<212> TYPE: PRT
<213> ORGANISM: Artificial Sequence
<220> FEATURE:
<223> OTHER INFORMATION: Synthesized

<400> SEQUENCE: 5

Leu Glu Pro Asn Arg Arg Arg Gly Tyr Ala Lys Ala Thr Arg Ile
1               5                   10                  15

Ala Leu Asn Ala Pro Gly Lys Val Arg Arg Ala Glu Tyr Ala Ala
            20                  25                  30

Met Gln Arg Gln Trp Lys Thr Lys Arg Gly Leu Cys Ala Arg Glu Ala
            35                  40                  45

Leu Glu Gly Thr Trp Lys Ile Pro Ala Arg Thr Val Ser Leu Ser Asp
50                  55                  60

Gln Glu Ala Phe Trp Arg Pro Leu Met Glu Ser Gln Ser Lys Asn Asp
65                  70                  75                  80

Leu Arg Glu Pro Ala Lys Val Gly Glu Thr Leu Trp Gly Leu Leu Asp
                85                  90                  95

Pro Ile Thr Pro Asp Glu Val Arg Gln Ile Leu Gly Ser Met Ser Ser
                100                 105                 110

Lys Ala Pro Gly Pro Asp Gly His Arg Leu Ser Asp Leu Arg Ser Ile
            115                 120                 125

Pro Ile Asp Gln Ile Cys Ser His Phe Asn Leu Trp Leu Leu Ala Gly
            130                 135                 140

Tyr Gln Pro Lys Ala Leu Arg Met Gly Glu Ser Cys Leu Ile Pro Lys
145                 150                 155                 160

Val Lys Asp Ala Ser Arg Pro Gln Gln Phe Arg Pro Ile Thr Leu Gly
                165                 170                 175

Ser Tyr Val Gly Arg Cys Leu His Lys Cys Leu Ala Ser Arg Phe Glu
            180                 185                 190

Arg Asp Leu Pro Ile Ser Ile Arg Gln Lys Ala Phe Arg Cys Met Asp
            195                 200                 205

Gly Val Ala Glu Asn Val Met Ile Leu Arg Ser Val Leu Asp Asp His
            210                 215                 220

Lys Lys Arg Leu Ala Glu Leu Asn Leu Val Phe Leu Asp Val Ser Lys
225                 230                 235                 240

Ala Phe Asp Ser Val Ser His Arg Ser Ile Leu His Ala Val Lys Arg
                245                 250                 255

Leu Gly Val Pro Pro Leu Leu Lys Tyr Val Glu Glu Leu Tyr Ala
            260                 265                 270

Asp Ser Glu Thr Phe Leu Arg Gly Ser Gly Glu Leu Ser Pro Ser Ile
            275                 280                 285

Lys Val Arg Arg Gly Val Lys Gln Gly Glu Pro Leu Ser Pro His Leu
            290                 295                 300

Phe Asn Ala Val Ile Asp Trp Ala Leu Ser Ser Leu Asp Gln Ser Phe
305                 310                 315                 320

Gly Val Thr Val Gly Glu Ala Arg Val Asn His Leu Ala Phe Ala Asp
                325                 330                 335

```
Asp Ile Val Leu Leu Ser Ser Gln Pro Gly Leu Gln Arg Leu Ile
                340             345             350

Asp Gln Leu Thr Thr His Leu Gly Glu Ser Gly Leu Arg Val Asn Ser
                355             360             365

Thr Lys Ser Ala Ser Ile Arg Ile Ala Val Asp Gly Lys Asn Lys Arg
            370             375             380

Trp Val Val Asp Pro Arg Asp Ser Val His Val Gly Val Arg Ile
385             390             395             400

Pro Ala Val Ala Val Ser Gly Ser Tyr Arg Tyr Leu Gly Val Asn Ile
                405             410             415

Ser Ala Ala Gly Met Arg Val Asp Ala Ala Asp Ser Leu Ala Ser Lys
            420             425             430

Leu Ala Asn Leu Ser Arg Ala Pro Leu Lys Pro Gln Gln Arg Leu Tyr
            435             440             445

Ile Leu Cys Thr His Leu Leu Pro Ser Ile Tyr His Gln Leu Val Leu
            450             455             460

Ser Ser Thr Ser Lys Lys Phe Leu Lys Tyr Leu Asp Arg Cys Val Arg
465             470             475             480

Val Ala Val Arg Arg Trp Leu Arg Leu Pro Lys Asp Thr Pro Lys Ala
                485             490             495

Tyr Phe His Ala Lys Cys Asn Asp Gly Gly Leu Gly Val Pro Glu Leu
                500             505             510

Gln Arg Val Ile Pro Leu Gln Lys Ala Gly Arg Trp Leu Lys Met Thr
            515             520             525

Arg Ser Gln Asp Pro Val Val Gln Ala Ala Val Gly Leu Glu Tyr Phe
            530             535             540

Gln Lys Leu Leu Glu Arg Trp Ser Thr Pro Glu Leu Tyr Gln Trp Gly
545             550             555             560

Gly Gly Gly Ile Thr Thr Ser Gly His Leu Ala Val Ala Gln Ala Arg
                565             570             575

Ser Leu Tyr Ser Ser Val Asn Gly Arg Gly Leu Arg Gln Ser Gly Leu
            580             585             590

Val Ser Thr Gln Phe Asp Trp Val Arg Ser Gly Cys Ser Leu Leu Ser
            595             600             605

Gly Arg Asn Phe Ile Gly Ala Met Gln Leu Arg Gly Asn Leu Leu Ala
            610             615             620

Thr Lys Leu Arg Ala Ser Arg Gly Arg Pro Arg Val Asp Ile Ser Cys
625             630             635             640

Asp Cys Cys Arg Thr Pro Glu Ser Ser Gly His Ile Leu Gln Val Cys
                645             650             655

Pro Arg Thr Ser Trp Gly Ala Arg Ile Gly Arg His Asp Asn Val Ala
                660             665             670

Lys Leu Val Ala Arg Glu Ser Ala Lys Arg His Trp Lys Val Ile Arg
            675             680             685

Glu Pro Ala Ile Pro Thr Pro Ala Gly Ile Arg Arg Pro Asp Leu Val
            690             695             700

Phe Ser Lys Gly Asp Thr Ala Ile Val Val Asp Val Thr Ile Val Pro
705             710             715             720

Asp Asn Ala Glu Leu Ser Asp Ala His Ser Ser Lys Val Ser Tyr Tyr
                725             730             735

Asp Asn Gly Ala Ile Arg Gly Trp Val Ala Leu Asn Thr Gly Ala Ser
                740             745             750
```

```
His Ile Thr Phe Ser Ser Val Asn Asn Asn Trp Ser Asp Cys Met Ala
        755                 760                 765

Glu Glu Ser Lys Arg Met Leu Lys Leu Gly Leu Gly Leu Pro Asn Ser
    770                 775                 780

Ile Arg Gly Thr Ile Ser Ala Val Val Leu Glu Lys Gly Phe His Met
785                 790                 795                 800

Tyr Leu Cys Phe Lys Arg Gly Thr Phe Arg Ala Ser Tyr
                805                 810

<210> SEQ ID NO 6
<211> LENGTH: 830
<212> TYPE: PRT
<213> ORGANISM: Artificial Sequence
<220> FEATURE:
<223> OTHER INFORMATION: Synthesized

<400> SEQUENCE: 6

Asn His Glu Arg Thr Thr Lys Gln Val Pro Glu Asn Asn Thr Pro Ala
1               5                   10                  15

Arg Arg Pro Phe Lys Arg Arg Leu His Arg Val Glu Arg Tyr Lys Arg
            20                  25                  30

Phe Gln Arg Met Tyr Asp Leu Gln Arg Lys Arg Leu Ala Glu Glu Ile
        35                  40                  45

Leu Asp Gly Arg Glu Ala Val Thr Cys Asn Leu Lys Lys Glu Glu Ile
50                  55                  60

Lys Asp His Tyr Asp Gln Val Tyr Gly Val Ser Asn Asp Arg Val Ser
65                  70                  75                  80

Leu Asp Asp Cys Pro Arg Pro Pro Gly Ala Asn Asn Thr Asp Leu Leu
                85                  90                  95

Lys Pro Phe Thr Pro Thr Glu Val Met Asp Ser Leu Gln Gly Met Lys
            100                 105                 110

Asn Gly Ala Pro Gly Pro Asp Lys Ile Thr Leu Pro Phe Leu Gln Lys
        115                 120                 125

Arg Leu Lys Asn Gly Ile His Val Ser Leu Ala Asn Val Phe Asn Leu
130                 135                 140

Trp Gln Phe Ser Gly Arg Ile Pro Glu Cys Met Lys Ser Asn Arg Ser
145                 150                 155                 160

Val Leu Ile Pro Lys Gly Lys Ser Asn Leu Arg Asp Val Arg Asn Trp
                165                 170                 175

Arg Pro Ile Thr Ile Ser Ser Ile Val Leu Arg Leu Tyr Thr Arg Ile
            180                 185                 190

Leu Ala Arg Arg Leu Glu Arg Ala Val Gln Ile Asn Pro Arg Gln Arg
        195                 200                 205

Gly Phe Val Pro Gln Ala Gly Cys Arg Asp Asn Ile Phe Leu Leu Gln
210                 215                 220

Ser Ala Met Arg Arg Ala Lys Arg Lys Gly Thr Leu Ala Leu Gly Leu
225                 230                 235                 240

Leu Asp Leu Ser Lys Ala Phe Asp Thr Val Gly His Lys His Leu Leu
                245                 250                 255

Thr Ser Leu Glu Arg Phe Ala Val His Pro His Phe Val Arg Ile Val
            260                 265                 270

Glu Asp Met Tyr Ser Gly Cys Ser Thr Ser Phe Arg Val Gly Ser Gln
        275                 280                 285

Ser Thr Arg Pro Ile Val Leu Met Arg Gly Val Lys Gln Gly Asp Pro
290                 295                 300
```

```
Met Ser Pro Ile Leu Phe Asn Ile Ala Leu Asp Pro Leu Leu Arg Gln
305                 310                 315                 320

Leu Glu Glu Ser Arg Gly Phe Met Phe Arg Glu Gly Gln Ala Pro
            325                 330                 335

Val Ser Ser Leu Ala Tyr Ala Asp Met Ala Leu Leu Ala Lys Asp
            340                 345                 350

His Ala Ser Leu Gln Ser Met Leu Gly Thr Val Asp Lys Phe Cys Ser
            355                 360                 365

Gly Asn Gly Leu Gly Leu Asn Ile Ala Lys Ser Ala Gly Leu Leu Ile
            370                 375                 380

Arg Gly Ala Asn Lys Thr Phe Thr Val Asn Asp Cys Pro Ser Trp Leu
385                 390                 395                 400

Val Asn Gly Glu Thr Leu Pro Met Ile Gly Pro Glu Gln Thr Tyr Arg
            405                 410                 415

Tyr Leu Gly Ala Ser Ile Cys Pro Trp Thr Gly Ile Asn Ser Gly Pro
            420                 425                 430

Val Lys Pro Thr Leu Glu Lys Trp Ile Ala Asn Ile Thr Glu Ser Pro
            435                 440                 445

Leu Lys Pro His Gln Arg Val Asp Ile Leu Cys Lys Tyr Ala Leu Pro
            450                 455                 460

Arg Leu Phe Tyr Gln Leu Glu Leu Gly Thr Leu Asn Phe Lys Glu Leu
465                 470                 475                 480

Lys Glu Leu Asp Ser Met Val Lys Gln Ala Val Lys Arg Trp Cys His
                485                 490                 495

Leu Pro Ala Cys Thr Ala Asp Gly Leu Leu Tyr Ser Arg His Arg Asp
            500                 505                 510

Gly Gly Leu Ala Val Val Lys Leu Glu Ser Leu Val Pro Cys Leu Lys
            515                 520                 525

Ile Lys Thr Asn Leu Arg Leu Val His Ser Thr Asp Pro Val Ile Ser
            530                 535                 540

Ser Leu Ala Glu Ser Asp Gly Leu Val Gly Ala Ile Glu Gly Ile Ala
545                 550                 555                 560

Gln Lys Ala Gly Leu Pro Ile Pro Thr Pro Asp Gln Arg Ser Gly Thr
            565                 570                 575

Tyr His Ser Asn Trp Arg Asp Met Glu Arg Arg Ser Trp Glu Arg Leu
            580                 585                 590

Ala Leu His Gly Gln Gly Val Glu Leu Phe Lys Gly Ser Arg Ser Ala
            595                 600                 605

Asn His Trp Leu Pro Arg Pro Val Gly Met Lys Pro His His Trp Val
            610                 615                 620

Lys Cys Leu Ala Met Arg Ala Asn Val Tyr Pro Thr Lys Arg Gly Leu
625                 630                 635                 640

Ser Arg Gly Asn Leu Ser Lys Asn Lys Asp Ser Ala Lys Cys Arg Gly
            645                 650                 655

Cys Thr Ser Met Arg Glu Thr Leu Cys His Leu Ser Gly Gln Cys Pro
            660                 665                 670

Lys Leu Lys Ser Met Arg Ile Arg Arg His Asn Lys Ile Cys Glu His
            675                 680                 685

Leu Ile Ala Glu Ala Ser Phe Lys Gly Trp Lys Val Leu Gln Glu Pro
            690                 695                 700

Thr Leu Val Thr Asp Asn Gly Glu Arg Arg Pro Asp Leu Ile Phe
705                 710                 715                 720

His Arg Asp Asp Lys Ala Val Val Val Asp Val Thr Val Arg Tyr Glu
```

```
                    725                 730                 735
Ile Ser Lys Asp Thr Leu Arg Glu Ala Tyr Ala Ser Lys Val Arg Arg
                740                 745                 750

Tyr Gly Cys Leu Thr Glu Gln Ile Lys Asp Leu Thr Gly Ala Thr Ser
            755                 760                 765

Val Val Phe His Gly Phe Pro Met Gly Ala Arg Gly Ala Trp Phe Pro
770                 775                 780

Glu Ser Ser Asp Val Met Ala Asp Leu Asn Ile Arg Ser Lys Tyr Phe
785                 790                 795                 800

Glu Glu Phe Leu Cys Arg Arg Thr Ile Leu Tyr Thr Leu Asp Leu Leu
                805                 810                 815

Trp Lys Ser Asn Asn Glu Gln Tyr Leu Glu Arg Leu Ala Pro
                820                 825                 830

<210> SEQ ID NO 7
<211> LENGTH: 821
<212> TYPE: PRT
<213> ORGANISM: Artificial Sequence
<220> FEATURE:
<223> OTHER INFORMATION: Synthesized

<400> SEQUENCE: 7

Asn Glu Gly Leu Gln Gly Asn Gln Arg Leu Pro Lys Glu Lys Pro Met
1               5                   10                  15

Thr Ala Arg Ala Lys Met Arg His Leu Arg Leu Leu Arg Tyr Arg Arg
                20                  25                  30

Leu Gln Glu Leu Tyr Lys Lys Asp Arg Ser Leu Ala Ala Lys Gln Val
            35                  40                  45

Leu Gln Asp Met Leu Asp Ser Lys Pro Gly Arg Asn Pro Glu Ala Val
        50                  55                  60

Lys Tyr Trp Ala Glu Thr Met Gly Lys Glu Ser Thr Gly Ile Asp Val
65              70                  75                  80

Ser Val Met Thr Gly Arg Pro Arg Tyr Arg Asp Asn Val Trp Ser Pro
                85                  90                  95

Ile Tyr Pro Gly Glu Val Ser Ala Ala Val Lys Leu Met Asp Ser Ser
            100                 105                 110

Gly Ala Thr Gly Pro Asp Gly Phe Ser Val Arg Ser Leu Lys Cys Thr
        115                 120                 125

Pro Ser Arg Val Leu Ala Lys Val Phe Asn Leu Phe Leu Leu Glu Glu
    130                 135                 140

Lys Leu Pro Ala Phe Leu Met Thr Ser Arg Thr Val Leu Val Pro Lys
145                 150                 155                 160

Val Lys Glu Pro Lys Ala Pro Thr Asp Tyr Arg Pro Ile Ser Val Ser
                165                 170                 175

Ser Thr Leu Val Arg Leu Phe His Lys Ile Leu Ala Arg Arg Leu Thr
            180                 185                 190

Leu Ala Ser Gly Leu Asp Ser Arg Gln Arg Gly Phe Val Pro Val Asp
        195                 200                 205

Gly Cys Ala Glu Asn Leu Val Val Leu Glu Ser Ala Ile Arg Ser Ala
    210                 215                 220

Lys Asn Tyr Lys Arg Ser Leu Phe Val Ala Met Asp Ile Lys Asn
225                 230                 235                 240

Ala Phe Gly Ser Val Ala His Glu Ala Ile Phe Glu Ala Leu Ser Lys
                245                 250                 255

Ser Gly Ala Pro Asp Ser Phe Val Thr Tyr Val Arg Asn Cys Tyr Asp
```

```
                    260                 265                 270
Gly Phe Ala Ser Val Val Lys Leu Gly Arg Asp Thr Ala Gln Thr Thr
                275                 280                 285
Val Arg Gln Gly Val Leu Gln Gly Asp Pro Leu Ser Pro Ile Leu Phe
            290                 295                 300
Asn Leu Val Ile Asp Gln Ile Ile Arg Ser Leu Pro Glu Thr Val Gly
305                 310                 315                 320
Val Gln Leu Asp Ala Asn Thr Lys Leu Asn Ser Met Ala Phe Ala Asp
                325                 330                 335
Asp Leu Ile Leu Leu Ser Ser Ser Glu Ala Gly Met Arg Arg Met Leu
            340                 345                 350
Gly Val Leu Ala Gly Val Ser Ser Lys Phe Gly Leu Ile Phe His Pro
        355                 360                 365
Gly Lys Cys Lys Tyr Leu Ala Met Ile Trp Ala Gly Lys Gln Lys Lys
    370                 375                 380
Met Lys Ile Ala Thr Asp Leu Ser Phe Glu Ile Gly Gly Gly Phe Met
385                 390                 395                 400
Thr Pro Val Gly Val Thr Glu Thr Trp Lys Tyr Leu Gly Ala Tyr Leu
                405                 410                 415
Gly Gln Ile Gly Ile Gln Pro Ala Arg Leu Ser Leu Gln Thr Phe Leu
            420                 425                 430
Glu Arg Ile Ala Lys Ser Pro Leu Lys Pro Gln Gln Lys Leu Tyr Leu
        435                 440                 445
Ile Arg Val His Leu Leu Pro Lys Leu Ile Tyr Pro Leu Val Met Ala
    450                 455                 460
Pro Ile Arg Ala Ser Met Leu Asn Lys Leu Asp Arg Met Val Arg Val
465                 470                 475                 480
Ala Leu Thr Gly Lys Asp Gly Ile Leu His Leu Pro Gln Ser Val Pro
                485                 490                 495
Ser Ala Phe Phe Tyr Ala Pro Ile Gly Glu Gly Gly Leu Gly Leu Met
            500                 505                 510
Glu Leu Arg Thr Ser Ile Pro Ala Met Val Lys Ala Arg Phe Glu Arg
        515                 520                 525
Met Met Asn Ser Thr Cys His His Val Arg Ala Ala Ala Lys Gly Ala
    530                 535                 540
Ala Asn Ser Asn Arg Ile Ala Leu Ala Asn Arg Phe Leu Arg Lys Thr
545                 550                 555                 560
Ala Asp Gly Ile Pro Val Thr Ser Ala Lys Leu Val Lys Glu Tyr Gln
                565                 570                 575
Ala Ala Lys Leu His Gly Ser Phe Asp Gly Lys Pro Leu Ser Glu Ala
            580                 585                 590
Gly Arg Val Lys Gly Ile His Ser Trp Thr Cys Asp Gly Arg Met Val
        595                 600                 605
Met Thr Gly Gln Ala Phe Cys Glu Ala Leu Lys Ile Arg Ile Asn Ala
    610                 615                 620
Leu Pro Cys Leu Ser Arg Tyr Asn Arg Gly Thr Glu Lys Pro Arg Glu
625                 630                 635                 640
Cys Arg Ala Gly Cys Lys Thr Thr Glu Ser Leu Asn His Val Leu Gln
                645                 650                 655
Val Cys Pro Arg Thr His Asp Met Arg Val Ala Arg His Asp Lys Leu
            660                 665                 670
Val Asn Arg Leu Gly Gly Tyr Leu Ser Gln Lys Gly Phe Glu Ile His
        675                 680                 685
```

```
Thr Glu Pro Arg Ile Ile Thr Ser Leu Gly Leu Arg Lys Pro Asp Ile
    690                 695                 700

Ile Ala Ile Lys Gly Glu Lys Gly Val Val Leu Asp Ala Gln Ile Gly
705                 710                 715                 720

Gly Ala Ala Asn Leu Asn Ala Ala His Asp Ala Lys Met Cys Tyr Tyr
                725                 730                 735

Ser Ser Ser Pro Glu Ile Lys Glu Trp Val Thr Gly Lys Gly Ala Pro
                740                 745                 750

Asp Val Ser Tyr Gly Ala Cys Ile Val Ser Pro Gln Gly Ile Met Ser
            755                 760                 765

Glu Glu Ser Trp Lys Thr Leu Arg Gly Leu Gly Phe Ser Lys Gly Met
    770                 775                 780

Leu Asn Ser Leu Val Val Thr Val Met Glu Gln Ser Thr Tyr Val Trp
785                 790                 795                 800

His Val Phe Asn Arg Ser Thr Ala Ser Tyr Gly Trp Lys Arg Arg Arg
                805                 810                 815

Lys Arg Lys Trp Asp
            820

<210> SEQ ID NO 8
<211> LENGTH: 811
<212> TYPE: PRT
<213> ORGANISM: Artificial Sequence
<220> FEATURE:
<223> OTHER INFORMATION: Synthesized

<400> SEQUENCE: 8

Met Ala Gln Asn Pro Cys Pro Lys Pro Pro Pro Ala Lys Asn Ser
1               5                   10                  15

Arg Glu Arg Arg Asp Arg Glu Tyr Ser Arg Val Gln Asn Phe Tyr Lys
            20                  25                  30

Lys Asn Arg Ser Ala Cys Ile Asn Ser Ile Leu Asp Gly Asn Thr Arg
        35                  40                  45

Ser Gln Asn Val Ile Pro Gly Leu Thr Lys Phe Trp Thr Glu Thr Phe
    50                  55                  60

Glu Lys Asn Ser Pro Pro Asp Asp Glu Ala Pro Asp Gln Phe Val Ala
65                  70                  75                  80

Asp Glu Pro Arg Asp Met Tyr Lys Trp Ile Thr Phe Tyr Glu Met Ser
                85                  90                  95

Gln Asp Tyr Leu Asp Ser Ser Thr Ala Pro Gly Val Asp Gly Phe Ser
                100                 105                 110

Ala Lys Gln Leu Arg Ser Met Ser Pro Arg Val Leu Asn Lys Ile Leu
            115                 120                 125

Asn Leu Leu Leu Ser Glu Asn Leu Pro Asn Ser Phe Lys Met His
        130                 135                 140

Lys Thr Val Leu Ile Pro Lys Ile Asp Pro Lys Ser Pro Gly Asp
145                 150                 155                 160

Phe Arg Pro Ile Thr Ile Ser Pro Val Leu Ala Arg Leu Leu Asn Lys
                165                 170                 175

Ile Leu Ala Ala Arg Leu Ser Lys Leu Val Pro Ile Ser Gln Arg Gln
            180                 185                 190

Lys Ala Phe Leu Pro Val Asp Gly Cys Gly Glu Asn Ile Phe Leu Leu
        195                 200                 205

Asp Tyr Ile Leu Arg Ser Ser Lys Lys Ser Ser Lys Ser Val Ala Met
    210                 215                 220
```

-continued

```
Ala Val Leu Asp Val Lys Lys Ala Phe Asp Ser Val His His Ser
225                 230                 235                 240

Ile Leu Arg Ala Leu Asn Glu Ala Lys Cys Pro Ile Asn Phe Ile Asn
            245                 250                 255

Phe Val Arg Asn Ser Tyr Asp Gly Cys Thr Thr Lys Leu Thr Cys Gly
        260                 265                 270

Gly Thr Ser Phe Pro Asp Ser Val Arg Met Asn Arg Gly Val Lys Gln
    275                 280                 285

Gly Asp Pro Leu Ser Pro Val Leu Phe Asn Leu Ile Ile Asp Ser Ala
290                 295                 300

Ile Arg Lys Leu Pro Asp Ser Ile Gly Tyr Val Ile Arg Asp Gly Leu
305                 310                 315                 320

Lys Ile Asn Cys Leu Ala Tyr Ala Asp Asp Leu Ile Leu Val Ala Ser
                325                 330                 335

Ser Arg Ala Gly Leu Lys Thr Leu Leu Asn Ile Val Ala Glu His Leu
            340                 345                 350

Ser Leu Arg Gly Leu Asp Leu Asn Ala Ala Lys Cys His Gly Leu Ser
        355                 360                 365

Ile Ile Ala Ser Gly Lys Ala Lys Thr Thr Tyr Val Ser Ala Ala Asp
370                 375                 380

Ser Leu Asp Leu Asp Gly Gln Pro Ile Lys Asn Leu Gly Val Leu Asp
385                 390                 395                 400

Thr Trp Thr Tyr Leu Gly Ile Pro Phe Ser His Leu Gly Arg Ala Glu
                405                 410                 415

Lys Val Ser Pro Asp Leu Thr Asn Leu Leu Asn Lys Leu Gln Lys Ala
            420                 425                 430

Pro Leu Lys Leu Gln Gln Lys Leu Tyr Ala Val Arg Asn Phe Val Ile
        435                 440                 445

Pro Arg Ala Leu His Gly Leu Ile Leu Ser Lys Thr Asn Leu Lys Glu
450                 455                 460

Leu Asn Thr Leu Asp Arg Ala Ile Arg Val Phe Leu Arg Thr Leu Leu
465                 470                 475                 480

Tyr Leu Pro Lys Asp Thr Pro Leu Gly Phe Phe His Ser Pro Ile Lys
                485                 490                 495

Ser Gly Gly Leu Gly Ile Thr Cys Phe Arg Thr Ser Val Leu Lys Cys
            500                 505                 510

Arg Leu Gln Arg Ile Ala Arg Met Arg Ser Ser Cys Asp Gly Val Ile
        515                 520                 525

Gln Ala Val Ala Glu Ser Asp Ile Phe Ala Asp Glu Tyr Ala Lys Leu
530                 535                 540

Arg Asp Leu Ile Arg Ile Asn Gly Asn Val Leu Asp Thr Thr Glu Ser
545                 550                 555                 560

Ile Lys Arg Tyr Trp Ala Gln Arg Leu His Ser Ser Val Asp Gly Lys
                565                 570                 575

Thr Leu Ala Tyr Met Asp Tyr Phe Pro Gln Gly Asn Leu Trp Met Ser
            580                 585                 590

Glu Asp Lys Val Ser Gln Arg Ser Tyr Val Phe Ala Asp Cys Val Lys
        595                 600                 605

Leu Arg Ile Asn Ala Ile Pro Thr Arg Val Arg Val Ser Arg Gly Arg
610                 615                 620

Pro Asn Lys Glu Met Cys Cys Arg Ala Lys Cys Phe Asp Ser Gln Arg
625                 630                 635                 640
```

```
Met Pro Ala Phe Glu Ser Leu Asn His Ile Thr Gln Val Cys Pro Arg
                645                 650                 655

Thr His Gly Ser Arg Ile Gln Arg His Asp Lys Ile Ala Lys Phe Leu
            660                 665                 670

Phe Lys Asn Leu Asn Asn Cys Pro Ser Arg Ser Val Leu Tyr Glu Pro
            675                 680                 685

His Phe Val Thr Val Asp Gly Leu Arg Lys Pro Asp Ile Ile Ile Tyr
690                 695                 700

Asp Asp Ser His Met Val Val Leu Asp Val Gln Val Val Ser Asp Ser
705                 710                 715                 720

Ala Asn Leu Glu Lys Glu Phe Glu Cys Lys Ala Lys Lys Tyr Ala Asn
            725                 730                 735

Asp Val Ala Leu Arg Ser Ala Met Leu Ile Lys Tyr Pro Phe Ile Lys
            740                 745                 750

Ser Phe Ser Phe Val Ala Ala Thr Tyr Asn Asn Arg Gly Leu Ile Ala
            755                 760                 765

Lys Ser Ser Val Gln Val Leu Arg Gln Leu Gly Leu Ser Pro Arg Ser
            770                 775                 780

Ile Met Val Ser Ile Leu Ile Cys Leu Glu Gly Thr Leu Glu Thr Trp
785                 790                 795                 800

Arg Ile Phe Asn Gln Ser Thr Met Asn Ala His
            805                 810

<210> SEQ ID NO 9
<211> LENGTH: 817
<212> TYPE: PRT
<213> ORGANISM: Artificial Sequence
<220> FEATURE:
<223> OTHER INFORMATION: Synthesized

<400> SEQUENCE: 9

Ser Asp Leu Glu Val Thr Gly Arg Lys Arg Val Ala Arg Gly Pro Arg
1               5                   10                  15

Ala Ile Pro Val Leu Ser Lys Arg Lys Ala Arg Ile Glu Tyr Arg
            20                  25                  30

Arg Met Gln Gln Leu Trp Arg Thr Asn Met Thr Lys Ala Ala His Lys
            35                  40                  45

Val Leu Asp Gly Asp Ala Gly Ser Leu Pro His Pro Thr Leu Ala Ala
        50                  55                  60

Gln Leu Gly Phe Trp Lys Pro Val Leu Glu Ala Glu Ser Val Asp Leu
65                  70                  75                  80

Ala Trp Pro Phe Ala Val Gly His Pro Gly Val Ala Val Gly Asp Leu
                85                  90                  95

Trp Ser Pro Ile Thr Glu Gly Glu Val Ile Asn Ile Arg Leu Pro Arg
            100                 105                 110

Thr Ser Ser Pro Gly Leu Asp Gly Leu Thr Val His Arg Trp Phe Thr
            115                 120                 125

Glu Val Pro Ala Ile Leu Arg Ala Thr Ile Leu Asn Ile Phe Met Ala
            130                 135                 140

Thr Gly Trp Val Pro Pro Arg Phe Arg His Ser Arg Thr Val Leu Ile
145                 150                 155                 160

Pro Lys Ser Ser Asp Leu Met Asp Pro Ala Tyr Tyr Arg Pro Ile Ser
                165                 170                 175

Val Ser Ser Val Ile Leu Arg His Phe His Lys Ile Leu Ala Arg Arg
            180                 185                 190
```

```
Val Ala Ala Cys Glu Leu Leu Asp Val Arg Gln Arg Ala Phe Ile Ala
        195                 200                 205

Ala Asp Gly Cys Ala Glu Asn Val Ala Val Leu Ser Ala Ile Leu Phe
    210                 215                 220

Asp Ala Arg Thr Asn Arg Arg Gln Leu His Val Ile Thr Leu Asp Val
225                 230                 235                 240

Arg Lys Ala Phe Asp Thr Val Ser His Asn Ala Ile Arg Tyr Val Leu
                245                 250                 255

Ser Lys His Gly Met Pro Gln Ile Met Val Glu Tyr Leu Ser Thr Leu
            260                 265                 270

Tyr Arg Thr Ala Ala Val Arg Leu Glu Val Asp Gly Glu Phe Ser Asp
        275                 280                 285

Glu Ile Leu Pro Gly Arg Gly Val Arg Gln Gly Asp Pro Leu Ser Pro
    290                 295                 300

Leu Leu Phe Asn Leu Ile Met Asn Glu Ile Leu Ala Glu Val Pro Asp
305                 310                 315                 320

Gln Val Gly Tyr Cys Met Met Asp Arg Asn Val Asn Ala Leu Ala Phe
                325                 330                 335

Ala Asp Asp Leu Val Leu Ile Gly Ala Thr Arg Asp Gly Ala Gln Arg
            340                 345                 350

Ser Leu Glu Arg Val Met Ala Ala Leu Tyr Arg Phe Gly Leu Glu Leu
        355                 360                 365

Ala Pro Ala Lys Cys Ala Ala Phe Ser Leu Val Pro Cys Gly Lys Thr
    370                 375                 380

Lys Arg Ile Lys Ile Leu Thr Asp Pro Gln Phe Val Ala Gly Asp Arg
385                 390                 395                 400

Pro Ile Pro Gln Leu Gly Val Leu His Thr Val Arg Tyr Leu Gly Val
                405                 410                 415

Arg Phe Gly Glu Thr Gly Pro Val Ile Gln Gly Val Glu Leu Leu Pro
            420                 425                 430

Leu Leu Glu Arg Ile Thr Arg Ala Pro Leu Lys Pro Gln Gln Arg Leu
        435                 440                 445

Lys Ile Leu Arg Thr Tyr Leu Ile Pro Arg Tyr Thr His Asn Leu Val
    450                 455                 460

Leu Gly Arg Val Ser Tyr Ser Met Leu Arg Lys Leu Asp Lys Gln Thr
465                 470                 475                 480

Arg Ala Ala Val Arg Arg Trp Leu Val Leu Pro Asp Asp Val Pro Val
                485                 490                 495

Ala Phe Phe His Cys Pro Ile Lys Gln Gly Gly Leu Gly Ile Gln Ser
            500                 505                 510

Phe Glu Thr Ala Ile Pro Arg Leu Thr Leu Leu Arg Leu Asn Arg Leu
        515                 520                 525

Lys Asp Ser Gln Tyr Glu Met Ala Arg Val Val Gly Ser Ser Ala Trp
    530                 535                 540

Ala Asp Arg Arg Met Arg Trp Cys Arg Phe Ala Arg Arg Asp Glu
545                 550                 555                 560

Asp Trp Pro Ser Glu Leu His Ala Lys Val Asp Gly Phe Glu Leu Arg
                565                 570                 575

Glu Ala Gly Asn Val Ser Val Ser Thr Arg Trp Leu Asp Asp Ala Met
            580                 585                 590

Val His Ile Pro Ser Ser Asp Trp Leu Gln Tyr Val Lys Val Trp Ile
        595                 600                 605

Asn Ala Leu Pro Thr Arg Ile Arg Thr Thr Arg Gly Ser Arg Arg Leu
```

```
                    610                 615                 620
Arg Glu Asp Val Asn Cys Arg Gly Gly Cys Gly Val Gln Glu Thr Ala
625                 630                 635                 640

Ala His Val Val Gln Gln Cys Phe Arg Thr His Gly Gly Arg Ile Met
                645                 650                 655

Arg His Asp Ala Val Ala Ser Ala Leu Ala Gly Glu Leu Gln Arg Gly
                    660                 665                 670

Gly Tyr Asn Val His Arg Glu Arg Val Phe Arg Thr Arg Glu Gly Val
                675                 680                 685

Arg Lys Pro Asp Ile Leu Ala Ala Lys Gly Thr His Gly His Val Leu
            690                 695                 700

Asp Val Gln Ile Ile Ser Gly Ala Arg Pro Leu Ser Asp Gly His Asp
705                 710                 715                 720

Arg Lys Arg Ser Tyr Tyr Ala Asn Asn Ala Asp Leu Leu Ala Arg Ile
                725                 730                 735

Ser Ala Leu Leu Gln Val Pro Val Arg Asn Leu Asp Val Ser Thr Val
                    740                 745                 750

Thr Leu Ser Trp Arg Gly Val Trp Ala Arg Glu Ser Ala Ala Val Leu
                755                 760                 765

Thr Ser Leu Gly Val Ser Lys Ala Val Leu Arg Gly Ile Thr Thr Arg
            770                 775                 780

Val Leu Lys Gly Ser Tyr Met Asn Phe Ser Arg Phe Asn Gln Thr Thr
785                 790                 795                 800

Ala Thr Cys Arg Gly Arg Ala Asn Leu Arg Met Ser Gly Trp Gly Pro
                805                 810                 815

Pro

<210> SEQ ID NO 10
<211> LENGTH: 805
<212> TYPE: PRT
<213> ORGANISM: Artificial Sequence
<220> FEATURE:
<223> OTHER INFORMATION: Synthesized

<400> SEQUENCE: 10

Asn Thr Ala Lys Cys Pro Lys Gly Pro Arg Phe Arg Lys Thr Ala Thr
1               5                   10                  15

His Ser Gly Thr Asn Lys Gln Gln Arg Gln Arg Tyr Ala Arg Val
                20                  25                  30

Gln Lys Leu Tyr Lys Met Asn Arg Lys Val Ala Ala Lys Met Val Leu
            35                  40                  45

Glu Glu Thr Asp Lys Ile Gln Ile Lys Leu Pro Asp His Asp Pro Met
50                  55                  60

Phe Lys Phe Trp Glu Ser Glu Phe Lys Glu Gly Met Pro Glu
65                  70                  75                  80

Arg Met Pro Lys Asp Leu Lys Glu Ser Pro Asp Leu Lys Ala Ile Trp
                85                  90                  95

Asp Pro Val Thr Glu Glu Val Arg Lys Ala Lys Val Ala Asn Asn
                100                 105                 110

Thr Ala Ala Gly Pro Asp Gly Ile Gln Pro Lys Ser Trp Asn Arg Ile
            115                 120                 125

Ser Leu Lys Tyr Lys Thr Leu Ile Tyr Asn Leu Leu Leu Tyr Tyr Glu
            130                 135                 140

Lys Val Pro His Lys Leu Lys Val Ser Arg Thr Val Phe Ile Pro Lys
145                 150                 155                 160
```

-continued

```
Lys Lys Asp Gly Ser Ser Asp Pro Gly Glu Phe Arg Pro Leu Thr Ile
            165                 170                 175
Cys Ser Val Val Leu Arg Gly Phe Asn Lys Ile Leu Val Gln Arg Leu
            180                 185                 190
Val Ser Leu Tyr Lys Tyr Asp Glu Arg Gln Thr Ala Tyr Leu Pro Ile
            195                 200                 205
Asp Gly Val Gly Thr Asn Ile His Val Leu Ala Ala Ile Leu Asn Asp
            210                 215                 220
Ser Asn Thr Lys Leu Ser Glu Leu His Val Ala Leu Leu Asp Ile Thr
225             230                 235                 240
Lys Ala Phe Asn Arg Leu His His Thr Ser Ile Ile Lys Ser Leu Val
                245                 250                 255
Gly Lys Gly Phe Pro Tyr Gly Phe Ile Thr Phe Ile Arg Arg Met Tyr
            260                 265                 270
Thr Gly Leu Gln Thr Met Met Gln Phe Glu Gly His Cys Lys Met Thr
            275                 280                 285
Gln Val Asn Arg Gly Val Tyr Gln Gly Asp Pro Leu Ser Gly Pro Ile
            290                 295                 300
Phe Leu Leu Ala Ile Glu Lys Gly Leu Gln Ala Leu Asp Lys Glu Val
305                 310                 315                 320
Gly Tyr Asp Ile Gly Asp Val Arg Val Asn Ala Gly Ala Tyr Ala Asp
                325                 330                 335
Asp Thr Asp Leu Val Ala Gly Thr Arg Leu Gly Leu Gln Asp Asn Ile
                340                 345                 350
Asn Arg Phe Ser Ser Thr Ile Lys Gln Val Gly Leu Glu Val Asn Pro
            355                 360                 365
Arg Lys Ser Met Thr Leu Ser Leu Val Pro Ser Gly Lys Glu Lys Lys
            370                 375                 380
Met Lys Val Glu Thr Gly Lys Pro Phe Arg Ala Asn Asp Val Pro Leu
385                 390                 395                 400
Lys Glu Leu Ser Ile Asn Asp Phe Trp Arg Tyr Leu Gly Ile Ser Tyr
                405                 410                 415
Thr Asn Glu Gly Pro Glu Arg Leu Ser Leu Thr Ile Glu Gln Asp Leu
            420                 425                 430
Glu Arg Leu Thr Lys Ala Pro Leu Lys Pro Gln Gln Arg Ile His Met
            435                 440                 445
Leu Asn Ala Tyr Val Ile Pro Lys Tyr Gln Asp Lys Leu Val Leu Ser
450                 455                 460
Lys Thr Thr Ala Lys Gly Leu Lys Arg Thr Asp Arg Gln Ile Arg Gln
465                 470                 475                 480
Tyr Val Arg Arg Trp Leu Lys Leu Pro His Asp Val Pro Ile Ala Tyr
                485                 490                 495
Leu His Ala Pro Val Lys Ser Gly Gly Leu Asn Ile Pro Cys Leu Gln
                500                 505                 510
Tyr Trp Ile Pro Leu Leu Arg Val Asn Arg Val Asn Lys Ile Thr Glu
            515                 520                 525
Ser Gln Arg Ser Val Leu Ala Ala Val Gly Lys Thr Ala Leu Leu Thr
            530                 535                 540
Ser Thr Val Tyr Lys Cys Asn Gln Ser Leu Ala Thr Leu Gly Gly Asn
545                 550                 555                 560
Pro Thr Met Leu Ala Tyr Arg Thr Tyr Trp Glu Lys Glu Leu Tyr Ala
                565                 570                 575
```

```
Lys Val Asp Gly Lys Asp Leu Gln Asn Ala Arg Asp Lys Ala Ser
            580                 585                 590

Thr Arg Trp Asn Gly Met Leu His Ser Asp Ile Ser Gly Glu Asp Tyr
            595                 600                 605

Leu Asn Tyr His Lys Leu Arg Thr Asn Ser Val Pro Thr Lys Val Arg
            610                 615                 620

Thr Ala Arg Gly Arg Pro Gln Lys Glu Thr Ser Cys Arg Gly Gly Cys
625                 630                 635                 640

Lys Ser Thr Glu Thr Leu Gln His Val Val Gln Gln Cys His Arg Thr
                    645                 650                 655

His Gly Gly Arg Thr Leu Arg His Asp Arg Ile Val Gly Leu Leu Gln
                    660                 665                 670

His Glu Leu Arg Arg Asp Tyr Asn Val Leu Ala Lys Gln Glu Leu Lys
                    675                 680                 685

Thr Gly Ile Gly Leu Arg Lys Pro Asp Leu Val Leu Ile Lys Asp Asp
            690                 695                 700

Thr Ala His Ile Val Asp Val Gln Val Ala Arg Cys Ser Lys Leu Asn
705                 710                 715                 720

Glu Ser His Val Arg Lys Arg Ser Lys Tyr Asp Lys Lys Glu Ile Glu
                    725                 730                 735

Val Glu Val Lys Ser Arg Tyr Arg Val Ser Lys Val Met Tyr Glu Ala
                    740                 745                 750

Cys Thr Ile Ser Tyr Lys Gly Ile Trp Asp Lys Gln Ser Val Met Ser
                    755                 760                 765

Met Arg Arg Leu Gly Val Ser Glu Tyr Cys Leu Phe Lys Ile Val Thr
            770                 775                 780

Ser Thr Leu Arg Gly Thr Trp Leu Cys Trp Lys Arg Phe Asn Met Ile
785                 790                 795                 800

Thr Ser Val Arg Ser
            805

<210> SEQ ID NO 11
<211> LENGTH: 809
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (63)..(63)
<223> OTHER INFORMATION: Xaa can be any naturally occurring amino acid

<400> SEQUENCE: 11

Phe Trp Lys Pro Leu Thr Pro Asn Leu Ala Arg Val Ser Leu Pro Ser
1               5                   10                  15

Lys Asp Lys Val Ser Arg Arg Leu Arg Arg Ala Asp Tyr Gly Arg
            20                  25                  30

Val Gln Arg Ala Trp Lys Arg Asn Arg Asn Thr Cys Leu Arg Asp Leu
            35                  40                  45

Leu Arg Asp Lys Arg Thr Glu Ser Ala Pro Pro Glu Glu Leu Xaa Val
    50                  55                  60

Pro Tyr Trp Glu Ser Val Leu Ser Gly Ser Ser Cys Thr Pro Gly
65                  70                  75                  80

Gln Arg Gly Arg Thr Ala Glu Arg Thr Glu Leu Trp Asp Pro Val Ser
                    85                  90                  95

Ser Lys Glu Val Glu Gln Ala Leu Pro Pro Leu Gly Thr Ala Pro Gly
            100                 105                 110
```

-continued

```
Pro Asp Ser Phe Thr Pro Lys Asp Phe Arg Ala Val Pro Ser Ala Val
        115                 120                 125
Trp Ala Cys Ile Phe Asn Ile Phe Met Leu Cys Gly Arg Leu Pro Asp
    130                 135                 140
Tyr Leu Leu Glu Ser Arg Thr Thr Leu Ile Pro Lys Arg Asp Gly Ala
145                 150                 155                 160
Cys Asn Pro Glu Asp Phe Arg Pro Ile Thr Val Ser Ser Val Val
                165                 170                 175
Arg Cys Phe His Lys Val Ile Ala Asn Arg Met Ser Arg His Ile Gln
            180                 185                 190
Leu Asp Pro Arg Gln Lys Ala Phe Arg Ser Leu Asp Gly Cys Ser Glu
        195                 200                 205
Gly Val Phe Leu Leu Asp Phe Ile Leu Gly His Ala Arg Arg Asn His
    210                 215                 220
Arg Pro Val His Leu Ala Ser Leu Asp Val Ala Lys Ala Phe Asp Ser
225                 230                 235                 240
Val Ser His Ala Ala Ile Leu Asp Val Leu Arg Ser Phe Gly Val Pro
                245                 250                 255
Asp Gln Met Val Glu Tyr Ile Ala Ser Val Tyr Ala Gly Ser Arg Thr
            260                 265                 270
Arg Leu Gln Gly Asp Gly Trp Gln Ser His Ala Ile His Pro Thr Cys
        275                 280                 285
Gly Val Lys Gln Gly Asp Pro Leu Ser Pro Met Ile Phe Asn Met Val
    290                 295                 300
Ile Asp Arg Leu Phe Thr Leu Phe Pro Arg Asp Thr Gly Val Ser Val
305                 310                 315                 320
Gly Asp Thr Val Leu Asn Gly Met Gly Tyr Ala Asp Asp Leu Val Leu
                325                 330                 335
Phe Ala Thr Thr Pro Val Gly Leu Gln Gln Leu Leu Asp Ile Thr Ala
            340                 345                 350
Glu Tyr Leu Ser Gln Cys Gly Leu Arg Val Asn Ala Ala Lys Cys Phe
        355                 360                 365
Ser Val Ser Leu Ala Ile Val Pro His Glu Lys Val Val Ala
    370                 375                 380
Thr Lys His Arg Phe Lys Cys Leu Gly Gln Pro Ile Pro Ala Leu Lys
385                 390                 395                 400
Arg Ser Asp Gln Trp Lys Tyr Leu Gly Val Pro Phe Ser Pro Glu Gly
                405                 410                 415
Arg Leu Lys Ile Asp Pro Leu Gly Arg Leu Lys Asp Glu Leu Glu Lys
            420                 425                 430
Leu Arg Arg Ala Pro Leu Lys Pro Gln Gln Arg Leu Tyr Ala Leu Arg
        435                 440                 445
Thr Val Val Pro Gly Leu Tyr His Leu Val Leu Gly Gly Thr
    450                 455                 460
Thr Ile Ser Ser Leu Asn Arg Leu Asp Ile Ala Val Arg Ser Thr Val
465                 470                 475                 480
Arg Lys Trp Leu Ser Leu Pro His Asp Val Pro Asn Ala Tyr Ile His
                485                 490                 495
Ala Asp Ala Arg Asp Gly Gly Leu Ser Ile Pro Ser Tyr Arg Trp Thr
            500                 505                 510
Val Pro Arg Leu Arg Phe His Arg Leu Lys Ala Leu Ser Val Leu Cys
        515                 520                 525
```

```
Asp Gly Gly Pro Asp Glu Met Val Ala Cys Val Gly Asp Glu Ile
    530             535                 540

Lys Arg Ala Ser Ala Arg Leu Gln Asp His Gly Met Asn Ile Asn Thr
545                 550                 555                 560

Arg Asn Thr Tyr Arg Val Arg Phe Ala Arg Leu Leu His Thr Ser Asn
                565                 570                 575

Asp Gly Ala Pro Leu Lys Gly Ser Lys Lys Val Glu Gly Gln His Arg
            580                 585                 590

Trp Val Thr Asp Gly Ser Leu Met Leu Ser Gly Arg Asp Tyr Ile Ala
        595                 600                 605

Cys Asn Trp Val Arg Ile Asn Ser Ile Pro Leu Arg Lys Arg Thr Ala
610                 615                 620

Arg Gly Arg Val Arg Asp Thr Arg Cys Arg Ala Gly Cys Asp Ser Thr
625                 630                 635                 640

Glu Thr Leu His His Val Leu Gln Gln Cys His Arg Thr His Asp Met
                645                 650                 655

Arg Ile Lys Arg His Asn Ala Cys Val Lys Tyr Leu Leu Asp Arg Gln
            660                 665                 670

Arg Ser Arg Gly Lys Thr Val Phe Trp Glu Pro His Phe His Thr Ala
        675                 680                 685

Gly Gly Leu Leu Lys Pro Asp Ser Val Ile Leu His Asp Ala Ser Thr
    690                 695                 700

Ala Val Val Val Asp Ala Leu Val Ala Gly Glu Arg Ser Asp Leu Asp
705                 710                 715                 720

Arg Glu His Asp Arg Lys Val Ser Lys Tyr Glu Pro Leu Val Asp Leu
                725                 730                 735

Val Lys Asp Arg Tyr Ser Val Asp Lys Val Ile Phe Ser Ser Leu Ile
            740                 745                 750

Ile Ser Ala Arg Gly Val Trp Gly Gly Arg Ser Phe Arg His Leu Ser
        755                 760                 765

Lys Leu Arg Leu Leu Asp Ile Ser Asp Ala Lys Val Leu Ser Thr Arg
    770                 775                 780

Val Leu Leu Gly Gly Met Gly Ala Val Arg Val Phe Asn Arg Arg Thr
785                 790                 795                 800

Ala Val Ser Gly Arg Val Asn Gly Trp
                805
```

<210> SEQ ID NO 12
<211> LENGTH: 809
<212> TYPE: PRT
<213> ORGANISM: Artificial Sequence
<220> FEATURE:
<223> OTHER INFORMATION: Synthesized

<400> SEQUENCE: 12

```
Glu Val Phe Pro Ala Pro Pro Arg Arg Glu Arg Arg Arg Lys Lys
1               5                   10                  15

Thr Pro Asn Pro Ala Pro Met Arg Lys Arg Glu Ala Arg Arg Cys Glu
                20                  25                  30

Tyr Gly Ala Ala Gln Ser Leu Trp Lys Arg Asp Arg Arg His Cys Ile
            35                  40                  45

Thr Asn Ile Leu Asn Glu Met Gly Pro Val Asn Gln Pro Pro Arg Glu
        50                  55                  60

Thr Met Glu Pro Tyr Trp Thr Arg Met Met Thr Thr Asp Gly Arg Thr
65                  70                  75                  80
```

```
Ser Pro Pro Ser Asp Lys Val Pro Ile Lys Glu Asp Ile Trp Thr Pro
                85                  90                  95
Ile Thr Gly Asn Asp Ile Lys Arg Ser Arg Ile Pro Arg Ala Ser Ala
            100                 105                 110
Pro Gly Pro Asp Gly Ile Ser Ala Arg Leu Tyr Arg Ser Ile Pro Thr
        115                 120                 125
Thr Val Ile Ile Arg Leu Phe Asn Leu Leu Leu Trp Cys Glu Arg Leu
    130                 135                 140
Pro Glu Asp Leu Leu Leu Ser Arg Thr Ile Phe Leu Pro Lys Lys Thr
145                 150                 155                 160
Asn Ala Ser Glu Pro Gly Asp Phe Arg Pro Ile Thr Ile Pro Pro Val
                165                 170                 175
Leu Val Arg Gly Leu His Lys Ile Leu Ala Lys Arg Leu Glu Thr Ala
            180                 185                 190
Leu Asp Ile Asp Pro Arg Gln Arg Ala Phe Arg Ser Met Asp Gly Cys
        195                 200                 205
Ala Asp Asn Thr Leu Leu Leu Asp Thr Leu Leu Arg Tyr His Arg Lys
    210                 215                 220
Gln Tyr Lys Ser Leu Tyr Met Ala Ser Ile Asp Val Ser Lys Ala Phe
225                 230                 235                 240
Asp Ala Val Thr His Pro Thr Ile Glu Ser Thr Leu Ile Ser Leu Gly
                245                 250                 255
Val Pro Pro Pro Met Ile Arg Tyr Leu Gly Gln Val Tyr Ala Asn Ser
            260                 265                 270
Arg Thr Arg Ile Glu Gly Asp Gly Trp Thr Ser Lys Pro Val His Pro
        275                 280                 285
Lys Arg Gly Val Arg Gln Gly Asp Pro Leu Ser Pro Ile Leu Phe Asn
    290                 295                 300
Ala Val Thr His Arg Leu Leu Gln Arg Leu Pro Arg Glu Val Gly Ala
305                 310                 315                 320
Arg Leu Gly Asn Ile Pro Ile Asn Ala Ala Tyr Ala Asp Asp Leu
                325                 330                 335
Leu Leu Phe Ala Ser Thr Ser Met Gly Leu Gln Gln Met Ile Asp Thr
        340                 345                 350
Met Thr Asp Tyr Leu Ala Glu Cys Gly Met Thr Ile Asn Val Glu Lys
    355                 360                 365
Ser Met Thr Val Ala Ile Arg Ala Ala Pro His Leu Lys Lys Thr Ala
370                 375                 380
Val Asp Ala Ser Leu Ser Phe Ser Cys Gly Gly Arg Gln Leu Pro Ser
385                 390                 395                 400
Leu Lys Arg Thr Asn Lys Trp Arg Tyr Leu Gly Val Val Phe Thr Pro
                405                 410                 415
Glu Gly Arg Ala Gln Cys Arg Pro Ala Glu Val Ala Pro Leu Leu
            420                 425                 430
Gly Ala Leu Thr Lys Ala Pro Leu Lys Pro Gln Gln Arg Leu Tyr Ala
        435                 440                 445
Leu Arg Thr Val Val Ile Pro Lys Leu Tyr His Gln Leu Ala Leu Gly
    450                 455                 460
Ala Val Thr Ile Gly Thr Leu Asn Lys Thr Asp Arg Leu Val Arg Gly
465                 470                 475                 480
Ala Leu Arg Lys Trp Leu Ala Leu Pro His Asp Thr Pro Asn Ala Tyr
                485                 490                 495
Phe His Thr Ser Val Arg Asp Gly Gly Leu Gly Ile Pro Ala Ile Arg
```

```
                500             505             510
Trp Thr Ala Pro Val Gln Arg Arg Gly Arg Leu Leu Gly Val Met Lys
            515                 520             525

Ala Leu Gly Gln Gln Gly Leu Asp Arg Phe Ile Gln Asp Glu Leu Asn
            530                 535             540

Thr Cys Lys Lys Arg Leu Thr Asp His Gly Val Leu Leu Gly Thr Pro
545                 550                 555                 560

Glu Met Val Ala Lys Arg Trp Ala Gln Gln Leu Tyr Gly Ser Ile Asp
                565                 570                 575

Gly Ala Gly Leu Lys Asp Ser Ala Lys Thr Pro His Gln His Gln Trp
                580                 585                 590

Ile Ala Asp Gly Ser Lys Phe Leu Thr Gly Lys Asp Phe Ile Asn Cys
            595                 600                 605

Asn Arg Ala Arg Ile Gly Ala Leu Pro Thr Arg Ser Arg Thr Thr Arg
            610                 615                 620

Gly Arg Pro Gln Asp Arg Arg Cys Arg Gly Cys Leu Ala Gln Glu
625                 630                 635                 640

Thr Leu Asn His Val Leu Gln His Cys His Arg Thr His Gly Gln Arg
                645                 650                 655

Ile Lys Arg His Asp Ala Val Val Lys Tyr Ile Ala Arg Asn Met Pro
            660                 665                 670

Arg Ser Gly Tyr Glu Val His Gln Glu Pro His Tyr Lys Thr Glu Leu
            675                 680                 685

Gly Leu Arg Lys Pro Asp Leu Val Ala Val Leu Gly Gln Thr Ala Ile
            690                 695                 700

Ile Ile Asp Ala Gln Val Val Ser Glu Gln Thr Asn Leu Asp Asp Ala
705                 710                 715                 720

His Thr Arg Lys Val Ala Tyr Tyr Asn Glu Pro Ala Thr Ile Arg Ala
                725                 730                 735

Ile Lys Ala Glu His Gly Val Arg Thr Val Lys Val Thr Ser Ala Thr
            740                 745                 750

Leu Ser Trp Lys Gly Val Trp Ser Pro Arg Ser Ala Glu Glu Leu Arg
            755                 760                 765

Lys Leu Gly Phe Ile Arg Ala Gly Asp Ala Lys Val Val Ala Thr Arg
            770                 775                 780

Val Leu Ile Gly Asn Ile Ala Ala Phe Arg Thr Phe Asn Ala Thr Thr
785                 790                 795                 800

Ser Val Glu His Arg Ala Gly Ile Gly
                805

<210> SEQ ID NO 13
<211> LENGTH: 823
<212> TYPE: PRT
<213> ORGANISM: Artificial Sequence
<220> FEATURE:
<223> OTHER INFORMATION: Synthesized

<400> SEQUENCE: 13

Ser Lys Glu Pro Ala Ala His Pro Leu Pro Phe Gly Ala Arg Arg
1               5                   10                  15

Pro Pro Asp Lys Lys Arg Ala Arg Arg Trp Glu Tyr Ala Ala Val
                20                  25                  30

Gln Arg Ala Phe Arg Lys Asn Ala Ala Arg Cys Val Asn Gly Leu Leu
            35                  40                  45

Asp Gly Thr Leu Leu His Gln Pro Pro Ser Ile Pro Gly Leu Val Glu
```

```
               50                  55                  60
Phe Trp Lys Asp Leu Phe Thr Ala Pro Cys Ala Ser Ser Arg Pro Arg
65                  70                  75                  80

Ser Lys Glu Gly Leu Ser Pro Met Leu Leu Ala Ser Ser Gln Pro Val
                85                  90                  95

Ser Phe Arg Asp Leu Trp Ala Pro Ile Thr Ser Glu Glu Ala Ala Ala
                100                 105                 110

Ala Leu Pro Pro Arg Asn Ser Ala Ala Gly Pro Asp Ala Leu Thr Pro
                115                 120                 125

Ala Gln Leu Arg Arg Leu Pro His Pro Val Phe Leu Lys Ile Leu Asn
130                 135                 140

Leu Phe Leu Leu Ala Arg Ser Leu Pro Ser Arg Leu Leu Arg Ala Arg
145                 150                 155                 160

Thr Thr Leu Leu Pro Lys Lys Thr Ser Pro Ala Ser Pro Ala Asp Phe
                165                 170                 175

Arg Pro Ile Thr Val Cys Ser Val Leu Ala Arg Ala Phe His Lys Val
                180                 185                 190

Leu Ala Gly Arg Leu Met Arg Tyr Cys Val Leu Asp Gly Arg Gln Arg
                195                 200                 205

Ala Phe Ile Pro Gln Asp Gly Met Leu His Asn Ser Phe Leu Leu Asp
210                 215                 220

Leu Ala Met Ala His Ser Arg Arg Thr Ala Cys Ser Leu Tyr Val Ala
225                 230                 235                 240

Ser Leu Asp Val Ser Lys Ala Phe Asp Ser Leu Asp His Gly Ala Leu
                245                 250                 255

Ser Pro Val Leu Arg Ala His Gly Leu Pro Val Glu Phe Val Glu Tyr
                260                 265                 270

Val Arg Gly Cys Tyr Gln Ala Ser Thr Thr Val Ile Cys Gly Gly Gly
                275                 280                 285

Ser Ser Ser Asp Leu Val Arg Pro Ser Lys Gly Val Arg Gln Gly Asp
290                 295                 300

Pro Leu Ser Pro Ile Leu Phe Asn Leu Ser Ile Asp Leu Leu Leu Ser
305                 310                 315                 320

Arg Leu Pro Gly Tyr Ile Gly Ala Arg Ile Phe Ser Arg Arg Val Asn
                325                 330                 335

Ala Ala Ala Phe Ala Asp Asp Ile Leu Leu Phe Ala Glu Thr Lys Gly
                340                 345                 350

Gly Leu Gln Glu Leu Leu Ser Thr Ala Thr Ser Ala Leu Gly Asp Leu
                355                 360                 365

Gly Leu Glu Val Asn Pro Phe Lys Cys Phe Ser Leu Ala Leu Val Ala
                370                 375                 380

Ser Gly Arg Glu Lys Lys Val Lys Val Asp Asn Ser Val Ile Phe Arg
385                 390                 395                 400

Ala Gly Asn Lys Asn Ile Pro Ala Leu Ala Met Gly Asp Thr Phe Arg
                405                 410                 415

Tyr Leu Gly Leu Gln Phe Ser Thr Ser Gly Leu Ser Gln Phe His Pro
                420                 425                 430

Arg Gln Glu Val Gln Glu Gln Leu Asp Ile Ile Lys Arg Ala Pro Leu
                435                 440                 445

Lys Pro Gln Gln Arg Leu Phe Ala Leu Arg Ser Val Ile Leu Pro Gly
                450                 455                 460

Thr Tyr His Gly Leu Ala Leu Gly Arg Thr Arg Leu Gly Ala Leu Lys
465                 470                 475                 480
```

-continued

```
Ser Leu Asp Val Cys Val Arg Ala Ala Val Arg Ala Trp Leu Arg Leu
            485                 490                 495

Pro Asp Asp Thr Pro Ile Gly Tyr Phe His Ala Pro Val Ile Tyr Gly
        500                 505                 510

Gly Leu Gly Ile Pro Ala Thr Arg Trp Leu Gly Pro Leu Leu Arg Arg
            515                 520                 525

Arg Arg Leu Ala Ser Met Glu Gly Leu Gly Val Ile Val Asp Glu Pro
        530                 535                 540

Ser Gln Asp Ile Leu Lys Arg Glu Ile Cys Arg Leu Asp Asn Tyr Leu
545                 550                 555                 560

Lys Trp Asp Gly Asp Val Ile Lys Thr Ser Tyr Gln Leu Gly Arg Phe
                565                 570                 575

Trp Ala Leu Arg Leu His Ser Ser Val Asp Gly Ala Ala Leu Arg Arg
            580                 585                 590

Ser Ala Gln Thr Pro Gly Gln His Ser Trp Val Ser Asn Thr Arg Leu
        595                 600                 605

Met Leu Ser Gly Arg Asp Phe Leu Ala Cys Val Arg Ala Arg Ile Ser
            610                 615                 620

Ala Leu Pro Ser Arg Ala Arg Leu Leu Arg Gly Arg Glu Gly Asp Thr
625                 630                 635                 640

Arg Cys Arg Ala Gly Cys Asn Ala Ser Glu Thr Asn Asn His Val Ile
                645                 650                 655

Gln His Cys Trp Arg Ser His Glu Ala Arg Val Glu Arg His Asp Ala
            660                 665                 670

Val Ala Leu Tyr Met Val Arg Gly Leu Arg Arg Gly Tyr Asp Val
            675                 680                 685

His Arg Glu Leu His Leu Arg Thr Ser Gln Gly Leu Lys Lys Pro Asp
        690                 695                 700

Ile Val Ala Val Ser Gly Thr Thr Ala Phe Val Ile Asp Ala Gln Val
705                 710                 715                 720

Ile Gly Asp His Leu Asp Ala Asp Arg Cys His Arg Glu Lys Val Glu
                725                 730                 735

Val Tyr Asp Gln Gln Pro Val His Thr Glu Ile Lys Arg Met Phe Pro
            740                 745                 750

Glu Val Gln Met Ile Thr Thr Thr Ser Ala Thr Leu Asn Trp Arg Gly
        755                 760                 765

Val Trp Ser Pro Ala Ser Ala Lys Ala Leu Ile Gly Ile Gly Phe Asn
        770                 775                 780

Ser Asn His Leu Ser Thr Met Ala Thr Arg Ala Leu Leu Gly Ser Ile
785                 790                 795                 800

Met Ala Ala Arg Arg Phe Asp Ser Met Thr Ala Pro Arg Arg Arg Met
                805                 810                 815

Met Pro Arg Thr Gly Val Gly
            820
```

<210> SEQ ID NO 14
<211> LENGTH: 794
<212> TYPE: PRT
<213> ORGANISM: Artificial Sequence
<220> FEATURE:
<223> OTHER INFORMATION: Synthesized

<400> SEQUENCE: 14

```
Asn Arg Asn Asp Arg Pro Ser Ser Ala Thr Val Pro Ala Arg Arg Pro
1               5                   10                  15
```

-continued

```
Arg Asn Arg Arg Ile Ser Arg Arg Gln Gln Tyr Ala Arg Cys Ile Lys
        20                  25                  30

Ser Leu Leu Asp Gly Thr Asp Glu Ser Ala Leu Pro Asn Gln Ser Ile
        35                  40                  45

Met Glu Pro Tyr Trp Arg Gln Val Met Thr Gln Pro Ser Pro Ser Leu
 50                  55                  60

Cys Ser Asn Thr Val Pro Arg Lys Gly Asn Met Gln Glu Gly Val Trp
 65                  70                  75                  80

Ser Pro Ile Thr Ser Arg Asp Leu Gln Val His Lys Val Pro Leu Thr
                85                  90                  95

Ser Ser Pro Gly Pro Asp Gly Ile Thr Ser Gln Thr Ala Arg Ser Ile
            100                 105                 110

Pro Ile Gly Ile Met Leu Arg Ile Val Asn Leu Ile Leu Trp Cys Gly
            115                 120                 125

Asp Leu Pro Val Pro Phe Arg Met Ala Arg Thr Ile Phe Ile Pro Lys
130                 135                 140

Thr Val Arg Ala Asn Arg Pro Gln Asp Phe Arg Pro Ile Ser Val Pro
145                 150                 155                 160

Ser Ile Val Val Arg Gln Leu Asn Ala Ile Leu Ala Ser Arg Leu Thr
                165                 170                 175

Ala Ala Val Ser Trp Asp Pro Arg Gln Arg Gly Phe Leu Pro Thr Asp
            180                 185                 190

Gly Cys Ala Asp Asn Ala Thr Ile Val Asp Leu Val Leu Arg Asp His
            195                 200                 205

His Lys Arg Tyr Ala Ser Cys Tyr Ile Ala Thr Leu Asp Val Ser Lys
        210                 215                 220

Ala Phe Asp Ser Val Ala His Asp Ala Val Phe Asn Thr Val Thr Ala
225                 230                 235                 240

Tyr Gly Ala Pro Lys Ser Phe Val Asp Tyr Val Arg Arg Trp Tyr Ser
                245                 250                 255

Gly Gly Gly Thr Tyr Phe Asn Gly Gly Asp Trp Arg Ser Glu Glu Phe
            260                 265                 270

Val Pro Ala Arg Gly Val Lys Gln Gly Asp Pro Leu Ser Pro Val Leu
            275                 280                 285

Phe Asn Leu Ile Ile Asp Arg Leu Leu Arg Ser Leu Pro Lys Asp Ile
290                 295                 300

Gly Val His Val Gly Asn Ala Lys Val Asn Ala Cys Ala Phe Ala Asp
305                 310                 315                 320

Asp Leu Met Leu Phe Ala Ser Thr Pro Lys Gly Leu Gln Glu Leu Leu
                325                 330                 335

Asn Thr Thr Val Lys Phe Leu Ser Ser Val Gly Leu Thr Leu Asn Ala
            340                 345                 350

Asp Lys Cys Phe Thr Ile Ser Ile Lys Gly Gln Pro Lys Gln Lys Val
            355                 360                 365

Thr Val Val Glu Gln Arg Thr Phe Cys Ile Gly Arg Ala Arg Val Gln
            370                 375                 380

Leu Lys Arg Ser Glu Glu Trp Lys Tyr Leu Gly Ile His Phe Thr Ala
385                 390                 395                 400

Asp Gly Arg Ala Arg Tyr Asn Pro Ser Glu Asp Ile Gly Pro Lys Leu
                405                 410                 415

Glu Arg Leu Met Gln Ser Pro Leu Lys Pro Gln Gln Lys Leu Phe Ala
            420                 425                 430
```

Leu Arg Thr Val Leu Val Pro Gln Leu Tyr His Lys Leu Thr Leu Gly
435                 440                 445

Ser Val Ala Leu Gly Val Leu Arg Lys Cys Asp Lys Leu Val Arg Ser
450                 455                 460

Phe Ala Arg Lys Leu Leu Gly Leu Pro Leu Asp Val Ser Val Ala Phe
465                 470                 475                 480

Tyr His Ala Pro His Ser Cys Gly Leu Gly Ile Pro Ser Val Arg
                485                 490                 495

Trp Ile Ala Pro Met Leu Arg Thr Lys Arg Leu Ala Gly Ile Asn Trp
                500                 505                 510

Pro His Leu Glu Gln Ser Glu Val Ala Ser Ala Phe Leu Ser Glu Glu
                515                 520                 525

Leu Arg Arg Ala Arg Asp Arg Ala Lys Ala Gly Val Asn Glu Leu Leu
530                 535                 540

Ser Gln Pro Lys Ile Asp Thr Tyr Trp Ala Asp Arg Leu Tyr Thr Ser
545                 550                 555                 560

Val Asp Gly Asn Gly Leu Arg Glu Ala Arg Arg Tyr Ala Pro Gln His
                565                 570                 575

Gly Trp Val Ser Gln Pro Thr Arg Leu Met Ser Gly Lys Ala Tyr Arg
                580                 585                 590

Thr Gly Ile Gln Leu Arg Ile Asn Ala Leu Pro Thr Arg Ser Arg Thr
                595                 600                 605

Thr Arg Gly Arg His Glu Met Asn Arg Gln Cys Arg Ala Gly Cys Asp
                610                 615                 620

Ala Pro Ser His Asn His Val Leu Gln Arg Cys His Arg Thr His Gly
625                 630                 635                 640

Ser Arg Val Ser Arg His Asn Gly Val Val Ser Tyr Leu Lys Lys Gly
                645                 650                 655

Leu Glu Thr Arg Gly Tyr Thr Val Tyr Ser Glu Gln Ser Leu His Gly
                660                 665                 670

Gln Asn Arg Val Tyr Lys Pro Asp Ile Val Ala Phe Arg His Asp Ser
                675                 680                 685

Thr Ile Val Val Asp Ala Gln Val Val Thr Asp Gly Leu Asp Leu Asp
690                 695                 700

Arg Ala His Gln Ser Lys Val Glu Ile Tyr Asn Arg Gln Asp Leu Leu
705                 710                 715                 720

Thr Thr Leu Arg Ser Val Tyr Arg Ala Arg Glu Asn Ile Glu Val Val
                725                 730                 735

Ser Ala Thr Leu Asn Trp Arg Gly Ile Trp Ser Phe Gln Ser Ile Thr
                740                 745                 750

Arg Leu Arg Thr Leu Gly Ile Leu Thr Ala Gly Asp Ser Asn Val Ile
                755                 760                 765

Ser Ser Arg Val Val Ser Gly Arg Val Tyr Ser Phe Lys Thr Phe Met
770                 775                 780

Phe His Ala Gly Phe His Arg Gly Met Ala
785                 790

<210> SEQ ID NO 15
<211> LENGTH: 802
<212> TYPE: PRT
<213> ORGANISM: Artificial Sequence
<220> FEATURE:
<223> OTHER INFORMATION: Synthesized

<400> SEQUENCE: 15

-continued

```
Ser Ser Gly Arg Lys Leu Pro Val Lys Ser Arg Gly Ala Arg Glu Thr
1               5                   10                  15

Val Gln Lys Lys Met Ala Asn Pro Arg Val Ala Lys Tyr Lys Arg Phe
            20                  25                  30

Gln Arg Leu Phe Arg Ser Asn Arg Lys Leu Ala Ser His Ile Phe
        35                  40                  45

Asp Lys Ala Ser Leu Glu Gln Phe Gly Gly Ser Ile Asp Glu Ala Ser
    50                  55                  60

Asp His Leu Glu Lys Phe Leu Ser Arg Pro Leu Glu Ser Asp Ser
65                  70                  75                  80

Tyr Ser Val Ile Asn Gly Asn Lys Ser Ile Gly Val Ala His Pro Ile
                85                  90                  95

Leu Ala Glu Glu Val Glu Leu Glu Leu Lys Ala Ser Arg Pro Thr Ala
                100                 105                 110

Val Gly Pro Asp Gly Ile Ala Leu Glu Asp Ile Lys Lys Leu Asn Ser
            115                 120                 125

Tyr Asp Leu Ala Ser Leu Phe Asn Leu Trp Leu Lys Ala Gly Asp Leu
    130                 135                 140

Pro Glu Ser Val Lys Ala Ser Arg Thr Ile Phe Leu Pro Lys Ser Asp
145                 150                 155                 160

Gly Thr Thr Asp Ile Ser Asn Cys Arg Pro Ile Thr Ile Ala Ser Ala
                165                 170                 175

Leu Tyr Arg Leu Phe Ser Lys Ile Ile Thr Arg Arg Leu Ala Ala Arg
                180                 185                 190

Leu Glu Leu Asn Val Arg Gln Lys Ala Phe Arg Pro Glu Met Asn Gly
                195                 200                 205

Val Phe Glu Asn Ser Ala Ile Leu Tyr Ala Leu Ile Lys Asp Ala Lys
    210                 215                 220

Ala Arg Ser Lys Glu Ile Cys Ile Thr Thr Leu Asp Leu Ala Lys Ala
225                 230                 235                 240

Phe Asp Thr Val Pro His Ser Arg Ile Val Arg Ala Leu Arg Lys Asn
                245                 250                 255

Asn Val Asp Pro Glu Ser Val Asp Leu Ile Ser Lys Met Leu Thr Gly
            260                 265                 270

Thr Thr Tyr Ala Glu Ile Lys Gly Leu Gln Gly Lys Pro Ile Thr Ile
        275                 280                 285

Arg Asn Gly Val Arg Gln Gly Asp Pro Leu Ser Pro Leu Leu Phe Ser
    290                 295                 300

Leu Phe Ile Asp Glu Ile Ile Gly Arg Leu Gln Ala Cys Gly Pro Ala
305                 310                 315                 320

Tyr Asp Phe His Gly Glu Lys Ile Cys Ile Leu Ala Phe Ala Asp Asp
                325                 330                 335

Leu Thr Leu Val Ala Asp Asn Ala Ala Gly Met Lys Ile Leu Leu Lys
            340                 345                 350

Ala Ala Cys Asp Phe Leu Glu Glu Ser Gly Met Ser Leu Asn Ala Glu
        355                 360                 365

Lys Cys Arg Thr Leu Cys Ile Ser Arg Ser Pro Arg Ser Arg Lys Thr
    370                 375                 380

Phe Val Asn Pro Ala Ala Lys Phe Asn Ile Ser Asp Trp Lys Thr Gly
385                 390                 395                 400

Ile Ser Ser Glu Ile Pro Ser Leu Cys Ala Thr Asp Thr Phe Arg Phe
                405                 410                 415

Leu Gly His Thr Phe Asp Gly Glu Gly Lys Ile His Ile Asp Met Glu
```

```
                    420             425             430
Glu Ile Arg Ser Met Leu Lys Ser Val Arg Ser Ala Pro Leu Lys Pro
            435                 440                 445

Glu Gln Lys Val Ala Leu Ile Arg Ser His Leu Leu Pro Arg Leu Gln
        450                 455                 460

Phe Leu Phe Ser Thr Ala Glu Ala Asp Ser Arg Lys Ala Trp Leu Ile
465                 470                 475                 480

Asp Ser Ile Ile Arg Gly Cys Val Lys Glu Ile Leu His Ser Val Lys
                485                 490                 495

Ala Gly Met Cys Thr Glu Ile Phe Tyr Ile Pro Ser Arg Asp Gly Gly
            500                 505                 510

Leu Gly Leu Thr Ser Leu Gly Glu Phe Ser Leu Phe Ser Arg Gln Lys
        515                 520                 525

Ala Leu Ala Lys Met Ala Gly Ser Ser Asp Pro Leu Ser Lys Arg Val
        530                 535                 540

Ala Glu Phe Phe Met Glu Arg Trp Asn Ile Ala Arg Asp Pro Lys Val
545                 550                 555                 560

Thr Glu Ala Ala Arg Arg Val Tyr Gln Lys Lys Arg Tyr Gln Arg Phe
                565                 570                 575

Phe Gln Thr Tyr Gln Ser Gly Gly Trp Asn Glu Phe Ser Gly Asn Thr
            580                 585                 590

Ile Gly Asn Ala Trp Leu Thr Asn Gly Arg Ala Arg Gly Arg Asn Tyr
        595                 600                 605

Val Met Ala Val Lys Phe Arg Ser Asn Thr Ala Thr Arg Ala Glu
        610                 615                 620

Asn Leu Arg Gly Arg Pro Gly Met Lys Glu Cys Arg Phe Cys Lys Ser
625                 630                 635                 640

Ala Thr Glu Thr Leu Ala His Ile Cys Gln Lys Cys Pro Ala Asn His
                645                 650                 655

Gly Leu Val Ile Gln Arg His Asn Ala Val Val Ser Phe Leu Gly Glu
            660                 665                 670

Val Ala Arg Lys Glu Gly Tyr Gln Val Met Ile Glu Pro Lys Val Ser
        675                 680                 685

Thr Pro Val Gly Ala Leu Lys Pro Asp Leu Leu Ile Lys Ala Asp
        690                 695                 700

Thr Ala Phe Ile Val Asp Val Gly Ile Ala Trp Glu Gly Gly Arg Pro
705                 710                 715                 720

Leu Lys Leu Val Asn Lys Met Lys Cys Asp Lys Tyr Lys Ile Ala Ile
                725                 730                 735

Pro Ala Ile Leu Glu Thr Phe His Val Gly His Ala Glu Thr Tyr Gly
            740                 745                 750

Val Ile Leu Gly Ser Arg Gly Cys Trp Leu Lys Ser Asn Asp Lys Ala
        755                 760                 765

Leu Ala Ser Ile Gly Leu Asn Ile Thr Arg Lys Met Lys Glu His Leu
        770                 775                 780

Ser Trp Leu Thr Phe Glu Asn Thr Ile Arg Ile Tyr Asn Ser Phe Met
785                 790                 795                 800

Lys Asn

<210> SEQ ID NO 16
<211> LENGTH: 809
<212> TYPE: PRT
<213> ORGANISM: Artificial Sequence
<220> FEATURE:
```

<223> OTHER INFORMATION: Synthesized

<400> SEQUENCE: 16

```
Thr Lys Trp Arg Pro Ser Lys Pro Arg Leu Pro Pro Thr Tyr Arg Ala
1               5                   10                  15
Asn Thr Ser Arg Lys His Leu Arg Arg Leu Gln Tyr Gly His Ile Gln
            20                  25                  30
Thr Leu Tyr Asn Arg Cys Arg Arg Asp Ala Ala Asn Thr Val Leu Asp
        35                  40                  45
Gly Arg Trp Arg Ser Pro His Thr Ser Ser Pro Phe Ser Ile Pro Glu
    50                  55                  60
Phe Glu Thr Phe Trp Lys Thr Ile Phe Thr Thr Pro Ser Thr Pro Asp
65                  70                  75                  80
Asn Arg Pro Val Val Pro Val Leu Pro Thr Cys Pro Ala Leu Leu Asp
                85                  90                  95
Pro Ile Thr Pro Asp Glu Ile Thr Trp Ala Leu Lys Asp Met Arg Asn
            100                 105                 110
Ser Ala Pro Gly Val Asp Arg Leu Ser Ala Gln His Phe Leu Asn Phe
        115                 120                 125
Asp Val Pro Ser Leu Ala Gly Tyr Leu Asn Met Val Leu Ala Phe Lys
    130                 135                 140
Phe Leu Pro Thr Asn Leu Ser Ile Ser Arg Val Thr Phe Ile Pro Lys
145                 150                 155                 160
Gly Ala Ser Pro Gln Gln Pro Asn Asp Phe Arg Pro Ile Ser Ile Ala
                165                 170                 175
Pro Val Ile Thr Arg Cys Leu His Lys Ile Leu Ala Lys Arg Trp Met
            180                 185                 190
Pro Leu Phe Pro Ser Ser Lys Leu Gln Phe Ala Phe Leu Gln Arg Asp
        195                 200                 205
Gly Cys Phe Glu Ala Ile Asn Leu Leu His Ser Leu Leu Arg His Ala
    210                 215                 220
His Glu Arg His Ser Gly Cys Ser Ile Ala Leu Leu Asp Ile Ser Arg
225                 230                 235                 240
Ala Phe Asp Ser Val Ser His His Ser Ile Leu Arg Ala Ala His Arg
                245                 250                 255
Phe Gly Ala Pro Asp Gly Leu Cys Gln Tyr Leu Gln Arg Val Tyr Asn
            260                 265                 270
Gly Ser Thr Ser Leu Phe Asn Thr Val Asp Cys Ala Pro Ser Arg Gly
        275                 280                 285
Val Lys Gln Gly Asp Pro Leu Ser Pro Leu Leu Phe Ile Met Ser Leu
    290                 295                 300
Asp Glu Ala Leu Glu Ser Ile Glu Thr Val Ser Pro Val Ile Val Asp
305                 310                 315                 320
Gly Leu Pro Ile Ser Tyr Ile Ala Tyr Ala Asp Asp Leu Val Ile Leu
                325                 330                 335
Ala Pro Asn Ala Asp Leu Leu Gln Lys Leu Asp Lys Leu Ala Ser
            340                 345                 350
Leu Leu Gln Arg Ser Gly Leu Ile Ile Asn Thr Ser Lys Ser Met Ser
        355                 360                 365
Ile Asp Leu Ile Ala Gly His Ser Lys Leu Thr Ala Leu Lys Pro
    370                 375                 380
Thr Val Phe Lys Ile Asp Gly Asn Gln Leu Gln Arg Leu Asn Val Ser
385                 390                 395                 400
```

```
Asp His Phe Asp Phe Leu Gly Ile Ser Phe Asp Tyr Lys Gly Arg Ser
                405                 410                 415

Lys Met Asp His Val Glu Thr Leu Ser Ala Tyr Leu Leu Asn Leu Thr
            420                 425                 430

Gln Ala Pro Leu Lys Pro Gln Gln Arg Met Ser Ile Leu Arg Glu Asn
        435                 440                 445

Leu Glu Pro Arg Leu Leu Tyr Pro Leu Thr Ile Gly Val Val His Lys
    450                 455                 460

Cys Thr Leu Arg Gln Met Asp Cys Leu Ile Arg Ser Ser Val Arg Lys
465                 470                 475                 480

Trp Leu Arg Leu Pro Ser Asp Thr Pro Thr Ser Phe Phe His Ser Ser
                485                 490                 495

Ile Ser Thr Gly Gly Leu Gly Ile Pro His Leu Ser Ser Ile Ile Pro
            500                 505                 510

Leu His Arg Arg Lys Arg Ala Ala Lys Leu Leu Ser Pro Cys Pro
        515                 520                 525

Ile Ile Arg Trp Val Ser Gln Ser Pro Ser Phe Ser Asn Phe Leu Arg
    530                 535                 540

Ile Cys Asn Leu Pro Ile Asn Val His Arg Asp Leu Ile His Ser Phe
545                 550                 555                 560

Asp Glu Ala Arg Cys Ser Trp Ser Lys Gln Leu His Ser Thr Cys Asp
                565                 570                 575

Gly Arg Gly Leu Ser Met Ser Ser Arg Asn Thr Val Ser His Leu Trp
            580                 585                 590

Leu Arg Tyr Pro Glu His Ile Phe Pro Arg Leu Tyr Ile Asn Ala Ile
        595                 600                 605

Lys Leu Arg Gly Gly Leu Leu Ser Thr Lys Val Arg Arg Ser Arg Gly
    610                 615                 620

Arg Gln Glu Asn Ala Asp Leu Leu Cys Arg Gly Arg Cys Gly His His
625                 630                 635                 640

Glu Ser Ile Gln His Ile Leu Gln His Cys Ser Leu Thr His Asp Ile
                645                 650                 655

Arg Cys Arg Arg His Asn Asp Ile Cys Arg Leu Val Ala Ser Arg Leu
            660                 665                 670

Arg Arg Asn Asn Ile Arg Phe Phe Gln Glu Pro Cys Ile Pro Thr Pro
        675                 680                 685

Val Ser Phe Cys Lys Pro Asp Phe Ile Ile Arg Asp Ser Ile Ala
    690                 695                 700

Tyr Val Leu Asp Val Ser Val Cys Asp Asp Ala Asn Val His Leu Ser
705                 710                 715                 720

Arg Gln Leu Lys Ile Asn Lys Tyr Gly Cys Ser Thr Val Val Ser Ser
                725                 730                 735

Ile Tyr Asn Phe Leu Asn Ala Thr Gly Leu Arg Ile Ser Ser Val Arg
            740                 745                 750

Gln Thr Pro Leu Ile Ile Thr Tyr Arg Gly Leu Ile Asp Pro Leu Ser
        755                 760                 765

Thr Thr Ser Leu Arg Arg Leu Ser Phe Ser Arg Asp Ile Ser Asp
    770                 775                 780

Leu Cys Val Ala Ser Ile Gln Gly Ser Met Arg Ile Tyr Asn Thr Tyr
785                 790                 795                 800

Met Arg Gly Thr Ser Pro Gln Asp Pro
                805
```

<210> SEQ ID NO 17
<211> LENGTH: 806
<212> TYPE: PRT
<213> ORGANISM: Artificial Sequence
<220> FEATURE:
<223> OTHER INFORMATION: Synthesized

<400> SEQUENCE: 17

```
Gln His Ala Leu Asp Cys Phe Pro Arg Leu Trp Ala Pro Ser Arg Pro
1               5                   10                  15

Arg Pro Asn His Pro Gln Pro Arg Ser Tyr Arg Ala Leu Arg Lys Ala
            20                  25                  30

Gln Tyr Ala Ser Leu Gln Arg Ile Leu His Thr Ser Pro Lys Asp Ala
        35                  40                  45

Ala Thr His Val Leu Asp Gly Ser Trp Arg Leu Leu His Gln Asn Arg
    50                  55                  60

Ala Leu Pro Pro Asp Leu His Ser Phe Trp Thr Asn Val Phe Arg Ile
65                  70                  75                  80

Pro Ser Phe Ser Asp Asn Arg Pro Val Ser Ala Thr Gln Pro Glu Leu
                85                  90                  95

Ser Leu Ile Ser Pro Ile Thr Cys Glu Glu Val Lys Lys Ala Ile Ala
            100                 105                 110

Gly Met Gly Gly Thr Ala Pro Gly Leu Asp Arg Leu Thr Pro Ala Asn
        115                 120                 125

Leu Lys Ser Phe Gly Leu Lys Pro Leu Thr Gly Tyr Leu Asn Leu Ile
    130                 135                 140

Leu Cys Tyr Gly Cys Pro Ala Ser Leu Ala Ala Ala Arg Val Thr Leu
145                 150                 155                 160

Ile Pro Lys Val Pro Asp Ala Thr Arg Pro Glu Gln Tyr Arg Pro Leu
                165                 170                 175

Ala Val Ser Ser Val Ile Val Arg Cys Leu His Lys Ile Leu Ala Phe
            180                 185                 190

Arg Trp Ala Ser Val Leu Lys Leu Ser Ser Leu Gln Leu Ala Phe Met
        195                 200                 205

Gln Arg Asp Gly Cys Leu Glu Ala Thr Thr Ile Leu Gln Gly Val Phe
    210                 215                 220

Arg Asp Ala His Ser Arg Arg Pro Ile Ala Met Ala Phe Leu Asp
225                 230                 235                 240

Val Ser Lys Ala Phe Asp Thr Val Leu His Asp Ser Val Phe Arg Ala
                245                 250                 255

Ala Ala Met Tyr Gly Ala Pro Pro Leu Leu Arg Tyr Leu Arg Lys
            260                 265                 270

Leu Tyr Ser Gln Gly Thr Val Thr Leu Gly Asp Ile Asp Ile Leu Pro
        275                 280                 285

Lys Arg Gly Val Arg Gln Gly Asp Pro Leu Ser Pro Leu Leu Phe Ile
    290                 295                 300

Leu Ala Met Glu Glu Ile Leu Met Ala Ala Asn Pro Asn Asp Gly Tyr
305                 310                 315                 320

Gln Leu Pro Ser Ser Thr Ile Ser Thr Leu Ala Tyr Ala Asp Asp Leu
                325                 330                 335

Val Leu Phe Ala His Ser Pro Gly Ala Leu Gly Leu Lys Leu Glu Arg
            340                 345                 350

Val Ala Ala Ala Leu Arg Leu Ala Gly Met Glu Ile Asn Ala Ala Lys
        355                 360                 365

Ser Ile Thr Phe Thr Ile Ser Ala Asn Thr His Asn Lys Asn Leu Cys
```

```
            370                 375                 380
Leu Glu Asn Ile Ala Tyr Thr Leu Asp Gly Val Ser Ile Ala Ala Ala
385                 390                 395                 400

Asp Thr Glu Thr Arg Val Lys Tyr Leu Gly Leu His Phe Asn Trp Lys
                405                 410                 415

Gly Gln Ile Ser Tyr Lys Asp Thr Ala Arg Leu Ala Gly Tyr Cys Gln
                420                 425                 430

Glu Leu Thr Ser Ala Pro Leu Lys Pro Gln Gln Arg Ile His Ile Leu
            435                 440                 445

Arg Gln Val Ala Leu Pro Lys Leu His His Gln Leu Val Leu Ser Ser
450                 455                 460

Ile His Arg Arg Thr Leu Lys Ala Met Asp Ile Ser Cys Arg His Tyr
465                 470                 475                 480

Val Arg Arg Trp Leu Lys Leu Pro Gln Asp Thr Ser Thr Ala Phe Phe
                485                 490                 495

His Ala Lys Ile Gly Asp Gly Gly Leu Gly Leu Thr Ser Leu Ala Thr
                500                 505                 510

Ser Ile Pro Leu Trp Arg Arg Thr Arg Leu Thr Lys Leu Ile Thr Ser
            515                 520                 525

Glu His Pro Val Val Arg Asp Val Val Ser Ile Cys Leu Thr Lys Ala
        530                 535                 540

Leu Ala Val Ala Asn Glu Pro Val Phe Val Met Gly Thr Val Val Ser
545                 550                 555                 560

Asp Lys Asp Glu Ala Ala Met Ala Trp Lys Leu Ala Met Tyr Ala Thr
                565                 570                 575

Leu Asp Cys Ala Asp Leu Gln Thr Ile His Glu Thr Pro Glu Ser Ser
            580                 585                 590

Asn Trp Val Val Arg Pro Leu Arg Met Thr Pro Ser Leu Tyr Ile Arg
        595                 600                 605

Gly Leu Gln Leu Arg Ala Gly Thr Leu Gly Thr Lys Ser Arg Gln Gln
    610                 615                 620

Arg Gly Arg Ala Gln Met Asp Lys Leu Cys Arg Arg Gly Cys Gly Gln
625                 630                 635                 640

Thr Glu Thr Leu Pro His Ile Leu Gln Ser Cys Pro Ala Ala His Ala
                645                 650                 655

Ala Arg Cys Val Arg His Asn Arg Val Ala Lys Ser Ile Ala Val Ser
                660                 665                 670

Leu Arg Arg Lys Gly Tyr Arg Val Tyr Glu Glu Pro Ile Ile Arg Thr
            675                 680                 685

Gly Thr Thr Tyr Cys Lys Pro Asp Ile Ile Ala Cys Gln Asp Gly Leu
        690                 695                 700

Gly Phe Val Ile Asp Val Ala Val Ser Gly His Arg Leu His Glu
705                 710                 715                 720

Ser Trp Asp Leu Lys Ile Ala Lys Tyr Asp Thr Asp Phe Ile Asn Thr
                725                 730                 735

Ala Ile Ile Asp Cys Leu Pro Glu Asp Val Glu Ile Leu Ser Leu Ile
            740                 745                 750

His Gln Pro Ala Ile Ile Ser Phe Lys Gly Val Trp Phe Pro Pro Ser
        755                 760                 765

Ala Lys Arg Leu Lys Thr Leu Gly Leu Ser Ala Asp Cys Leu Ala Gly
    770                 775                 780

Leu Gly Leu Val Thr Ile Lys Gly Ser Leu Ala Cys Phe Asp Met Phe
785                 790                 795                 800
```

Met Met Gly Ser Asn Gly
            805

<210> SEQ ID NO 18
<211> LENGTH: 834
<212> TYPE: PRT
<213> ORGANISM: Artificial Sequence
<220> FEATURE:
<223> OTHER INFORMATION: Synthesized

<400> SEQUENCE: 18

Lys Glu Asn Leu Lys Lys Arg Ala Cys Lys Thr Leu Thr Arg Arg Ile
1               5                   10                  15

Lys Pro Lys Lys Ser Lys Lys His Glu Tyr Trp Lys Met Gln Gln Met
            20                  25                  30

Tyr His Arg Asp Arg Ala Gly Leu Ala Lys Leu Ile Leu Glu Gly Glu
        35                  40                  45

Ala Arg Asp Ile Cys Pro Ile Pro Leu Thr Arg Leu Thr Thr Ala Phe
50                  55                  60

Lys Glu Lys Trp Glu Lys Glu Asp Arg Phe Val Ser Leu Gly Gln Phe
65                  70                  75                  80

Lys Ser Ser Cys Lys Ala Val Asn Asp Ile Phe Ala Ser Pro Ile Ser
                85                  90                  95

Pro Glu Glu Val Cys Lys Ile Arg Ser Lys Met Lys Asn Lys Ala Ala
            100                 105                 110

Thr Gly Leu Asp Gly Ile Ser Lys Thr Cys Leu Met Arg Gly Asp Pro
        115                 120                 125

Lys Gly Ile Asn Leu Ala Asn Leu Phe Thr Ala Ile Leu Leu Asn Gly
130                 135                 140

Tyr Ile Pro Arg Ala Leu Lys Lys Asn Arg Thr Thr Leu Leu Pro Lys
145                 150                 155                 160

Thr Gln Asp Lys Arg Lys Leu Ser Asp Thr Ser Gln Trp Arg Pro Ile
                165                 170                 175

Thr Ile Gly Ser Thr Ile Gln Arg Leu Leu Ser Gly Val Ile Asn Asp
            180                 185                 190

Arg Leu Lys Glu Ala Cys Glu Ile His Pro Arg Gln Arg Gly Phe Ile
        195                 200                 205

Ser Ser Pro Gly Cys Ala Glu Asn Leu Met Leu Leu Arg Glu Leu Ile
210                 215                 220

Ala Leu Ser Lys Arg Glu Leu Lys Pro Leu Ala Val Ile Phe Ile Asp
225                 230                 235                 240

Phe Ala Lys Ala Phe Asp Thr Val Ser His Lys His Ile Lys Ala Val
                245                 250                 255

Leu Gln Gln Arg Gly Val Asp Lys Met Ile Ile Asp Leu Ile Ser Asn
            260                 265                 270

Ser Tyr Glu Gly Arg Thr Thr Ile Leu Lys Ala Lys Gly Ser Tyr Ser
        275                 280                 285

Arg Glu Ile Arg Leu Lys Met Gly Val Lys Gln Gly Asp Pro Leu Ser
290                 295                 300

Pro Leu Leu Phe Asn Leu Ala Ile Asp Pro Leu Leu Cys Lys Leu Asp
305                 310                 315                 320

Lys Val Gly Glu Gly Ala Ile Val Asp Gly Ile Glu Ile Thr Ser Leu
                325                 330                 335

Ala Phe Ala Asp Asp Ile Val Leu Leu Ser Asn Ser Trp Ser Gly Met
            340                 345                 350

```
Arg Lys Asn Leu Lys Ile Leu Glu Val Phe Cys Glu Leu Thr Gly Leu
            355                 360                 365

Thr Leu Asn Val Met Lys Cys His Gly Phe Phe Ile Asp Ser Met Asn
    370                 375                 380

Arg Cys Leu Ala Ile Asn Glu Cys Pro Pro Trp Arg Leu Gln Gln Asn
385                 390                 395                 400

Asp Leu His Met Ile Gly Ser Lys Glu Lys Tyr Leu Gly Met
                405                 410                 415

Glu Ile Ser Pro Trp Leu Gly Ile Ile Glu Pro Asn Ile Gln Lys Met
            420                 425                 430

Ile Asn Ile Met Leu Asn Asn Leu Thr Ala Ser Leu Leu Lys Pro Ser
            435                 440                 445

Gln Lys Leu Glu Leu Leu Arg Thr Tyr Ala Val Pro Lys Leu Thr Tyr
        450                 455                 460

Met Ala Asp Asn Gly Met Val Thr Gln Thr Thr Leu Ile Thr Thr Asp
465                 470                 475                 480

Arg Lys Ile Arg Met Thr Ile Lys Lys Trp Phe His Leu Asn His Ala
                485                 490                 495

Thr Thr Asp Gly Leu Leu Tyr Thr Gly Cys Lys Ser Gly Gly Met Gly
                500                 505                 510

Leu Val Lys Leu Ala Arg Val Ile Pro Arg Ile Gln Val Asn Arg Ile
        515                 520                 525

Leu Gly Leu Cys Asn Ser Glu Asp Ser Cys Thr Arg Thr Met Ala Arg
        530                 535                 540

Lys Ala His Arg Pro Ser Glu Phe Arg Lys Ile Trp Lys Met Gly Met
545                 550                 555                 560

Gly Lys Gly Gly Glu Thr Thr Ile Gln Gly Ala Ser Asp Ile Arg Thr
                565                 570                 575

Pro Tyr Trp Asn Thr Pro Lys Ile His Ser Asp Trp Arg Ile Asn Glu
            580                 585                 590

Leu Asp Lys Trp Lys Lys Met Lys Thr Gln Gly Glu Gly Ile Glu Val
        595                 600                 605

Phe Glu Asn Asp Lys Ile Ser Asn Ser Trp Leu Arg His Pro Thr Leu
        610                 615                 620

Ser Asn Phe Ser Glu Arg Asp Tyr Ile Leu Ala Leu Lys Leu Arg Thr
625                 630                 635                 640

Asn Thr Tyr Pro Met Lys Ala Ile Leu Ala Arg Gly Arg Met Ala Lys
                645                 650                 655

Asn Lys Gly Thr Lys Cys Arg Leu Cys Gly Tyr Ile Lys Lys Thr Thr
            660                 665                 670

Lys His Val Leu Gly Ser Cys Ile Gly Thr Arg Pro Asn Arg Met Gln
        675                 680                 685

Arg His Asn Lys Ile Cys Ala Leu Leu Ala Lys Ala Ala Arg Gln Leu
    690                 695                 700

Gly Trp Glu Thr Leu Thr Glu His His Leu Lys Met Asp Asn Gly Lys
705                 710                 715                 720

Thr Leu Val Pro Asp Leu Ile Met Met Lys Asp Thr Arg Ala Ile Val
                725                 730                 735

Ala Asp Val Thr Ile Cys Tyr Glu Thr Asn Gln Tyr Ser Leu Arg Lys
            740                 745                 750

Ala Tyr Glu Val Lys Val Lys Lys Tyr Ala Pro Leu Glu Leu Pro Ile
        755                 760                 765
```

Lys Glu Arg Trp Pro Gly Ile Lys Asp Val Arg Ile His Gly Phe Pro
770                 775                 780

Leu Gly Thr Arg Gly Lys Trp Pro Ser Leu Asn Trp Arg Leu Leu Glu
785                 790                 795                 800

Glu Leu Asp Met Asp Lys Ser Lys Arg Arg Lys Phe Ala Ser Leu Leu
                805                 810                 815

Ser Lys Arg Ser Leu Leu Tyr Thr Ile Asp Ile Leu Lys Trp Phe Ser
                820                 825                 830

Lys Asn

<210> SEQ ID NO 19
<211> LENGTH: 812
<212> TYPE: PRT
<213> ORGANISM: Artificial Sequence
<220> FEATURE:
<223> OTHER INFORMATION: Synthesized

<400> SEQUENCE: 19

Thr Arg Ser Ala Pro Ser Ser Thr Ser Ser Gly Lys Ser Thr Arg Asn
1               5                   10                  15

Ala Lys Arg Leu Glu Lys Leu Lys Lys Tyr Gly Tyr Tyr Gln His Leu
                20                  25                  30

Tyr Tyr Asn Asn Lys Lys Lys Leu Val Ala Glu Ile Leu Asp Gly Glu
            35                  40                  45

Thr Ser Gly Ala Lys Pro Pro Pro Met Asn Leu Val Glu Asp Tyr Tyr
    50                  55                  60

Lys Asn Ile Trp Ser Arg Ser Thr Ile Asp Asp Ser Pro Val Asn Asn
65                  70                  75                  80

Ile Lys Thr Val Asn Ser Asp Ser Ile Phe Ala Pro Ile Ser Arg Asp
                85                  90                  95

Glu Ile Lys Leu Ala Leu Ser Asn Thr Lys Lys Asp Ser Ala Ala Gly
                100                 105                 110

Pro Asp Ser Val Thr Ile Lys Glu Ala Lys Ala Ile Ile Asp Asn Leu
            115                 120                 125

Tyr Val Ala Tyr Asn Ile Trp Leu Gly Val Gln Gly Ile Pro Glu Gln
    130                 135                 140

Leu Lys Leu Asn Lys Thr Ile Leu Ile Pro Lys Gly Asn Ser Asp Leu
145                 150                 155                 160

Ser Leu Leu Lys Asn Trp Arg Pro Ile Thr Ile Ser Ser Ile Ile Leu
                165                 170                 175

Arg Val Tyr Asn Arg Leu Leu Ala Tyr Arg Met Asn Lys Val Phe Lys
                180                 185                 190

Thr Asn Asp Lys Gln Val Gly Phe Lys Pro Val Asn Gly Cys Gly Ile
                195                 200                 205

Asn Ile Ser Trp Leu His Ser Leu Leu Lys His Ala Arg Leu Asn Lys
210                 215                 220

Asn Pro Ile Tyr Ala Cys Leu Val Asp Val Ser Lys Ala Phe Asp Ser
225                 230                 235                 240

Val Ser His Gln Ser Ile Val Arg Ala Leu Thr Met Asn Gly Ala Pro
            245                 250                 255

Ser Leu Leu Val Lys Leu Ile Met Asp Gln Tyr Thr Asn Ile Asn Thr
            260                 265                 270

Ile Ile Thr Cys Ser Gly Ser Ile Ser Asn Lys Ile Asn Ile Ser Ser
        275                 280                 285

Gly Val Lys Gln Gly Asp Pro Leu Ser Ser Leu Leu Phe Asn Met Val

-continued

```
                290                 295                 300
Ile Asp Glu Leu Phe Asp Val Ile Lys Asp Gln Tyr Gly Tyr Thr Ile
305                 310                 315                 320

Asp Asn Ile Gly Thr Thr Asn Ala Arg Cys Phe Ala Asp Asp Leu Thr
                325                 330                 335

Leu Ile Ser Ser Ser Arg Met Gly Met Asn Lys Leu Leu Glu Leu Thr
                340                 345                 350

Thr Glu Phe Phe Lys Glu Arg Gly Leu Asn Val Asn Pro Ser Lys Cys
                355                 360                 365

Met Ser Ile Gly Met Ser Lys Gly Tyr Lys Gly Lys Ser Lys Ile
                370                 375                 380

Glu Ser Glu Pro Leu Phe Ser Ile Ala Asp Ala Gln Ile Pro Met Leu
385                 390                 395                 400

Gly Tyr Ile Asp Lys Thr Thr Arg Tyr Leu Gly Val Asn Phe Thr Ser
                405                 410                 415

Ile Gly Ala Ile Asp Ala Lys Arg Ile Lys Lys Asp Leu His Asp Thr
                420                 425                 430

Leu Asp Lys Leu Glu His Leu Lys Leu Lys Ala Gln Cys Lys Met Asp
                435                 440                 445

Leu Leu Arg Thr Tyr Met Ile Pro Arg Phe Met Phe Gln Leu Ile His
                450                 455                 460

Thr Glu Leu Tyr Pro Lys Leu Leu Ile Lys Met Asp Ile Leu Ile Arg
465                 470                 475                 480

Lys Leu Ala Lys Arg Ile Leu His Leu Pro Ile Ser Thr Ser Ser Glu
                485                 490                 495

Phe Phe Tyr Leu Pro Phe Lys Glu Gly Leu Gln Leu Thr Ser Leu
                500                 505                 510

Lys Glu Ala Val Gly Leu Ala Lys Ile Lys Leu His Lys Lys Ile Met
                515                 520                 525

Ser Ser Asn Asp Pro Met Leu Cys Tyr Leu Ile Glu Ser Gln Arg Ser
530                 535                 540

Arg Ile Ile Glu His Phe Met Lys Asp Leu Lys Leu Gly Asp Ser Leu
545                 550                 555                 560

Thr Leu Asn Glu Met Asp Asn Ile Lys Glu Cys Phe Met Lys Glu Lys
                565                 570                 575

Arg Ile Ser Phe Ala Gln Lys Ile His Gly Val Gly Phe Glu Val Phe
                580                 585                 590

Ser Ser Ser Pro Leu Thr Asn Gln Trp Ile Asn Gly Glu Ile Lys Thr
                595                 600                 605

Met Thr Thr Arg Thr Tyr Ile Asn Ser Ile Lys Leu Arg Thr Asn Thr
                610                 615                 620

Leu Glu Thr Arg Val Thr Thr Ser Arg Gly Leu Asn Ile Ile Lys Thr
625                 630                 635                 640

Cys Arg Arg Cys His Val Ala Asp Glu Ser Leu Met His Val Leu Gln
                645                 650                 655

Tyr Cys Ser Ser Thr Lys Gly Leu Arg Tyr Ser Arg His His Arg Ile
                660                 665                 670

Cys Ala Lys Val Ala Asn Lys Leu Met Lys Asn Gly Tyr Gly Val Tyr
                675                 680                 685

Arg Glu Lys Ser Tyr Pro Asp Pro Asn Asn Ser Gly Ser Tyr Leu Arg
                690                 695                 700

Pro Asp Leu Ile Ala Val Lys Asp Gly His Val Ile Val Leu Asp Val
705                 710                 715                 720
```

```
Thr Val Val Tyr Glu Val Gly Ala Thr Phe Ile Asn Ala Tyr Gln
                725                 730                 735

Thr Lys Val Asn Lys Tyr Asn Thr Ile Met Val Gln Ile Glu Gln Met
        740                 745                 750

Phe Asn Cys Val Ser Gly Val Leu His Gly Leu Val Ile Gly Ser Arg
        755                 760                 765

Gly Ser Ile His His Ser Gln Leu His Ile Trp His Gln Met Gly Phe
    770                 775                 780

Ser Ser Thr Glu Leu Lys Tyr Val Ala Ile Gly Cys Met Glu Asp Ser
785                 790                 795                 800

Leu Arg Ile Met Ser Thr Phe Ser Lys Ala Ile Leu
                805                 810

<210> SEQ ID NO 20
<211> LENGTH: 797
<212> TYPE: PRT
<213> ORGANISM: Artificial Sequence
<220> FEATURE:
<223> OTHER INFORMATION: Synthesized

<400> SEQUENCE: 20

Lys Ser Lys Ser Leu Pro Arg Leu Lys Arg Thr Gly Arg Ala Phe His
1               5                   10                  15

Arg Arg Glu Lys Tyr Ala Ile Cys Gln Lys Ser Leu Asp Lys Asp Phe
            20                  25                  30

Ser Gly Thr Ile Ser Lys Ile Leu Asp Gly Val Glu Ile Ser Glu Ala
        35                  40                  45

Glu Val Arg Pro Glu Met Ala Lys Ile Glu Glu Val Tyr Gln Gln Arg
    50                  55                  60

Leu Gly Asn Thr Ser Gly Ala Leu Pro Glu Asn Thr Asp Thr Pro Val
65                  70                  75                  80

Val Glu Gly Leu Arg Phe Glu Arg Lys Thr Ala Pro Phe Asp Ala Gln
                85                  90                  95

Glu Val Thr Arg Ala Ile Arg Glu Ser Asn Lys Ser Thr Ala Ala Gly
            100                 105                 110

Pro Asp Arg Trp Phe Asn Gly Arg Cys Leu Lys Asn Leu Asp Cys Glu
        115                 120                 125

Thr Val Ala Ala Leu Phe Asn Leu Trp Arg Phe Lys Gln Lys Ile Pro
    130                 135                 140

Ser Ala Leu Arg Glu Asn Arg Thr Ile Leu Leu Pro Lys Gly Gly Asp
145                 150                 155                 160

Leu Thr Asp Ala Asn Asn Trp Arg Pro Leu Thr Ile Gly Ser Leu Leu
                165                 170                 175

Leu Arg Leu Tyr Ala Lys Ser Leu Thr Thr Arg Trp Ser Asp Ala Pro
            180                 185                 190

Ile Cys Glu Arg Gln Lys Ala Phe Arg Pro Val Asp Gly Cys Trp Glu
        195                 200                 205

Asn Ile Asn Leu Leu Leu Gly Ala Leu Lys Ser Ala His Lys Lys Arg
    210                 215                 220

Arg Gln Ile Asn Leu Ile Ser Ile Asp Leu Ala Lys Ala Phe Asp Asn
225                 230                 235                 240

Ile Gln His Gly Ala Ile Phe Asn Ala Met Arg Arg Phe Gly Phe Ser
                245                 250                 255

Pro Ser Glu Ile Ser Val Val Lys Asp Leu Tyr Thr Asn Val Trp Thr
            260                 265                 270
```

```
Lys Ile Ser Ile Gly Asn Glu Ile Ser Gly Pro Ile Asn Ile Ser Arg
        275                 280                 285

Gly Val Lys Gln Gly Cys Pro Leu Ser Pro Phe Leu Phe Asn Leu Val
    290                 295                 300

Leu Asp Glu Leu Ile Asn Glu Leu Gln Ser Ser Gly Tyr Gly Tyr Pro
305                 310                 315                 320

Val Glu Gly Phe Lys Val Pro Val Leu Ala Tyr Ala Asp Asp Leu Ile
                325                 330                 335

Leu Cys Gly Ala Thr Asp Tyr Glu Thr Lys Arg Met Val Glu Ile Thr
                340                 345                 350

Glu Lys Phe Phe Ala Arg Gln Met Leu Ala Val Asn Leu Lys Lys Cys
        355                 360                 365

Lys Ala Leu Arg Leu Leu Pro Val Lys Gly Lys Arg Thr Leu Lys Val
    370                 375                 380

Ser Ser Asp Pro Met Leu Trp Lys Gly Glu Gln Leu Pro Met Val Lys
385                 390                 395                 400

Ser Ile Asp Asp Phe Ile Ser Tyr Leu Gly Val Lys Val Ser Val Thr
                405                 410                 415

Gly Lys Val Ile Trp Ser Val Asp Gln Leu Arg Leu Trp Leu Asp Arg
                420                 425                 430

Val Met Lys Ala Pro Leu Lys Pro Asp Gln Lys Ile Lys Gly Ile Lys
        435                 440                 445

Glu Val Leu Ile Gly Arg Leu Thr Tyr Gln Leu Arg Leu Ser Glu Ala
    450                 455                 460

Arg Val Cys Glu Leu Arg Arg Val Thr Arg Met Val Arg Lys Ala Cys
465                 470                 475                 480

Lys Gln Ile Leu His Met Gln Leu Gly Ala Pro Asn Ala Trp Ala His
                485                 490                 495

Leu Pro Leu Arg Lys Cys Gly Leu Gly Leu Pro Asp Phe Glu Leu Thr
                500                 505                 510

Ile Pro Leu Met Arg Arg Ala Ala Cys Glu Lys Met Lys Ser Ser Pro
        515                 520                 525

Asp Pro Val Val Ala Asn Ile Ser Glu Lys Ile Pro Ile Tyr Glu Ser
    530                 535                 540

Gly Leu Thr Arg Gly Leu Asp Val Arg Ala Ala Lys Arg Ala Ile Gln
545                 550                 555                 560

Asp Lys Tyr Glu Gln Ala Tyr Leu Ser Thr Gln Arg Gly Lys Leu Met
                565                 570                 575

Asn Ala Arg Trp Ile Ser Ala Val Lys Pro Tyr Trp Leu His Gly Gly
                580                 585                 590

Thr Gly Val Val Lys Ala Gly Glu Tyr Val Ser Ile Asn Lys Leu Val
        595                 600                 605

Thr Arg Thr Ile Glu Thr Arg Gln Phe Ile His Pro Gly Val Thr Asp
    610                 615                 620

Phe Glu Thr Leu Lys Cys Arg Arg Cys Gly Lys Ala Val Glu Thr Asp
625                 630                 635                 640

Leu His Val Leu Asn Glu Cys Pro Phe Thr Arg Leu Ala Gln Cys Arg
                645                 650                 655

Arg His Asn Phe Ile Ala Asp Tyr Leu Gly Lys Val Leu Val Asp His
                660                 665                 670

Gly Trp Glu Val Trp Arg Glu Arg Leu Val Lys Lys Asp Leu Glu Asn
        675                 680                 685
```

```
Phe Lys Pro Asp Leu Ile Cys Arg Lys Gly Ala Glu Gly Ala Ile Ile
        690                 695                 700
Asp Val Thr Val Pro Tyr Glu Ser Asn Glu Ala Val Leu Gln Ser Lys
705                 710                 715                 720
Glu Arg Phe Lys Glu Ala Lys Tyr Ala Gly Leu Lys Gly Gln Val Ala
                725                 730                 735
Glu Leu Leu Asn Ile Asn Gly Val Lys Val Gly Ile Ala Val
                740                 745                 750
Gly Ala Leu Gly Thr Ile Leu Thr Ser Thr Leu Glu Lys Ala Lys Gly
                755                 760                 765
Leu Gly Leu Asp Pro Val Lys Val Gly Lys Ser Leu Gln Ile Ser Ala
        770                 775                 780
Leu Arg Gly Ser Gly His Val Trp Lys Ala Phe Arg Ser
785                 790                 795
```

<210> SEQ ID NO 21
<211> LENGTH: 69
<212> TYPE: PRT
<213> ORGANISM: Artificial Sequence
<220> FEATURE:
<223> OTHER INFORMATION: Synthesized

<400> SEQUENCE: 21

```
Met Pro Ser Val Gln Glu Val Glu Lys Leu Leu His Val Leu Asp Arg
1               5                   10                  15
Asn Gly Asp Gly Lys Val Ser Ala Glu Leu Lys Ala Phe Ala Asp
            20                  25                  30
Asp Ser Lys Cys Pro Leu Asp Ser Asn Lys Ile Lys Ala Phe Ile Lys
        35                  40                  45
Glu His Asp Lys Asn Lys Asp Gly Lys Leu Asp Leu Lys Glu Leu Val
    50                  55                  60
Ser Ile Leu Ser Ser
65
```

<210> SEQ ID NO 22
<211> LENGTH: 210
<212> TYPE: DNA
<213> ORGANISM: Artificial Sequence
<220> FEATURE:
<223> OTHER INFORMATION: Synthesized

<400> SEQUENCE: 22

```
atgccgtctg ttcaggaagt tgaaaaactg ctgcacgttc tggaccgtaa cggtgacggt      60
aaagtttctg cggaagaact gaaagcgttc gcggacgact ctaaatgccc gctggactct     120
aacaaaatca agcgttcat caaagaacac gacaaaaaca agacggtaa actggacctg      180
aaagaactgg tttctatcct gtcttcttag                                     210
```

<210> SEQ ID NO 23
<211> LENGTH: 220
<212> TYPE: DNA
<213> ORGANISM: Artificial Sequence
<220> FEATURE:
<223> OTHER INFORMATION: Synthesized

<400> SEQUENCE: 23

```
ctgcagtaat acgactcact ataggatcct ctagagtcga cctgcaggca tgcaagcttg      60
gcactggccg tcgttttaca acgtcgtgac tgggaaaacc ctggcgttac ccaacttaat     120
cgccttgcag cacatccccc tttcgccagc tggcgtaata gcgaagaggc ccgcaccgat     180
```

-continued cgcccttccc aacagttgcg cagcctgaat ggcgaatggc              220

<210> SEQ ID NO 24
<211> LENGTH: 45
<212> TYPE: DNA
<213> ORGANISM: Artificial Sequence
<220> FEATURE:
<223> OTHER INFORMATION: Synthesized

<400> SEQUENCE: 24
ctgcagtaat acgactcact ataggatcct ctagagtcga cctgc        45

<210> SEQ ID NO 25
<211> LENGTH: 24
<212> TYPE: DNA
<213> ORGANISM: Artificial Sequence
<220> FEATURE:
<223> OTHER INFORMATION: Synthesized

<400> SEQUENCE: 25
cagtcagtca gtcagtcagt gcca                               24

<210> SEQ ID NO 26
<211> LENGTH: 38
<212> TYPE: RNA
<213> ORGANISM: Artificial Sequence
<220> FEATURE:
<223> OTHER INFORMATION: Synthesized

<400> SEQUENCE: 26
cagucaguca gucagucagu gccaaaugcc ucgucauc                38

<210> SEQ ID NO 27
<211> LENGTH: 19
<212> TYPE: DNA
<213> ORGANISM: Artificial Sequence
<220> FEATURE:
<223> OTHER INFORMATION: Synthesized

<400> SEQUENCE: 27
tgatgacgag gcatttggc                                     19

<210> SEQ ID NO 28
<211> LENGTH: 23
<212> TYPE: DNA
<213> ORGANISM: Artificial Sequence
<220> FEATURE:
<223> OTHER INFORMATION: Synthesized

<400> SEQUENCE: 28
acactctttc cctacacgac gct                                23

<210> SEQ ID NO 29
<211> LENGTH: 22
<212> TYPE: DNA
<213> ORGANISM: Artificial Sequence
<220> FEATURE:
<223> OTHER INFORMATION: Synthesized

<400> SEQUENCE: 29
gcgtcgtgta gggaaagagt gt                                 22

<210> SEQ ID NO 30
<211> LENGTH: 22
<212> TYPE: DNA

```
<213> ORGANISM: Artificial Sequence
<220> FEATURE:
<223> OTHER INFORMATION: Synthesized

<400> SEQUENCE: 30
cactctttcc ctacacgacg ct                                          22

<210> SEQ ID NO 31
<211> LENGTH: 45
<212> TYPE: DNA
<213> ORGANISM: Artificial Sequence
<220> FEATURE:
<223> OTHER INFORMATION: Synthesized

<400> SEQUENCE: 31
agcgtcgtgt agggaaagag tgtcactctt tccctacacg acgct                 45

<210> SEQ ID NO 32
<211> LENGTH: 42
<212> TYPE: DNA
<213> ORGANISM: Artificial Sequence
<220> FEATURE:
<223> OTHER INFORMATION: Synthesized

<400> SEQUENCE: 32
acactttatg cttccggctc cactctttcc ctacacgacg ct                    42

<210> SEQ ID NO 33
<211> LENGTH: 41
<212> TYPE: DNA
<213> ORGANISM: Artificial Sequence
<220> FEATURE:
<223> OTHER INFORMATION: Synthesized

<400> SEQUENCE: 33
taagttgggt aacgccaggc actctttccc tacacgacgc t                     41

<210> SEQ ID NO 34
<211> LENGTH: 33
<212> TYPE: DNA
<213> ORGANISM: Artificial Sequence
<220> FEATURE:
<223> OTHER INFORMATION: Synthesized

<400> SEQUENCE: 34
acactctttc ccactctttc cctacacgac gct                              33

<210> SEQ ID NO 35
<211> LENGTH: 31
<212> TYPE: DNA
<213> ORGANISM: Artificial Sequence
<220> FEATURE:
<223> OTHER INFORMATION: Synthesized

<400> SEQUENCE: 35
agcgtcgtgc actctttccc tacacgacgc t                                31

<210> SEQ ID NO 36
<211> LENGTH: 65
<212> TYPE: DNA
<213> ORGANISM: Artificial Sequence
<220> FEATURE:
<223> OTHER INFORMATION: Synthesized

<400> SEQUENCE: 36
ttccaatgat acggcgacca ccgauacugu cauagctagc tcctcactct ttccctacac  60
```

```
gacgc                                                              65

<210> SEQ ID NO 37
<211> LENGTH: 65
<212> TYPE: DNA
<213> ORGANISM: Artificial Sequence
<220> FEATURE:
<223> OTHER INFORMATION: Synthesized

<400> SEQUENCE: 37
ggagctagct atgacagtat cggtggtcgc cgtatcatta cttcactctt tccctacacg    60
acgct                                                              65

<210> SEQ ID NO 38
<211> LENGTH: 33
<212> TYPE: DNA
<213> ORGANISM: Artificial Sequence
<220> FEATURE:
<223> OTHER INFORMATION: Synthesized

<400> SEQUENCE: 38
acactctttc cctacacgac gctcttccga tct                                33

<210> SEQ ID NO 39
<211> LENGTH: 34
<212> TYPE: DNA
<213> ORGANISM: Artificial Sequence
<220> FEATURE:
<223> OTHER INFORMATION: Synthesized

<400> SEQUENCE: 39
gtgactggag ttcagacgtg tgctcttccg atct                               34

<210> SEQ ID NO 40
<211> LENGTH: 56
<212> TYPE: DNA
<213> ORGANISM: Artificial Sequence
<220> FEATURE:
<223> OTHER INFORMATION: Synthesized

<400> SEQUENCE: 40
aatgatacgg cgaccaccga gatctacact aatcttaaca ctctttccct acacga        56

<210> SEQ ID NO 41
<211> LENGTH: 50
<212> TYPE: DNA
<213> ORGANISM: Artificial Sequence
<220> FEATURE:
<223> OTHER INFORMATION: Synthesized

<400> SEQUENCE: 41
caagcagaag acggcatacg agatattact cggtgactgg agttcagacg               50

<210> SEQ ID NO 42
<211> LENGTH: 37
<212> TYPE: DNA
<213> ORGANISM: Artificial Sequence
<220> FEATURE:
<223> OTHER INFORMATION: Synthesized

<400> SEQUENCE: 42
acactctttc cctacacgac gctcttccga tctaggg                            37

<210> SEQ ID NO 43
```

```
<211> LENGTH: 38
<212> TYPE: DNA
<213> ORGANISM: Artificial Sequence
<220> FEATURE:
<223> OTHER INFORMATION: Synthesized

<400> SEQUENCE: 43
acactctttc cctacacgac gctcttccga tctcaggg                              38

<210> SEQ ID NO 44
<211> LENGTH: 39
<212> TYPE: DNA
<213> ORGANISM: Artificial Sequence
<220> FEATURE:
<223> OTHER INFORMATION: Synthesized

<400> SEQUENCE: 44
acactctttc cctacacgac gctcttccga tcttctggg                             39

<210> SEQ ID NO 45
<211> LENGTH: 34
<212> TYPE: DNA
<213> ORGANISM: Artificial Sequence
<220> FEATURE:
<223> OTHER INFORMATION: Synthesized

<400> SEQUENCE: 45
acactctttc cctacacgac gctcttccga tctg                                  34

<210> SEQ ID NO 46
<211> LENGTH: 33
<212> TYPE: DNA
<213> ORGANISM: Artificial Sequence
<220> FEATURE:
<223> OTHER INFORMATION: Synthesized

<400> SEQUENCE: 46
acactctttc cctacacgac gctcttccga tct                                   33

<210> SEQ ID NO 47
<211> LENGTH: 39
<212> TYPE: DNA
<213> ORGANISM: Artificial Sequence
<220> FEATURE:
<223> OTHER INFORMATION: Synthesized

<400> SEQUENCE: 47
acactctttc cctacacgac gctcttccga tctrgrgrg                             39

<210> SEQ ID NO 48
<211> LENGTH: 39
<212> TYPE: DNA
<213> ORGANISM: Artificial Sequence
<220> FEATURE:
<223> OTHER INFORMATION: Synthesized

<400> SEQUENCE: 48
acactctttc cctacacgac gctcttccga tctrgrgrg                             39

<210> SEQ ID NO 49
<211> LENGTH: 34
<212> TYPE: DNA
<213> ORGANISM: Artificial Sequence
<220> FEATURE:
<223> OTHER INFORMATION: Synthesized
<220> FEATURE:
<221> NAME/KEY: misc_feature
```

<222> LOCATION: (34)..(34)
<223> OTHER INFORMATION: n is a, c, g, or t

<400> SEQUENCE: 49
acactctttc cctacacgac gctcttccga tctn                            34

<210> SEQ ID NO 50
<211> LENGTH: 35
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (34)..(35)
<223> OTHER INFORMATION: n is a, c, g, or t

<400> SEQUENCE: 50
acactctttc cctacacgac gctcttccga tctnn                           35

<210> SEQ ID NO 51
<211> LENGTH: 33
<212> TYPE: DNA
<213> ORGANISM: Artificial Sequence
<220> FEATURE:
<223> OTHER INFORMATION: Synthesized

<400> SEQUENCE: 51
acactctttc cctacacgac gctcttccga tct                             33

<210> SEQ ID NO 52
<211> LENGTH: 34
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (34)..(34)
<223> OTHER INFORMATION: n is a, c, g, or t

<400> SEQUENCE: 52
acactctttc cctacacgac gctcttccga tctn                            34

<210> SEQ ID NO 53
<211> LENGTH: 32
<212> TYPE: DNA
<213> ORGANISM: Artificial Sequence
<220> FEATURE:
<223> OTHER INFORMATION: Synthesized

<400> SEQUENCE: 53
acactctttc cctacacgac gctcttccga tc                              32

<210> SEQ ID NO 54
<211> LENGTH: 36
<212> TYPE: DNA
<213> ORGANISM: Artificial Sequence
<220> FEATURE:
<223> OTHER INFORMATION: Synthesized

<400> SEQUENCE: 54
ccgtgactgg agttcagacg tgtgctcttc cgatct                          36

<210> SEQ ID NO 55
<211> LENGTH: 61
<212> TYPE: DNA

```
<213> ORGANISM: Artificial Sequence
<220> FEATURE:
<223> OTHER INFORMATION: Synthesized
<220> FEATURE:
<221> NAME/KEY: misc_feature
<222> LOCATION: (37)..(44)
<223> OTHER INFORMATION: n is a, c, g, or t

<400> SEQUENCE: 55
ccgtgactgg agttcagacg tgtgctcttc cgatctnnnn nnnnttttt tttttttttt      60 t                                                                    61

<210> SEQ ID NO 56
<211> LENGTH: 33
<212> TYPE: DNA
<213> ORGANISM: Artificial Sequence
<220> FEATURE:
<223> OTHER INFORMATION: Synthesized

<400> SEQUENCE: 56
acactctttc cctacacgac gctcttccga tct                                  33

<210> SEQ ID NO 57
<211> LENGTH: 59
<212> TYPE: DNA
<213> ORGANISM: Artificial Sequence
<220> FEATURE:
<223> OTHER INFORMATION: Synthesized

<400> SEQUENCE: 57
aatgatacgg cgaccaccga gatctacacg tactgacaca ctctttccct acacgacgc      59

<210> SEQ ID NO 58
<211> LENGTH: 53
<212> TYPE: DNA
<213> ORGANISM: Artificial Sequence
<220> FEATURE:
<223> OTHER INFORMATION: Synthesized

<400> SEQUENCE: 58
caagcagaag acggcatacg agatattact cggtgactgg agttcagacg tgt            53

<210> SEQ ID NO 59
<211> LENGTH: 829
<212> TYPE: PRT
<213> ORGANISM: Bombyx mori

<400> SEQUENCE: 59
```

Lys Thr Ala Gly Arg Arg Asn Asp Leu His Asp Arg Thr Ala Ser
1               5                  10                  15

Ala His Lys Thr Ser Arg Gln Lys Arg Arg Ala Glu Tyr Ala Arg Val
            20                  25                  30

Gln Glu Leu Tyr Lys Lys Cys Arg Ser Arg Ala Ala Ala Glu Val Ile
        35                  40                  45

Asp Gly Ala Cys Gly Gly Val Gly His Ser Leu Glu Glu Met Glu Thr
    50                  55                  60

Tyr Trp Arg Pro Ile Leu Glu Arg Val Ser Asp Ala Pro Gly Pro Thr
65                  70                  75                  80

Pro Glu Ala Leu His Ala Leu Gly Arg Ala Glu Trp His Gly Asn
                85                  90                  95

Arg Asp Tyr Thr Gln Leu Trp Lys Pro Ile Ser Val Glu Glu Ile Lys
            100                 105                 110

```
Ala Ser Arg Phe Asp Trp Arg Thr Ser Pro Gly Pro Asp Gly Ile Arg
            115                 120                 125

Ser Gly Gln Trp Arg Ala Val Pro Val His Leu Lys Ala Glu Met Phe
130                 135                 140

Asn Ala Trp Met Ala Arg Gly Glu Ile Pro Glu Ile Leu Arg Gln Cys
145                 150                 155                 160

Arg Thr Val Phe Val Pro Lys Val Glu Arg Pro Gly Pro Gly Glu
                165                 170                 175

Tyr Arg Pro Ile Ser Ile Ala Ser Ile Pro Leu Arg His Phe His Ser
            180                 185                 190

Ile Leu Ala Arg Arg Leu Leu Ala Cys Cys Pro Pro Asp Ala Arg Gln
        195                 200                 205

Arg Gly Phe Ile Cys Ala Asp Gly Thr Leu Glu Asn Ser Ala Val Leu
    210                 215                 220

Asp Ala Val Leu Gly Asp Ser Arg Lys Lys Leu Arg Glu Cys His Val
225                 230                 235                 240

Ala Val Leu Asp Phe Ala Lys Ala Phe Asp Thr Val Ser His Glu Ala
                245                 250                 255

Leu Val Glu Leu Leu Arg Leu Arg Gly Met Pro Glu Gln Phe Cys Gly
            260                 265                 270

Tyr Ile Ala His Leu Tyr Asp Thr Ala Ser Thr Thr Leu Ala Val Asn
        275                 280                 285

Asn Glu Met Ser Ser Pro Val Lys Val Gly Arg Gly Val Arg Gln Gly
    290                 295                 300

Asp Pro Leu Ser Pro Ile Leu Phe Asn Val Val Met Asp Leu Ile Leu
305                 310                 315                 320

Ala Ser Leu Pro Glu Arg Val Gly Tyr Arg Leu Glu Met Glu Leu Val
                325                 330                 335

Ser Ala Leu Ala Tyr Ala Asp Asp Leu Val Leu Leu Ala Gly Ser Lys
            340                 345                 350

Val Gly Met Gln Glu Ser Ile Ser Ala Val Asp Cys Val Gly Arg Gln
        355                 360                 365

Met Gly Leu Arg Leu Asn Cys Arg Lys Ser Ala Val Leu Ser Met Ile
    370                 375                 380

Pro Asp Gly His Arg Lys Lys His His Tyr Leu Thr Glu Arg Thr Phe
385                 390                 395                 400

Asn Ile Gly Gly Lys Pro Leu Arg Gln Val Ser Cys Val Glu Arg Trp
                405                 410                 415

Arg Tyr Leu Gly Val Asp Phe Glu Ala Ser Gly Cys Val Thr Leu Glu
            420                 425                 430

His Ser Ile Ser Ser Ala Leu Asn Asn Ile Ser Arg Ala Pro Leu Lys
        435                 440                 445

Pro Gln Gln Arg Leu Glu Ile Leu Arg Ala His Leu Ile Pro Arg Phe
    450                 455                 460

Gln His Gly Phe Val Leu Gly Asn Ile Ser Asp Asp Arg Leu Arg Met
465                 470                 475                 480

Leu Asp Val Gln Ile Arg Lys Ala Val Gly Gln Trp Leu Arg Leu Pro
                485                 490                 495

Ala Asp Val Pro Lys Ala Tyr Tyr His Ala Ala Val Gln Asp Gly Gly
            500                 505                 510

Leu Ala Ile Pro Ser Val Arg Ala Thr Ile Pro Asp Leu Ile Val Arg
        515                 520                 525

Arg Phe Gly Gly Leu Asp Ser Ser Pro Trp Ser Val Ala Arg Ala Ala
```

```
               530                 535                 540
Ala Lys Ser Asp Lys Ile Arg Lys Leu Arg Trp Ala Trp Lys Gln
545                 550                 555                 560

Leu Arg Arg Phe Ser Arg Val Asp Ser Thr Thr Gln Arg Pro Ser Val
                565                 570                 575

Arg Leu Phe Trp Arg Glu His Leu His Ala Ser Val Asp Gly Arg Glu
            580                 585                 590

Leu Arg Glu Ser Thr Arg Thr Pro Thr Ser Thr Lys Trp Ile Arg Glu
        595                 600                 605

Arg Cys Ala Gln Ile Thr Gly Arg Asp Phe Val Gln Phe Val His Thr
    610                 615                 620

His Ile Asn Ala Leu Pro Ser Arg Ile Arg Gly Ser Arg Gly Arg Arg
625                 630                 635                 640

Gly Gly Gly Glu Ser Ser Leu Thr Cys Arg Ala Gly Cys Lys Val Arg
                645                 650                 655

Glu Thr Thr Ala His Ile Leu Gln Gln Cys His Arg Thr His Gly Gly
            660                 665                 670

Arg Leu Leu Arg His Asn Lys Ile Val Ser Phe Val Ala Lys Ala Met
        675                 680                 685

Glu Glu Asn Lys Trp Thr Val Glu Leu Glu Pro Arg Leu Arg Thr Ser
    690                 695                 700

Val Gly Leu Arg Lys Pro Asp Ile Ile Ala Ser Arg Asp Gly Val Gly
705                 710                 715                 720

Val Ile Val Asp Val Gln Val Val Ser Gly Gln Arg Ser Leu Asp Glu
                725                 730                 735

Leu His Arg Glu Lys Arg Asn Lys Tyr Gly Asn His Gly Glu Leu Val
            740                 745                 750

Glu Leu Val Ala Gly Arg Leu Gly Leu Pro Lys Ala Glu Cys Val Arg
        755                 760                 765

Ala Thr Ser Cys Thr Ile Ser Trp Arg Gly Val Trp Ser Leu Thr Ser
    770                 775                 780

Tyr Lys Glu Leu Arg Ser Ile Ile Gly Leu Arg Glu Pro Thr Leu Gln
785                 790                 795                 800

Ile Val Pro Ile Leu Ala Leu Arg Gly Ser His Met Asn Trp Thr Arg
                805                 810                 815

Phe Asn Gln Met Thr Ser Val Met Gly Gly Gly Val Gly
            820                 825

<210> SEQ ID NO 60
<211> LENGTH: 38
<212> TYPE: RNA
<213> ORGANISM: Artificial Sequence
<220> FEATURE:
<223> OTHER INFORMATION: Synthesized

<400> SEQUENCE: 60
cagucaguca gucagucagu gccaaaugcc ucgucauc                          38

<210> SEQ ID NO 61
<211> LENGTH: 19
<212> TYPE: DNA
<213> ORGANISM: Artificial Sequence
<220> FEATURE:
<223> OTHER INFORMATION: Synthesized

<400> SEQUENCE: 61
tgatgacgag gcatttggc                                               19
```

<210> SEQ ID NO 62
<211> LENGTH: 28
<212> TYPE: DNA
<213> ORGANISM: Artificial Sequence
<220> FEATURE:
<223> OTHER INFORMATION: Synthesized

<400> SEQUENCE: 62
gttaataacg aaatgagcag ccrgrgrg                                       28

<210> SEQ ID NO 63
<211> LENGTH: 22
<212> TYPE: DNA
<213> ORGANISM: Artificial Sequence
<220> FEATURE:
<223> OTHER INFORMATION: Synthesized

<400> SEQUENCE: 63
cagggttatt gtctcatgag cg                                             22

<210> SEQ ID NO 64
<211> LENGTH: 21
<212> TYPE: DNA
<213> ORGANISM: Artificial Sequence
<220> FEATURE:
<223> OTHER INFORMATION: Synthesized

<400> SEQUENCE: 64
gccattcgcc attcaggctg c                                              21

<210> SEQ ID NO 65
<211> LENGTH: 204
<212> TYPE: DNA
<213> ORGANISM: Artificial Sequence
<220> FEATURE:
<223> OTHER INFORMATION: Synthesized

<400> SEQUENCE: 65
acggccagtg aattgtaata cgactcacta tagggcgaat tgggtaccgc ctcgaggtcg    60
acggtatcga taagcttgat atcgaattcc tgcagcggat ccactagttc tagagcggcc   120
gccaccgcgg tggagctcca gcttttgttc cctttagtga gggttaattt cgagcttggc   180
gtaatcatgg tcatagctgt ttcc                                          204

<210> SEQ ID NO 66
<211> LENGTH: 24
<212> TYPE: DNA
<213> ORGANISM: Artificial Sequence
<220> FEATURE:
<223> OTHER INFORMATION: Synthesized

<400> SEQUENCE: 66
acggccagtg aattgtaata cgac                                           24

<210> SEQ ID NO 67
<211> LENGTH: 19
<212> TYPE: DNA
<213> ORGANISM: Artificial Sequence
<220> FEATURE:
<223> OTHER INFORMATION: Synthesized

<400> SEQUENCE: 67
ggaaacagct atgaccatg                                                 19

METHODS FOR PRODUCING MODIFIED REVERSE TRANSCRIPTASES

CROSS-REFERENCE TO RELATED APPLICATIONS

This application is 35 U.S.C. § 371 national phase application of PCT/US2019/032701, filed May 16, 2019, which claims priority to U.S. Provisional Application No. 62/672,480, filed on May 16, 2018, and to U.S. Provisional Application No. 62/779,371 filed on Dec. 13, 2018, the contents of each of which are hereby incorporated by reference in their entirety.

BACKGROUND

A common technique used to study gene expression in living cells is to produce complementary deoxyribonucleic acid (cDNA) from a ribonucleic acid (RNA) molecule. This technique provides a means to study RNA from living cells which avoids the direct analysis of inherently unstable RNA. As a first step in cDNA synthesis, the RNA molecules from an organism are isolated from an extract of cells or tissues of the organism. After messenger RNA (mRNA) isolation, using methods such as affinity chromatography utilizing oligo dT (a short sequence of deoxy-thymidine nucleotides), oligonucleotide sequences are annealed to the isolated mRNA molecules and enzymes with reverse transcriptase activity can be utilized to produce cDNA copies of the RNA sequence, utilizing the RNA/DNA primer as a template. Thus, reverse transcription of mRNA is a key step in many forms of gene expression analyses. Generally, mRNA is reverse transcribed into cDNA for subsequent analysis by primer extension or polymerase chain reaction.

Reverse transcriptase has both an RNA-directed DNA polymerase activity and a DNA-directed DNA polymerase activity. The reverse transcription of RNA templates may require a primer sequence which is annealed to an RNA template in order for DNA synthesis to be initiated from the 3' OH of the primer. At room temperature, reverse transcriptase enzymes may allow formation of both perfectly matched as well as mismatched DNA/RNA hybrids. In some instances, a reverse transcriptase enzyme can produce large amounts of non-specific cDNA products as a result of such non-specific priming events. The products of non-specific reverse transcription can interfere with subsequent cDNA analyses, such as cDNA sequencing, real-time polymerase chain reaction (PCR), and alkaline agarose gel electrophoresis, among others. Non-specific cDNA templates produced by non-specific reverse transcriptase activity can present particular difficulties in applications such as real-time PCR. In particular, such non-specific cDNA products can give rise to false signals which can complicate the analysis of real-time PCR signals and products. Thus, the reduction of non-specific reverse transcriptase activity may result in greater specificity of cDNA synthesis. Currently, there are no reliable and easy to use methods for improving the specificity of reverse transcription. The present disclosure satisfies these and other needs.

Several approaches may be used for obtaining transcriptome data from single cells. A pioneer approach used reverse transcriptase and oligo-dT primers with a T7 phage RNA polymerase promoter sequence attached to the 5' end of the oligo-dT run. The resulting cDNA was transcribed into multiple copies of RNA which were then converted back to cDNA (Phillips, et al., Methods 10(3):283-288 (1996)). This often truncates the cDNA molecule, losing 5' sequences of the original mRNA, especially for relatively long transcripts, and requires multiple rounds of processing when starting with low quantity (LQ) of cells, further exacerbating cDNA truncation. A recent modification (Hashimshony, et al., Cell Rep. 2(3):666-673 (2012)) enables multiplex analyses, but this is still 3' end sequence biased. Other methods are based on PCR amplification of cDNA (Liu, et al., Methods Enzymol. 303:45-55 (1999), Ozsolak, et al., Genome Res. 20(4):519-525 (2010), Gonzalez, et al., PLoS ONE. 5(12):e14418 (2010), Kanamori, et al., Genome Res. 21(7):1150-1159 (2011), Islam, et al., Genome Res. 21(7):1160-1167 (2011), Tang, et al., Nat. Methods. 6(5):377-382 (2009), Kurimoto, et al., Nucleic Acids Res. 34(5):e42 (2006), Qiu S, et al., Front Genet. 3:124 (2012)).

These approaches, however, may yield biased representations of sequences along the mRNA, and fail to give complete sequences for mRNAs (e.g., long mRNAs) because DNA templates (e.g., long DNA templates) are discriminated against even when a long PCR reaction is used.

SUMMARY

In some aspects, the disclosure provides a method for generating a non-naturally occurring enzyme comprising: a) expressing a heterologous sequence encoding said non-naturally occurring enzyme in a host, wherein said non-naturally occurring enzyme comprises: a first domain, such as a finger domain, derived from an R2 retrotransposon; a second domain, such as a thumb domain, derived from an R2 retrotransposon; a third domain, such as a palm domain, derived from an R2 retrotransposon; and an endonuclease domain derived from an R2 retrotransposon; b) purifying said non-naturally occurring enzyme from said host, thereby generating said non-naturally occurring enzyme. In some instances, said non-naturally occurring enzyme further comprises a fusion-tag molecule. In other instances, said fusion tag-molecule stabilizes said non-naturally occurring enzyme and said fusion-tag molecule is selected from the group consisting of: Fh8, MBP, NusA, Trx, SUMO, GST, SET, GB1, ZZ, HaloTag, SNUT, Skp, T7PK, EspA, Mocr, Ecotin, CaBP, ArsC, IF2-domain I, an IF2-domain I derived tag, RpoA, SlyD, Tsf, RpoS, PotD, Crr, msyB, yjgD, rpoD, and His6. In other cases, said fusion-tag molecule is selected from the group consisting of: His-tag, His6-tag, Calmodulin-tag, CBP, CYD (covalent yet dissociable NorpD peptide), Strep II, FLAG-tag, HA-tag, Myc-tag, S-tag, SBP-tag, Softag-1, Softag-3, V5-tag, Xpress-tag, Isopeptag, SpyTag, B, HPC (heavy chain of protein C) peptide tags, GST, MBP, biotin, biotin carboxyl carrier protein, glutathione-S-transferase-tag, green fluorescent protein-tag, maltose binding protein-tag, Nus-tag, Strep-tag, and thioredoxin-tag. In some instances, at least one of said first domain, said second domain, said third domain, or said endonuclease domain, is derived from an arthropod. In some instances at least one of said first domain, said second domain, said third domain, or said endonuclease is derived from a vertebrate, an echinoderm, a flatworm, a hydra, or silkmoth. In some instances, said non-naturally occurring enzyme has at least 90% identity to SEQ ID NOs: 1-20. In some aspects, said host is selected from bacteria, yeast, algae, cyanobacteria, fungi, a plant cell, E. coli, or any combination thereof. In some instances, said non-naturally occurring enzyme comprises a mutagenized motif-1 sequence. In some instances, said mutagenized motif-1 sequence has an improved jumping activity as compared to a wild-type sequence. In some instances, said non-naturally occurring enzyme comprises a mutagenized motif 0 sequence. In some instances, said mutagenized motif 0 sequence has an improved jumping activity as compared to a wild-type sequence. In some instances, said non-naturally occurring enzyme comprises a mutagenized thumb sequence. In some instances, said mutagenized second domain sequence has an improved single-stranded priming efficiency or an improved processivity.

In some instances, the disclosure provides a non-naturally occurring enzyme, comprising (i) a first domain, such as a finger domain, from an R2 retrotransposon; (ii) a second domain, such as a thumb domain, derived from an R2 retrotransposon; (iii) a third domain, such as a palm domain, derived from an R2 retrotransposon; and (iv) an endonuclease domain derived from an R2 retrotransposon. In some instances, said non-naturally occurring enzyme has at least 80% identity to SEQ ID NOs: 1-20.

In some instances, the disclosure provides a method for simultaneously amplifying a ribonucleic acid (RNA) molecule and a deoxyribonucleic (DNA) molecule, comprising: (a) providing a reaction mixture comprising said RNA, DNA and non-naturally occurring enzymes, each of said non-naturally occurring enzymes comprising (i) a first domain, such as a finger domain, derived from a non-retroviral transposon or from an R2 retrotransposon; (ii) a second domain, such as a thumb domain, derived from an R2 retrotransposon; (iii) a third domain, such as a palm domain, derived from an R2 retrotransposon; and (iv) an endonuclease domain derived from an R2 retrotransposon; and (b) subjecting said reaction mixture to conditions sufficient to amplify said RNA and DNA, thereby yielding amplified products of said RNA and said DNA. In some instances, said DNA is complementary DNA derived from a subset of RNA in said reaction mixture.

In some instances, the disclosure provides a method for preparing a complementary deoxyribonucleic acid (cDNA) molecule comprising: (a) partitioning a cell and a non-naturally occurring reverse transcriptase, which cell comprises ribonucleic acid (RNA) molecules; (b) releasing said RNA molecules from said cell in said partition; and (c) in said partition, using said non-naturally occurring reverse transcriptase to synthesize a complementary deoxyribonucleic acid (cDNA) library from said RNA molecule, which non-naturally occurring transcriptase synthesizes said cDNA library at a processivity of 20 nucleotides or longer. In some instances, said non-naturally occurring reverse transcriptase has at least 80% identity to SEQ ID NOs: 1-20. In some instances, said partition further comprises: i) one or more acceptor nucleic acid molecules; and ii) a non-naturally occurring reverse transcriptase, wherein said non-naturally occurring reverse transcriptase has at least 80% identity to SEQ ID NOs: 1-20.

In some aspects, said partition is a reaction space or chamber that may be a droplet, a well, or a tube. In some instances, said droplet may be formed by bringing a first phase in contact with a second phase that is immiscible with the first phase, such as bringing an aqueous phase in contact with an oil phase.

In some instances, the disclosure provides, a method for processing a sample comprising various types of ribonucleic acids (RNAs), comprising using said RNA molecules to synthesize complementary deoxyribonucleic acid (cDNA) molecules in presence of ribosomal ribonucleic acid (rRNA) molecules blocked from transcription, such that less than 30% of said cDNA molecules comprise sequences from said rRNA molecules. In some instances, rRNA may not have been degraded and may be present during reverse transcription.

In some instances, the disclosure provides, a method for processing a mixture comprising ribonucleic acid (RNA) molecules, comprising: (a) in said mixture, fragmenting said RNA molecules to yield a plurality of RNA fragments; (b) bringing one or more single stranded nucleic sequences in contact with said plurality of RNA fragments, which one or more single-stranded nucleic acids sequences have complementarity with at least a subset of said RNA fragments, thereby providing one or more RNA fragment complexes comprising said one or more single-stranded nucleic acids sequences hybridized to said at least said subset of said RNA fragments; and (c) using a reverse transcriptase to synthesize at least one complementary deoxyribonucleic acid (cDNA) molecule from said RNA in presence of said one or more RNA fragment complexes.

In some instances, the disclosure provides a method for sequencing a single stranded nucleic acid molecule, comprising: (a) providing a reaction mixture comprising said single stranded nucleic acid molecule and a non-naturally occurring enzyme, wherein said non-naturally occurring enzyme comprises: a first domain, such as a finger domain, derived from an R2 retrotransposon; a second domain, such as a thumb domain, derived from an R2 retrotransposon; a third domain, such as a palm domain, derived from an R2 retrotransposon; and an endonuclease domain derived from an R2 retrotransposon, (b) subjecting said reaction mixture to conditions sufficient to use said non-naturally occurring enzyme to incorporate individual nucleotides into a growing strand complementary to said single stranded nucleic acid molecule, wherein incorporation of said individual nucleotides into said growing strand yields detectable signals; and (c) detecting said detectable signals, thereby sequencing said single stranded nucleic acid molecule. In some aspects, said single stranded nucleic acid molecule is an RNA molecule or a single stranded DNA molecule. In some aspects, said conditions sufficient to directly sequence said single stranded nucleic acid molecule comprise optic based single-molecule sequencing conditions. In some aspects, said conditions sufficient to directly sequence said single stranded nucleic acid molecule comprise microscopy based single-molecule sequencing conditions. In some aspects, said conditions sufficient to directly sequence said single stranded nucleic acid molecule comprise nanopore based single-molecule sequencing conditions. In some aspects, said conditions sufficient to directly sequence said single stranded nucleic acid molecule comprise field-effect transistors based single-molecule sequencing conditions.

In some aspects, the disclosure provides a method comprising: (a) preparing a complementary deoxyribonucleic acid (cDNA) molecule from one or more ribonucleic acid (RNAs), wherein said one or more ribonucleic acid (RNAs) are derived from an in situ tissue of a subject or from a fixed ex vivo tissue of said subject with a non-naturally occurring enzyme, wherein said non-naturally occurring enzyme comprises: a first domain, such as a finger domain, derived from an R2 retrotransposon; a second domain, such as a thumb domain, derived from an R2 retrotransposon; a third domain, such as a palm domain, derived from an R2 retrotransposon; and an endonuclease domain derived from an R2 retrotransposon; thereby generating a cDNA molecule from said in situ tissue of said subject or from said fixed ex vivo tissue of said subject; and (b) sequencing the said cDNA molecule generated in (a). In some aspects, said fixed ex vivo tissue of said subject is fixed in formaldehyde or in paraffin.

In some aspects, the disclosure provides a method for preparing a complementary deoxyribonucleic acid molecule comprising: (a) fragmenting a ribonucleic molecule to yield a plurality of RNA fragments; (b) removing a 3'-phosphate group, a 2'-phosphate group, and cyclic 2'3' phosphate from one or more of said RNA fragments, thereby generating one or more dephosphorylated fragmented RNAs; (c) adding a poly-A tail to said one or more dephosphorylated fragmented RNAs; (d) adding, to said one or more dephosphorylated fragmented RNAs: a primer adapter comprising an oligo-T sequence; an acceptor adapter; and a non-naturally occurring R2 enzyme having a processivity of 20 nucleotides or longer wherein said non-naturally occurring R2 enzyme reverse transcribes a sequence from said one or more dephosphorylated fragmented RNAs in a 3' to 5' order, wherein said R2 enzyme jumps to a 3'-end of said acceptor adapter upon reaching the 5' end of said one or more dephosphorylated fragmented RNAs. In some aspects, said acceptor adapter comprises a nucleotide analogue. In some aspects, said nucleotide analogue is at the 5' end of said acceptor adapter, of said primer adapter, or both. Some aspects further comprise removing one or more non-annealed primer-adapter of (d)(i) prior to adding said non-naturally occurring R2 enzyme. In some instances, said one or more non-annealed primer-adapter is removed with an immobilized poly A oligo. In some aspects, said acceptor adapter comprises a 3'-dideoxy nucleotide at the acceptor-adapter 3'-end.

In some aspects, the disclosure provides a method for preparing a complementary deoxyribonucleic acid molecule comprising: (a) fragmenting a ribonucleic (RNA) molecule to yield a plurality of fragmented RNA fragments; (b) adding, to said one or more fragmented RNAs: a primer adapter; an acceptor adapter; and a non-naturally occurring R2 enzyme having a processivity of 20 nucleotides or longer wherein said non-naturally occurring R2 enzyme primes the reverse transcription using a plurality of ssDNA primers that are not complementary to a template, wherein said R2 enzyme jumps to a 3'-end of said acceptor adapter upon reaching the 5' end of said fragmented RNAs.

In some aspects, the disclosure provides a method for preparing a complementary deoxyribonucleic acid molecule comprising: a) fragmenting a ribonucleic (RNA) molecule to yield a plurality of fragmented RNA fragments; b) adding, to said one or more fragmented RNAs: i. a primer adapter; ii. an acceptor adapter; and enzyme; wherein said enzyme primes the reverse transcription using a plurality of ssDNA primers that are not complementary to a template, wherein said enzyme jumps to a 3'-end of said acceptor adapter upon reaching the 5' end of said fragmented RNAs. In some instances, said enzyme is a non-naturally occurring R2 enzyme.

In some aspects, the disclosure provides a method for preparing a complementary deoxyribonucleic acid molecule comprising: a) adding to a non-fragmented ribonucleic (RNA) molecule: i. a primer adapter; ii. an acceptor adapter; and iii. an enzyme wherein said enzyme primes the reverse transcription using a plurality of ssDNA primers that are not complementary to a template, wherein said enzyme jumps to a 3'-end of said acceptor adapter upon reaching the 5' end of said fragmented RNAs. In some instances, said enzyme is a non-naturally occurring R2 enzyme.

In some aspects, the disclosure provides a method for depleting a plurality of ribonucleic acid (RNAs) from a sample, comprising: (a) synthesizing a complementary deoxyribonucleic acid (cDNA) molecule from a ribonucleic acid template from said sample, (b) incorporating a first adapter molecule to a 3' of said synthesized cDNA molecule and incorporating a second adapter molecule to a 5' end of said synthesized cDNA; (c) performing at most 10 cycles of a polymerase chain reaction (PCR) with a modified-oligo probe complementary to said rDNA sequence, wherein said modified-oligo probe is configured to permit binding of said probe to a solid support, thereby generating a hybridized product that is bound to said solid support in the reaction mixture; (d) removing the synthesized cDNA from said reaction mixture while the hybridized product is bound to said solid support, thereby depleting said plurality of ribonucleic acid (RNAs) from said sample.

In some aspects the disclosure provides a method for depleting a plurality of ribonucleic acid (RNAs) from a sample, comprising: a) synthesizing an asymmetric double stranded deoxyribonucleic acid molecule that is protected from enzymatic degradation at a first 5' end and unprotected at a second 5' end from a ribonucleic (RNA) molecule by adding to a reaction vessel comprising an RNA molecule i. a primer, wherein said primer comprises a modification at its 5' end that is configured to prevent enzymatic degradation by a 5' to 3' exonuclease; and ii. an enzyme; under conditions sufficient to allow for the synthesis of said asymmetric double stranded deoxyribonucleic acid molecule; (b) adding a 5' to 3' exonuclease to the product of step (a), thereby generating a ssDNA having a pre-determined polarity; and (c) depleting said plurality of RNAs from the product of said (b) by hybridizing one of more probes to said plurality of RNAs and performing a pull-down reaction.

In some aspects, the disclosure provides a method for preparing a sample for ribonucleic acid (RNA) sequencing, comprising: (a) individually labeling a plurality of single cells with a plurality of unique barcodes; (b) combining said plurality of single cells in a single pot; (c) performing an RNA sequencing reaction on said plurality of single cells; (d) selecting a cell of interest based on said RNA sequencing reaction and identifying a unique barcode associated with said cell of interest, wherein said selecting and said identifying are performed in a computer program product; (e) hybridizing a primer to said unique barcode associated with said cell of interest and performing an amplification reaction in said hybridized sample, thereby generating a plurality of amplicons.

In some aspects, the disclosure provides a method for preparing a sample for ribonucleic acid (RNA) sequencing, comprising: (a) dissociating a tissue sample in a lysis reaction, thereby generating a plurality of nucleic acid templates from said dissociated sample, wherein said nucleic acid templates comprise ribonucleic acid; (b) synthesizing a complementary deoxyribonucleic acid (cDNA) molecule from said plurality of nucleic acid templates from said dissociated sample, wherein said cDNA molecule is synthesized with a non-naturally occurring R2 enzyme having a processivity of 20 nucleotides or longer, wherein the synthesis is performed in the presence of one or more regents used in said lysis reaction or in the presence of a plurality of cell debris from said tissue sample.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications, and NCBI accession numbers mentioned in this specification are herein incorporated by reference to the same extent as if each individual publication, patent, patent application, or NCBI accession number was specifically and individually indicated to be incorporated by reference. To the extent publications and patents, patent applications, or NCBI accession numbers incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative instances, in which the principles of the disclosure are utilized, and the accompanying drawings (also "Figure" and "FIG." herein), of which:

Figure 1A:
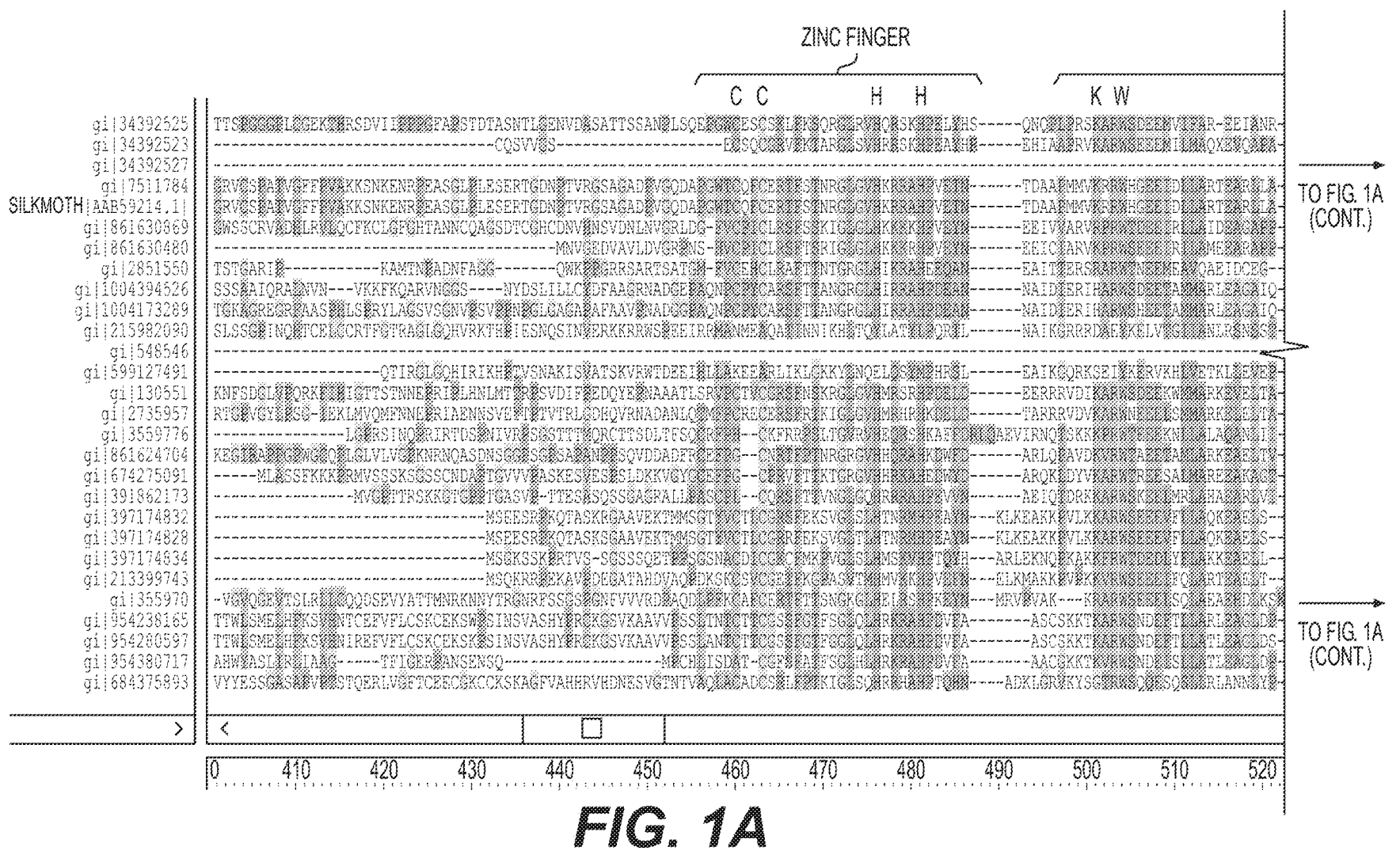
Figure 1A:
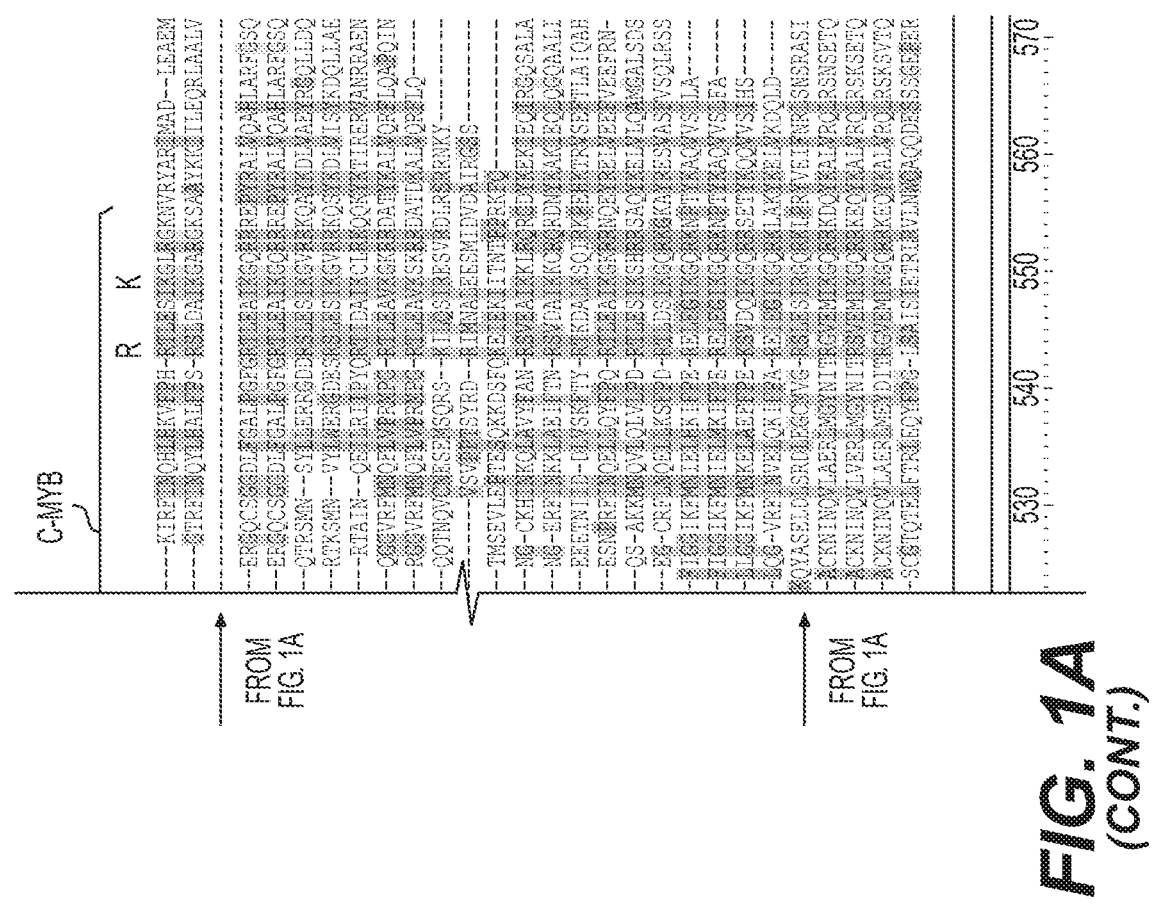
Figure 1B:
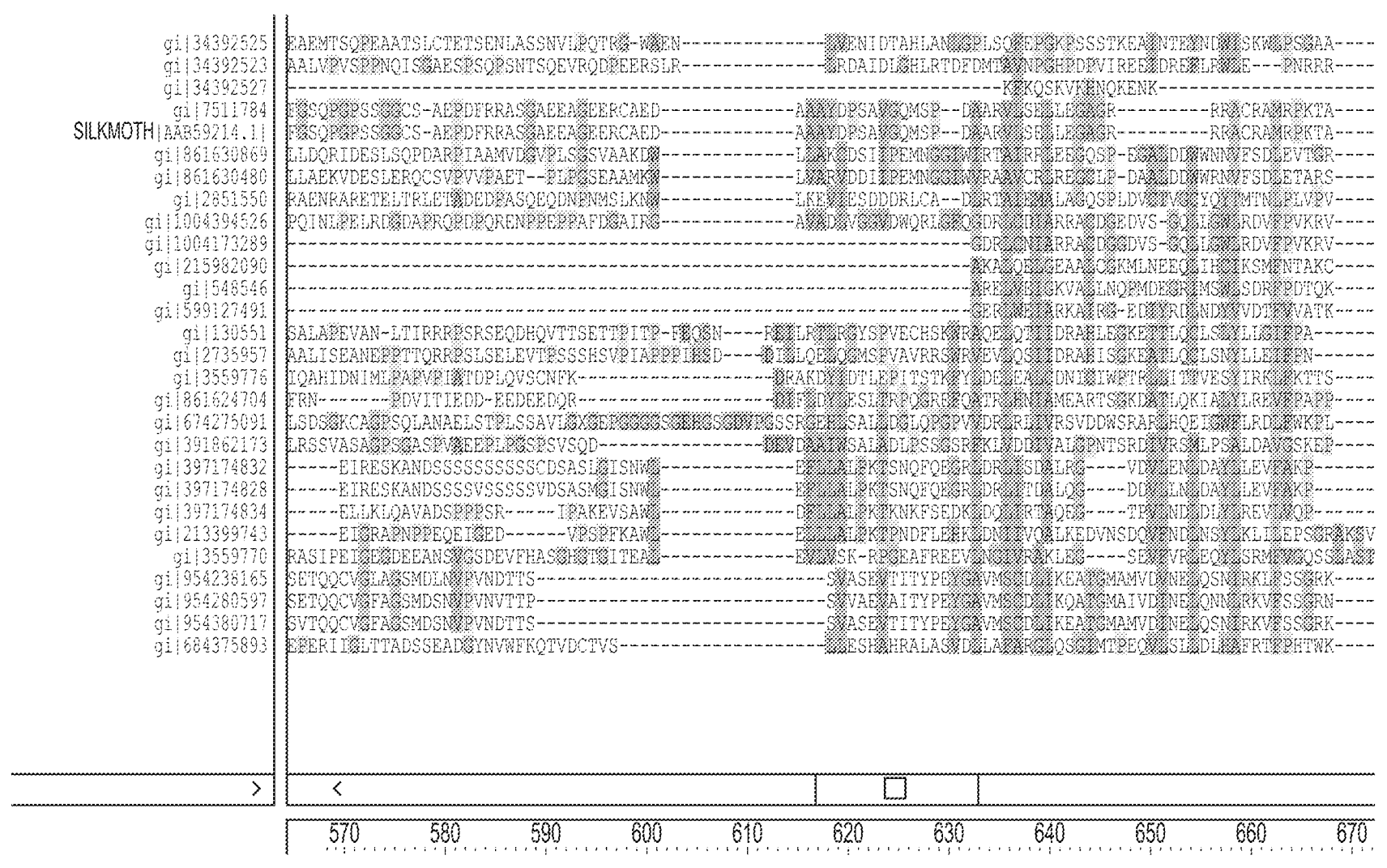

FIG. 1A illustrates the R2 N-terminal Domain. This figure illustrates the comparison of the conserved sequence motifs in the amino-terminal domains of the R2 elements. This figure also highlights the CCHH zinc finger and the KWRK c-myb DNA-binding motifs. The continuation of the N-terminal domain alignment is shown in FIG. 1B.

FIG. 1B illustrates the R2 N-terminal domain. This figure is a continuation of the alignment from FIG. 1A and as such, also illustrates the comparison of the conserved sequence in the N-terminal domains of R2 elements. The following sequences at the C-terminal are the RT and endonuclease domains, which are not shown in this figure.

FIG. 3 illustrates the R2 reverse transcriptase (RT) thumb domain. This figure illustrates the comparison of the conversed sequence motifs. The R2 RT thumb domain is subjected to engineering/mutagenesis in the method of the present disclosure.

FIG. 4 illustrates the R2 reverse transcriptase (RT) thumb domain. This figure is a continuation of FIG. 3 and illustrates a comparison of the conserved sequence motifs. The R2 RT thumb domain is subjected to engineering/mutagenesis in the method of the present disclosure.

FIG. 5B, however, illustrates a method in which an RCA product, which is rRNA complementary, is used instead of the circular ssDNA (DNA-sponge).

FIG. 14 illustrates the silkmoth R2 reference sequence (SEQ ID NO: 97).

FIG. 15 illustrates motif-1 point mutations.

FIG. 16 illustrates motif 0 point mutations.

FIG. 17 illustrates thumb subunit substitutions, continued in FIG. 18.

FIG. 18 illustrates thumb subunit substitutions. This figure is a continuation of FIG. 17.

FIG. 19 illustrates a method to remove specific artifacts.

DETAILED DESCRIPTION

Figure 1C:
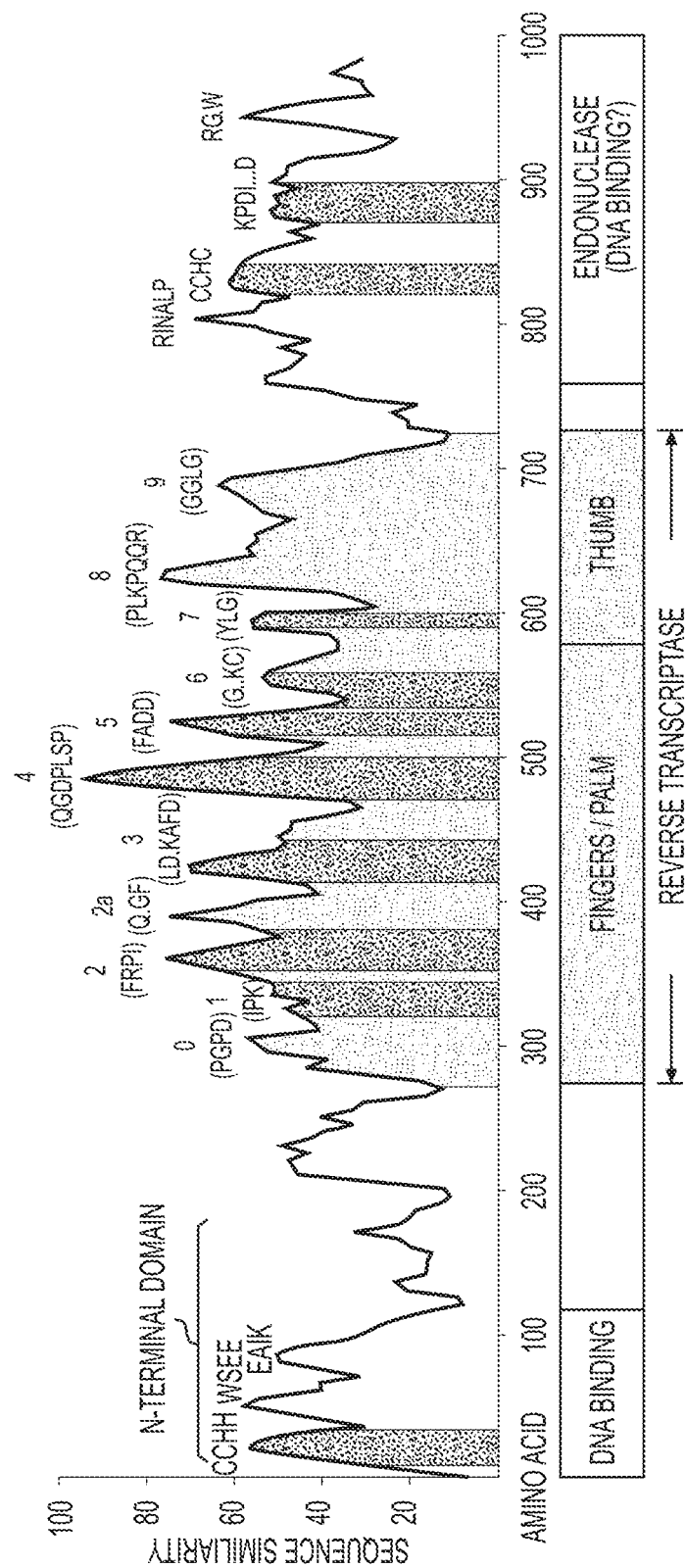
FIG. 1C illustrates a schematic diagram of the amino acid sequence similarity of nine arthropod R2 elements whereby the N-terminal domain is labeled.

While various embodiments of the disclosure have been shown and described herein, it will be obvious to those skilled in the art that such embodiments are provided by way of example only. Numerous variations, changes, and substitutions may occur to those skilled in the art without departing from the disclosure. It should be understood that various alternatives to the embodiments of the disclosure described herein may be employed.

Unless defined otherwise, all technical and scientific terms used herein have the same meaning as commonly understood by one of ordinary skill in the art to which the present disclosure belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference. In order to further define the present disclosure, the following terms, abbreviations and definitions are provided.

The term "about" generally refers to variations in the numerical quantity that may occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In some instances, the term "about" means within 10% of the reported numerical value, or within 5% of the reported numerical value, or within 20% of the reported numerical value.

The indefinite articles "a" and "an" preceding an element or component of the present disclosure are intended to be nonrestrictive regarding the number of instances, i.e., occurrences of the element or component. Therefore "a" or "an" should be read to include one or at least one, and the singular word form of the element or component also includes the plural unless the number is meant to be singular.

As used herein, "non-LTR retrotransposon" generally refers to naturally occurring proteins encoded by non-LTR retrotransposons and polypeptide fragments thereof which possess reverse transcriptase activity, as well as proteins or polypeptides derived therefrom which contain one or more amino acid substitutions that either enhance the reverse transcriptase activity thereof or have no deleterious effect thereon. A class of non-LTR retrotransposon is R2 proteins or polypeptides. Thus, as used herein, "R2 protein or R2 enzyme or polypeptide or a functional fragment thereof" refers to naturally occurring proteins encoded by R2 elements and polypeptide fragments thereof which possess reverse transcriptase activity, as well as proteins or polypeptides derived therefrom which contain one or more amino acid substitutions that either enhance the reverse transcriptase activity thereof or have no deleterious effect thereon.

As used herein, the terms "variant," "modified," "non-naturally occurring," and "mutant" are synonymous and refer to a polypeptide or enzyme differing from a specifically recited polypeptide or enzyme by one or more amino acid insertions, deletions, mutations, and substitutions, created using, e.g., recombinant DNA techniques, such as mutagenesis. Guidance in determining which amino acid residues may be replaced, added, or deleted without abolishing activities of interest, may be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences. In some instances, the terms "derivative," "variant," "modified," "non-naturally occurring," and "mutant" are used interchangeably.

The terms "anneal", "hybridize" or "bind," generally refer to the combining of one or more single-stranded polynucleotide sequences, segments or strands, and allowing them to form a double-stranded molecule through base pairing. Two complementary sequences (e.g., ribonucleic acid (RNA) and/or deoxyribonucleic acid (DNA)) can anneal or hybridize by forming hydrogen bonds with complementary bases to produce a double-stranded polynucleotide or a double-stranded region of a polynucleotide.

As used herein the term "incorporating" when used with respect to the incorporation of an adapter may refer to the physical attachment of the adapter, to an extension of said adapter, or to the generation of a sequence that is complementary to an adaptor sequence in a nucleic acid molecule.

The term "subject" can be any animal which may benefit from the methods of the disclosure, including, e.g., humans and non-human mammals, such as primates, rodents, horses, dogs and cats. Subjects include without limitation a eukaryotic organism, a mammal such as a primate, e.g., chimpanzee or human, cow; dog; cat; a rodent, e.g., guinea pig, rat, mouse; rabbit; or a bird; reptile; or fish. Subjects specifically intended for treatment using the methods described herein include humans. A subject may be an individual or a patient.

As used herein, the term "primer extension reaction" generally refers to the denaturing of a double-stranded nucleic acid, binding of a primer to one or both strands of the denatured nucleic acid, followed by elongation of the primer(s).

As used herein, the term "reaction mixture" generally refers to a composition comprising reagents necessary to complete nucleic acid amplification (e.g., DNA amplification, RNA amplification), with non-limiting examples of such reagents that include primer sets having specificity for target RNA or target DNA, DNA produced from reverse transcription of RNA, a DNA polymerase, a reverse transcriptase (e.g., for reverse transcription of RNA), suitable buffers (including zwitterionic buffers), co-factors (e.g., divalent and monovalent cations), dNTPs, and other enzymes (e.g., uracil-DNA glycosylase (UNG)), etc). In some cases, reaction mixtures can also comprise one or more reporter agents.

As used herein, a "reporter agent" generally refers to a composition that yields a detectable signal, the presence or absence of which can be used to detect the presence of amplified product.

As used herein, the term "target nucleic acid" generally refers to a nucleic acid molecule in a starting population of nucleic acid molecules having a nucleotide sequence whose presence, amount, and/or sequence, or changes in one or more of these, are desired to be determined. A target nucleic acid may be any type of nucleic acid, including DNA, RNA, and analogues thereof.

The terms "polynucleotides", "nucleic acid", "nucleotides" and "oligonucleotides" can be used interchangeably. They can refer to a polymeric form of nucleotides of any length, either deoxyribonucleotides or ribonucleotides, fragments, or analogs thereof. The following are non-limiting examples of polynucleotides: coding or non-coding regions of a gene or gene fragment, loci (locus) defined from linkage analysis, exons, introns, messenger RNA (mRNA), transfer RNA, transfer-messenger RNA, ribosomal RNA, antisense RNA, small nuclear RNA (snRNA), small nucleolar RNA (snoRNA), micro-RNA (miRNA), small interfering RNA (siRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogues. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A nucleic acid described herein can contain phosphodiester bonds. In some instances, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A polynucleotide is intended to encompass a singular nucleic acid as well as plural nucleic acids. The polynucleotide may be composed of any polyribonucleotide or polydeoxyribonucleotide, which may be unmodified RNA or DNA or modified RNA or DNA. For example, polynucleotides may be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

The term "primer", as used herein, refers to an oligonucleotide, occurring naturally as in a purified restriction digest or produced synthetically that is characterized by an ability to be extended against a template oligonucleotide, so that an oligonucleotide whose sequence is complementary to that of at least a portion of the template molecule is linked to the primer, when all are placed in the presence of nucleotides at a suitable temperature and pH. However, the mere ability to be used in this fashion does not require that primers be fully extended against a template, and in some instances, primers are used only as a site for the addition of a small number of non-templated nucleotides. Primers such as primer hexamers having a length of at least 6 nucleotides long can be used. In some instances, a primer may be fluorescently labeled (e.g., 5'-/56FAM/TGATGACGAGG-CATTTGGC/3'). In some instances, primers have a length within the range of about 6 to about 100 nucleotides, or in some instances from about 10 to about 70 nucleotides. In some instances, larger primers can be used. In some instances, random primers may be used. In some instances, a primer may be a random primer. In some instances, one or more primer(s) may be one or more random primer(s).

The term "one or more primer(s)" can comprise any number of primers or random primers. For example, "one or more primer(s)" can include at least, at most, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 20, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 primers or random primers. One or more primer(s) can include about 1 to about 2, about 1 to about 3, about 1 to about 4, about 1 to about 5, about 1 to about 6, about 1 to about 7, about 1 to about 8, about 1 to about 9, about 1 to about 10, about 1 to about 15, about 1 to about 20, about 1 to about 25, about 1 to about 30, about 1 to about 35, about 5 to about 15, about 3 to about 10, about 5 to about 20, about 10 to about 50, about 30 to about 100, or more than about 100 primers. One or more primer(s) can comprise any number of primers.

The term "random primer," as used herein, refers to a primer containing a random base sequence therein, and is intended to encompass primers whether they consist partially or wholly of random base sequences.

As used herein, "homologue" refers to a protein that is functionally equivalent i.e. has the same enzymatic activity as an enzyme having an amino acid sequence of the specified sequence identification number, but may have a limited number of amino acid substitutions, deletions, insertions or additions in the amino acid sequence. In order to maintain the function of the protein, the substitutions may be conservative substitutions, replacing an amino acid with one having similar properties.

The term "heterologous" refers to a molecule or activity derived from a source other than the referenced species whereas "homologous" refers to a molecule or activity derived from the host microbial organism. Accordingly, exogenous expression of an encoding nucleic acid of the present disclosure may use either or both a heterologous or homologous encoding nucleic acid.

The tem "acceptor template," as used herein, generally refers to a nucleic acid molecule that is used to synthesize complementary DNA (cDNA) molecules. The acceptor nucleic acid may be modified. The acceptor nucleic acid molecule may be modified at the 3' end, for example to protect it from being mistaken as an RNA primer. The modification of the acceptor nucleic acid molecule may comprise a dideoxy 3' end. The modification may comprise a phosphorylated 3' end. In some instances, the phosphorylated 3' end of a polynucleotide or of an acceptor nucleic acid molecule, which typically has a hydroxyl group on its 3' end, can act as a 3' block because extension by an enzyme of the present disclosure, or of DNA polymerase for example may be inhibited or ligation by a ligase may be inhibited. Another non-limiting example of a 3' block includes the addition of a 3' C3 spacer (three-carbon spacer) to the 3' end of a polynucleotide which can function as an effective blocking agent against polymerase extension. Zhou, et al., Clin. Chem., 50: 1328-1335 (2004). Thus, the 3' end can be blocked by the addition of, for example, a C3 spacer, a phosphate, an amine group (NH2), or any other chemical modification that inhibits formation of a subsequent phosphodiester bond between the 3' end of the polynucleotide and another nucleotide.

An "overhang sequence," as used herein, generally refers to a single stranded region of nucleic acid extending from a double stranded region.

An "isolated" polynucleotide, as used herein, generally refers a polynucleotide that has been either removed from its natural environment, produced using recombinant techniques, or chemically or enzymatically synthesized. A polynucleotide can also be purified, i.e., essentially free from any other polynucleotides and associated cellular products or other impurities.

The term "polymerase" as used herein, generally refers to an enzyme that links individual nucleotides together into a strand, using another strand as a template. In some instances, the polymerase is a polymerase with editing capabilities. In some instances, the polymerase with editing capabilities may be 3' to 5' exonuclease, T4 DNA polymerase, exonuclease I, Phi29, Pfu, Vent, KOD, exonuclease III, and exonuclease T. Examples of polymerases can include a DNA polymerase, an RNA polymerase, an RNA-directed DNA polymerase, reverse transcriptase, a polypeptide having reverse transcriptase activity, or any variant thereof, a thermostable polymerase, a wild-type polymerase, a modified polymerase, E. coli DNA polymerase I, T7 DNA polymerase, bacteriophage T4 DNA polymerase PHI 29 (phi29) DNA polymerase, Taq polymerase, Tth polymerase, Tli polymerase, Pfu polymerase VENT polymerase, DEEP-VENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Tth polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some instances, the polymerase may be a reverse transcriptase or a modified reverse transcriptase of the present disclosure. In some instances, the polymerase is a single subunit polymerase. The polymerase can have high processivity, namely the capability of the polymerase to consecutively incorporate nucleotides into a nucleic acid template without releasing the nucleic acid template. In some cases a polymerase can be a polymerase described in PCT/US2017/061197, such as P2. PCT/US2017/061197 is incorporated herein in its entirety.

The term "reverse transcriptase" or RT, as used herein, generally refers to an enzyme with both an RNA-directed DNA polymerase and a DNA-directed DNA polymerase. RT refers to a group of enzymes having reverse transcriptase activity (e.g., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-long terminal repeat (LTR) retrotransposon reverse transcriptases, retroplasmid reverse transcriptases, retron reverse transcriptases, and group II intron reverse transcriptases. Further bacterial reverse transcriptases are described by Simon D & Zimmerly S (2008) "A diversity of uncharacterized retroelements in bacteria" Nucleic Acids Res 36(22):7219-7229, and Kojima, KK & Kanehisa, M (2008) "Systematic survey for novel types of prokaryotic retroelements based on gene neighborhood and protein architecture" Mol Biol Evol 25:1395-1404, which describe many classes of non-retroviral reverse transcriptases (i.e., retrons, group II introns, and diversity-generating retroelements among others). Reverse transcriptase has been used primarily to transcribe RNA into cDNA, which can then be cloned into a vector for further manipulation or used in various amplification methods such as polymerase chain reaction, nucleic acid sequence-based amplification (NASBA), transcription mediated amplification (TMA), self-sustained sequence replication (3SR), diverse primer extension reactions, 5'RACE, detection of chemical modifications or other techniques that require synthesis of DNA using an RNA template.

Reverse Transcriptases

Reverse transcriptase enzymes may be isolated from a large number of mobile genetic elements which are of retroviral and non-retroviral origin. Such mobile genetic elements are resident in the genomes of higher order species and play a function role in life cycle of these mobile genetic elements. Mobile genetic elements may encode genes for reverse transcriptase enzymes (reviewed in Howard M Temin, Reverse Transcription in the Eukaryotic Genome: Retroviruses. Pararetroviruses, Retrotransposons, and Retrotranscripts, Mol. Biol. Evol. 2(6):455-468). These elements include, but are not limited, to retrotransposons. Retrotransposons include the non-long terminal repeat (LTR) retrotransposon and LTR mobile elements (e.g., TY3, TY5, non-LTR, LINE-L1, R2, R1). (Reviewed by Cordaux and Batzer, Nature Reviews, October 2009, volume 10, pp 691-703).

Retroelements, genetic elements that encode RTs, are divided into two major families denoted LTR-containing retroelements and non-LTR-containing retroelements (Xiong Y, Eickbush T H (1990) "Origin and evolution of retroelements based upon their reverse transcriptase sequences" EMBO J 9:3353-62). Non-LTR-retroelements are a diverse family of RT-encoding elements that includes retroplasmids, non-LTR-retrotransposons, retrons, and mobile group II introns.

The mutants of the present disclosure may be generated in accordance with any suitable method, including, but not limited to, methods described and exemplified herein. Mutations, such as substitutions, insertions, deletions, and/or side chain modifications, may be introduced into the nucleotide and amino acid sequences of the gene of interest using any suitable technique, including site-directed mutagenesis (Wu, ed., Meth. Enzymol. 217, Academic Press (1993)). The lambda red recombinase method may be used to "knock out" genes (Datsenko et al., PNAS USA 97: 6640-6645 (2000)). Permanent, marker-free, multiple gene disruptions may be created. Non-naturally occurring nucleotides and amino acids also may be used.

Methods of Expressing Non-Naturally Occurring Enzymes from a Host System

Non-naturally occurring enzymes, including R2 enzymes, can be difficult to manufacture, in part because of their size, structural complexity, and amino acid composition. In addition, R2 retroelements are multi-domain elements with molecular masses usually over 100 kD, which increases the challenges in manufacturing R2 enzymes recombinantly. Furthermore, naturally occurring R2 enzymes need to be expressed at low levels in host organisms largely because of their toxic effects to the host. In addition, naturally occurring R2 retroelements are believed to function as dimers.

In some aspects, the disclosure provides recombinantly manufactured enzymes comprising select sequences derived from an R2 retrotransposon and vectors comprising a nucleic acid sequence encoding the recombinantly manufactured enzymes disclosed herein. R2 retroelements are usually composed of three major domains (FIGS. 1A, 1B, 1C): an N-terminal domain, a reverse transcriptase domain, and an endonuclease domain. The N-terminal domain may include zinc-finger and c-myb DNA binding motifs, which are believed to contribute to specific recognition and binding to target DNA (target primed reverse transcription mechanism (TPRT). The reverse transcriptase domain is responsible for copying R2 RNA template. Lastly, the endonuclease domain is responsible for specific cleavage of target DNA.

In some aspects, the disclosure provides non-naturally occurring enzymes that are phylogenetically related to one or more elements of an R2 retroelement. In some instances, the enzymes of the disclosure do not comprise the N-terminal domain of an R2 enzyme. In some aspects, the disclosure provides a method for generating a non-naturally occurring enzyme comprising: expressing a heterologous sequence encoding said non-naturally occurring enzyme in a host, wherein said non-naturally occurring enzyme comprises a first, a second, and a third domain derived from an R2 retrotransposon; such as for example, a palm, a finger, and a thumb domain derived from an R2 retrotransposon; an endonuclease domain derived from an R2 retrotransposon; and purifying said non-naturally occurring enzyme from said host, thereby generating said non-naturally occurring enzyme.

In some aspects, the disclosure provides non-naturally occurring enzymes whereby the N-terminal domain is removed. The N-terminal domain is believed to interfere with the expression and stability of R2 retroelements. As such, the removal of parts of the entire N-terminal or parts of the N-terminal is believed to improve the expression and stability of the R2 retroelement without necessarily affecting the disclosed enzyme's ability and performance in RNA library preparation for sequencing. In some aspects, the disclosure identifies the said N-terminal domain using sequence analysis of the R2 retrotransposon and other phylogenetically related R2 retroelements. In some instances, the enzyme of the disclosure is an enzyme that is phylogenetically related to one or more elements of an R2 retroelement and in some instances, the N-terminal domain is removed from said enzyme.

In some aspects, the disclosure provides non-naturally occurring enzymes comprising fusion-tag molecules, whereby the fusion-tag molecule stabilizes the non-naturally occurring enzymes disclosed herein. In some aspects, the fusion-tag molecules are selected from the group consisting of: Fh8, MBP, NusA, Trx, SUMO, GST, SET, GB1, ZZ, HaloTag, SNUT, Skp, T7PK, EspA, Mocr, Ecotin, CaBP, ArsC, IF2-domain I, an IF2-domain I derived tag, RpoA, SlyD, Tsf, RpoS, PotD, Crr, msyB, yjgD, rpoD, and His6.

In some aspects, the disclosure provides non-naturally occurring enzymes comprising fusion-tag molecules, whereby the fusion-tag molecule stabilizes the non-naturally occurring enzymes disclosed herein. In some aspects, the fusion-tag molecules are selected from the group consisting of: His-tag, His6-tag, Calmodulin-tag, CBP, CYD (covalent yet dissociable NorpD peptide), Strep II, FLAG-tag, HA-tag, Myc-tag, S-tag, SBP-tag, Softag-1, Softag-3, V5-tag, Xpress-tag, Isopeptag, SpyTag, B, HPC (heavy chain of protein C) peptide tags, GST, MBP, biotin, biotin carboxyl carrier protein, glutathione-S-transferase-tag, green fluorescent protein-tag, maltose binding protein-tag, Nus-tag, Strep-tag, and thioredoxin-tag.

In some aspects, the disclosure provides non-naturally occurring enzymes, whereby at least one of said palm and finger domain from an R2 retrotransposon, said thumb domain of an R2 retrotransposon, or said endonuclease domain of an R2 retrotransposon are derived from an arthropod.

In some aspects, the disclosure provides non-naturally occurring enzymes, whereby at least one of said palm and finger domain from an R2 retrotransposon, said thumb domain of an R2 retrotransposon, or said endonuclease domain of an R2 retrotransposon is derived from silkmoth.

In some aspects, the disclosure provides non-naturally occurring enzymes, whereby at least one of said palm and finger domain from an R2 retrotransposon, said thumb domain of an R2 retrotransposon, or said endonuclease domain of an R2 retrotransposon is derived from a vertebrate or an echinoderm.

In some aspects, the disclosure provides non-naturally occurring enzymes, whereby at least one of said palm and finger domain from an R2 retrotransposon, said thumb domain of an R2 retrotransposon, or said endonuclease domain of an R2 retrotransposon is derived from a flatworm or a hydra.

In some aspects, the disclosure provides non-naturally occurring enzymes with at least 80% identify to SEQ ID Nos: 1-20, with at least 81% identify to SEQ ID Nos: 1-20, with at least 82% identify to SEQ ID Nos: 1-20, with at least 83% identify to SEQ ID Nos: 1-20, with at least 84% identify to SEQ ID Nos: 1-20, with at least 85% identify to SEQ ID Nos: 1-20, with at least 86% identify to SEQ ID Nos: 1-20, with at least 87% identify to SEQ ID Nos: 1-20, with at least 88% identify to SEQ ID Nos: 1-20, with at least 89% identify to SEQ ID Nos: 1-20, with at least 90% identify to SEQ ID Nos: 1-20, with at least 91% identify to SEQ ID Nos: 1-20, with at least 92% identify to SEQ ID Nos: 1-20, with at least 93% identify to SEQ ID Nos: 1-20, with at least 94% identify to SEQ ID Nos: 1-20, with at least 95% identify to SEQ ID Nos: 1-20, with at least 96% identify to SEQ ID Nos: 1-20, with at least 97% identify to SEQ ID Nos: 1-20, with at least 98% identify to SEQ ID Nos: 1-20, with at least 99% identify to SEQ ID Nos: 1-20, with at least 100% identify to SEQ ID Nos: 1-20.

In some aspects, the disclosure provides non-naturally occurring enzymes wherein the host is selected from bacteria, yeast, algae, cyanobacteria, fungi, a plant cell, or any combination thereof. In some instances, the disclosure provides non-naturally occurring enzymes wherein the host is *E. coli*.

Figure 2:
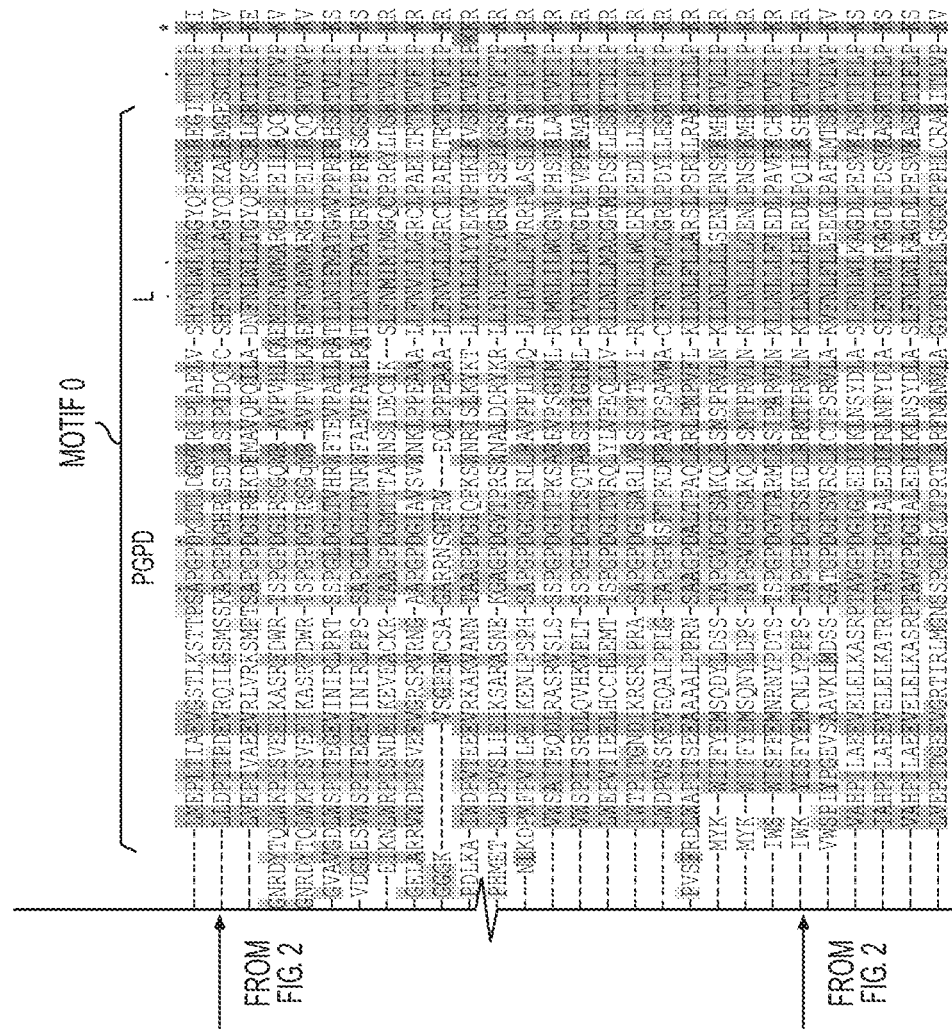
FIG. 2 illustrates the R2 reverse transcriptase. This figure illustrates the comparison of the conserved sequence motifs of the N-terminal portion of the reverse transcriptase R2 elements. This figure highlights motif-1 and motif 0. Both motifs are subjected to engineering/mutagenesis in the method of the present disclosure.
Figure 3:
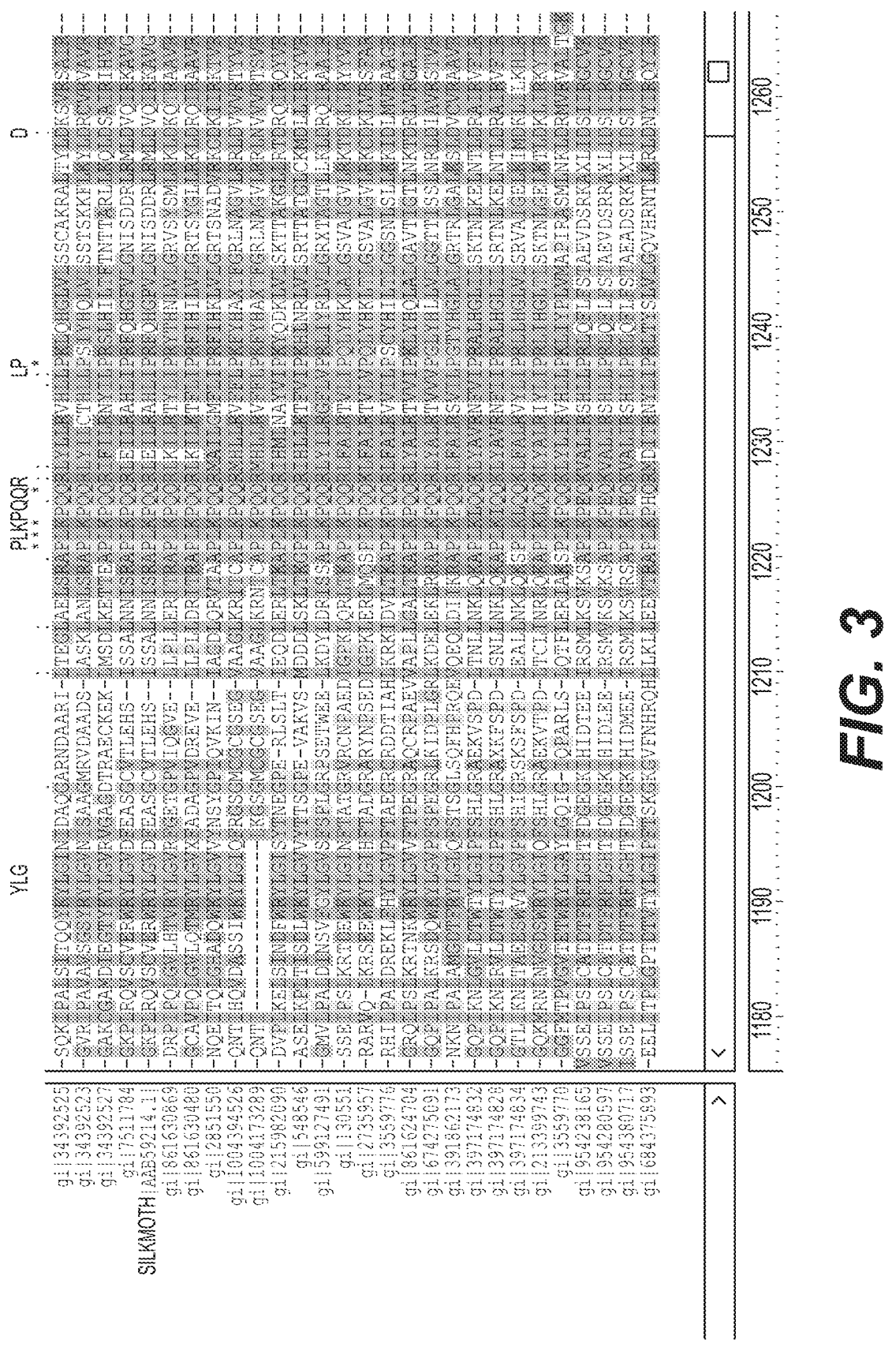
Figure 4:
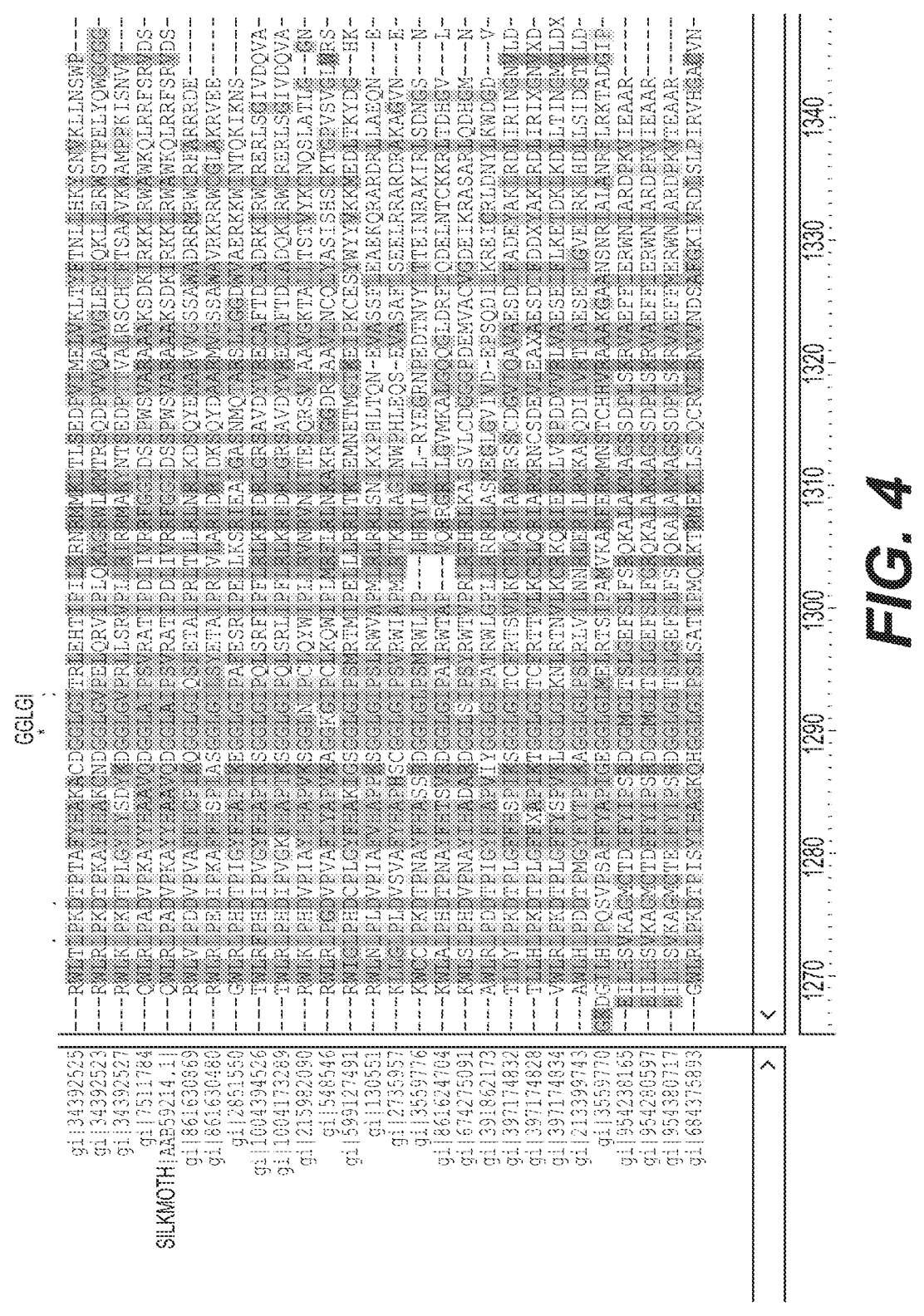
Figure 15:
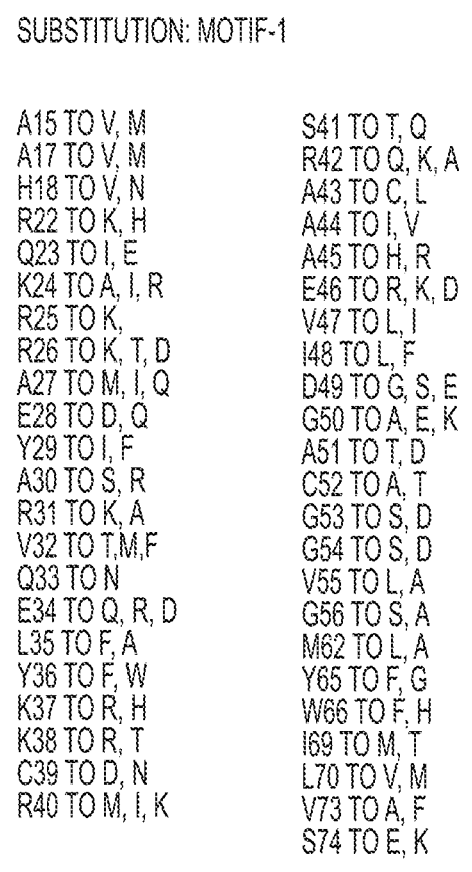

In some aspects, the disclosure provides a non-naturally occurring enzyme, which can comprise one or more amino acid mutations in motif-1, motif-0, and the thumb subunit (FIGS. 2, 3, and 4). Suitable amino acid modifications for improving a property of an R2 related enzyme can be conservative or non-conservative mutations. In some instances, motif-1 and motif-0 can be present in non-long terminal repeat (LTR) retrotransposons and telomerase, but not retroviral transposons and LTR retroelements. A mutation can be made such that the encoded amino acid is modified to a polar, non-polar, basic or acidic amino acid. FIGS. 15 and 16 disclose potential mutations in motif-1 or motif-0 that can improve one or more properties of an R2 enzyme derived from silkmoth, whereby the silkmoth R2 reference sequence is disclosed in FIG. 14. For instance, the following amino acid substitutions may be engineered in motif-1: A15→V15, A15→M15, A17→V17, A17→M17, H18→V18, H18→N18, R22→K22, R22→H22, Q23→I23, Q23→E23, K24→A24, K24→I24, K24→R24, R25→K25, R26→K26, R26→T26, R26→D26, A27→M27, A27→I27, A27→Q27, E28→D28, E28→Q28, Y29→I29, Y29→F29, A30→530, A30→R30, R31→K31, R31→A31, V32→T32, V32→M32, V32→F32, Q33→N33, E34→Q34, E34→R34, E34→D34, L35→F35, L35→A35, Y36→F36, Y36→W36, K37→R37, K37→H37, K38→R38, K38→T38, C39→D39, C39→N39, R40→M40, R40→I40, R40→K40, S41→T41, S41→Q41, R42→Q42, R42→K42, R42→A42, A43→C43, A43→L43, A44→I44, A44→V44, A45→H45, A45→R45, E46→R46, E46→K46, E46→D46, V47→L47, V47→I47, I48→L48, I48→F48, D49→G49, D49→S49, D49→E49, G50→A50, G50→E50, G50→K50, A51→T51, A51→D51, C52→A52, C52→T52, G53→553, G53→D53, G54→554, G54→D54, V55→L55, V55→A55, G56→556, G56→A56, M62→L62, M62→A62, Y65→F65, Y65→G65, W66→F66, W66→H66, I69→M69, I69→T69, L70→V70, L70→M70, V73→A73, V73→F73, S74→E74, S74→K74.

In some aspects, the disclosure provides a non-naturally occurring enzyme, which can comprise one or more amino acid mutations in motif-1, motif-0, and the thumb subunit (FIGS. 2, 3, and 4). A mutation can be made such that the encoded amino acid is modified to a polar, non-polar, basic or acidic amino acid. FIG. 16 discloses potential mutations in motif-0 that can improve one or more properties of an R2 enzyme derived from silkmoth, whereby the silkmoth R2 reference sequence is disclosed in FIG. 14. In some instances, the following amino acid substitutions may be engineered in motif-0: Q101→N101, Q101→S101, L102→V102, L102→I102, W103→M103, W103→V103, K104→R104, K104→S104, K104→D104, P105→A105, I106→L106, I106→V106, S107→T107, S107→V107, V108→N108, V108→L108, V108→S108, E109→D109, E109→Q109, E109→L109, E110→D110, I111→V111, I111→M111, K112→I112, K112→R112, R115→H115, F116-L116, F116→A116, D117→C117, D117→S117, D117→E117, R119→T119, R119-N119, T120→S120, S121→A121, P122→A122, G123→A123, P124→L124, D125→N125, D125→E125, G126→S126, G126→K126, I127→M127, I127→V127, R128→T128, R128→K128, S129→L129, S129→H129, G130→K130, G130→S130, Q131→D131, Q131→R131, W132→L132, W132→A132, R133→N133, R133→Y133, R133→K133, A134→L134, A134→M134, V135→T135, V135→S135, P136→S136, V137→A137, V137→Q137, H138→I138, H138→A138, L139→A139, L139→M139, L139→V139, K140→R140, K140→N140, K140→L140, A141→deletion, E142→S142, E142→K142, E142→D142, M143→I143, M143→V143, F144→L144, F144→Y144, N145→D145, A146→L146, A146→V146, W147→F147, W147→L147, M148→L148, M148→V148, A149→L149, A149→F149, R150→T150, R150→H150, R150→K150, G151→R151, G151→E151, E152→R152, E152→N152, E152→D152, I153→V153, I153→C153, P154→A154, E155→K155, E155→P155, E155→Q155, E155→A155, E155→D155, I156→E156, I156→R156, I156→V156, L157→V157, L157→F157, R158→K158, R158→L158, R158→K158, Q159→L159, Q159→M159, Q159→H159, Q159→N159, C160→G160, C160→S160, C160→H160, R161→K161.

In some aspects, the disclosure provides a non-naturally occurring enzyme, which can comprise one or more amino acid mutations in motif-1, motif-0, and the thumb subunit (FIGS. 2 and 3). A mutation can be made such that the encoded amino acid is modified to a polar, non-polar, basic or acidic amino acid. FIG. 17 discloses potential mutations in the thumb subunit that can improve one or more properties of an R2 enzyme derived from silkmoth, whereby the silkmoth R2 reference sequence is disclosed in FIG. 14. In some instances, the following amino acid substitutions may be engineered in the thumb subunit: G403→D403, G403→S403, G404→D404, G404→R404, G404→S404, K405→Q405, K405→V405, K405→R405, P406→V406, P406→Q406, P406→K406, L407→V407, L407→M407, R408→G408, R408→P408, R408→H408, R408→T408, R408→K408, Q409→A409, Q409→E409, Q409→S409, V410→M410, V410→L410, S411→D411, S411→G411, S411→K411, C412→I412, C412→H412, C412→A412, C412→R412, V413→E413, V413→L413, V413→A413, V413→G413, E414→G414, E414→H414, E414→Q414, E414→K414, W416→Y416, W416→V416, W416→F416, R417→K417, R417→H417, R417→T417, R417→G417, Y418→F418, L419→V419, L419→I419, G420→A420, V421→I421, V421→A421, V421→H421, D422→R422, D422→W422, D422→N422, D422→T422, D422→P422, D422→E422, F423→V423, F423→Y423, F423→I423, E424→G424, E424→A424, E424→N424, E424→R424, E424→T424, E424→5424, E424→D424, A425→5425, A425→H425, A425→G425, S426→T426, S426→A426, S426→E426, G427→A427, C428→T428, C428→P428, C428→R428, C428→C428→M428, V429→C429, V429→I429, V429→E429, V429→A429, T430→I430, T430→D430, T430→Q430, T430→R430, T430→T430→H430, S434→E434, S434→N434, I435→V435, I435→L435, I435→M435, S436→M436, S436→L436, S436→A436, S436→D436, S436→K436, S437→P437, S437→G437, S437→A437, S437→D437, S437→T437, A438→L438, A438→G438, A438→K438, A438→D438, A438→L438, L439→I439, L439→V439, N440→E440, N440→D440, N440→Q440, N440→K440, N441→E441, N441→R441, N441→A441, N441→Q441, I442→T442, I442→V442, S443→T443, S443→K443, S443→Q443, R444→A444, R444→C444, R444→S444, R444→Q444, R444→K444, A445→G445, A445→S445, P446→G446, L447→I447, K448→R448, P449→L449, Q450→E450, Q450→H450, Q451→E451, Q451→H451, L453→V453, L453→M453, E454→K454, E454→H454, E454→F454, E454→A454, E454→D454, I455→L455, I455→M455, I455→A455, L456→I456, R457→C457, R457→G457, R457→N457, R457→R457→K457, A458→N458, A458→T458, A458→V458, A458→S458, H459→Y459, H459→F459, H459→V459, L460→F460, L460→V460, I461→L461, I461→V461, P462→G462, R463→K463, R463→Q463, R463→G463, F464→Y464, F464→S464, F464→A464, F464→H464, Q465→T465, Q465→Y465, H466→Y466, H466→F466, G467→N467, G467→I467, G467→K467, G467→A467, F468→L468, F468→W468, V469→T469, V469→A469, V469→S469, V469→L469, L470→F470, L470→M470, L470→T470, G471→S471, G471→T471, G471→A471, N472→R472, N472→S472, N472→G472, R477→L477, R477→M477, R477→D477, R477→K477, L478→V478, L478→A478, R479→N479, R479→K479, R479→C479, R479→L479, R479→W479, M480→Q480, M480→K480, M480→T480, M480→R480, L481→G481, L481→T481, L481→M481, D482→N482, D482→E482, V483→S483, V483→K483, V483→R483, V483→L483, Q484→A484, Q484→I484, Q484→V484, Q484→M484, I485→T485, I485→V485, R486→K486, R486→L486, K487→A487, K487→T487, K487→Q487, K487→G487, K487→V487, K487→R487, A488→H488, A488→T488, A488→Y488, A488→S488, G490→R490, G490→K490, Q491→R491, Q491→T491, Q491→K491.

In some aspects, the mutagenized motif-1 sequence has an improved jumping activity compared to the wild-type sequence. In some aspects, the mutagenized motif-0 sequence has an improved jumping activity compared to the wild-type sequences. In some aspects, the mutagenized thumb domain sequence has an improved single-stranded priming efficiency compared to the wild-type sequences. In some instances, the mutagenized thumb domain sequence has an improved processivity compared to the wild-type sequences. Jumping efficiency, single-stranded priming efficiency, and processivity are essential parameters for the conversion efficiency of RNA samples to DNA library.

In some instances, a host cell may be selected from, and the modified or non-naturally occurring enzyme generated in, for example, bacteria, yeast, fungus or any of a variety of other organisms may be used as a host organism.

In some instances, the host is not particularly restricted and the enzymatic activity or activities may be incorporated into any suitable host organism using methods, for example, as described herein. In some instances, the host is selected from bacteria, yeast, algae, cyanobacteria, fungi, or a plant cell, or any combination thereof. *E. coli* and *S. cerevisiae* are particularly useful host organisms since they are well characterized microorganisms suitable for genetic engineering. In some instances, the host is *E. coli*.

Each of the enzymes described herein may be attached to an additional amino acid sequence as long as it retains an activity functionally equivalent to that of the enzyme. As mentioned above, it is understood that each enzyme or a homologue thereof may be a (poly)peptide fragment as long as it retains an activity functionally equivalent to that of the enzyme.

In some instances, the enzyme is selected and/or engineered to exhibit high fidelity with low error rates. The fidelity of a nucleotide polymerase is typically measured as the error rate, i.e., the frequency of incorporation of a nucleotide in a manner that may violate the widely known Watson-Crick base pairing rules. The fidelity or error rate of a polymerase (e.g., DNA polymerase) may be measured using any suitable assay. See, for example, Lundburg et al., 1991 Gene, 108:1-6. The term "fidelity" can be used to refer to the accuracy of polymerization, or the ability of the polymerase to discriminate correct from incorrect substrates, (e.g., nucleotides) when synthesizing nucleic acid molecules (e.g. RNA or DNA) which are complementary to a template. The higher the fidelity of an enzyme, the less the enzyme misincorporates nucleotides in the growing strand during nucleic acid synthesis; that is, an increase or enhancement in fidelity results in a more faithful polymerase having decreased error rate (decreased misincorporation rate). In some instances, the misincorporation error rate is at most about $10^{-2}$, $10^{-4}$, $10^{-6}$, or $10^{-8}$.

In some aspects, the present disclosure relates to a non-naturally occurring or modified enzyme that can be readily expressed in a recombinant system in a functional form. In some instances, the non-naturally occurring or modified enzyme is an enzyme with reverse transcriptase activity. In some instances, the non-naturally occurring or modified enzyme is a modified reverse transcriptase. In some instances, the non-naturally occurring or modified enzyme is a modified non-retroviral reverse transcriptase. In some instances, the non-naturally occurring or modified enzyme is a modified non-LTR retrotransposon. In some instances, the non-naturally occurring or modified enzyme is a modified R2 reverse transcriptase, comprising mutations in an R2 Motif-1 or Motif-0. In some instances, a non-naturally occurring or modified enzyme or a modified polypeptide having reverse transcriptase activity can amplify a template nucleic acid molecule at a processivity of at least about 80% per base, of at least 81% per base, of at least 82% per base, of at least 83% per base, of at least 84% per base, of at least about 85% per base, of at least 86% per base, of at least 87% per base, of at least about 88% per base, of at least about 89% per base, of at least about 90% per base, of at least about 91% per base, of at least about 92% per base, of at least about 93% per base, of at least about 94% per base, of at least about 95% per base, of at least about 96% per base, of at least about 97% per base, of at least about 98% per base, of at least about 99% per base, of at least about 99.5% per base, or of about 100% per base.

In some instances, a non-naturally occurring or modified enzyme or a modified polypeptide having reverse transcriptase activity can amplify or is capable of amplifying a template nucleic acid molecule at a processivity measured at a temperature of between about 12° C. and about 40° C. In some instances, the temperature is between about 10° C. and about 35° C., between about 12° C. and about 30° C., between about 25° C. and about 40° C., or between about 12° C. and about 42° C. In some instances, the temperature is between about 8° C. to about 50° C., between about 2° C. to about 60° C., between about 8° C. to about 42° C., between about 6° C. to about 32° C., or between about 7° C. to about 35° C.

In some instances, a non-naturally occurring or modified enzyme or a modified polypeptide having reverse transcriptase activity can amplify or is capable of amplifying a template nucleic acid molecule at a processivity of at least about 80% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; of at least about 89% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 90% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; of at least about 91% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; of at least about 95% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; of at least about 99% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; of at least about 99.5% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; or of about 100% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.

In some instances, the non-naturally occurring or modified enzyme or a modified polypeptide having reverse transcriptase activity can amplify or is capable of amplifying a template nucleic acid molecule at a processivity of at least about 80% per base at a temperature of at most about 35° C., of at least about 85% per base at a temperature of at most about 40° C., of at least about 88% per base at a temperature of at most about 35° C., of at least about 89% per base at a temperature of at most about 40° C., of at least about 90% per base at a temperature of at most about 35° C., of at least about 91% per base at a temperature of at most about 35° C., of at least about 92% per base at a temperature of at most about 40° C., of at least about 93% per base at a temperature of at most about 35° C., of at least about 94% per base at a temperature of at most about 40° C., of at least about 95% per base at a temperature of at most about 35° C., of at least about 96% per base at a temperature of at most about 40° C., of at least about 97% per base at a temperature of at most about 35° C., of at least about 98% per base at a temperature of at most about 40° C., of at least about 99% per base at a temperature of at most about 40° C., of at least about 99.5% per base at a temperature of at most about 40° C., or of about 100% per base at a temperature of at most about 40° C.

In some instances, the improved enzyme property is selected from at least one of the following: improved stability (e.g., improved thermostability), improved specific activity, improved protein expression, improved purification, improved processivity, improved strand displacement, improved template jumping, improved DNA/RNA affinity, improved single strand DNA priming, and improved fidelity. In some instances, a non-naturally occurring enzyme or a modified enzyme or a modified polypeptide having reverse transcriptase activity amplifies a template nucleic acid molecule. In some instances, the non-naturally occurring enzyme or the modified enzyme or the modified polypeptide having reverse transcriptase activity that amplifies a template nucleic acid molecule has a performance index greater than about 1, greater than about 2, greater than about 3, greater than about 4, greater than about 5, greater than about 6, greater than about 7, greater than about 8, greater than about 9, greater than about 10, greater than about 15, greater than about 20, greater than about 25, greater than about 30, greater than about 35, greater than about 40, greater than about 45, greater than about 50, greater than about 60, greater than about 70, greater than about 80, greater than about 90, or greater than about 100 for at least one enzyme property. In some instances, the enzyme property and/or the performance index is performed at a temperature equal to or lower than or at most about 50° C., equal to or lower than or at most about 42° C., equal to or lower than or at most about 40° C., equal to or lower than or at most about 39° C., equal to or lower than or at most about 38° C., equal to or lower than or at most about 37° C., equal to or lower than or at most about 36° C., equal to or lower than or at most about 35° C., equal to or lower than or at most about 34° C., equal to or lower than or at most about 33° C., equal to or lower than or at most about 32° C., equal to or lower than or at most about 31° C., equal to or lower than or at most about 30° C., equal to or lower than or at most about 29° C., equal to or lower than or at most about 28° C., equal to or lower than or at most about 27° C., equal to or lower than or at most about 26° C., equal to or lower than or at most about 25° C., equal to or lower than or at most about 23° C., equal to or lower than or at most about 20° C., equal to or lower than or at most about 15° C., equal to or lower than or at most about 13° C., equal to or lower than or at most about 12° C., equal to or lower than or at most about 10° C., equal to or lower than or at most about 8° C., equal to or lower than or at most about 4° C. In some instances, the non-naturally occurring enzyme or the modified enzyme (e.g., modified reverse transcriptase) or the modified polypeptide having reverse transcriptase activity exhibits a processivity for a given nucleotide substrate that is at least about 5%, at least about 10%, at least about 15%, at least about 20%, at least about 25%, at least about 30%, at least about 35%, at least about 37.5%, at least about 40%, at least about 45%, at least about 50%, at least about 60%, at least about 70%, at least about 75%, at least about 80%, at least about 90%, at least about 95%, at least about 100%, at least about 110%, at least about 125%, at least about 150%, at least about 170%, at least about 190%, at least about 200%, at least about 250%, at least about 500%, at least about 750%, at least about 1000%, at least about 5000%, or at least about 10000% higher than the processivity of a reference enzyme or a reference polypeptide for the same nucleotide substrate. In some instances, the non-naturally occurring enzyme is a non-naturally occurring reverse transcriptase enzyme. In some instances, the modified enzyme is a modified reverse transcriptase.

The present disclosure relates to processes and/or methods that require considerably less hands-on time, the protocol is much simpler to perform and requires a much shorter duration time than other methods used for RNA sequencing and/or liquid biopsy, for example. In some instances, the methods and processes of the present disclosure comprises a protocol that is less than about 2 hours and/or less than about 30 minutes of hands-on time. In some instances, the protocol is less than about 20 hours, less than about 15 hours, less than about 12 hours, less than about 11 hours, less than about 10 hours, less than about 9 hours, less than about 8 hours, less than about 7 hours, less than about 6 hours, less than about 5 hours, less than about 4 hours, less than about 3 hours, less than about 2.5 hours, less than about 2 hours, less than about 1.5 hours, less than about 1 hour, or less than about 30 minutes. In some instances, the hands-on time is less than about 5 hours, less than about 4 hours, less than about 3 hours, less than about 2.5 hours, less than about 2 hours, less than about 1.5 hours, less than about 1 hour, less than about 50 minutes, less than about 40 minutes, less than about 35 minutes, less than about 30 minutes, less than about 25 minutes, less than about 20 minutes, or less than about 15 minutes.

In some aspects, the disclosure provides a method for simultaneously amplifying a messenger ribonucleic (mRNA) molecule and a deoxyribonucleic (DNA) molecule. In some instances, said method comprises providing a reaction mixture comprising said mRNA, DNA and non-naturally occurring enzymes, each of said non-naturally occurring enzymes comprising (i) a palm and finger domain derived from an R2 retrotransposon; (ii) a thumb domain derived from an R2 retrotransposon; and (iii) an endonuclease domain derived from an R2 retrotransposon. In some instances, said method comprises subjecting said reaction mixture to conditions sufficient to amplify said mRNA and DNA, thereby yielding amplified products of said mRNA and said DNA. In some instances, said DNA is complementary DNA derived from a subset of mRNA in said reaction mixture.

In some instances, the non-naturally occurring or modified enzyme (e.g., non-naturally occurring or modified reverse transcriptase, non-naturally occurring or modified non-LTR retrotransposon, non-naturally occurring or modified R2 reverse transcriptase) or a modified polypeptide having reverse transcriptase activity exhibits a misincorporation error rate of equal to or less than about 50%, equal to or less than about 45%, equal to or less than about 40%, equal to or less than about 35%, equal to or less than about 30%, equal to or less than about 25%, equal to or less than about 20%, equal to or less than about 15%, equal to or less than about 10%, equal to or less than about 9%, equal to or less than about 8%, equal to or less than about 7%, equal to or less than about 6%, equal to or less than about 5%, equal to or less than about 4%, equal to or less than about 3%, equal to or less than about 2%, equal to or less than about 1%, equal to or less than about 0.01%, equal to or less than about 0.001%, equal to or less than about 0.0001%, equal to or less than about 0.00001%, equal to or less than about 0.000001%, or equal to or less than about 0.0000001%.

In some instances, the non-naturally occurring or modified enzyme (e.g., non-naturally occurring or modified reverse transcriptase, non-naturally occurring or modified non-LTR retrotransposon, non-naturally occurring or modified R2 reverse transcriptase) or a modified polypeptide having reverse transcriptase activity generates one or more nucleic acid (e.g., cDNA) molecule(s) complementary to a template at an error rate that is at least about 10000 times lower, at least about 1500 times lower, at least about 1000 times lower, at least about 500 times lower, at least about 100 times lower, at least about 95 times lower, at least about 90 times lower, at least about 85 times lower, at least about 80 times lower, at least about 75 times lower, at least about 70 times lower, at least about 65 times lower, at least about 60 times lower, at least about 55 times lower, at least about 50 times lower, at least about 45 times lower, at least about 40 times lower, at least about 35 times lower, at least about 30 times lower, at least about 25 times lower, at least about 20 times lower, at least about 15 times lower, at least about 10 times lower, at least about 9 times lower, at least about 8 times lower, at least about 7 times lower, at least about 6 times lower, at least about 5 times lower, at least about 4 times lower, at least about 3 times lower, at least about 2 times lower, or at least about 1 time lower than the unmodified or naturally occurring enzyme or unmodified polypeptide having reverse transcriptase activity.

In some instances, the sequencing error rate will be equal to or less than about 1 in 100,000 bases. In some instances, the error rate of nucleotide sequence determination is equal to or less than about 1 in 10 bases, 1 in 20 bases, 3 in 100 bases, 1 in 100 bases, 1 in 1000 bases, and 1 in 10,000 bases.

In some instances, the modified enzyme (e.g., modified reverse transcriptase), modified reverse transcriptase, non-naturally occurring enzyme, modified polypeptide having reverse transcriptase activity comprises at least one modification relative to the wild type, unmodified counterpart, or naturally occurring enzyme. In some instances, the modified non-LTR retrotransposon comprises at least one modification of a wild-type or unmodified non-LTR retrotransposon. In some instances, the modified R2 reverse transcriptase comprises at least one modification of a wild-type or unmodified R2 reverse transcriptase. In some instances, the modified reverse transcriptase comprises at least one modification of a wild-type or unmodified reverse transcriptase. In some instances, the modified polypeptide having reverse transcriptase activity comprises at least one modification of a wild-type or unmodified polypeptide having reverse transcriptase activity. In some instances, the modification comprises at least one truncation (e.g., N-terminal truncation, C-terminal truncation, and/or N- and C-terminal truncations). In some instances, the modification comprise(s) site-specific incorporation, and/or addition, and/or deletion, and/or substitution of amino acid(s) at positions of interest. In some instances, the modification enhances the biological properties of the modified enzyme or modified polypeptide relative to the wild-type or unmodified enzyme or polypeptide. In some instances, the modification improves at least one enzyme property of the modified enzyme or polypeptide relative to the wild-type or unmodified enzyme or polypeptide. In some instances, the modification(s) serve as a point of attachment for, e.g., labels and protein half-life extension agents, and for purposes of affixing the variants to the surface of a solid support. In some instances, the present disclosure is related to methods of producing cells capable of producing the modified enzymes (e.g., modified reverse transcriptase) or modified polypeptides, and of producing vectors containing DNA or RNA encoding the modified enzymes (e.g., modified reverse transcriptase) or modified polypeptides. In some instances, the truncation is based on a two-step process. In some instances, the first step for selecting a truncation includes analyzing the domains and motifs structure(s) and function(s) of a class of enzymes, or proteins, or polypeptides. In some instances, the enzymes, or proteins, or polypeptides are non-LTR retrotransposons, reverse transcriptases, R2 reverse transcriptase, LTR retrotransposons, R2 non-LTR retrotransposons, or any combination thereof. In some instances, the enzymes, or proteins, or polypeptides are from different organisms. In some instances, all the domains of the enzymes, or proteins, or polypeptides are present. In some instances, all the domains are present to ensure reverse transcriptase activity. In some instances, all the domains are present to ensure the unique properties essential for the present disclosure. In some instances, the domains responsible for reverse transcriptase activity are not modified. In some instances, the R2 domain does not comprise modifications. In some instances, the R2 domain may comprise modifications. In some instances, the truncated variants show expression level. In some instances, the truncated variants that show promising expression level are further subject to small adjustment(s) in the sequence (step two). In some instances, the small adjustment(s) in the sequence include deletion, insertion, and/or substitution of amino acid(s). In some instances, the deletion, insertion, and/or substitution of amino acid(s) may include one or several amino acid(s). In some instances, the deletion, insertion, and/or substitution of amino acid(s) further optimize expression and/or stability (e.g., thermostability).

In some instances, the modified enzyme (e.g., modified reverse transcriptase), modified reverse transcriptase, or modified polypeptides has an N-terminal truncation, a C-terminal truncation, or both, relative to the wild type or unmodified enzyme (e.g., wild-type reverse transcriptase) or wild-type or unmodified polypeptide. In some instances, the polymerase comprises an N-terminal truncation, a C-terminal truncation, or both. In some instances, the modified reverse transcriptase comprises N-terminal truncation, C-terminal truncation, or a combination of N-terminal and C-terminal truncation(s). In some instances, the modified enzyme comprises N-terminal truncation, C-terminal truncation, or a combination of N-terminal and C-terminal truncation(s). In some instances, the modified polypeptide comprises N-terminal truncation, C-terminal truncation, or a combination of N-terminal and C-terminal truncation(s). In some instances, the modified reverse transcriptase, modified enzyme, modified polypeptide, modified non-LTR retrotransposon, or modified R2 reverse transcriptase comprises a truncation of less than about 100 amino acid residues. In some instances, the modified reverse transcriptase, modified enzyme, modified polypeptide, modified non-LTR retrotransposon, or modified R2 reverse transcriptase comprises at least one of: (a) an amino-terminal truncation of less than about 400 amino acid residues and (b) a carboxyl-terminal truncation of less than about 400 amino acid residues. In some instances, the modified reverse transcriptase, modified enzyme, modified polypeptide, modified non-LTR retrotransposon, or modified R2 reverse transcriptase lacks up to: about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 50, about 75, about 100, about 120, about 150, about 175, about 200, about 220, about 250, about 275, about 280, about 290, about 300, about 325, about 350, about 375, about 380, about 390, about 400, or about 450 amino acids from the N-terminus, C-terminus, or both. In some instances, the modified reverse transcriptase, modified enzyme, modified polypeptide, modified non-LTR retrotransposon, or modified R2 reverse transcriptase may alternately or additionally have one or more internal deletions of up to: about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 amino acids, about 30, about 50, about 75, about 100, about 120, about 150, about 175, about 200, about 220, about 250, about 275, about 280, about 290, about 300, about 325, about 350, about 375, about 380, about 390, or a total of about 450 amino acids. In some instances, the N-terminal truncation, C-terminal truncation, or both, may comprise deletions from about 1 to about 50 amino acids, from about 1 to about 25, from about 1 to about 70, from about 10 to about 50, from about 20 to about 30, from about 15 to about 100, from about 1 to about 150, from about 15 to about 60, from about 15 to about 40, from about 1 to about 10, from about 10 to 35, from about 50 to about 100, from about 20 to about 150, from about 200 to about 350, from about 25 to about 350, from about 150 to about 400, from about 50 to about 400, from about 50 to about 450, from about 200 to about 400, or from about 50 to about 350, or from about 50 to about 400 amino acids. In some instances, the N-terminal truncation removes at least about 5, at least about 10, at least about 15, at least about 20, at least about 25, at least about 30, at least about 35, at least about 40, at least about 50, at least about 60, at least about 65, at least about 70, at least about 75, at least about 80, at least about 90, at least about 95, at least about 100, at least about 120, at least about 130, at least about 140, at least about 150, at least about 175, at least about 200, at least about 220, at least about 250, at least about 275, at least about 300, at least about 325, at least about 350, at least about 375, or at least about 400 amino acids. In some instances, the C-terminal truncation removes at least about 5, at least about 10, at least about 15, at least about 20, at least about 25, at least about 30, at least about 35, at least about 40, at least about 50, at least about 60, at least about 65, at least about 70, at least about 75, at least about 80, at least about 90, at least about 95, at least about 100, at least about 120, at least about 130, at least about 140, at least about 150, at least about 175, at least about 200, at least about 220, at least about 250, at least about 275, at least about 300, at least about 325, at least about 350, at least about 375, or at least about 400 amino acids. In some instances, the N-terminal truncation lacks about 5, about 10, about 15, about 20, about 25, about 30, about 35, about 40, about 50, about 60, about 65, about 70, about 75, about 80, about 90, about 95, about 100, about 120, about 130, about 140, about 150, about 175, about 200, about 220, about 250, about 275, about 300, about 325, about 350, about 375, or about 400 amino acids. In some instances, the C-terminal truncation lacks about 5, about 10, about 15, about 20, about 25, about 30, about 35, about 40, about 50, about 60, about 65, about 70, about 75, about 80, about 90, about 95, about 100, about 120, about 130, about 140, about 150, about 175, about 200, about 220, about 250, about 275, about 300, about 325, about 350, about 375, or about 400 amino acids. In some instances, the N-terminal truncation lacks no more than about 5, no more than about 10, no more than about 15, no more than about 20, no more than about 25, no more than about 30, no more than about 35, no more than about 40, no more than about 50, no more than about 60, no more than about 65, no more than about 70, no more than about 75, no more than about 80, no more than about 90, no more than about 95, no more than about 100, no more than about 120, no more than about 130, no more than about 140, no more than about 150, no more than about 175, no more than about 200, no more than about 220, no more than about 250, no more than about 275, no more than about 300, no more than about 325, no more than about 350, no more than about 375, or no more than about 400 amino acids. In some instances, the C-terminal truncation lacks no more than about 5, no more than about 10, no more than about 15, no more than about 20, no more than about 25, no more than about 30, no more than about 35, no more than about 40, no more than about 50, no more than about 60, no more than about 65, no more than about 70, no more than about 75, no more than about 80, no more than about 90, no more than about 95, no more than about 100, no more than about 120, no more than about 130, no more than about 140, no more than about 150, no more than about 175, no more than about 200, no more than about 220, no more than about 250, no more than about 275, no more than about 300, no more than about 325, no more than about 350, no more than about 375, or no more than about 400 amino acids. In some instances, the truncation comprises an N-terminal truncation that removes at least about, at most about, or about 5, 10, 15, 20, 25, 30, 40, 50, 75, 100, 125, 150, 175, 200, 225, 250, 275, 300, 325, 350, 375, 400, 425, 450, 475, or 500 amino acids. In some instances, the truncation comprises a C-terminal truncation that removes at least about, at most about, or about 5, 10, 15, 20, 25, 30, 40, 50, 75, 100, 125, 150, 175, 200, 225, 250, 275, 300, 325, 350, 375, 400, 425, 450, 475, or 500 amino acids. In some instances, the N-terminal truncation, the C-terminal truncation, or both, may be more than about 500 amino acids, more than about 1000 amino acids, more than about 1500 amino acids, more than about 2000 amino acids, more than about 5000 amino acids, more than about 10000 amino acids, more than about 100000 amino acids, more than about 1000000 amino acids.

In some instances, truncations of regions which do affect functional activity of a protein or enzyme may be engineered. In some instances, truncations of regions which do not affect functional activity of a protein or enzyme may be engineered. A truncation may comprise a truncation of less than about 5, less than about 10, less than about 15, less than about 20, less than about 25, less than about 30, less than about 35, less than about 40, less than about 45, less than about 50, less than about 60, less than about 70, less than about 80, less than about 90, less than about 100, less than about 125, less than about 150, less than about 200, less than about 250, less than about 300, less than about 350, less than about 400 or more amino acids. A truncation may comprise a truncation of more than about 5, more than about 10, more than about 15, more than about 20, more than about 25, more than about 30, more than about 35, more than about 40, more than about 45, more than about 50, more than about 60, more than about 70, more than about 80, more than about 90, more than about 100, more than about 125, more than about 150, more than about 200, more than about 250, more than about 300, more than about 350, more than about 400 or more amino acids. A truncation may comprise a truncation of about 5%, about 10%, about 15%, about 20%, about 25%, about 30%, about 35%, about 40%, about 45%, about 50%, about 55%, about 60%, about 65%, about 70%, about 75%, about 80%, about 85%, about 87%, about 90%, about 92%, about 95% or about 100% of the polypeptide or enzyme.

In some instances, the variant or modified enzyme or modified protein may comprise one or more modification(s) at an amino acid position. In some instances, a variant, a mutant, or modified polypeptides or enzymes of the present disclosure may possess an increased activity, such as an increased RNA-dependent DNA polymerase activity or a DNA-dependent DNA polymerase activity, compared to the corresponding unmutated or unmodified or wildtype polymerase or as compared to one or more polymerases (e.g., RNA-dependent DNA polymerase, or a reverse transcriptase). In some instances, a polymerase or a reverse transcriptase having an increase in activity may be a modified polymerase or a modified reverse transcriptase that has at least about a 5% increase, at least about a 10% increase, at least about a 25% increase, at least about a 30% increase, at least about a 50% increase, at least about a 100% increase, at least about a 150% increase, at least about a 200% increase, at least about a 300% increase, at least about a 500% increase, at least about a 1,000% increase, at least about a 2,500% increase or at least about a 5,000% increase as compared to (1) the corresponding unmutated or wild-type enzyme; or (2) a particular polymerase (e.g., RNA-dependent DNA polymerase, reverse transcriptase) or a particular reverse transcriptase, or a group of polymerases, or a group of reverse transcriptases. In some instances, the modified polymerase or the modified reverse transcriptase of the present disclosure may have an increase in activity of from about 5% to about 5,000%, from about 5% to about 2,500%, from about 5% to about 1000%, from about 5% to about 500%, from about 5% to about 250%, from about 5% to about 100%, from about 5% to about 50%, from about 5% to about 25%, from about 25% to about 5,000%, from about 25% to about 2,500%, from about 25% to about 1,000%, from about 25% to about 500%, from about 25% to about 250%, from about 25% to about 100%, from about 100% to about 5,000%, from about 100% to about 2,500%, from about 100% to about 1000%, from about 100% to about 500%, or from about 100% to about 250%. An increase in RNA-dependent DNA polymerase activity and/or DNA-dependent DNA polymerase for a modified polymerase or modified reverse transcriptase of the present disclosure may also be measured according to relative activity compared to (1) the corresponding unmodified or wild-type enzyme; or (2) a particular polymerase (e.g., RNA-dependent DNA polymerase, reverse transcriptase) or a particular reverse transcriptase, or a group of polymerases, or a group of reverse transcriptases. In some instances, the increase in such relative activity is at least about 1.1, 1.2, 1.5, 2, 5, 10, 25, 50, 75, 100, 150, 200, 300, 500, 1,000, 2,500, 5,000, 10,000, or 25,000 fold when the activity of a modified polymerase or modified reverse transcriptase of the present disclosure is compared to (1) the corresponding unmutated or wild-type enzyme; or (2) a particular polymerase (e.g., RNA-dependent DNA polymerase, reverse transcriptase) or a particular reverse transcriptase, or a group of polymerases, or a group of reverse transcriptases. Thus a modified polymerase or modified reverse transcriptase of the present disclosure may have an increased RNA-dependent DNA polymerase and/or an increased DNA-dependent DNA polymerase activity of from about 1.1 fold to about 25,000 fold, from about 1.1 fold to about 10,000 fold, from about 1.1 fold to about 5,000 fold, from about 1.1 fold to about 2,500 fold, from about 1.1 fold to about 1,000 fold, from about 1.1 fold to about 500 fold, from about 1.1 fold to about 250 fold, from about 1.1 fold to about 50 fold, from about 1.1 fold to about 25 fold, from about 1.1 fold to about 10 fold, from about 1.1 fold to about 5 fold, from about 5 fold to about 25,000 fold, from about 5 fold to about 5,000 fold, from about 5 fold to about 1,000 fold, from about 5 fold to about 500 fold, from about 5 fold to about 100 fold, from about 5 fold to about 50 fold, from about 5 fold to about 25 fold, from about 50 fold to about 25,000 fold, from about 50 fold to about 5,000 fold, from about 50 fold to about 1,000 fold, from about 50 fold to about 500 fold, from about 50 fold to about 100 fold, from about 100 fold to about 25,000 fold, from about 1,000 fold to about 25,000 fold, from about 4,000 fold to about 25,000 fold, from about 10,000 fold to about 25,000 fold, from about 15,000 fold to about 25,000 fold, from about 1,000 fold to about 10,000 fold, from about 2,500 fold, to about 10,000 fold, from about 5,000 fold to about 10,000 fold, from about 7,500 fold to about 10,000 fold, from about 1,000 fold to about 15,000 fold, from about 2,500 fold, to about 15,000 fold, from about 5,000 fold to about 15,000 fold, from about 7,500 fold to about 15,000 fold, from about 10,000 fold to about 15,000 fold, or from about 12,500 fold to about 15,000 fold.

In some instances, the polypeptides, proteins, enzymes, modified enzymes (e.g., modified reverse transcriptase), modified polypeptides, non-naturally occurring enzymes, or variants comprise a fusion with, but not limited to, a protein, a domain, a fusion partner, a carrier protein, a target sequence, an antigenic determinant, or any combination thereof. In some instances, the reverse transcriptase or modified reverse transcriptase is fused to a protein, a domain, a fusion partner, a target sequence, an antigenic determinant, or any combination thereof. In some instances, the non-LTR retrotransposon or modified non-LTR retrotransposon is fused to a protein, a domain, a fusion partner, a target sequence, an antigenic determinant, or any combination thereof. In some instances, the modified LTR retrotransposon is fused to a protein, a domain, a fusion partner, a target sequence, an antigenic determinant, or any combination thereof. In some instances, the modified R2 non-LTR retrotransposon is fused to a protein, a domain, a fusion partner, a target sequence, an antigenic determinant, or any combination thereof. In some instances, the modified R2 reverse transcriptase is fused to a protein, a domain, a fusion partner, a target sequence, an antigenic determinant, or any combination thereof. In some instances, the modified reverse transcriptase is fused to a protein, a domain, a fusion partner, a target sequence, an antigenic determinant, or any combination thereof. In some instances, the variant is fused to a protein, a domain, a fusion partner, a target sequence, an antigenic determinant, or any combination thereof. In some instances, the polypeptide having reverse transcriptase activity is fused to a protein, a domain, a fusion partner, a target sequence, an antigenic determinant, or any combination thereof.

In some instances, the fused polypeptides, proteins, enzymes, modified enzymes (e.g., modified reverse transcriptase), modified polypeptides, non-naturally occurring enzymes, or variants thereof increase stability (e.g., increase thermostability), increase shelf life, increase active fraction(s), and/or improve purification compared to the wild-type counterpart, naturally occurring enzyme, or unfused polypeptides, proteins, enzymes, or variants thereof. In some instances, a modified reverse transcriptase comprises a fusion partner or a carrier protein. In some instances, the selection of the fusion protein, domain, fusion partner, target sequence, antigenic determinant, or any combination thereof is based on the mechanism causing reduced or increased stability (e.g., increased thermostability), reduced or increased shelf life, and/or reduced or increased expression level (Costa et al., "Fusion tags for protein solubility, purification and immunogenicity in *Escherichia coli*: the novel Fh8 system. Front Microbiol. 2014 Feb. 19; 5:63). In some instances, the fusion tags enhance the solubility of their partner proteins. In some instances, the fusion proteins form micelle-like structures. In some instances, the micelle-like structures are misfolded or unfolded proteins that are sequestered and protected from the solvent and/or the soluble protein domains face outward. In some instances, the fusion partners attract chaperones. In some instances, the fusion tag drives its partner protein into a chaperone-mediated folding pathway. In some instances, the MBP and/or N-utilization substance (NusA) are two fusion tags that present this mechanism. In some instances, the fusion partners have an intrinsic chaperone-like activity. In some instances, the hydrophobic patches of the fusion tag interact with partially folded passenger proteins, preventing self-aggregation, and promoting proper folding. In some instances, the solubility enhancer partners may play a passive role in the folding of their target proteins, reducing the chances for protein aggregation. In some instances, the fusion partners net charges. In some instances, the highly acidic fusion partners inhibit protein aggregation. In some instances, the fusion is with, but it is not limited to, Fh8, MBP, NusA, Trx, SUMO, GST, SET, GB1, ZZ, HaloTag, SNUT, Skp, T7PK, EspA, Mocr, Ecotin, CaBP, ArsC, IF2-domain I, an expressivity tag, an expressivity tag that is part of IF2-domain I, RpoA, SlyD, Tsf, RpoS, PotD, Crr, msyB, yjgD, rpoD, His6, or any combination thereof. In some instances, the fusion enhances protein solubility and/or purification. In some instances, the Fh8 may act as an effective solubility enhancer partner and/or robust purification. In some instances, the Fh8 fusion tag has an amino acid sequence comprising MPSVQEVEKLLHVLDRNGDGKV-SAEELKAFADDSKCPLDSNKIKAFIKEHDKNKDGKL DLKELVSILSS (SEQ ID NO: 21). In some instances, the codon optimized sequence comprises ATGCCGTCTGTTCAGGAAGTT-GAAAAACTGCTGCACGTTCTGGACCGTAACGGTGA CGGTAAAGTTTCTGCGGAAGAACT-GAAAGCGTTCGCGGACGACTCTAAATGCCCGC TGGACTCTAACAAAATCAAAGCGTTCAT-CAAAGAACACGACAAAAACAAAGACGG TAAACTGGACCTGAAAGAACTGGTTTC-TATCCTGTCTTCTTAG (SEQ ID NO: 22). In some instances, an enzyme, or a modified enzyme (e.g., modified reverse transcriptase), or a protein (e.g., modified protein), or a polypeptide (e.g., modified polypeptide), or a variant, or a product, or a nucleic acid molecule, or a cDNA molecule, or a template, or an acceptor nucleic acid molecule, or a primer, or an RNA, or a DNA, or a fragment nucleic acid, or a degraded nucleic acid, of the present disclosure may comprise one or more tag(s). In some instances, the fragmented or degraded RNA or DNA, or a variant thereof may comprise one or more tag(s). In some instances, the R2 reverse transcriptase, or a variant thereof, may comprise one or more tag(s). In some instances, the non-LTR retrotransposon protein or polypeptide having reverse transcriptase activity, or a variant thereof, may comprise one or more tag(s). In some instances, the cDNA molecule may comprise one or more tag(s). In some instances, the tag may be captured on a solid support, facilitating the isolation of the enzyme, or protein, or polypeptide, or a variant, or a product of the present disclosure. In some instances, the tag may be biotin that can be recognized by avidin. The affinity tag may include multiple biotin residues for increased binding to multiple avidin molecules. In some instances, the tag may include a functional group such as an azido group or an acetylene group, which enables capture through copper(I) mediated click chemistry (see H. C. Kolb and K. B. Sharpless, Drug Discovery Today, 2003, 8(24), 1128-1137). In some instances, the tag may include an antigen that may be captured by an antibody bound on a solid support. In some instances, the tag may include, but is not limited to, His-tag, His6-tag, Calmodulin-tag, CBP, CYD (covalent yet dissociable NorpD peptide), Strep II, FLAG-tag, HA-tag, Myc-tag, S-tag, SBP-tag, Softag-1, Softag-3, V5-tag, Xpress-tag, Isopeptag, SpyTag, B, HPC (heavy chain of protein C) peptide tags, GST, MBP, biotin, biotin carboxyl carrier protein, glutathione-S-transferase-tag, green fluorescent protein-tag, maltose binding protein-tag, Nus-tag, Strep-tag, thioredoxin-tag, and combinations thereof. In some instances, the tagged molecule may be subjected to sequencing.

In some instances, a molecular barcode may be attached to any region of a molecule. For example, the molecular barcode may be attached to the 5' or 3' end of a polynucleotide (e.g., DNA, RNA). For example, the target-specific region of the molecular barcode comprises a sequence that is complementary to a sequence in the 5' region of the molecule. The target-specific region of the molecular barcode may also comprise a sequence that is complementary to a sequence in the 3' region of the molecule. In some instances, the molecular barcode is attached a region within a gene or gene product. For example, genomic DNA is fragmented and a sample tag or molecular identifier label is attached to the fragmented DNA. In other instances, an RNA molecule is alternatively spliced and the molecular barcode is attached to the alternatively spliced variants. In another example, the polynucleotide is digested and the molecular barcode is attached to the digested polynucleotide. In another example, the target-specific region of the molecular barcode comprises a sequence that is complementary to a sequence within the molecule.

In some instances the method of the present disclosure comprises introducing a biotin moiety or another affinity purification moiety to, for example, a nucleic acid molecule, such as DNA, RNA, or a combination of DNA and RNA. In some instances, the method further comprises immobilizing the affinity purification tagged nucleic acid molecule on a solid support. In some instances the solid support is a sepharose resin or magnetic beads having an affinity purification material, such as avidin, streptavidin, chitin, glutathione and the like, bound thereto. In some instances, the enzyme, or protein, or polypeptide, or a variant, or a product of the present disclosure may be bound to a solid support. In some instances, the fragmented or degraded nucleic acid (e.g., RNA or DNA), or a variant thereof may be bound to a solid support. In some instances, the R2 reverse transcriptase, or a variant thereof, may be bound to a solid support. In some instances, the non-LTR retrotransposon protein or polypeptide having reverse transcriptase activity, or a variant thereof, may be bound to a solid support. In some instances, the cDNA molecule may be bound to a solid support. In some instances, the solid support may be glass, plastic, porcelain, resin, sepharose, silica, or other material. In some instances, the solid support may be a plate that is substantially flat substrates, gel, microbeads, magnetic beads, membrane, or other suitable shape and size. In some instances, the microbeads may have diameter between 10 nm to several millimeters. In some instances, the solid support may be non-porous or porous with various density and size of pores. In some instances the DNA and/or RNA fragment may be captured on a solid support, unwanted DNA and/or RNA may be washed away. In some instances, the DNA and/or RNA fragment may be released from the solid support, for example, by using restriction enzyme.

In some instances, the solid support may comprise the target nucleic acid binding region, wherein the target nucleic acid binding region comprises a sequence selected from the group consisting of a gene-specific sequence, an oligo-dT sequence, a random multimer, and any combination thereof. In some instances, the solid support further comprises a target nucleic acid or complement thereof. In some instances, the solid support comprises a plurality of target nucleic acids or complements thereof comprising from about 0.01% to about 100% of transcripts of a transcriptome of an organism or complements thereof, or from about 0.01% to about 100% of genes of a genome of an organism or complements thereof. In some instances, the cellular labels of the plurality of oligonucleotides comprise a first random sequence connected to a second random sequence by a first label linking sequence; and the molecular labels of the plurality of oligonucleotides comprise random sequences. In some instances, the solid support is selected from the group consisting of a polydimethylsiloxane (PDMS) solid support, a polystyrene solid support, a glass solid support, a polypropylene solid support, an agarose solid support, a gelatin solid support, a magnetic solid support, a pluronic solid support, and any combination thereof. In some instances, the plurality of oligonucleotides comprise a linker comprising a linker functional group, and the solid support comprises a solid support functional group; wherein the solid support functional group and linker functional group connect to each other. In some instances, the linker functional group and the solid support functional group are individually selected from the group consisting of C6, biotin, streptavidin, primary amine(s), aldehyde(s), ketone(s), and any combination thereof. In some instances, molecular labels of the plurality of oligonucleotides comprise at least 15 nucleotides.

In some instances, fusion partners may be removed from their target protein by enzymatic cleavage, chemical cleavage, and/or by using an in vivo cleavage strategy. In some instances, proteases may be used for tag removal. In some instances, the protease may be an endoprotease, serine protease, factor Xa, enterokinase, alpha-thrombin, a viral protease, tobacco etch virus (TEV), the human rhinovirus 3C protease, SUMO protease, exoprotease, metallocarboxypeptidase, or aminopeptidase. In some instances, a fusion tag may be removed by two purification steps. In some instances, the initial affinity purification step includes (e.g., via a histidine tag located at the N-terminal of the fusion protein), the purified fusion protein mixed in solution with the endoprotease (e.g., a his-tagged protease) to cleave off the tag. The cleaved target protein may be recovered in the flow-through sample after a second affinity purification step, in which the cleaved fusion tag and the added protease are collected in the eluted sample.

In some instances, the modified enzyme, modified reverse trancriptase, non-naturally occurring enzyme, or modified polypeptide having reverse transcriptase activity of the present disclosure shows activity, is capable of template jumping, and/or generate a nucleic acid molecule (e.g., cDNA molecule) without thermal cycling. In some instances, the modified reverse trancriptase, modified enzyme, non-naturally occurring enzyme, or the modified polypeptide having reverse transcriptase activity of the present disclosure shows activity, is capable of template jumping, and/or generate a nucleic acid, cDNA molecule at a temperature ranging from about 25° C. to about 42° C., from about 12° C. to about 42° C., from about 8° C. to about 50° C., from about 4° C. to about 60° C., from about 27° C. to about 35° C., from about 28° C. to about 33° C., from about 29° C. to about 32° C., from about 30° C. to about 37° C., from about 26° C. to about 38° C., from about 30° C. to about 37° C., from about 25° C. to about 32° C., from about 29° C. to about 31° C., from about 27° C. to about 38° C., from about 29° C. to about 38° C. In some instances, the non-naturally occurring enzyme, modified reverse trancriptase, modified enzyme, or modified polypeptide having reverse transcriptase activity of the present disclosure shows activity, is capable of template jumping, and/or generate a nucleic acid molecule (e.g., cDNA molecule) at about 30° C., or at about 35° C., or at about 25° C. In some instances, the modified enzyme, modified reverse trancriptase, non-naturally occurring enzyme, or modified polypeptide having reverse transcriptase activity of the present disclosure shows activity, is capable of template jumping, and/or generate a nucleic acid molecule (e.g., cDNA molecule) at a temperature equal to less than about 38° C., equal to less than about 42° C., equal to less than about 50° C., equal to less than about 60° C., equal to less than about 35° C., equal to less than about 30° C., equal to less than about 28° C., equal to less than about 25° C., equal to less than about 20° C., equal to less than about 12° C., equal to less than about 8° C., or equal to less than about 4° C. In some instances, the modified enzyme, modified reverse trancriptase, non-naturally occurring enzyme, or modified polypeptide having reverse transcriptase activity of the present disclosure shows activity, is capable of template jumping, and/or generate a nucleic acid molecule (e.g., cDNA molecule) at a temperature equal to less than about 36° C. In some instances, the modified enzyme, modified reverse trancriptase, non-naturally occurring enzyme, or modified polypeptide having reverse transcriptase activity of the present disclosure shows activity, is capable of template jumping, and/or generate a nucleic acid molecule (e.g., cDNA molecule) at room temperature. In some instances, the modified enzyme, modified reverse trancriptase, non-naturally occurring enzyme, or modified polypeptide having reverse transcriptase activity of the present disclosure shows activity, is capable of template jumping, and/or generate a nucleic acid molecule (e.g., cDNA molecule) at a temperature of at about or of at most about 8° C., at about or of at most about 12° C., at about or of at most about 20° C., at about or of at most about 25° C., at about or of at most about 28° C., at about or of at most about 30° C., at about or of at most about 31° C., at about or of at most about 32° C., at about or of at most about 33° C., at about or of at most about 34° C., at about or of at most about 35° C., at about or of at most about 36° C. at about or of at most about 39° C., at about or of at most about 40° C., at about or of at most about 41° C., at about or of at most about 42° C., at about or of at most about 50° C., at about or of at most about 55° C., at about or of at most about 60° C. In some instances, the modified enzyme, modified reverse trancriptase, non-naturally occurring enzyme, or modified polypeptide having reverse transcriptase activity of the present disclosure shows activity, is capable of template jumping, and/or generate a nucleic acid molecule (e.g., cDNA molecule) at a temperature equal to or less than about any temperature between about 42° C. to about 80° C., or between about 35° C. to about 80° C., or between about 30° C. to about 50° C., or between about 8° C. to about 50° C., or between about 12° C. to about 42° C.

In some instances, a modified enzyme, modified reverse trancriptase, modified polypeptide having reverse transcriptase activity, or a non-naturally occurring enzyme of the present disclosure has at least one altered characteristic relative to an unmodified or naturally occurring enzyme. In some instances, the altered characteristic enables the modified enzyme, modified reverse trancriptase, non-naturally occurring enzyme, or modified polypeptide having reverse transcriptase activity to generate a nucleic acid molecule and/or a complementary deoxyribonucleic acid (cDNA) molecule from a template nucleic acid molecule without thermal cycling. In some instances, a modified enzyme, modified reverse trancriptase, modified polypeptide having reverse transcriptase activity, or a non-naturally occurring enzyme of the present disclosure is capable of generating one or more copies of the nucleic acid molecule or cDNA molecule at an error rate of at most about 0.5%, of at most about 1%, of at most about 1.5%, of at most about 2%, of at most about 2.5%, of at most about 3%, of at most about 3.5%, of at most about 4%, of at most about 4.5%, of at most about 5%, of at most about 6%, of at most about 7%, of at most about 8%, of at most about 9%, of at most about 10%, of at most about 15%, of at most about 20%, of at most about 25%, of at most about 30%, of at most about 40%, of at most about 45%, of at most about 50%, of at most about 60%, of at most about 65%, of at most about 70%, of at most about 75%, or of at most about 80%. In some instances, the modified enzyme, modified reverse trancriptase, modified polypeptide having reverse transcriptase activity, or the non-naturally occurring enzyme of the present disclosure is a variant of any one of the sequences disclosed herein. In some instances, the modified enzyme, modified reverse trancriptase, modified polypeptide having reverse transcriptase activity, or the non-naturally occurring enzyme of the present disclosure is a variant of any one of the sequences provided in SEQ ID Nos: 1-20. In some instances, a modified enzyme, modified reverse trancriptase, modified polypeptide having reverse transcriptase activity, or a non-naturally occurring enzyme of the present disclosure has at least one altered characteristic that improves enzyme property relative to an unmodified or a naturally occurring enzyme. In some instances, the at least one altered characteristic that improves enzyme property comprises at least one of increased/improved stability (e.g., increased/improved thermostability), increased/improved specific activity, increased/improved protein expression, increased/improved purification, increased/improved processivity, increased/improved strand displacement, increased/improved template jumping, improved single strand DNA priming, and increased/improved fidelity.

In one embodiment, the present disclosure relates to a non-naturally occurring enzyme that subjects a template nucleic acid molecule to reverse transcription to generate a complementary deoxyribonucleic acid (cDNA) product and amplification of the cDNA product at a processivity of at least about 80%, at least about 85%, at least about 87%, at least about 90%, at least about 92%, at least about 95%, at least about 96%, at least about 97%, at least about 98%, at least about 99%, or at least about 99.5% per base as measured at about 12° C., about 15° C., about 20° C., about 25° C., about 30° C., about 32° C., about 35° C., about 40° C.

In some instances, the non-naturally occurring enzyme has a performance index greater than about 1.0 for at least one enzyme property. In some instances, enzyme property is at least one of the group consisting of improved stability (e.g., improved thermostability), specific activity, protein expression, purification, processivity, strand displacement, template jumping, increased DNA/RNA affinity, and fidelity.

In one embodiment, the present disclosure relates to a non-naturally occurring enzyme that subjects a template nucleic acid molecule to reverse transcription to generate a complementary deoxyribonucleic acid (cDNA) product, a nucleic acid product, and amplification of the cDNA product in a time period of about 3 hours or less and/or at a performance index greater than about 1.0 for at least one enzyme property selected from the group consisting of improved stability (e.g., improved thermostability), specific activity, protein expression, purification, processivity, strand displacement, template jumping, increased DNA/RNA affinity, and fidelity. In some instances, the temperature is from about 25° C. to about 40° C. (e.g., about 28° C., about 30° C., about 32° C., about 35° C., or about 37° C.). In some instances, the temperature is from about 8° C. to about 50° C. (e.g., about 8° C., about 20° C., about 42° C., about 45° C., or about 50° C.).

In one embodiment, the present disclosure relates to a non-naturally occurring enzyme that subjects a template nucleic acid molecule to reverse transcription to generate a complementary deoxyribonucleic acid (cDNA) product and amplification of the cDNA product in a time period of 3 hours or less (e.g., 2.5 hours or less, 2 hours or less, 1.5 hours or less, 1 hour or less, or 30 minutes or less) and/or at a processivity for a given nucleotide substrate that is at least about 5%, at least about 10%, at least about 20%, at least about 30%, at least about 40%, at least about 50%, at least about 60%, at least about 70%, at least about 80%, at least about 85%, at least about 88%, at least about 90%, at least about 95%, or at least about 98% higher than the processivity of a reference enzyme for the same nucleotide substrate.

In one embodiment, the present disclosure relates to a non-naturally occurring enzyme that subjects a template nucleic acid molecule to reverse transcription to generate a nucleic acid product and amplification of the nucleic acid product in a time period of 3 hours or less (e.g., 2.5 hours or less, 2 hours or less, 1.5 hours or less, 1 hour or less, or 30 minutes or less) and/or at a processivity for a given nucleotide substrate that is at least about 5%, at least about 10%, at least about 20%, at least about 30%, at least about 40%, at least about 50%, at least about 60%, at least about 70%, at least about 80%, at least about 85%, at least about 88%, at least about 90%, at least about 95%, or at least about 98% higher than the processivity of a reference enzyme for the same nucleotide substrate.

In one embodiment, the present disclosure provides a method of amplifying a nucleic acid molecule, comprising subjecting the nucleic acid molecule to nucleic acid amplification using a modified reverse transcriptase. In some instances, the reverse transcriptase is capable of amplifying the nucleic acid molecule at processivity of at least about 80%, at least about 88%, at least about 90%, at least about 95%, or at least about 98% per base at about 4° C., about 8° C., about 12° C., about 30° C., about 28° C., about 29° C., about 32° C., about 35° C., about 37° C., about 42° C., about 50° C., or higher than about 42° C.

Methods of Preparing RNA Libraries

In some aspects, the disclosure provides a method for preparing a complementary deoxyribonucleic acid (cDNA) molecule comprising: partitioning a cell and a non-naturally occurring reverse transcriptase, which cell comprises ribonucleic acid (RNA) molecules; releasing said RNA molecules from said cell in said partition; and in said partition, using said non-naturally occurring reverse transcriptase to synthesize a complementary deoxyribonucleic acid (cDNA) library from said RNA molecule, which non-naturally occurring transcriptase synthesizes said cDNA library at a processivity of 20 nucleotides or longer per continuous run, whereby processivity is defined as the number of reaction enzymes generated in one continuous run without dissociation. In some aspects, the processivity of the enzyme is about 15 nucleotides, 16 nucleotides, 17 nucleotides, 18 nucleotides, 19 nucleotides, 20 nucleotides per second, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, or more.

In some aspects, said non-naturally occurring reverse transcriptase has at least 80% identity to SEQ ID NOs: 1-20. In some aspects said partition further comprises: one or more acceptor nucleic acid molecules; and a non-naturally occurring reverse transcriptase, wherein said non-naturally occurring reverse transcriptase has at least 80% identity to SEQ ID NOs: 1-20.

Methods currently used to conduct library preparation for single cell and low input methods include various confinement methods, such as emulsion-based techniques, nano-fabrication-based techniques, cell-sorting techniques, and serial dilution-based techniques. Library preparation for single cell and low input methods includes many challenges including but not limited to a risk of artifact amplification due to an excess of reaction reagents such as oligo adapters and primers rather than the RNA sample in itself. Achieving quality library preparation requires high RNA to DNA conversion efficiency and low oligo adapter-adapter products.

In some aspects, the disclosure provides a method for preparing a complementary deoxyribonucleic acid (cDNA) molecule for single cell or low RNA sample input, whereby the RNA sample input is from 5 to 50 pg, from 10 to 50 pg, from 15 to 50 pg, from 20 to 50 pg, from 25 to 50 pg, from 30 to 50 pg, from 35 to 50 pg, from 40 to 50 pg, from 45 to 50 pg.

In some aspects, the disclosure provides an enzymatic platform for preparing a complementary deoxyribonucleic acid (cDNA) molecule for single cell or low RNA sample input, which provides the necessary high RNA-sample-library conversion efficiency. In some instances, the method disclosed herein provides a relatively simple protocol with a small number of steps, assuring a small amount of sample loss.

In some aspects, the disclosure provides an enzymatic platform for preparing a complementary deoxyribonucleic acid (cDNA) molecule for single cell or low RNA sample input that is not only limited to target poly-adenylated ribonucleic acid (RNA) from cells. In some instances, the enzymatic platform disclosed herein captures non-polyadenylated RNA, such as micro RNA (miRNA), non-coding RNA (ncRNA), long intergenic noncoding RNA (lincRNA), long non-coding RNA (lnRNA). In some instances, the enzymatic platform disclosed herein captures the full transcriptome, and thus, including but not limited to messenger RNA (mRNA), ribosomal RNA (rRNA), transfer RNA (tRNA), microRNA (miRNA), small interfering RNA (siRNA), small nucleolar RNA (snoRNA), piwi-interacting RNA (piRNA), tRNA-derived small RNA (tsRNA), and small rDNA-derived RNA (srRNA).

In one embodiment, the present disclosure relates to a method for preparing a concatemer of nucleic acid molecules. In some instances, the method comprises processing ends of a plurality of double-stranded nucleic acid molecules. In some instances, the method comprises adding a first plurality of adaptor molecules to the plurality of double stranded nucleic acid molecules. In some instances, the first plurality of adaptor molecules comprise one or more overhang sequences. In some instances, at least two of the one or more overhang sequences are complementary to each other. In some instances, the method provides a first plurality of adaptor connected double-stranded nucleic acid molecules. In some instances, the method comprises adding a polymerizing enzyme (e.g., adding a polymerase enzyme to the first plurality of adaptor connected double-stranded nucleic acid molecules). In some instances, adding a polymerase enzyme is in the absence of a primer. In some instances, the method does not comprise adding a primer. In some instances, the polymerizing enzyme forms a first set of adaptor connected double-stranded nucleic acid concatemers. In some instances, forming a first set of adaptor connected double-stranded nucleic acid concatemers is by joining two or more adaptor connected double-stranded nucleic acid molecules by the one or more overhang sequences. In some instances, the method comprises adding a second plurality of adaptor molecules to the first set (e.g., first adaptor molecules). In some instances, the second plurality of adaptor molecules comprises one or more overhang sequences. In some instances, at least two of the one or more overhang sequences are complementary to each other. In some instances, the method provides a second set of adaptor connected double-stranded nucleic acid molecules. In some instances, any one of the previous instances can be repeated with a set of adaptor molecules to yield a concatemer comprising a predetermined average length.

In one embodiment, the present disclosure relates to a method for preparing a concatemer of nucleic acid molecules. In some instances, the method comprises subjecting at least one nucleic acid molecule and/or a plurality of double-stranded nucleic acid molecules to end-repair. In some instances, the method comprises adding at least one or a plurality of adaptor molecules to the at least one nucleic acid molecule and/or the plurality of double-stranded nucleic acid molecules. In some instances, adding at least one or a (first) plurality of adaptor molecules to the at least one nucleic acid molecule and/or the plurality of double stranded nucleic acid molecules comprises ligation. In some instances, adding at least one or a (first) plurality of adaptor molecules to the at least one nucleic acid molecule and/or the plurality of double stranded nucleic acid molecules comprises a reverse transcriptase (e.g., R2 reverse transcriptase, or a modified reverse transcriptase). In some instances, In some instances, the at least one or a plurality of adaptor molecules comprise one or more overhang sequences. In some instances, at least two overhang sequences are complementary to each other (e.g., thereby providing a (first) plurality of adaptor connected double-stranded nucleic acid molecules). In some instances, the at least one or a plurality of adaptor molecules comprise a sequence (e.g., overhang sequence) that attaches/ligates to the 3' end of the nucleic acid molecule and/or a sequence (e.g., overhang sequence) that attaches/ligates to the 5' end of the nucleic acid molecule. In some instances, the nucleic acid molecule comprises adaptors on both the 3' and the 5' end. In some instances, the adaptor that binds to the 3' end is complementary to the adaptor that binds to the 5' end. In some instances, the sequence of the adaptors is unknown. In some instances, the sequence of the adaptors is pre-determined. In some instances, the adaptor serves as a template and/or as a primer. In some instances, the adaptor that binds to the 3' end of one nucleic acid molecule can bind to an adaptor on the 5' end of another nucleic acid molecule. In some instances, the method further comprises adding a polymerase enzyme to the adaptor connected to a nucleic acid molecule. In some instances, the method further comprises adding a polymerase to the (first) plurality of adaptor connected double-stranded nucleic acid molecules. In some instances, the polymerase is added in the absence of a primer. In some instances, the polymerase enzyme forms a first set of adaptor connected double-stranded nucleic acid concatemers by joining two or more adaptor connected double-stranded nucleic acid molecules by the one or more overhang sequences. In some instances, the polymerase permits that the adaptor connected to the nucleic acid molecule form concatemers. In some instances, the method comprises adding a second plurality of adaptor molecules to the first set. In some instances, the second plurality of adaptor molecules comprise one or more overhang sequences. In some instances, the at least two overhang sequences are complementary to each other. In some instances, a second set of adaptor connected double-stranded nucleic acid molecules is formed. In some instances, the concatemer length or the number of attached templates can be determined, for example, by tagging the adaptors with modified nucleotides (e.g., by introducing methylated nucleotides or by inserting dUTP). In some instances the length of the concatemer can be regulated based on the ratio between modified/unmodified adaptors. In some instances the adaptor sequences can serve as a homology priming location (annealed to the homology spot ssDNA fragments serve as template and primer). In some instances, the method comprises amplifying the concatemers by PCR or isothermal reaction. In some instances, the reaction in the PCR undergoes a selected number of cycles (the more cycles, the longer the concatemer) or time (isothermal amplification). In some instances, the reaction is stopped and the (long) dsDNA concatemers are ligated with two unique dsDNA adaptors. In some instances, the length of the concatemer can be manipulated. In some instances, the length of the concatemer can be determined at least based on the number of PCR cycles, and/or the amount of time (e.g., in an isothermal amplification), and/or based on the modified nucleotide present in the adaptor. In some instances, the adaptor comprises a unique molecular identifier sequence (UMI). In some instances, the polymerase enzyme joins two or more adaptor connected double-stranded nucleic acid molecules in a PCR or isothermal amplification reaction. In some instances, the adaptor comprises at least one modified nucleotide.

In some instances, the method for preparing a nucleic acid library and/or a complementary cDNA library comprises preparing the library in at most about 1 hour, at most about 2 hours, at most about 3 hours, at most about 4 hours, at most about 5 hours, at most about 7 hours, at most about 10 hours, at most about 15 hours, or at most about 20 hours.

In one embodiment, the present disclosure relates to methods and processes that enable the discovery of novel markers and mutations for cancer, and/or provides approaches for precision medicine. In some instances, the methods and processes disclosed herein provides for higher sensitivity to capture minor allele in ctDNA of <0.1% (available current methods have sensitivity >1%). In some instances, the methods and/or processes of the present disclosure comprise a 1-pot (e.g., single vessel), 1-step protocol, and the library is prepared from a sample in an amount of time that is equal to or less than about 2 hours.

The present disclosure relates to methods for preparing a complementary deoxyribonucleic acid (cDNA) molecule. In some instances, the method comprises annealing a primer to a template nucleic acid molecule, thereby generating an annealed template nucleic acid molecule. In some instances, the method further comprises mixing, in the presence of nucleotides, the annealed template nucleic acid molecule, a one or more acceptor nucleic acid molecules, and a modified reverse transcriptase. In some instances, the modified reverse transcriptase generates a plurality of continuous complementary deoxyribonucleic acid molecules. In some instances, the plurality of continuous complementary deoxyribonucleic acid molecules are prepared in at most about 2 hours. In some instances, the plurality of continuous complementary deoxyribonucleic acid molecules is generated by having the modified reverse transcriptase reverse transcribe a sequence of the annealed template nucleic acid molecule. In some instances, the modified reverse transcriptase then migrates to an acceptor nucleic acid molecule (e.g., one or more acceptor nucleic acid molecules). In some instances, the reverse transcriptase (e.g., modified reverse transcriptase) is able to reverse transcribe a sequence of the template and/or the acceptor nucleic acid molecule at a temperature of from about 12° C. to about 42° C. In some instances, the reverse transcriptase (e.g., modified reverse transcriptase) is able to reverse transcribe a sequence of the template and/or the acceptor nucleic acid molecule at a temperature of from about 8° C. to about 50° C. (e.g., about 8° C., about 15° C., about 20° C., about 25° C., about 30° C., about 35° C., about 40° C., about 45° C., about 48° C.). In some instances, the reverse transcriptase (e.g., modified reverse transcriptase) is able to reverse transcribe a sequence of the template and/or the acceptor nucleic acid molecule at a temperature of at most about 4° C., at most about 8° C., at most about 15° C., at most about 20° C., at most about 25° C., at most about 30° C., at most about 35° C., at most about 40° C., at most about 45° C., or at most about 48° C. In some instances, reverse transcription occurs at an error rate of at most about 5%. In some instances, the reverse transcriptase (e.g., modified reverse transcriptase) is capable of reverse transcribing the template and/or the acceptor nucleic acid molecule at an error rate of at most about 45%, at most about 40%, at most about 35%, at most about 30%, at most about 25%, at most about 20%, at most about 15%, at most about 10%, at most about 8%, at most about 7%, at most about 6%, at most about 5%, at most about 4%, at most about 3%, at most about 2%, or at most about 1%. In some instances, the reverse transcriptase (e.g., modified reverse transcriptase) can migrate from the template to the acceptor nucleic acid molecule independently of sequence identity between the template and the acceptor nucleic acid molecule. In some instances, the method is prepared in a single vessel. In some instances, the template nucleic acid molecule is a fragmented DNA template, a fragmented RNA template, a non-fragmented DNA template, a non-fragmented RNA template, or a combination thereof. In some instances, the method further comprises adding a tag to a template nucleic acid molecule, thereby generating a plurality of tagged continuous complementary deoxyribonucleic acid molecules. In some instances, the method further comprises performing a polymerase chain reaction amplification reaction, thereby forming one or more amplicons.

The present disclosure relates to methods for preparing a complementary deoxyribonucleic acid (cDNA) molecule using a modified reverse transcriptase. In some instances, the method for preparing a cDNA molecule is via template jumping. In some instances, the modified reverse transcriptase has an improved enzyme property compared to a naturally occurring or unmodified or wild type enzyme (e.g., wild type reverse transcriptase). In some instances, the method for preparing a cDNA molecule comprises: (a) annealing a primer to a template; and (b) mixing, in the presence of nucleotides (e.g., dNTPs), the template annealed to the primer with a modified reverse transcriptase and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the enzyme (e.g., modified reverse transcriptase) generates a continuous cDNA molecule by migrating from the template to the acceptor nucleic acid molecule. In some instances, template jumping is independent of sequence identity between the template and the acceptor nucleic acid molecule. In some instances, step (a) and step (b) are done at the same time. In some instances, step (a) comprises step (b) (e.g., step (a) and step (b) are merged into one step). In some instances, at least one of step (a) and/or step (b) further comprises addition of a hot start thermostable polymerase. In some instances, the method of the present disclosure is performed in a single tube. In some instances, the method of the present disclosure further comprises a polymerase chain reaction (PCR) amplification reaction. In some instances, the PCR amplification reaction is performed in a single tube (e.g., the same one tube from steps (a) and (b)). In some instances, all the steps of the method of the present disclosure are performed in a single tube.

The present disclosure relates to a method for preparing a concatemer of nucleic acid molecules for sequencing. In some instances, the method comprises ligating a nucleic acid molecule with a first adaptor. In some instances, the method further comprises amplifying the ligated nucleic acid molecule by performing a nucleic acid amplification reaction to form a concatemer. In some instances, the amplification reaction is performed in the absence of a primer. In some instances, the method further comprises ligating the concatemer with a second adaptor. In some instances, the adaptor(s) (first and/or second adaptor) is/are designed to allow recombination or homology based annealing and extension of molecules (e.g., nucleic acid molecules, and/or a template, and/or a primer, and/or an acceptor). In some instances, the nucleic acid amplification reaction is polymerase chain reaction (PCR) or isothermal amplification. In some instances, the first adaptor comprises a unique molecular identifier (UMI) sequence. In some instances, the first adaptor serves as a primer. In some instances, the first adaptor comprises single stranded nucleic acid. In some instances, the single stranded nucleic acid comprises single stranded DNA (ssDNA). In some instances, the second adaptor comprises double stranded nucleic acid. In some instances, the double stranded nucleic acid comprises double stranded DNA (dsDNA). In some instances, the first adaptor is different from the second adaptor. In some instances, the first adaptor comprises two or more adaptors. In some instances, the second adaptor comprises two or more adaptors. In some instances, both ends of the nucleic acid molecule comprise an adaptor. In some instances, only one end of the nucleic acid molecule comprises an adaptor. In some instances, both the 3' and the 5' ends of a nucleic acid molecule comprise an adaptor.

The present disclosure relates to methods for preparing a complementary deoxyribonucleic acid (cDNA) molecule using a modified reverse transcriptase. In some instances, the method for preparing a cDNA molecule is via template jumping. In some instances, the modified reverse transcriptase has an improved enzyme property compared to a naturally occurring or unmodified or wild type enzyme (e.g., wild type reverse transcriptase). In some instances, the method for preparing a cDNA molecule comprises mixing, in the presence of nucleotides (e.g., dNTPs), a primer, a template, a modified reverse transcriptase and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the method comprises addition of a hot start thermostable polymerase (e.g., to the mixing step). In some instances, the method of the present disclosure is performed in a single tube. In some instances, the method of the present disclosure further comprises a polymerase chain reaction (PCR) amplification reaction. In some instances, the PCR amplification reaction is performed in a single tube (e.g., the same one tube as the mixing step). In some instances, all the steps of the method of the present disclosure is performed in a single tube (single vessel).

In some instances, the method for preparing a cDNA molecule comprises: (a) annealing one or more primer(s) to a template; and (b) mixing, in the presence of nucleotides (e.g., dNTPs), the template annealed to one or more primer(s) with a modified reverse transcriptase and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the method for preparing a cDNA molecule is via template jumping. In some instances, step (a) and step (b) are done at the same time. In some instances, step (a) comprises step (b) (e.g., step (a) and step (b) are merged into one step). In some instances, at least one of step (a) and/or step (b) further comprises addition of a hot start thermostable polymerase. In some instances, the method of the present disclosure is performed in a single tube. In some instances, the method of the present disclosure further comprises a polymerase chain reaction (PCR) amplification reaction. In some instances, the PCR amplification reaction is performed in a single tube (e.g., the same one tube used in or from steps (a) and (b)). In some instances, all the steps of the method of the present disclosure is performed in a single tube (i.e. one-pot or single pot).

In some instances, the method for preparing a cDNA molecule comprises mixing, in the presence of nucleotides (e.g., dNTPs), one or more primer(s), a template, a modified reverse transcriptase, and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the method for preparing a cDNA molecule is via template jumping. In some instances, the method comprises addition of a hot start thermostable polymerase (e.g., to the mixing step). In some instances, the method of the present disclosure is performed in a single tube. In some instances, the method of the present disclosure further comprises a polymerase chain reaction (PCR) amplification reaction. In some instances, the PCR amplification reaction is performed in a single tube (e.g., the same one tube as the mixing step). In some instances, all the steps of the method of the present disclosure is performed in a single tube.

ssDNA Sponges for RNA Depletion

Ribosomal RNAs can makeup as much as 80% or more of the total RNA in a sample. It is often desirable to separate mRNA from rRNA because rRNA can adversely affect the quantitative analysis of mRNA. One approach to separating rRNA from the other RNA biotypes, including mRNA, miRNA, lncrna, and lincRNA is to deplete the rRNA from the sample. One example is the hybridization of rRNA molecules using oligonucleotides, for example, oligonucleotides homologous to the 5.8S rRNA, 17S rRNA, 18S rRNA, or 28S rRNA in the case of eukaryotic rRNAs, or to the 5S rRNA, 16S rRNA, or 23S rRNA in the case of bacterial rRNA. The oligonucleotides are designed such that they can be "captured" and the hybridization product removed from the sample. For example, the oligonucleotides may be immobilized on a surface such as a column or a bead. MICROBExpress (Registered Trademark) and MICROBEnrich (Registered Trademark) (Ambion, Austin, Tex.) are examples of commercially available kits for the depletion of rRNA. Methods and compositions for the depletion or rRNA from a sample are described in U.S. application Ser. No. 10/029,397, which is incorporated by reference. The poly(A) tail at the 3' end of most eukaryotic mRNAs can be used to separate these molecules away from rRNA and other non-mRNA species that lack this poly(A) tail.

Rather than removing the rRNA from samples, in some instances, the method of the present disclosure contemplates blocking the RNA from any potential amplification or additional reaction. In some instances, the disclosure provides a method for processing a sample comprising messenger ribonucleic acid (mRNA), ribosomal ribonucleic acid (rRNA) molecules, microRNAs (miRNA), long non-coding RNAs (lncRNA), long intergenic noncoding RNAs (lincRNA), and other RNA biotypes, including comprising using said mRNA molecules or other RNA biotypes, including miRNA, lncRNA, and lincRNA, to synthesize complementary deoxyribonucleic acid (cDNA) molecules in presence of said rRNA molecules blocked from transcription, such that less than 30% of said cDNA molecules comprise sequences from said rRNA molecules.

In some aspects, the disclosure provides a method for processing a sample comprising messenger ribonucleic acid (mRNA) and ribosomal ribonucleic acid (rRNA) molecules; comprising using said mRNA molecules to synthesize complementary deoxyribonucleic acid (cDNA) molecules in presence of said rRNA molecules blocked from transcription, such that less than 30% of said cDNA molecules comprise sequences from said rRNA molecules.

Figure 5A:
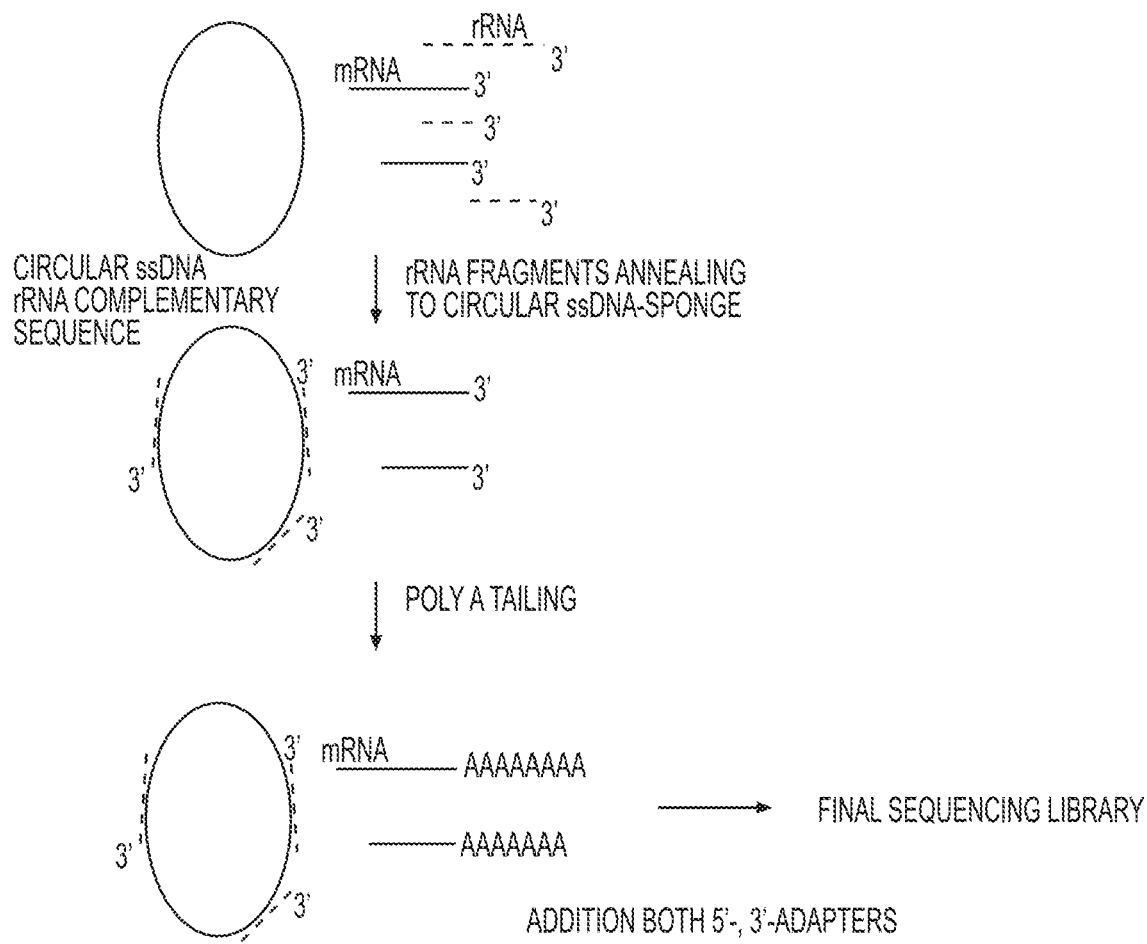
FIG. 5A illustrates a method for rRNA sequence depletion as described in the present disclosure whereas the rRNA depletion is integrated into the process of sample preparation. This figure illustrates the different steps of the procedure whereby during or right after RNA sample fragmentation, the ssDNA (DNA-sponge), which is complementary to rRNA, is included in the library preparation reaction. DNA-sponges are large ssDNA fragments that are at least partially complementary to a sequence of an rRNA subunit.
Figure 5B:
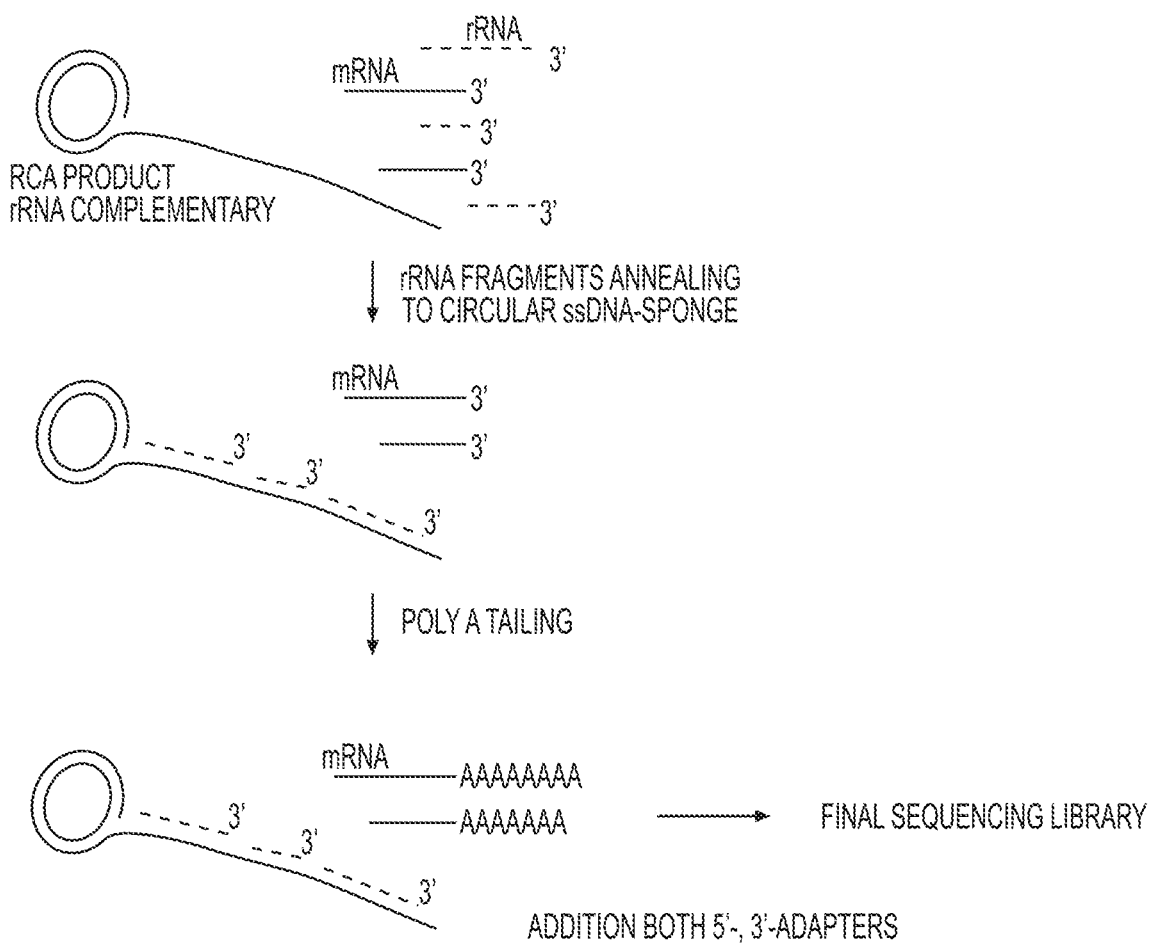
FIG. 5B illustrates a method for rRNA sequence depletion as described in the present disclosure and illustrated in FIG. 5A.
Figure 6:
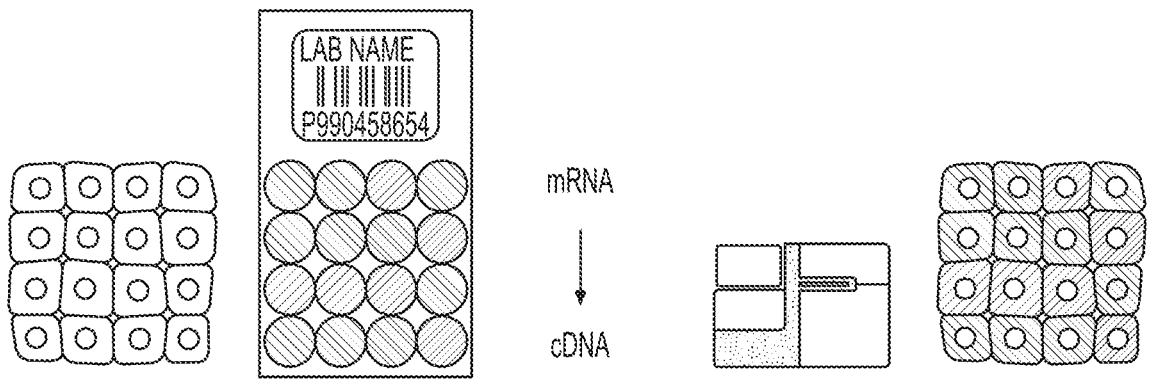
FIG. 6 illustrates the ability of in situ RNA-seq to allow genome-wide profiling of gene expression in situ in fixed cells and tissues. This figure illustrates the steps of in situ RNA-seq whereby RNA is converted into cDNA and either directly sequenced using single-molecule method or converted to a sequencing library. This figure also illustrates the spatial-specific barcoding technique in which a glass plate with printed barcoded primer oligonucleotide is used.

In some aspects, the disclosure provides a method for processing a mixture comprising a messenger ribonucleic acid (mRNA) and a ribosomal ribonucleic (rRNA) molecule, comprising: in said mixture, fragmenting said ribosomal ribonucleic (rRNA) molecule to yield a plurality of rRNA fragments; bringing one or more single stranded nucleic sequences in contact with said plurality of rRNA fragments, which one or more single-stranded nucleic acids sequences have complementarity with at least a subset of said rRNA fragments, thereby providing one or more rRNA fragment complexes comprising said one or more single-stranded nucleic acids sequences hybridized to said at least said subset of said rRNA fragments; and using a reverse transcriptase to synthesize at least one complementary deoxyribonucleic acid (cDNA) molecule from said mRNA in presence of said one or more rRNA fragment complexes (FIGS. 5 and 6).

In some aspects, the complementary to rRNA ssDNA (DNA-sponge) has a linear form with blocked 3' ends. In some instances, the DNA-sponge has a circular form. In some instances, the DNA-sponge is concatemerized. FIG. 5 illustrates a DNA-sponge with a circular form, whereas FIG.

5B illustrates a rolling-circle amplification (RCA) product. This figure illustrates the function of the DNA-sponge, which is to anneal to rRNA fragments. The annealing of the rRNA fragments to large complementary ssDNA make the 3'-end of the rRNA fragment not available to Poly A polymerase or to 3'-priming by R2 enzyme. As such, rRNA fragments without available 3'-ends will not be converted to the sequencing library, as illustrated in FIG. 5.

Direct RNA and ssDNA Sequencing with R2 Enzyme

In some aspects, the disclosure provides a method for sequencing a single stranded nucleic acid molecule, comprising providing a reaction mixture comprising said single stranded nucleic acid molecule and a non-naturally occurring enzyme, wherein said non-naturally occurring enzyme comprises a finger domain derived from an R2 retrotransposon, a plam domain derived from an R2 retrotransposon, a thumb domain derived from an R2 retrotransposon; and an endonuclease domain derived from an R2 retrotransposon. In some instances, the method disclosed herein comprises subjecting said reaction mixture to conditions sufficient to use said non-naturally occurring enzyme to incorporate individual nucleotides into a growing strand complementary to said single stranded nucleic acid molecule, wherein incorporation of said individual nucleotides into said growing strand yields detectable signals. In some instances, the method disclosed herein comprises detecting said detectable signals, thereby sequencing said single stranded nucleic acid molecule.

In some aspects, the disclosure provides a method for sequencing a single stranded nucleic acid molecule, wherein the said single stranded nucleic acid molecule is an RNA molecule. In some instances, the method disclosed herein is for sequencing a single stranded nucleic acid molecule, wherein the single stranded nucleic acid molecule is a single stranded DNA molecule.

In some aspects, the disclosure provides a method for sequencing a single stranded nucleic acid molecule, wherein said conditions sufficient to directly sequence said single stranded nucleic acid molecule comprise optic based single-molecule sequencing conditions.

In some aspects, the disclosure provides a method for sequencing a single stranded nucleic acid molecule, wherein said conditions sufficient to directly sequence said single stranded nucleic acid molecule comprise microscopy based single-molecule sequencing conditions.

In some aspects, the disclosure provides a method for sequencing a single stranded nucleic acid molecule, wherein said conditions sufficient to directly sequence said single stranded nucleic acid molecule comprise nanopore based single-molecule sequencing conditions.

In some aspects, the disclosure provides a method for sequencing a single stranded nucleic acid molecule, wherein said conditions sufficient to directly sequence said single stranded nucleic acid molecule comprise field-effect transistors based single-molecule sequencing conditions.

Common single-molecule sequencing techniques are based on long-reads, whereby several kb fragments are read in one continuous read. In some aspects, the disclosure provides a method whereby the enzyme disclosed herein is capable of efficient template jumping, whereby a large number of templates can be sequenced in a single continuous sequencing run.

In Situ RNAseq with Non-Naturally Occurring Enzymes

Unlike in situ RNA-sequencing, conventional RNA-sequencing profiles gene expression over the whole transcriptome, yet still lacks spatial context. In situ RNA sequencing, however, allows genome-wide profiling of gene expression in situ in fixed cells and fixed tissue (FIG. 6).

In some aspects, the disclosure provides a method comprising preparing a complementary deoxyribonucleic acid (cDNA) molecule from one or more ribonucleic acid (RNAs), wherein said one or more ribonucleic acid (RNAs) are derived from an in situ tissue of a subject or from a fixed ex vivo tissue of said subject with a non-naturally occurring enzyme, wherein said non-naturally occurring enzyme comprises a palm and finger domain derived from an R2 retrotransposon, a palm domain derived from an R2 retrotransposon, a thumb domain derived from an R2 retrotransposon, and an endonuclease domain derived from an R2 retrotransposon; thereby generating a cDNA molecule from said in situ tissue of said subject or from said fixed ex vivo tissue of said subject; and sequencing the said cDNA molecule generated in with the non-naturally occurring enzyme disclosed herein.

In some aspects, the disclosure provides a method comprising preparing a complementary deoxyribonucleic acid (cDNA) molecule from one or more ribonucleic acid (RNAs), wherein said one or more ribonucleic acid (RNAs) are derived from an in situ tissue of a subject or from a fixed ex vivo tissue of said subject with a non-naturally occurring enzyme, wherein said fixed ex vivo tissue of said subject is fixed in formaldehyde.

In some aspects, the disclosure provides a method comprising preparing a complementary deoxyribonucleic acid (cDNA) molecule from one or more ribonucleic acid (RNAs), wherein said one or more ribonucleic acid (RNAs) are derived from an in situ tissue of a subject or from a fixed ex vivo tissue of said subject with a non-naturally occurring enzyme, wherein said fixed ex vivo tissue of said subject is fixed and embedded in paraffin.

In some aspects, the method disclosed herein consists of cDNA that is tagged with a barcode, including but not limited to spatial information (FIG. 6). The said cDNA can then be converted to a sequencing library. In some instances, the spatial-specific barcoding technique consists of using a glass plate with oligonucleotide primers that are printed in a spatial-specific manner. In some instances, the primer used in the method disclosed herein is a specifically-barcoded polyT oligonucleotide. In some aspects, the method disclosed herein is highly sensitive and can operate with very low sample input. In some aspects, the method disclosed herein has a protocol where a random primer is used. In some instances, the method disclosed herein has a protocol where a specific primer is used.

In some instances, a biological sample has been purified. In some instances, a biological sample has not been purified. In some instances, the nucleic acid of a biological sample has not been extracted when the biological sample is provided to a tube. For example, the RNA or DNA in a biological sample may not be extracted from the biological sample when providing the biological sample to a tube. In some instances, a target nucleic acid (e.g., a target RNA or target DNA) present in a biological sample may not be concentrated prior to providing the biological sample to a reaction vessel (e.g., a tube). Any suitable biological sample that comprises nucleic acid may be obtained from a subject.

In some instances, nucleic acid from a biological sample obtained from a subject is amplified. In some cases, the biological sample is obtained directly from the subject. In some instances, a biological sample obtained directly from a subject refers to a biological sample that has been further processed after being obtained from the subject. In some instances, a biological sample obtained directly from a subject refers to a biological sample that has not been further processed after being obtained from the subject, with the exception of any approach used to collect the biological sample from the subject for further processing. For example, blood is obtained directly from a subject by accessing the subject's circulatory system, removing the blood from the subject (e.g., via a needle), and entering the removed blood into a receptacle. The receptacle may comprise reagents (e.g., anti-coagulants) such that the blood sample is useful for further analysis. In another example, a swab may be used to access epithelial cells on an oropharyngeal surface of the subject. After obtaining the biological sample from the subject, the swab containing the biological sample can be contacted with a fluid (e.g., a buffer) to collect the biological fluid from the swab.

The present disclosure relates to methods of detecting, diagnosing, and/or prognosing a disease (e.g., cancer) in a subject comprising: (a) obtaining sequence information of a nucleic acid sample (e.g., a cell-free nucleic acid sample) derived from a subject and (b) using the sequence information derived from step (a) to detect circulating tumor nucleic acid in the sample. In some instances, obtaining sequence information according to step (a) comprises using one or more adaptor(s). In some instances, the one or more adaptor(s) comprises a molecular barcode. An adaptor can comprise one or more end modifications. An adaptor can comprise one 5' phosphate. An adaptor can comprise two 5' phosphates. An adaptor can comprise one 3' hydroxyl. An adaptor can comprise two 3' hydroxyls. An adaptor can lack a 3' hydroxyl.

In some instances, the molecular barcode comprises a randomer sequence. In some instances, the method is capable of detecting cell-free nucleic acid that is less than or equal to about 0.75%, 0.50%, 0.25%, 0.1%, 0.9%, 0.8%, 0.7%, 0.6%, 0.5%, 0.4%, 0.3%, 0.2%, 0.1%, 0.05%, 0.01%, 0.009%, 0.008%, 0.007%, 0.006%, 0.005%, 0.004%, 0.003%, 0.002%, 0.001%, 0.0005%, or 0.00001%, 1%, 1.75%, 1.5%, 1.25%, 2%, 3%, 4%, 5%, 6%, 8%, 9%, 10%, 11%, 12%, 13%, 14% 15%, 16%, 17%, 18%, 19%, 20%, 22%, 25%, 27%, 30%, 32%, 35%, 40%, 45%, 50%, 55%, 60%, 65%, 70%, 75%, 80%, 85%, 90%, 95%, or 100% of total cell-free nucleic acid. In some instances, the method is capable of detecting circulating tumor nucleic acid that is less than or equal to about 0.75%, 0.50%, 0.25%, 0.1%, 0.9%, 0.8%, 0.7%, 0.6%, 0.5%, 0.4%, 0.3%, 0.2%, 0.1%, 0.05%, 0.01%, 0.009%, 0.008%, 0.007%, 0.006%, 0.005%, 0.004%, 0.003%, 0.002%, 0.001%, 0.0005%, or 0.00001%, 1%, 1.75%, 1.5%, 1.25%, 2%, 3%, 4%, 5%, 6%, 8%, 9%, 10%, 11%, 12%, 13%, 14% 15%, 16%, 17%, 18%, 19%, 20%, 22%, 25%, 27%, 30%, 32%, 35%, 40%, 45%, 50%, 55%, 60%, 65%, 70%, 75%, 80%, 85%, 90%, 95%, or 100% of total circulating nucleic acid. In some instances, the method is capable of detecting a percentage of circulating tumor nucleic acid (ct nucleic acid) that is less than or equal to 1.75%, 1.5%, 1.25%, 1%, 0.75%, 0.50%, 0.25%, 0.1%, 0.9%, 0.8%, 0.7%, 0.6%, 0.5%, 0.4%, 0.3%, 0.2%, 0.1%, 0.05%, 0.01%, 0.009%, 0.008%, 0.007%, 0.006%, 0.005%, 0.004%, 0.003%, 0.002%, 0.001%, 0.0005%, or 0.00001% of the total cell-free nucleic acid. In some instances, the sequence information comprises information related to at least about 1, 2, 3, 4, 5, 6, 7, 8, 9, 10, 15, 20, 25, 30, 35, 40, 50, 70, 80, 100, 200, or 300 genomic regions. In some instances, the sequence information comprises information related to partially all, mostly all, or all genome sequencing. In some instances, concentrations as low as 50 ng of cfDNA may provide for full genome sequencing.

In some instances, the method of the present disclosure may be used to determine the presence of a disease (e.g., cancer) in a subject. In some instances, determining the presence of cancer in a subject comprises obtaining a sample from a subject and detecting a nucleic acid molecule (e.g., nucleic acid fragment) in the sample according to any of the methods described herein. In some instances, determining the presence of a disease (e.g., cancer) in a subject comprises amplifying and/or sequencing the nucleic acid molecule. In some instances, the presence of a nucleic acid molecule is indicative of cancer. In some instances, the presence of a nucleic acid molecule is indicative of a prenatal condition. In some instances, the nucleic acid molecule and/or template comprises an unknown sequence. In some instances, the sample is a biological sample. In some instances, the biological sample comprises circulating tumor DNA. In some instances, the biological sample comprises a tissue sample.

In some instances, the method of the present disclosure comprises detecting an amplicon generated by the amplification primers, wherein the presence of the amplicon determines whether the modified reverse transcriptase is present in the sample.

In some instances, the method of the present disclosure comprises providing a prenatal diagnosis based on the presence or absence of a nucleic acid molecule (e.g., cDNA molecule).

Preparations of RNA Libraries for Sequencing

In some aspects, the disclosure provides a method for preparing a complementary deoxyribonucleic acid (cDNA) molecule comprising fragmenting a ribonucleic acid (RNA) molecule to yield a plurality of RNA fragments; removing a 3'-phosphate, a 2'-phosphate, and a cyclic 2'3'-phosphate group from one or more of said RNA fragments, thereby generating one or more dephosphorylated fragmented rRNAs; adding a poly-A tail to said one or more dephosphorylated fragmented RNAs; adding, to said one or more dephosphorylated fragmented RNAs: a primer adapter comprising an oligo-T sequence, a poly-T and another adapter sequence compatible with major sequencing technologies; an acceptor adapter; and a non-naturally occurring R2 enzyme having a processivity of 20 nucleotides or longer.

In some aspects, the disclosure provides a method for preparing a complementary deoxyribonucleic acid (cDNA) molecule, comprising a non-naturally occurring R2 enzyme, wherein said non-naturally occurring R2 enzyme reverse transcribes a sequence from said one or more dephosphorylated fragmented RNAs in a 3' to 5' order, wherein said R2 enzyme jumps to a 3'-end of said acceptor adapter upon reaching the 5' end of said one or more dephosphorylated fragmented RNAs.

Figure 9:
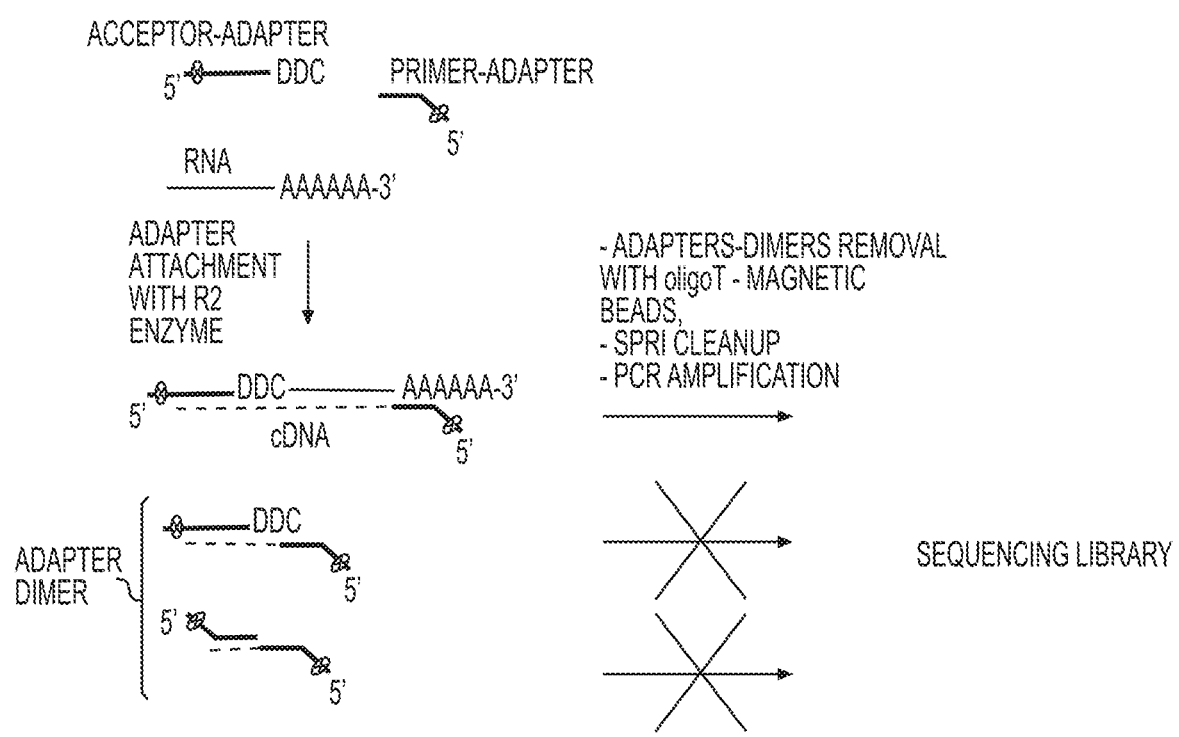
FIG. 9 illustrates the library product and adapter-dimer artifacts that can be generated in the reaction with the R2 enzyme. The adapter dimers artifacts including acceptor extension are prevented by 3'-dideoxy nucleotide at the acceptor-adapter 3'-end (alternatively different extension blockers can be applied like 3'phospho-dNTP, 3'amino-dNTP). The artifacts primed by primer-adapter (including poly-T sequence) are removed from the reaction with oligo-A attached to magnetic beads. The artifacts are primed without annealing (template primer duplex formation) so the primer sequence remained single-stranded.

In some aspects, the method disclosed herein consists of acceptor-adapter that comprises a nucleotide analogue (FIG. 9). In some instances, the said nucleotide analogue is at the 5' end of said acceptor-adapter. In some instances, the said acceptor-adaptor comprises a 3'-dideoxy nucleotide at the acceptor-adapter 3'-end.

Figure 10:
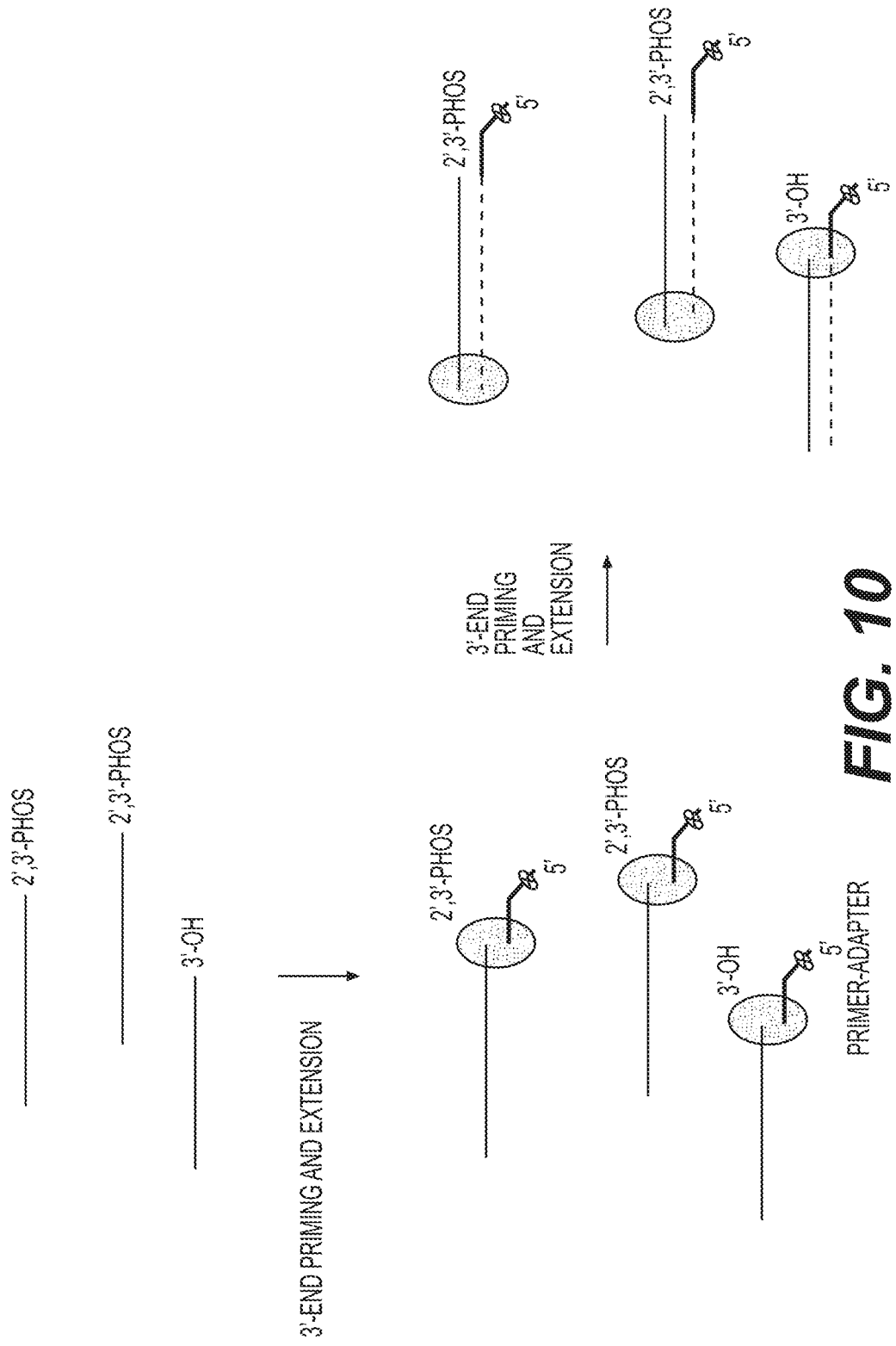
FIG. 10 illustrates 3'-end priming and extension with ssDNA primer-adapter and R2. In this mechanism, extension is primed on the 3'-end of the template by ssDNA primer without complementary sequence annealing to the template. This figure illustrates that the library products are a full length copy of the template.
Figure 11:
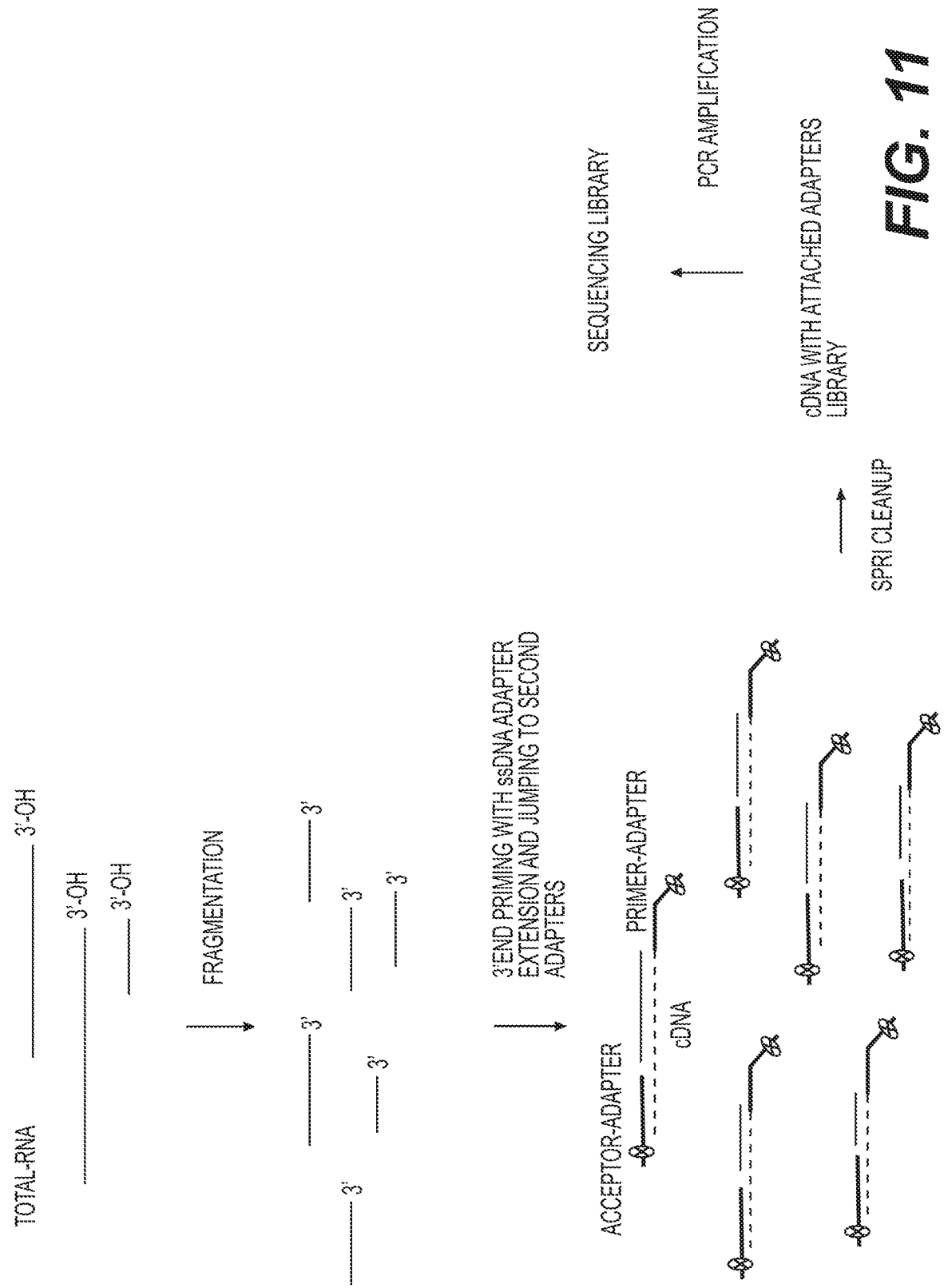
FIG. 11 illustrates a method of random priming by random fragmentation. This figure illustrates the first step, whereby the RNA sample is fragmented. This figure also illustrates the second step, whereby the RNA sample is mixed with primer-adapter (ssDNA), R2 enzyme, and acceptor-adaptor (ssDNA or RNA). The figure illustrates the third step, the cleanup by solid phase reversible immobilization (SPRI), whereby size selection is used to remove some adapter-adapter dimer artifacts. The figure illustrates the last step, which is a polymerase chain reaction (PCR) amplification using primer complementary to both the primer- and the acceptor-adapter.
Figure 12:
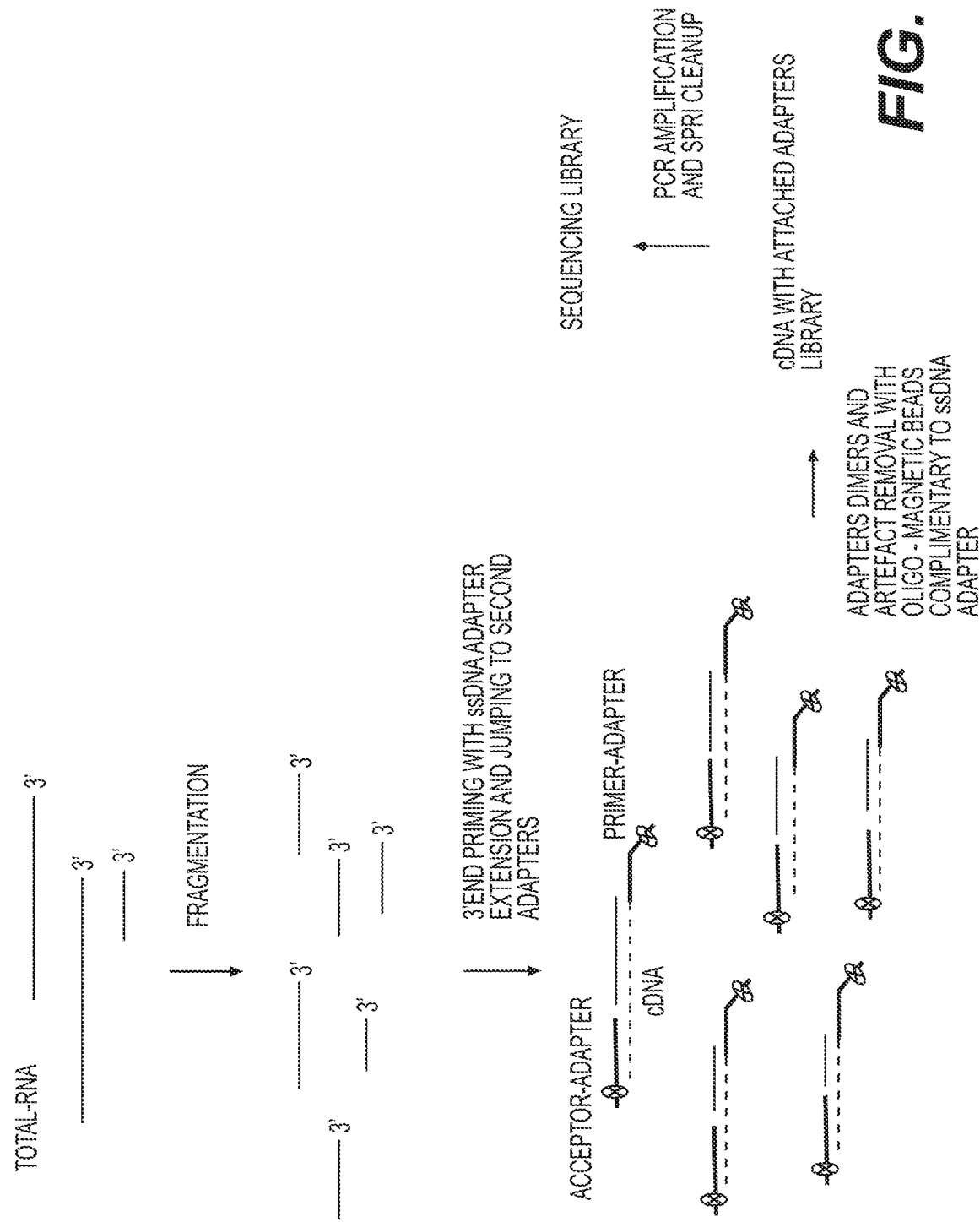
FIG. 12 illustrates the same method described in FIG. 11, however, with a different cleanup reaction. This figure illustrates the fragmentation step, the 3'-end priming, and finally the cleanup reaction, whereby adapter dimers and artifacts are removed with oligo-magnetic beads complementary to the ssDNA adapter.
Figure 13:
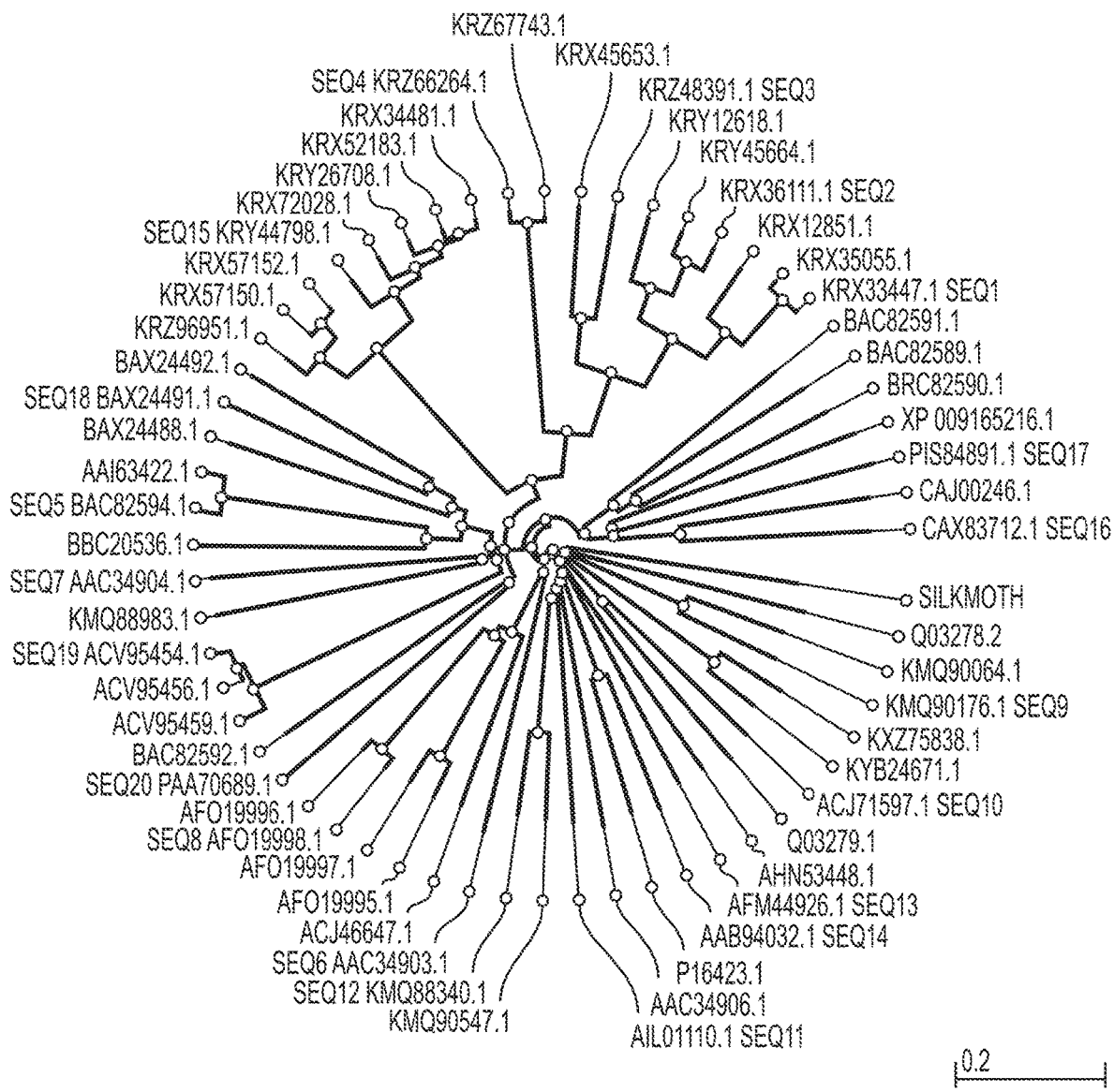
FIG. 13 illustrates a phylogenic tree, which highlights the inferred evolutionary relationships between non-LTR retroelements and silkmoth, here with a minimum 27% identity to silkmoth, and R2 retrotransposon focused on fragments of RT-endonuclease.
Figure 20:
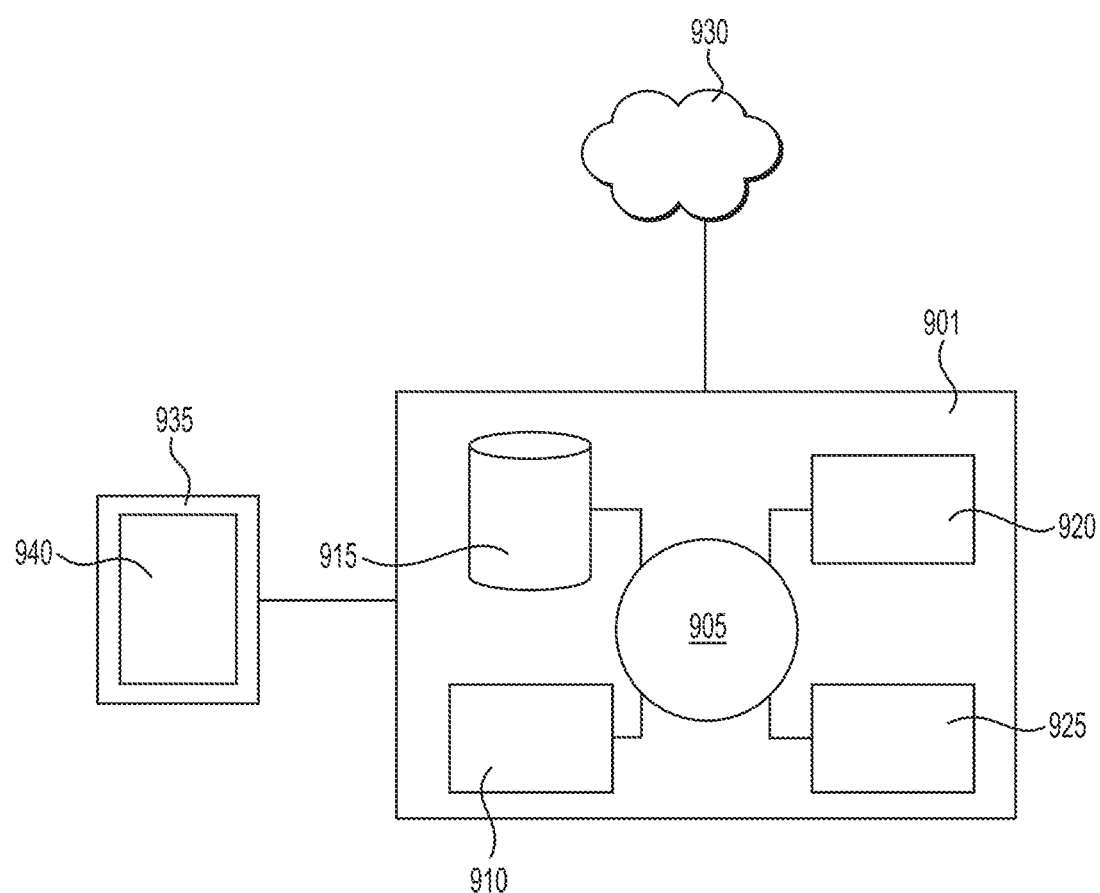
FIG. 20 illustrates a computer system that is programmed or otherwise configured to implement methods provided herein.

In some aspects, the method disclosed herein comprises a non-naturally occurring R2 enzyme, wherein said non-naturally occurring R2 enzyme reverse transcribes a sequence from said one or more fragmented RNAs in a 3' to 5' order, wherein said R2 enzyme jumps to a 3'-end of said acceptor adapter upon reaching the 5' end of said one or more fragmented RNAs (FIGS. 10, 11, and 12).

In some instances, a primer may comprise an adaptor sequence. In some instances, the 5' tail sequence of a primer comprises a sequence which does not hybridize to a target (the adaptor sequence). The adapter sequence may be selected such that it is the same in a variety of primers which have different 3' target binding sequences (i.e., a "universal" 5' tail sequence). The adapter sequence is compatible with major sequencing technologies including but not limited to, Illumina, Ion Torrent, PacBio, and Roche 454. This allows a single reporter probe sequence to be used for detection of any desired target sequence, which is an advantage in that synthesis of the reporter probe is more complex due to the labeling. In some instances, a primer may comprise an RNA primer. In some instances, a primer may comprise a DNA primer. In some instances, a primer may comprise an R2 RNA primer. In some instances, a primer may comprise one or more random primer(s).

The present disclosure relates to methods for preparing a nucleic acid molecule comprising: mixing, in the presence of nucleotides (e.g., dNTPs), a fragment or degraded template (e.g., a nucleic acid fragment), a primer, a modified reverse transcriptase, and an acceptor nucleic acid molecule under conditions sufficient to generate a nucleic acid molecule. In some instances, the acceptor nucleic acid molecule comprises a modified nucleotide. In some instances, the primer extension stops at the modified nucleotide. In some instances, the modified reverse transcriptase comprises at least one improved enzyme property relative to a wild type, naturally occurring, or unmodified reverse transcriptase. In some instances, the primer is an RNA primer. In some instances, the primer is an engineered primer (e.g., engineered RNA primer). In some instances, the primer has been optimized. In some instances, the primer is an optimized and/or engineered primer (e.g., optimized and/or engineered RNA primer). In some instances, the primer is RNA R2 primer. In some instances, the method for preparing a nucleic acid molecule is via template jumping. In some instances, the mixing step of the method of the present disclosure further comprises addition of a hot start thermostable polymerase. In some instances, the method of the present disclosure is performed in a single tube. In some instances, the method of the present disclosure further comprises a polymerase chain reaction (PCR) amplification reaction. In some instances, the PCR amplification reaction is performed in the same single tube. In some instances, all the steps of the method of the present disclosure is performed in a single tube.

The present disclosure relates to methods for preparing a nucleic acid molecule comprising: mixing, in the presence of nucleotides (e.g., dNTPs), a fragment or degraded template (e.g., a nucleic acid fragment), a donor complex, a modified reverse transcriptase, and an acceptor nucleic acid molecule under conditions sufficient to generate a nucleic acid molecule. In some instances, the acceptor nucleic acid molecule comprises a modified nucleotide. In some instances, the primer extension stops at the modified nucleotide. In some instances, the modified reverse transcriptase comprises at least one improved enzyme property relative to a wild type or naturally occurring or unmodified reverse transcriptase. In some instances, the donor complex comprises a template and a primer. In some instances, the donor complex is a donor R2 complex. In some instances, the donor R2 complex comprises an RNA R2 primer. In some instances, the method for preparing a nucleic acid molecule is via template jumping. In some instances, the mixing step of the method of the present disclosure further comprises addition of a hot start thermostable polymerase. In some instances, the method of the present disclosure is performed in a single tube. In some instances, the method of the present disclosure further comprises a polymerase chain reaction (PCR) amplification reaction. In some instances, the PCR amplification reaction is performed in the same single tube (e.g., the same single tube used to prepare a nucleic acid molecule). In some instances, all the steps of the method of the present disclosure is performed in a single tube.

The present disclosure relates to methods for preparing a complementary deoxyribonucleic acid (cDNA) library using a modified reverse transcriptase. In some instances, the method for preparing a cDNA library uses template jumping. In some instances, the modified reverse transcriptase has an improved enzyme property compared to a naturally occurring or wild type or unmodified enzyme (e.g., wild type reverse transcriptase). In some instances, the method for preparing a cDNA library comprises: (a) annealing a primer or one or more primer(s) to a template; and (b) mixing, in the presence of nucleotides (e.g., dNTPs), the template annealed to the primer or the template annealed to one or more primer(s) with a modified reverse transcriptase and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the method for preparing a cDNA library comprises mixing, in the presence of nucleotides (e.g., dNTPs), a primer or one or more primer(s), a template, a modified reverse transcriptase, and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the enzyme (e.g., modified reverse transcriptase) generates a continuous cDNA molecule by migrating from the template to the acceptor nucleic acid molecule. In some instances, template jumping is independent of sequence identity between the template and the acceptor nucleic acid molecule. In some instances the method further comprises amplifying the cDNA molecule to generate a cDNA library. In some instances, step (a) and step (b) are done at the same time. In some instances, step (a) comprises step (b) (e.g., step (a) and step (b) are merged into one step). In some instances, the mixing step or at least one of step (a) and/or step (b) further comprises addition of a hot start thermostable polymerase. In some instances, the method of the present disclosure is performed in a single tube. In some instances, the method of the present disclosure further comprises a polymerase chain reaction (PCR) amplification reaction. In some instances, the PCR amplification reaction is performed in a single tube (e.g., the same one tube used in or from the mixing step, or in or from steps (a) and (b)). In some instances, all the steps of the method of the present disclosure is performed in a single tube.

The present disclosure relates to methods for preparing a cDNA and/or DNA library comprising: mixing, in the presence of nucleotides (e.g., dNTPs), a fragment or degraded template (e.g., a nucleic acid fragment), a primer, a modified reverse transcriptase, and an acceptor nucleic acid molecule under conditions sufficient to generate a nucleic acid (e.g., cDNA and/or DNA) molecule. In some instances, the acceptor nucleic acid molecule comprises a modified nucleotide. In some instances, the primer extension stops at the modified nucleotide. In some instances, the modified reverse transcriptase comprises at least one improved enzyme property relative to a wild type or unmodified reverse transcriptase. In some instances, the primer is an RNA R2 primer. In some instances, the method further comprises amplifying the nucleic acid (e.g., cDNA and/or DNA) molecule to generate a cDNA library. In some instances, the method for preparing a cDNA and/or DNA and/or nucleic acid molecule is via template jumping.

The present disclosure relates to methods for preparing a cDNA and/or DNA library comprising: mixing, in the presence of nucleotides (e.g., dNTPs), a fragment or degraded template (e.g., a nucleic acid fragment), a donor complex, a modified reverse transcriptase, and an acceptor nucleic acid molecule under conditions sufficient to generate a nucleic acid (e.g., cDNA and/or DNA) molecule. In some instances, the acceptor nucleic acid molecule comprises a modified nucleotide. In some instances, the primer extension stops at the modified nucleotide. In some instances, the modified reverse transcriptase comprises at least one improved enzyme property relative to a wild type or unmodified reverse transcriptase. In some instances, the donor complex comprises a template and a primer. In some instances, the donor complex is a donor R2 complex. In some instances, the donor R2 complex comprises an RNA R2 primer. In some instances, the method further comprises amplifying the nucleic acid (e.g., cDNA and/or DNA) molecule to generate a cDNA and/or DNA library. In some instances, the method for preparing a cDNA and/or DNA and/or nucleic acid molecule is via template jumping.

In some instances, the method of the present disclosure may comprise a donor complex. In some instances, the donor complex comprises a template and a primer. In some instances, the method of the present disclosure may comprise a template. In some instances, the template is a fragmented and/or degraded template. In some instances, the template is not fragmented. In some instances, the template is RNA, DNA, or a combination of DNA and RNA. In some instances, the RNA is mRNA. In some instances, the template is mRNA.

The present disclosure relates to methods for preparing a library for sequencing comprising: (a) obtaining a sample with cell-free nucleic acid from a subject; and (b) adding a modified reverse transcriptase enzyme, a template (e.g., a nucleic acid template), nucleotides, an acceptor nucleic acid molecule, and one or more primer(s) to the nucleic acid. In some instances, the method further comprises conducting an amplification reaction on the cell-free nucleic acid (cf nucleic acid) derived from the sample to produce a plurality of amplicons. In some instances, the amplification reaction comprises 35 or fewer amplification cycles. In some instances, the method comprises producing a library for sequencing. In some instances, the library comprises a plurality of amplicons. In some instances, the modified reverse transcriptase is capable of template jumping and/or comprises at least one improved enzyme property relative to a wild type or unmodified reverse transcriptase. In some instances, the nucleic acid is DNA, RNA, or a combination of RNA and DNA.

The present disclosure relates to a method for preparing a complementary deoxyribonucleic acid (cDNA) molecule using template jumping, comprising mixing, in a single tube, a primer or one or more primer(s), a messenger RNA (mRNA) template, nucleotides, a modified reverse transcriptase, an acceptor nucleic acid molecule, and a catalytic metal under conditions sufficient to generate a continuous cDNA molecule. In some instances, the continuous cDNA molecule is complementary to the mRNA template and/or to the acceptor nucleic acid molecule. In some instances, the modified reverse transcriptase comprises at least one improved enzyme property relative to a wild type or unmodified reverse transcriptase. In some instances, a continuous cDNA molecule is produced. In some instances, the modified reverse transcriptase undergoes migration from the template to the acceptor nucleic acid molecule.

The present disclosure relates to a method for preparing a library for sequencing comprising mixing, in a single tube, a cell-free nucleic acid, a modified reverse transcriptase enzyme, a template, nucleotides, an acceptor nucleic acid molecule, a catalytic metal, and one or more primer(s), under conditions sufficient to generate a library. In some instances, the modified reverse transcriptase comprises at least one improved enzyme property relative to a wild type or unmodified reverse transcriptase.

In some instances, the nucleic acid molecule comprises an unknown nucleic acid sequence. In some instances, the template comprises an unknown nucleic acid sequence. In some instances, the migration from the template to the acceptor nucleic acid molecule is independent of sequence identity between the template and the acceptor nucleic acid molecule. In some instances, the acceptor nucleic acid molecule comprises a modified nucleotide that may cause primer extension to stop. In some instances, the cell-free nucleic acid is cell-free DNA (cfDNA), circulating tumor DNA (ctDNA), and/or formalin-fixed, paraffin-embedded DNA (FFPE DNA), or combinations thereof.

In some instances, a hot start thermostable polymerase may be added to a method of the present disclosure at or prior to any step of the method and/or at the same time that a mixing step takes place. For example, a hot start thermostable polymerase may be added at the same time that the modified reverse transcriptase is added to the reaction. The hot start thermostable polymerase may be added at the same time that the acceptor nucleic acid molecule is added, and/or at the same time that the template, and/or primer, and/or reverse transcriptase, and/or nucleotides is added to the reaction tube. In some instances, the hot start thermostable polymerase is added prior to the start of the PCR reaction. In some instances, the hot start thermostable polymerase is added prior to or at the same time as the RT reaction. In some instances, the hot start thermostable polymerase is hot start taq polymerase. Amplification of target nucleic acids can occur on a bead. In some instances, amplification does not occur on a bead. Amplification can be by isothermal amplification, e.g., isothermal linear amplification. In some instances, a hot start PCR can be performed wherein the reaction is heated to 95° C. e.g., for two minutes prior to addition of a polymerase or the polymerase can be kept inactive until a first heating step in cycle 1. Hot start PCR can be used to minimize nonspecific amplification.

In some instances, the PCR amplification is performed at a temperature sufficient to inactivate the reverse transcriptase enzyme. In some instances, the PCR amplification is performed at a temperature sufficient to activate the hot start thermostable polymerase.

The present disclosure relates to methods of amplifying a cell-free nucleic acid molecule from a sample. In some instances, the sample is a biological sample. In some instances, the cell-free nucleic acid molecule is subjected to nucleic acid amplification comprising a reverse transcriptase (e.g., modified reverse transcriptase). In some instances, the cell-free nucleic acid molecule is subjected to nucleic acid amplification comprising a reverse transcriptase (e.g., modified reverse transcriptase) under conditions that amplify the nucleic acid molecule at a specified processivity. In some instances the processivity is of at least about 80% per base, at least about 81% per base, at least about 82% per base, at least about 83% per base, at least about 84% per base, at least about 85% per base, at least about 86% per base, at least about 87% per base, at least about 88% per base, at least about 89% per base, at least about 90% per base, at least about 91% per base, at least about 92% per base, at least about 93% per base, at least about 94% per base, at least about 95% per base, at least about 96% per base, at least about 97% per base, at least about 98% per base, at least about 99% per base, or at least about 100% per base. In some instances, the processivity is performed at a temperature of about or at most about or at least about 12° C., of about or at most about or at least about 13° C., of about or at most about or at least about 14° C., of about or at most about or at least about 15° C., of about or at most about or at least about 16° C., of about or at most about or at least about 17° C., of about or at most about or at least about 18° C., of about or at most about or at least about 19° C., of about or at most about or at least about 20° C., of about or at most about or at least about 21° C., of about or at most about or at least about 22° C., of about or at most about or at least about 23° C., of about or at most about or at least about 24° C., of about or at most about or at least about 25° C., of about or at most about or at least about 26° C., of about or at most about or at least about 27° C. of about or at most about or at least about 28° C., of about or at most about or at least about 29° C., of about or at most about or at least about 30° C., of about or at most about or at least about 31° C., of about or at most about or at least about 32° C., of about or at most about or at least about 33° C., of about or at most about or at least about 34° C., of about or at most about or at least about 35° C., of about or at most about or at least about 36° C., of about or at most about or at least about 37° C., of about or at most about or at least about 38° C., of about or at most about or at least about 39° C., of about or at most about or at least about 40° C., of about or at most about or at least about 45° C., of about or at most about or at least about 50° C., of about or at most about or at least about 60° C., of about or at most about or at least about 70° C., of about or at most about or at least about 80° C., of about or at most about or at least about 8° C. In some instances the processivity is of at least about 80% per base, at least about 81% per base, at least about 82% per base, at least about 83% per base, at least about 84% per base, at least about 85% per base, at least about 86% per base, at least about 87% per base, at least about 88% per base, at least about 89% per base, at least about 90% per base, at least about 91% per base, at least about 92% per base, at least about 93% per base, at least about 94% per base, at least about 95% per base, at least about 96% per base, at least about 97% per base, at least about 98% per base, at least about 99% per base, or at least about 100% per base, at a temperature of about or at most about or of at least about 30° C., or of about or at most about or of at least about 12° C., of about or at most about or of at least about 45° C., of about or at most about or of at least about 35° C. In some instances, the reverse transcriptase is a non-LTR retrotransposon or a modified non-LTR retrotransposon. In some instances, the reverse transcriptase is an R2 reverse transcriptase or a modified R2 reverse transcriptase. In some instances, the reverse transcriptase is an R2 non-LTR retrotransposon or a modified R2 non-LTR retrotransposon.

The present disclosure relates to methods for preparing a complementary deoxyribonucleic acid (cDNA) library and/or a DNA library from a plurality of single cells. In some instances, the method comprises the steps of: releasing nucleic acid from each single cell to provide a plurality of individual nucleic acid samples. In some instances, the nucleic acid in each individual nucleic acid sample is from a single cell. In some instances, the method further comprises annealing the nucleic acid template to one or more primer(s). In some instances, the method further comprises mixing the nucleic acid template annealed to one or more primer(s) with an acceptor template (or an acceptor nucleic acid molecule) and a modified reverse transcriptase, in the presence of nucleotides, under conditions effective for producing a cDNA and/or a DNA molecule. In some instances, the modified reverse transcriptase is capable of template jumping and/or comprises at least one improved enzyme property relative to a wild type or unmodified reverse transcriptase. In some instances, the method further comprises amplifying the cDNA molecule and/or DNA molecule to generate a cDNA and/or DNA library.

The present disclosure relates to methods of detecting a nucleic acid molecule. In some instances, the method comprises mixing a sample comprising a nucleic acid molecule with an acceptor template (or an acceptor nucleic acid molecule), a modified reverse transcriptase, a primer, and nucleotides, under conditions effective for generating a nucleic acid molecule. In some instances, the modified reverse transcriptase comprises at least one improved enzyme property relative to a wild type or unmodified reverse transcriptase. In some instances, the acceptor template (or an acceptor nucleic acid molecule) comprises at least one modified nucleotide. In some, the modified nucleotide may cause primer extension to stop. In some instances, the method further comprises amplifying the nucleic acid molecule.

The present disclosure relates to any method disclosed herein wherein the methods may further comprise detecting at least one amplicon generated by the amplification primers. In some instances, the presence of at least one amplicon indicates the presence of at least one modified reverse transcriptase in a sample.

In some instances, any of the methods of the present disclosure does not comprise a purification step. In some instances, any of the methods of the present disclosure comprises at least one purification step. In some instances, any of the methods of the present disclosure comprises at least two purification steps. In some instances, any of the methods of the present disclosure comprises at least three, at least four, at least five, at least six, at least seven, at least eight, at least nine, at least ten, at least fifteen, or at least twenty purification steps.

The present disclosure relates to a method for preparing a library for sequencing.

In some instances, the modified reverse transcriptase is a modified non-retroviral reverse transcriptase. In some instances, the modified reverse transcriptase is a modified non-LTR retrotransposon. In some instances, the modified reverse transcriptase is a modified R2 reverse transcriptase.

In some instances, the sample is a biological sample. In some instances, the biological sample comprises a circulating tumor DNA. In some instances, the biological sample comprises a tissue sample. In some instances, the nucleic acid is from a sample. In some instances, the sample is a liquid biopsy sample. In some instances, a sample may be an RNA sample. In some instances, an RNA sample may be used for various purposes, including but not limited to PCR, ligation, transcriptome analysis, microarray analysis, northern analysis, and cDNA library construction. In some instances, the present disclosure is directed to methods for amplifying cDNA libraries from low quantities of cells and/or single cells in suitable quantity and quality for transcriptome analysis through, for example, sequencing or microarray analysis.

In some instances, the nucleic acid and/or a template is of an unknown sequence. In some instances, the nucleic acid and/or a template is RNA, DNA, or a combination of RNA and DNA. In some instances, the RNA is mRNA. In some instances, the mRNA comprises internal priming. In some instances, the nucleic acid may be a fragmented nucleic acid and/or a degraded nucleic acid. In some instances, the template may be a fragmented template and/or a degraded template. In some instances, the nucleic acid may be a non-fragmented nucleic acid and/or a non-degraded nucleic acid. In some instances, the template may be a non-fragmented template and/or a non-degraded template. In some instances, the nucleic acid and/or template is indicative of a disease. In some instances, the nucleic acid and/or template is indicative of cancer. In some instances, the nucleic acid is equal to or less than about 0.01 micromolar. In some instances, the nucleic acid is between about 0.1 nM to about 100 nM. In some instances, the nucleic acid is equal to or less than about 500 femtomolar.

In some instances, the RNA is obtained from a source selected from the group consisting of single cells, cultured cells, tissues, RNA transcription-based amplified RNA (such as TTR-amplified RNA or other DNA-dependent RNA polymerase transcribed RNA), RNA-promoter-driven transcribed RNA, aRNA, aRNA-amplified RNA, single-cell mRNA library, isolated mRNA, RNA contained within cells, and combinations of RNA sources. In some instances, the RNA is prepared from a plurality of fixed cells, wherein said fixed cells are protected from RNA degradation and also subjected to permeabilisation for enzyme penetration. In some instances, the fixed cells are obtained from fixative-treated cultural cells, frozen fresh tissues, fixative-treated fresh tissues or paraffin-embedded tissues on slides.

In some instances, the RNA molecule can be the product of in vitro synthesis or can have been isolated from cells or tissues (Ausubel, et. al., Short Protocols in Molecular Biology, 3rd ed., Wiley, 1995). Cells and tissues suitable for use in obtaining RNA useful in the practice of the present disclosure may include both animal cells and plant cells. In some instances, the cells include mammalian cells and insect cells. RNA may also be isolated from prokaryotic cells such as bacteria.

In some instances, the template is RNA, DNA, or a combination of RNA and DNA. In some instances, the template may be a fragmented template and/or a degraded template. In some instances, the template is not degraded and/or fragmented. In some instances, the RNA is mRNA. In some instances, the template is an RNA template. In some instances, the template is a DNA template. In some instances, the template is a DNA and/or RNA template. In some instances, the template is a mixture of DNA and RNA. In some instances, the RNA comprises any type of RNA (e.g., one or more of rRNA, tRNA, mRNA, ncRNA, lincRNA, miRNA, and/or snRNA). In some instances the RNA comprises a mixture of at least one type of RNA. In some instances, the DNA can comprise a mixture of, or at least one of, genomic DNA or nuclear DNA, mitochondrial DNA, Y-line DNA, autosomal DNA, ribosomal DNA, or a combination thereof. In some instances, the template is a polymer of any length. In some instances, the template is from about 20 bases to about 100 bases, from about 30 bases to about 500 bases, from about 30 bases to about 1000 bases, from about 50 bases to about 300 bases, about 100 bases to about 600 bases, about 200 bases to about 800 bases, about 200 bases to about 600 bases, about 100 bases to about 2000 bases, about 100 bases and about 2500 bases, about 200 bases to about 5000 bases, about 200 bases to about 1000 bases, about 200 to about 10000 bases. In some instances, the template is at least about 10 bases, at least about 20 bases, at least about 30 bases, at least about 40 bases, at least about 50 bases, at least about 60 bases, at least about 70 bases, at least about 80 bases, at least about 90 bases, at least about 100 bases, at least about 150 bases, at least about 200 bases, at least about 250 bases, at least about 300 bases, at least about 350 bases, at least about 400 bases, at least about 450 bases, at least about 500 bases, at least about 550 bases, at least about 600 bases, at least about 650 bases, at least about 700 bases, at least about 750 bases, at least about 800 bases, at least about 850 bases, at least about 900 bases, at least about 950 bases, at least about 1000 bases, at least about 1100 bases, at least about 1200 bases, at least about 1300 bases, at least about 1400 bases, at least about 1500 bases, at least about 1700 bases, at least about 2000 bases, at least about 2200 bases, at least about 2500 bases, at least about 2700 bases, at least about 3000, at least about 3500 bases, at least about 4000 bases, at least about 4500 bases, at least about 5000 bases, at least about 10,000 bases, or at least about 50,000 bases. In some instances, the template is about or at least about or at most about 10 bases, about or at least about or at most about 20 bases, about or at least about or at most about 30 bases, about or at least about or at most about 40 bases, about or at least about or at most about 50 bases, about or at least about or at most about 60 bases, about or at least about or at most about 70 bases, about or at least about or at most about 80 bases, about or at least about or at most about 90 bases, about or at least about or at most about 100 bases, about or at least about or at most about 150 bases, about or at least about or at most about 200 bases, about or at least about or at most about 250 bases, about or at least about or at most about 300 bases, about or at least about or at most about 350 bases, about or at least about or at most about 400 bases, about or at least about or at most about 450 bases, about or at least about or at most about 500 bases, about or at least about or at most about 550 bases, about or at least about or at most about 600 bases, about or at least about or at most about 650 bases, about or at least about or at most about 700 bases, about or at least about or at most about 750 bases, about or at least about or at most about 800 bases, about or at least about or at most about 850 bases, about or at least about or at most about 900 bases, about or at least about or at most about 950 bases, about or at least about or at most about 1000 bases, about or at least about or at most about 1100 bases, about or at least about or at most about 1200 bases, about or at least about or at most about 1300 bases, about or at least about or at most about 1400 bases, about or at least about or at most about 1500 bases, about or at least about or at most about 1700 bases, about or at least about or at most about 2000 bases, about or at least about or at most about 2200 bases, about or at least about or at most about 2500 bases, about or at least about or at most about 2700 bases, about or at least about or at most about 3000, about or at least about or at most about 3500 bases, about or at least about or at most about 4000 bases, about or at least about or at most about 4500 bases, about or at least about or at most about 5000 bases, about or at least about or at most about 10,000 bases, or about or at least about or at most about 50,000 bases. In some instances, the template DNA may be a double-stranded DNA template (dsDNA template) or a single-stranded DNA template (ssDNA template). In some instances, the template RNA may be a double-stranded RNA template (dsRNA template) or a single-stranded RNA template (ssRNA template).

In some instances, the template is from a single cell. In some instances, the template is from a plurality of cells. In some instances, the template comprises low copy number DNA, or RNA, or a combination of DNA and/or RNA. In some instances, low copy number refers to samples that contain equal to or less than about 250 picograms (e.g. 100 picograms) of for example the template and/or DNA and/or RNA and/or a mixture of DNA and RNA. In some instances, the RNA can comprise at least one of messenger RNA (mRNA), transfer RNA, transfer-messenger RNA, ribosomal RNA, antisense RNA, small nuclear RNA (snRNA), small nucleolar RNA (snoRNA), micro-RNA (miRNA), small interfering RNA (siRNA), long non-coding RNA (lncRNA), long intervening noncoding (lincRNA), or any combination thereof. In some instances, the template is from a sample. In some instances, the total amount of template is the total amount of template in a sample. In some instances, the total amount of template is the total amount of template in a reaction mixture. In some instances, the total amount of template is the total amount of template in one pot (e.g., single vessel). In some instances, the total amount of the template is from about 1 femtomolar (fM) to about 100 micromolar, from about 40 femtomolar to about 0.01 micromolar, from about 50 femtomolar to about 500 femtomolar, from about 50 femtomolar to about 0.01 micromolar, from about 50 femtomolar to about 0.1 micromolar, from about 50 femtomolar to about 500 picomolar, from about 50 femtomolar to about 500 nanomolar, from about 50 femtomolar to about 500 micromolar, from about 50 femtomolar to about 1 picomolar, from about 40 femtomolar to about 1 nanomolar, from about 1 femtomolar to about 1 picolomar, from about 0.0001 micromolar to about 0.01 micromolar, from about 0.0001 micromolar to about 0.1 micromolar, or from about 0.1 nM to about 100 nM. In some instances, the total about of template is equal to or at least about or lower than about 1000 micromolar, equal to or at least about or lower than about 500 micromolar, equal to or at least about or lower than about 250 micromolar, equal to or at least about or lower than about 100 micromolar, equal to or at least about or lower than about 50 micromolar, equal to or at least about or lower than about 25 micromolar, equal to or at least about or lower than about 10 micromolar, equal to or at least about or lower than about 1 micromolar, equal to or at least about or lower than about 0.1 micromolar, equal to or at least about or lower than about 0.01 micromolar, equal to or at least about or lower than about 0.001 micromolar, equal to or at least about or lower than about 0.0001 micromolar, equal to or at least about or lower than about 2000 nanomolar, equal to or at least about or lower than about 500 nanomolar, equal to or at least about or lower than about 250 nanomolar, equal to or at least about or lower than about 200 nanomolar, equal to or at least about or lower than about 50 nanomolar, equal to or at least about or lower than about 25 nanomolar, equal to or at least about or lower than about 20 nanomolar, equal to or at least about or lower than about 2 nanomolar, equal to or at least about or lower than about 0.2 nanomolar, equal to or at least about or lower than about 0.01 nanomolar, equal to or at least about or lower than about 0.001 nanomolar, equal to or at least about or lower than about 0.0001 nanomolar, equal to or at least about or lower than about 3000 picomolar, equal to or at least about or lower than about 500 picomolar, equal to or at least about or lower than about 250 picomolar, equal to or at least about or lower than about 300 picomolar, equal to or at least about or lower than about 50 picomolar, equal to or at least about or lower than about 25 picomolar, equal to or at least about or lower than about 30 picomolar, equal to or at least about or lower than about 3 picomolar, equal to or at least about or lower than about 0.3 picomolar, equal to or at least about or lower than about 0.01 picomolar, equal to or at least about or lower than about 0.001 picomolar, equal to or at least about or lower than about 0.0001 picomolar, equal to or at least about or lower than about 5000 femtomolar, equal to or at least about or lower than about 500 femtomolar, equal to or at least about or lower than about 250 femtomolar, equal to or at least about or lower than about 50 femtomolar, equal to or at least about or lower than about 25 femtomolar, equal to or at least about or lower than about 10 femtomolar, equal to or at least about or lower than about 1 femtomolar, equal to or at least about or lower than about 0.1 femtomolar, equal to or at least about or lower than about 0.01 femtomolar, equal to or at least about or lower than about 0.001 femtomolar, equal to or at least about or lower than about 0.0001 femtomolar.

In some instances, the template may be present in any nucleic acid sample of interest, including but not limited to, a nucleic acid sample isolated from a single cell, a plurality of cells (e.g., cultured cells), a tissue, an organ, or an organism (e.g., bacteria, yeast, or the like). In some instances, the nucleic acid sample is isolated from a cell(s), tissue, organ, and/or the like of a mammal (e.g., a human, a rodent (e.g., a mouse), or any other mammal of interest). In some instances, the nucleic acid sample is isolated from a source other than a mammal, such as bacteria, yeast, insects (e.g., *drosophila*), amphibians (e.g., frogs (e.g., *Xenopus*)), viruses, plants, or any other non-mammalian nucleic acid sample source.

In some instances, the template is optimized. In some instances, the acceptor template or acceptor nucleic acid molecule comprises at least one modified nucleotide. In some instances, the acceptor template or acceptor nucleic acid molecule is engineered to improve template jumping and/or conversion efficiency. In some instances, the acceptor template or acceptor nucleic acid molecule is optimized at the 3'-end. In some instances, the optimization prevents secondary structure formation and/or nucleotide composition.

In some instances, the methods disclosed in the present disclosure may further comprise optimization of the template (e.g. donor template). In some instances, optimization of the template comprises contacting the template (e.g. RNA) with an agent capable of removing the 5' cap structure of the template (e.g., mRNA). In some instances, the removal of the cap structure is performed under conditions permitting the removal of the cap structure by the agent. In some instances, the methods disclosed in the present disclosure further include dephosphorylation of for example, the decapped template. In some instances, the method further includes adding a dephosphorylating agent to the decapped template under conditions permitting dephosphorylation.

In some instances, any method of the present disclosure may further comprise optimization of the template. In some instances, optimization of the template comprises: contacting a sample comprising a template with an agent that removes a 5' cap structure of the template, under conditions permitting the removal of the cap structure by the agent. In some instances, the optimization of the template may further comprise adding a dephosphorylating agent under conditions permitting the dephosphorylation of the decapped template by the agent. In some instances, the template (e.g. RNA molecule) is dephosphorylated after synthesis or isolation. In some instances, the dephosphorylation is achieved by treatment of the nucleic acid (e.g., RNA) molecule with alkaline phosphatase. In some instances, the isolated donor template, such as RNA or mRNA, is decapped and dephosphorylated after isolation. Methods of decapping nucleic acids (e.g., RNAs) include both enzymatic methods (such as by using a pyrophosphatase such as tobacco pyrophosphatase) and chemical methods (such as periodate oxidation and beta elimination). Methods for dephosphorylation of nucleic acid (e.g., RNA) may use alkaline phosphatase. In some instances, the isolated mRNA is decapped (using tobacco acid pyrophosphatase, for example) and dephosphorylated (e.g., by using alkaline phosphatase). In some instances, the removal of the RNA cap structure is by either enzymatic treatment of the mRNA with a pyrophosphatase or chemical decapping (e.g., by periodate oxidation and beta elimination). In some instances, the mRNA is modified with a tag.

In some instances, template jumping is dependent on the concentration of the acceptor nucleic acid molecule.

In some instances, the method of the present disclosure further comprises using the modified reverse transcriptase to subject a template nucleic acid molecule to reverse transcription to yield the nucleic acid molecule. In some instances, the nucleic acid molecule is a cell-free nucleic acid molecule. In some instances, the template nucleic acid molecule is a cell-free nucleic acid molecule.

In some instances, primer extension or elongation reactions are utilized to generate amplified product. Primer extension/elongation reactions may comprise a cycle of incubating a reaction mixture at a denaturation temperature for a denaturation duration and incubating a reaction mixture at an elongation temperature for an elongation duration.

Any type of nucleic acid amplification reaction may be used to amplify a target nucleic acid and generate an amplified product. Moreover, amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction, ligase chain reaction, helicase-dependent amplification, asymmetric amplification, rolling circle amplification, and multiple displacement amplification (MDA). In some instances, the amplified product may be DNA. In cases where a target RNA is amplified, DNA can be obtained by reverse transcription of the RNA and subsequent amplification of the DNA can be used to generate an amplified DNA product. The amplified DNA product may be indicative of the presence of the target RNA in the biological sample. In cases where DNA is amplified, any DNA amplification may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). In some cases, DNA amplification is linear. In some cases, DNA amplification is exponential. In some cases, DNA amplification is achieved with nested PCR, which can improve sensitivity of detecting amplified DNA products.

Denaturation temperatures may vary depending upon, for example, the particular biological sample analyzed, the particular source of target nucleic acid (e.g., viral particle, bacteria) in the biological sample, the reagents used, and/or the desired reaction conditions. In some instances, a denaturation temperature may be from about 80° C. to about 110° C. In some instances, a denaturation temperature may be from about 90° C. to about 100° C. In some instances, a denaturation temperature may be from about 90° C. to about 97° C. In some examples, a denaturation temperature may be from about 92° C. to about 95° C. In still other examples, a denaturation temperature may be about 80°, 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

Denaturation durations may vary depending upon, for example, the particular biological sample analyzed, the particular source of target nucleic acid (e.g., viral particle, bacteria) in the biological sample, the reagents used, and/or the desired reaction conditions. In some instances, a denaturation duration may be less than or equal to about 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. For example, a denaturation duration may be no more than about 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

Elongation or extension temperatures may vary depending upon, for example, the particular biological sample analyzed, the particular source of target nucleic acid (e.g., viral particle, bacteria) in the biological sample, the reagents used, and/or the desired reaction conditions. In some instances, an elongation temperature may be from about 30° C. to about 80° C. In some instances, an elongation temperature may be from about 35° C. to about 72° C. In some instances, an elongation temperature may be from about 45° C. to about 68° C. In some instances, an elongation temperature may be from about 35° C. to about 65° C. In some instances, an elongation temperature may be from about 40° C. to about 67° C. In some instances, an elongation temperature may be from about 50° C. to about 68° C. In some instances, an elongation temperature may be about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 34° C., 33° C., 32° C., 31° C., 30° C., 20° C., 21° C., 22° C., 23° C., 24° C., 25° C., 26° C., 27° C., 28° C., 29° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C.

Elongation durations may vary depending upon, for example, the particular biological sample analyzed, the particular source of target nucleic acid (e.g., viral particle, bacteria) in the biological sample, the reagents used, and/or the desired reaction conditions. In some instances, an elongation duration may be less than or equal to about 360 seconds, less than or equal to about 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. In some instances, an elongation duration may be no more than about 120 seconds, 90 seconds, 80 seconds, 70 seconds, 65 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

In some instances, multiple cycles of a primer extension reaction can be conducted. Any suitable number of cycles may be conducted. In some instances, the number of cycles conducted may be less than about 100, 90, 80, 70, 60, 50, 40, 30, 20, 10, or 5 cycles. The number of cycles conducted may depend upon, for example, the number of cycles (e.g., cycle threshold value (Ct)) necessary to obtain a detectable amplified product (e.g., a detectable amount of amplified DNA product that is indicative of the presence of a target RNA in a biological sample). In some instances, the number of cycles necessary to obtain a detectable amplified product (e.g., a detectable amount of DNA product that is indicative of the presence of a target RNA in a biological sample) may be less than about or about 100 cycles, 75 cycles, 70 cycles, 65 cycles, 60 cycles, 55 cycles, 50 cycles, 40 cycles, 35 cycles, 30 cycles, 25 cycles, 20 cycles, 15 cycles, 10 cycles, 8 cycles, 7 cycles, 5 cycles, or 4 cycles. Moreover, in some instances, a detectable amount of an amplifiable product (e.g., a detectable amount of DNA product that is indicative of the presence of a target RNA in a biological sample) may be obtained at a cycle threshold value (Ct) of less than 100, 75, 70, 65, 60, 55, 50, 45, 40, 35, 30, 25, 20, 15, 10, 9, 8, 7, 6, 5, 4, 3, 2, 1.

In some instances, an amplification step (e.g., primer amplification, template amplification, nucleic acid amplification) comprises a PCR step. In some instances, each PCR cycle may comprise a denaturing step, an annealing step, and an extension step. In some instances, each PCR cycle may comprise a denaturing step and an extension step. In some instances, the PCR comprises at least about or about or at most about 1 cycle, at least about or about or at most about 4 cycles, at least about or about or at most about 5 cycles, at least about or about or at most about 10 cycles, at least about or about or at most about 15 cycles, at least about or about or at most about 20 cycles, at least about or about or at most about 25 cycles, at least about or about or at most about 30 cycles, at least about or about or at most about 35 cycles, at least about or about or at most about 40 cycles, at least about or about or at most about 45 cycles, at least about or about or at most about 50 cycles, at least about or about or at most about 55 cycles, at least about or about or at most about 60 cycles, at least about or about or at most about 65 cycles, at least about or about or at most about 70 cycles, at least about or about or at most about 75 cycles, at least about or about or at most about 80 cycles, at least about or about or at most about 90 cycles, at least about or about or at most about 95 cycles, at least about or about or at most about 100 cycles, at least about or about or at most about 110 cycles, at least about or about or at most about 120 cycles, at least about or about or at most about 130 cycles, at least about or about or at most about 140 cycles, at least about or about or at most about 150 cycles, at least about or about or at most about 160. In some instances, the PCR comprises from about 10 cycles to 40 cycles, from about 20 cycles to 40 cycles, from about 20 cycles to 38 cycles, from about 20 cycles to 35 cycles, from about 10 cycles to 35 cycles, from about 10 cycles to 30 cycles, from about 25 cycles to 30 cycles, from about 20 cycles to 30 cycles, from about 4 cycles to 8 cycles, or from about 28 cycles to 32 cycles. In some instances, the reaction is heated to 95° C. for 3 minutes before the PCR cycle begins. In some instances, each PCR cycle comprises 95° C. for 3 seconds and 62° C. for 20 seconds. In some instances, each PCR cycle comprises 95° C. for 3 seconds, 54° C. for 10 seconds, and 64° C. for 20 seconds. In some instances, each PCR cycle comprises 95° C. for 3 seconds and 64° C. for 20 seconds. In some instances, each PCR cycle comprises 95° C. for 3 seconds and 62° C. for 60 seconds. In some instances, each PCR cycle comprises 95° C. for 3 seconds, 54° C. for 10 seconds, and 64° C. for 10 seconds. In some instances, the PCR comprises 30 cycles. In some instances, the reaction is heated to 68° C. after the completion of the PCR cycles. In some instances, the reaction is heated to 68° C. from about 1 second to about 5 seconds, from about 1 second to about 5 minutes, from about 1 minute to about 5 minutes after the completion of the PCR cycles. In some instances, the PCR methods described herein comprises an extension or elongation step that is at least about 5 seconds long, at least about 6 seconds long, at least about 7 seconds long, at least about 8 seconds long, at least about 9 seconds long, at least about 10 seconds long, at least about 11 seconds long, at least about 12 seconds long, at least about 13 seconds long, at least about 14 seconds long, at least about 15 seconds long, at least about 20 seconds long, at least about 30 seconds long, at least about 40 seconds long, at least about 50 seconds long, at least about 60 seconds long, at least about 90 seconds long, at least about 120 seconds long, at least about 150 seconds long, at least about 180 seconds long, at least about 210 seconds long, at least about 240 seconds long, at least about 270 seconds long, at least about 300 seconds long, at least about 330 seconds long, at least about 360 seconds long, at least about 390 seconds long, or more.

The time for which amplification yields a detectable amount of amplified product indicative of the presence of a target nucleic acid amplified can vary depending upon the biological sample from which the target nucleic acid was obtained, the particular nucleic acid amplification reactions to be conducted, and the particular number of cycles of amplification reaction desired. In some instances, amplification of a target nucleic acid may yield a detectable amount of amplified product indicative to the presence of the target nucleic acid at time period of 120 minutes or less; 90 minutes or less; 60 minutes or less; 50 minutes or less; 45 minutes or less; 40 minutes or less; 35 minutes or less; 30 minutes or less; 25 minutes or less; 20 minutes or less; 15 minutes or less; 10 minutes or less; or 5 minutes or less.

In some instances, a biological sample may be preheated prior to conducting a primer extension reaction. The temperature (e.g., a preheating temperature) at which and duration (e.g., a preheating duration) for which a biological sample is preheated may vary depending upon, for example, the particular biological sample being analyzed. In some examples, a biological sample may be preheated for no more than about 60 minutes, 50 minutes, 40 minutes, 30 minutes, 25 minutes, 20 minutes, 15 minutes, 10 minutes, 9 minutes, 8 minutes, 7 minutes, 6 minutes, 5 minutes, 4 minutes, 3 minutes, 2 minutes, 1 minute, 45 seconds, 30 seconds, 20 seconds, 15 seconds, 10 seconds, or 5 seconds. In some examples, a biological sample may be preheated at a temperature from about 80° C. to about 110° C. In some examples, a biological sample may be preheated at a temperature from about 90° C. to about 100° C. In some examples, a biological sample may be preheated at a temperature from about 90° C. to about 97° C. In some examples, a biological sample may be preheated at a temperature from about 92° C. to about 95° C. In some instances, a biological sample may be preheated at a temperature of about 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

In some instances, reagents necessary for conducting nucleic acid amplification may also include a reporter agent that yields a detectable signal whose presence or absence is indicative of the presence of an amplified product. The intensity of the detectable signal may be proportional to the amount of amplified product. In some cases, where amplified product is generated of a different type of nucleic acid than the target nucleic acid initially amplified, the intensity of the detectable signal may be proportional to the amount of target nucleic acid initially amplified. For example, in the case of amplifying a target RNA via parallel reverse transcription and amplification of the DNA obtained from reverse transcription, reagents necessary for both reactions may also comprise a reporter agent, may yield a detectable signal that is indicative of the presence of the amplified DNA product, and/or the target RNA amplified. The intensity of the detectable signal may be proportional to the amount of the amplified DNA product and/or the original target RNA amplified. The use of a reporter agent also enables real-time amplification methods, including real-time PCR for DNA amplification.

Reporter agents may be linked with nucleic acids, including amplified products, by covalent or non-covalent linkages or interactions. Non-limiting examples of non-covalent linkates or interactions include ionic interactions, Van der Waals forces, hydrophobic interactions, hydrogen bonding, and combinations thereof. In some instances, reporter agents may bind to initial reactants and changes in reporter agent levels may be used to detect amplified product. In some instances, reporter agents may only be detectable (or non-detectable) as nucleic acid amplification progresses. In some instances, an optically-active dye (e.g., a fluorescent dye) may be used as may be used as a reporter agent. Non-limiting examples of dyes include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5-(or 6-) iodoacetamidofluorescein, 5-{[2 (and 3)-5-(Acetylmercapto)-succinyl] amino}fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

In some instances, a reporter agent may be a sequence-specific oligonucleotide probe that is optically active when hybridized with an amplified product. Due to sequence-specific binding of the probe to the amplified product, use of oligonucleotide probes can increase specificity and sensitivity of detection. A probe may be linked to any of the optically-active reporter agents (e.g., dyes) and may also include a quencher capable of blocking the optical activity of an associated dye. Non-limiting examples of probes that may be useful used as reporter agents include TaqMan probes, TaqMan Tamara probes, TaqMan MGB probes, or Lion probes. In some instances, a reporter agent may be a radioactive species. Non-limiting examples of radioactive species include 14C, 123I, 124I, 125I, 131I, 99mTc, 355, or 3H. In some instances, a reporter agent may be an enzyme that is capable of generating a detectable signal. Detectable signal may be produced by activity of the enzyme with its substrate or a particular substrate in the case the enzyme has multiple substrates. Non-limiting examples of enzymes that may be used as reporter agents include alkaline phosphatase, horseradish peroxidase, I2-galactosidase, alkaline phosphatase, β-galactosidase, acetylcholinesterase, and luciferase.

In some instances, an amplified product (e.g., amplified DNA product, amplified RNA product) may be detected. Detection of amplified product, including amplified DNA, may be accomplished with any suitable detection method. The particular type of detection method used may depend, for example, on the particular amplified product, the type of reaction vessel used for amplification, other reagents in a reaction mixture, whether or not a reporter agent was included in a reaction mixture, and if a reporter agent was used, the particular type of reporter agent use. Non-limiting examples of detection methods include optical detection, spectroscopic detection, electrostatic detection, electrochemical detection, and the like. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis, SDS-PAGE gel. Electrochemical detection methods include, but are not limited to, electrochemical detection of amplified product after high-performance liquid chromatography separation of the amplified products.

In some instances, the time required to complete the elements of a method may vary depending upon the particular steps of the method. In some instances, an amount of time for completing the elements of a method may be from about 5 minutes to about 120 minutes. In some instances, an amount of time for completing the elements of a method may be from about 5 minutes to about 60 minutes. In some instances, an amount of time for completing the elements of a method may be from about 5 minutes to about 30 minutes. In some instances, an amount of time for completing the elements of a method may be less than or equal to 120 minutes, less than or equal to 90 minutes, less than or equal to 75 minutes, less than or equal to 60 minutes, less than or equal to 45 minutes, less than or equal to 40 minutes, less than or equal to 35 minutes, less than or equal to 30 minutes, less than or equal to 25 minutes, less than or equal to 20 minutes, less than or equal to 15 minutes, less than or equal to 10 minutes, or less than or equal to 5 minutes.

In some instances, the reaction may have a pH suitable for producing the product, for primer extension, protein expression, PCR amplication, or template jumping. In some instances, the pH of the reaction may range from about 5 to about 9, from about 6 to about 9, from about 7 to about 9, from about 8 to about 9. In some instances, the pH range is from about pH 2 to about pH 10, from about pH 4 to about pH 10, from about pH 2 to about pH 8, from about pH 4 to about pH 8, from about pH 5 to about pH 8, from about pH 5 to about pH 7, from about pH 6 to about pH 11, from about pH 6 to about pH 12, from about pH 5 to pH 13, from about pH 5 to about pH 14. In some instances, the pH is about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10.0, about 10.5, about 11, about 11.5, about 12, about 12.5, about 13, about 13.5, about 14.

In some instances, any method of the present disclosure may comprise a detergent. In some instances, the detergent is non-ionic and/or a zwitterionic detergent. In some instances, a non-ionic detergent is selected from a group consisting of tween, triton, Triton CF-21, Triton CF-32, Triton DF-12, Triton DF-16, Triton GR-SM, Triton N-101 (Polyoxyethylene branched nonylphenyl ether), Triton QS-15, Triton QS-44, Triton RW-75 (Polyethylene glycol 260 monoChexadecyl/octadecyl) ether and 1-Octadecanol), Triton X-100 (Polyethylene glycol tert-octylphenyl ether), Triton X-102, Triton X-15, Triton X-151, Triton X-200, Triton X-207, Triton X-114, Triton X-165, Triton X-305, Triton X-405 (polyoxyethylene(40) isooctylphenyl ether), Triton X-405 reduced (polyoxyethylene(40) isooctylcyclohexyl ether), Triton X-45 (Polyethylene glycol 4-tert-octylphenyl ether), Triton X-705-70, TWEEN in any form including: TWEEN 20 (Polyoxyethylene sorbitan monolaurate), TWEEN 21 (Polyoxyethylene sorbitan monolaurate), TWEEN 40 (polyoxyethylene(20) sorbitan monopalmitate), TWEEN 60 (Polyethylene glycol sorbitan monostearate), TWEEN 61 (Polyethylene glycol sorbitan monostearate), TWEEN 65 (Polyoxyethylene sorbitan Tristearate), TWEEN 80 (Polyoxyethylene sorbitan monooleate), TWEEN 81 (Polyoxyethylene sorbitan monooleate), TWEEN 85 (polyoxyethylene(20) sorbitan trioleate), Brij, Brij 30 (Polyoxyethylene 4 lauryl ether) Brij 35 (Polyoxyethylene 23 lauryl ether), Brij 52 (Polyoxyethylene 2 cetyl ether), Brij56 (Polyoxyethylene 10 cetyl ether), Brij 58 (Polyoxyethylene 20 cetyl ether), Brij 72 (Polyoxyethylene 2 stearyl ether), Brij 76 (Polyoxyethylene 10 stearyl ether), Brij 78 (Polyoxyethylene 20 stearyl ether), Brij 92 (Polyoxyethylene 2 oleyl ether), Brij 97 (Polyoxyethylene 10 oleyl ether), Brij 98 (Polyoxyethylene 20 oleyl ether), Brij700 (Polyoxyethylene 100 stearyl ether, octyl thioglucoside, maltosides, and combinations thereof In some instances, any method disclosed herein for producing any molecule according to the present disclosure comprises at least one salt. In some instances, the salt is at least one member selected from the group consisting of NaCl, LiCl, $AlCl_3$, $CuCl_2$, $MgC_2$, $InC_3$, $SnCl_4$, $CrCl_2$, $CrCl_3$, KCl, NaI, KI, TMACl (tetramethyl ammonium chloride), TEACl (tetraethyl ammonium chloride), KSCN, CsSCN, $KCH_3COO$, $CH_3COONa$, $C_5H_8KNO_4$, $C_5H_8NNaO_4$, CsCl, and any combination thereof. In some instances, any method disclosed herein for producing any molecule according to the present disclosure comprises NaCl. In some instances, the conditions sufficient for producing a molecule or a library comprises NaCl. In some instances, the reaction may have a salt concentration and/or NaCl suitable for producing a product, for primer extension, protein expression, PCR amplification, or template jumping. In some instances, the NaCl concentration is from about 50 mM to about 1000 mM, from about 100 mM to about 500 mM, from about 200 mM to about 300 mM, from about 200 mM to about 600 mM. In some instances, the NaCl concentration is at least about, at most about, or about 50 mM, at least about, at most about, or about 100 mM, at least about, at most about, or about 150 mM, at least about, at most about, or about 200 mM, at least about, at most about, or about 250 mM, at least about, at most about, or about 300 mM, at least about, at most about, or about 350 mM, at least about, at most about, or about 400 mM, at least about, at most about, or about 450 mM, at least about, at most about, or about 500 mM, at least about, at most about, or about 550 mM, at least about, at most about, or at least about, at most about, or about 600 mM, at least about, at most about, or about 650 mM, at least about, at most about, or about 700 mM, at least about, at most about, or about 750 mM, at least about, at most about, or about 800 mM, at least about, at most about, or about 850 mM, at least about, at most about, or about 900 mM, at least about, at most about, or about 950 mM, or at least about, at most about, or about 1000 mM. In some instances, the NaCl may improve enzyme activity and/or template jumping of an enzyme or polypeptide of the present disclosure (e.g., of a reverse transcriptase).

In some instances, the reaction may have a nucleotide (e.g. dNTPs) concentration suitable for producing a product, for primer extension, protein expression, PCR amplication, or template jumping. In some instances, the total dNTP concentration in a reaction may be from about 50 µM to about 1000 µM, from about 100 µM to about 500 µM, from about 200 µM to about 300 µM, from about 200 µM to about 600 µM. In some instances, the total dNTP concentration is at least about, at most about, or about 50 µM, at least about, at most about, or about 100 µM, at least about, at most about, or about 150 µM, at least about, at most about, or about 200 µM, at least about, at most about, or about 250 µM, at least about, at most about, or about 300 µM, at least about, at most about, or about 350 µM, at least about, at most about, or about 400 µM, at least about, at most about, or about 450 µM, at least about, at most about, or about 500 µM, at least about, at most about, or about 550 µM, at least about, at most about, or at least about, at most about, or about 600 µM, at least about, at most about, or about 650 µM, at least about, at most about, or about 700 µM, at least about, at most about, or about 750 µM, at least about, at most about, or about 800 µM, at least about, at most about, or about 850 µM, at least about, at most about, or about 900 µM, at least about, at most about, or about 950 µM, or at least about, at most about, or about 1000 µM. In some instances, the total concentration of each dNTP is at least about, at most about, or about 1 µM; at least about, at most about, or about 2 µM; at least about, at most about, or about 3 µM; at least about, at most about, or about 4 µM; at least about, at most about, or about 5 µM; at least about, at most about, or about 6 µM; at least about, at most about, or about 7 µM; at least about, at most about, or about 8 µM; at least about, at most about, or about 9 µM; at least about, at most about, or about 10 µM; at least about, at most about, or about 15 µM; at least about, at most about, or about 20 µM; at least about, at most about, or about 25 µM; at least about, at most about, or about 30 µM; at least about, at most about, or about 35 µM; at least about, at most about, or about 40 µM; at least about, at most about, or about 45 µM; at least about, at most about, or about 50 µM; at least about, at most about, or about 55 µM; at least about, at most about, or about 60 µM; at least about, at most about, or about 65 µM; at least about, at most about, or about 70 µM; at least about, at most about, or about 75 µM; at least about, at most about, or about 80 µM; at least about, at most about, or about 85 µM; at least about, at most about, or about 90 µM; at least about, at most about, or about 95 µM; at least about, at most about, or about 100 µM; at least about, at most about, or about 250 µM; at least about, at most about, or about 500 µM; at least about, at most about, or about 1000 µM; at least about, at most about, or about 10000 µM. In some instances, the total concentration of each dNTP is from about 2 µM to about 5 µM, from about 2 µM to about 10 µM, from about 2 µM to about 20 µM, from about 2 µM to about 50 µM, from about 2 µM to about 100 µM, from about 2 µM to about 250 µM, from about 5 µM to about 10 µM, from about 5 µM to about 50 µM, from about 5 µM to about 250 µM, from about 5 µM to about 1000 µM.

In some instances, the concentration of each dNTP may be independent and different from the concentration of one or more dNTP. In some instances, the concentration of each dNTP for example the concentration of each dCTP, dGTP, dTTP, or dATP may be independent and different from the concentration of at least one other dNTP. In some instances, the concentration of one dNTP (e.g., dCTP, dGTP, dTTP, or dATP) may be at least about or at most about or about 1 fold, 2 fold, 3 fold, 4 fold, 5 fold, 7 fold, 10 fold, 20 fold, 35 fold, 50 fold, 75 fold, 90 fold, 100 fold, 200 fold, 500 fold, or 1000 fold different from at least one other dNTP (e.g., dCTP, dGTP, dTTP, or dATP).

In some instances, the reaction mixture includes a pH adjusting agent. pH adjusting agents of interest include, but are not limited to, sodium hydroxide, hydrochloric acid, phosphoric acid buffer solution, tris buffer, citric acid buffer solution, and the like. For example, the pH of the reaction mixture can be adjusted to the desired range by adding an appropriate amount of the pH adjusting agent.

The temperature range suitable for production of a product may vary according to factors such as the particular polymerase employed, the melting temperatures of any optional primers employed, etc. In some instances, the polymerase may include, but it is not limited to, a reverse transcriptase, a Moloney Murine Leukemia Virus (MMLV) reverse transcriptase, an R2 reverse transcriptase, an RNA-directed DNA polymerase, an DNA-directed DNA polymerase, a non-LTR retrotransposon, an R2 non-LTR retrotransposon, a polypeptide having reverse transcriptase activity, or any variant thereof, or any combination thereof.

In some instances, the conditions sufficient to produce a product include bringing the reaction mixture to a temperature ranging from about 4° C. to about 72° C., from about 16° C. to about 70° C., from about 37° C. to about 50° C., from about 40° C. to about 45° C., from about 30° C. to about 42° C., from about 25° C. to about 42° C., from about 25° C. to about 30° C., from about 28° C. to about 32° C., from about 29° C. to about 31° C. In some instances, the temperature is about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., or about 75° C. In some instances, the temperature is about or at most about 42° C. In some instances, the temperature is about or at most about 50° C. In some instances, the temperature is about or at most about 35° C. In some instances, the temperature is about or at most about 25° C. In some instances, the temperature is about or at most about 30° C. In some instances, the reaction is incubated from about 20 minutes to about 3 hours, from about 30 minutes to about 1.5 hours, from about 30 minutes to about 1 hour, from about 30 minutes to about 2 hours, from about 1 hour to about 2 hours, from about 1 hour to about 1.5 hours, from about 30 minutes to about 5 hours, from about 1 hour to about 3 hours, from about 1 hour to about 4 hours, from about 1 hour to about 5 hours. In some instances, the reaction is incubated for about 1 hour. In some instances, the reaction is incubated for about 20 minutes, about 30 minutes, about 40 minutes, about 50 minutes, about 1 hour, about 1.5 hours, about 2 hours, about 2.5 hours, about 3 hours, about 3.5 hours, about 4 hours, about 4.5 hours, or about 5 hours. In some instances, the reaction is incubated for at least at least about 20 minutes, at least about 30 minutes, at least about 40 minutes, at least about 50 minutes, at least about 1 hour, at least about 1.5 hours, at least about 2 hours, at least about 2.5 hours, at least about 3 hours, at least about 3.5 hours, at least about 4 hours, at least about 4.5 hours, or at least about 5 hours. In some instances, the reaction is incubated at about 30° C. for about 1 hour, or at about 42° C. for about 1 hour. In some instances, the conditions sufficient for generating a molecule or a nucleic acid molecule comprises a temperature of about 12° C. to about 42° C. for about 1 minute to about 5 hours. In some instances, the conditions sufficient for generating a molecule or a nucleic acid molecule comprises a temperature of about 8° C. to about 50° C. for about 1 minute to about 24 hours.

In some instances, a primer can be designed to be a certain length. In some instances, a primer can be from about 6 to about 100 nucleotides, from about 6 to about 90 nucleotides, from about 6 to about 80 nucleotides, from about 6 to about 70 nucleotides, from about 6 to about 60 nucleotides, from about 6 to about 50 nucleotides, from about 6 to about 40 nucleotides, from about 6 to about 30 nucleotides, from about 6 to about 20 nucleotides, or from about 6 to about 10 nucleotides in length. In some instances, a primer can be from about 25 to about 80, from about 25 to about 75, from about 25 to about 70, from about 25 to about 65, from about 25 to about 60, from about 25 to about 55, from about 25 to about 50, from about 25 to about 45, from about 25 to about 40, from about 25 to about 35, or from about 25 to about 30 bases in length. In some instances, a primer can be at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95 or at least about 100 bases in length. In some instances, a primer can be about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95 or about 100 bases in length. In some instances, a primer can be at least about, no more than about, or about 120, 130, 140, 150, 160, 170, 180, 190, 200, 230, 250, 270, 290, 300, 320, 340, 350, 370, 400, 420, 450, 470, 490, or 500.

In some instances, a primer can be designed to anneal to a target at a given melting temperature (Tm). In some instances, a Tm can be from about 20° C. to about 100° C., about 20° C. to about 90° C., about 20° C. to about 80° C., about 20° C. to about 70° C., about 20° C. to about 60° C., about 20° C. to about 50° C., about 20° C. to about 40° C., or about 20° C. to about 30° C. In some instances, a Tm can be at least about, at most about, or about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 83° C., 84° C., 85° C., 96° C., 97° C., 98° C., 99° C., or 100° C. A plurality of primers can be designed to have Tms within a range, e.g., within a range spanning 15° C., 10° C., 9° C., 8° C., 7° C., 6° C., 5° C., 4° C., 3° C., 2° C., or 1° C. A plurality of primers can be designed to have identical Tms.

In some instances the enzyme, or modified enzyme (e.g., modified reverse transcriptase), or protein, or polypeptide, or a variant, or a PCR product, or a cDNA molecule, or a template, or a nucleic acid molecule, or any component of the present disclosure may be purified. In some instances, the fragmented or degraded nucleic acid (e.g., RNA or DNA) may be purified. In some instances, the reverse transcriptase or a modified reverse transcriptase may be purified. In some instances, the R2 reverse transcriptase or a modified R2 reverse transcriptase may be purified. In some instances, the non-LTR retrotransposon protein or polypeptide having reverse transcriptase activity, or a modified non-LTR retrotransposon protein or a modified polypeptide having reverse transcriptase activity may be further purified. In some instances, the cDNA molecule may be purified. In some instances, the template may be purified. In some instances, the acceptor nucleic acid molecule may be purified.

Purification may comprise precipitation, ultracentrifugation, chromatographic method based on size, charge, hydrophobicity, affinity, metal binding, HPLC. In some instances, the purification comprises column chromatography. In some instances, the column chromatography may be size exclusion (SEC), ion exchange (IEX), affinity chromatography, immobilized metal ion affinity chromatography (IMAC), Ni-IMAC chromatography, and/or hydrophobic interaction (HIC). In some instances, the purification comprises His-tag affinity resin. In some instances, the purification may comprise one step. In some instances, the purification may comprise two steps. In some instances, the two step purification comprises nickel and heparin. In some instances, the two step purification comprises nickel and heparin affinity purifications. In some instances, the two purification steps provide higher activity and/or increased template jumping compared to one step purification. In some instances, the purification comprises heparin-affinity purification. In some instances, purification may include affinity purification, Ni-NTA affinity, fast protein liquid chromatography (FPLC) (e.g., AKTA and Bio-Rad FPLC systems), high-pressure liquid chromatography (HPLC) (e.g., Beckman and Waters HPLC). In some instances, purification may include, but not limited to, ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD (Registered trademark) ion exchange chromatography, and hydrophobic interaction columns (HIC). Also included are analytical methods such as SDS-PAGE (e.g., coomassie, silver stain), immunoblot, Bradford, and ELISA, which may be utilized during any step of the production or purification process, typically to measure the purity of the protein or enzyme composition.

In some instances, the overall activity of the purified enzyme, protein, polypeptide, the R2 reverse transcriptase, the non-LTR retrotransposon protein or polypeptide having reverse transcriptase activity, the reverse transcriptase, or variants thereof, or products thereof using a two-step purification is at least about 2%, at least about 5%, at least about 7%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99% higher than the overall activity using the one-step purification. In some instances, the overall activity of the purified enzyme, protein, polypeptide, the R2 reverse transcriptase, the non-LTR retrotransposon protein or polypeptide having reverse transcriptase activity, the reverse transcriptase, or variants thereof, or products thereof is at least about 0.5%, at least about 1%, at least about 1.5%, at least about 2%, at least about 5%, at least about 7%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99% higher than the overall activity of the non-purified enzyme, protein, polypeptide, R2 reverse transcriptase, non-LTR retrotransposon protein or polypeptide having reverse transcriptase activity, reverse transcriptase, or variants thereof, or products thereof. In some instances, a purified enzyme, protein, polypeptide, R2 reverse transcriptase, the non-LTR retrotransposon protein, or polypeptide having reverse transcriptase activity, reverse transcriptase, modified enzyme, modified reverse transcriptase, modified polypeptide having reverse transcriptase activity, or variants thereof, or products thereof is at least about 0.5%, at least about 1%, at least about 3%, at least about or about 5%, at least about or about 10%, at least about or about 15%, at least about or about 20%, at least about or about 25%, at least about or about 30%, at least about or about 35%, at least about or about 40%, at least about or about 45%, at least about or about 50%, at least about or about 55%, at least about or about 60%, at least about or about 61%, at least about or about 62%, at least about or about 63%, at least about or about 64%, at least about or about 65%, at least about or about 66%, at least about or about 67%, at least about or about 68%, at least about or about 69%, at least about or about 70%, at least about or about 71%, at least about or about 72%, at least about or about 73%, at least about or about 74%, at least about or about 75%, at least about or about 76%, at least about or about 77%, at least about or about 78%, at least about or about 79%, at least about or about 80%, at least about or about 81%, at least about or about 82%, at least about or about 83%, at least about or about 84%, at least about or about 85%, at least about or about 86%, at least about or about 87%, at least about or about 88%, at least about or about 89%, at least about or about 90%, at least about or about 91%, at least about or about 92%, at least about or about 93%, at least about or about 94%, at least about or about 95%, at least about or about 96%, at least about or about 97%, at least about or about 98%, or at least about or about 99% pure.

In some instances, the purified enzyme, protein, polypeptide, R2 reverse transcriptase, non-LTR retrotransposon protein or polypeptide having reverse transcriptase activity, reverse transcriptase, or variants thereof, or products thereof produces template jumping that is at least about or about one time, at least about or about two times, at least about or about three times, at least about or about four times, at least about or about five times, at least about or about six times, at least about or about seven times, at least about or about eight times, at least about or about nine times, at least about or about ten times, at least about or about fifteen times, at least about or about twenty times, at least about or about twenty five times, at least about or about thirty times, at least about or about forty times, at least about or about fifty times, at least about or about seventy times, at least about or about eighty times, at least about or about ninety times, at least about or about 100 times, at least about or about 150 times, at least about or about 200 times, at least about or about 250 times, at least about or about 300 times, at least about or about 350 times, at least about or about 400 times, at least about or about 500 times, at least about or about 700 times, at least about or about 1000 times, at least about or about 10000 times more and/or higher intensity than the non-purified enzyme, protein, polypeptide, R2 reverse transcriptase, non-LTR retrotransposon protein or polypeptide having reverse transcriptase activity, reverse transcriptase, or variants thereof, or products thereof.

Mutation of Enzymes

In some instances, a modified enzyme, or derivatives and variants may be prepared during synthesis of the peptide or by post-production modification. In some instances, a modified enzyme, or derivatives and variants may be produced by site-directed mutagenesis (e.g. Q5@ Site-Directed Mutagenesis Kit Protocol), random mutagenesis, or enzymatic cleavage and/or ligation of nucleic acids. In some instances, the derivatives and variants, or a modified enzyme are produced by random mutagenesis. In some instances, a rational design and/or mutagenesis is based on sequence alignment analysis. In some instances, the rational design/mutagenesis is based on sequence alignment analysis with defined and known enzymes and proteins. In some instances, sequence alignment analysis or homology modeling is performed with enzymes and/or elements with homology to R2, including, but not limited to, non-LTR retrotransposons, telomerase, group II introns, LTR retrotransposons, reverse transcriptase, retroviral reverse transcriptase (e.g., HIV, MMLV), and viral RNA dependent RNA polymerase.

In some instances, variants or modified enzymes of the present disclosure can be produced by, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches. Methods for making modified enzymes, polynucleotides and proteins (e.g., variants) include DNA shuffling methodologies, methods based on non-homologous recombination of genes, such as ITCHY (See, Ostermeier et al., 7:2139-44 [1999]), SCRACHY (See, Lutz et al. 98:11248-53 [2001]), SHIPREC (See, Sieber et al., 19:456-60 [2001]), and NRR (See, Bittker et al., 20:1024-9 [2001]; Bittker et al., 101:7011-6 [2004]), and methods that rely on the use of oligonucleotides to insert random and targeted mutations, deletions and/or insertions (See, Ness et al., 20:1251-5 [2002]; Coco et al., 20:1246-50 [2002]; Zha et al., 4:34-9 [2003]; Glaser et al., 149:3903-13 [1992]). In some instances, polynucleotides, polypeptides, proteins, or enzymes of the present disclosure may be altered by being subjected to random mutagenesis by error-prone PCR, random nucleotide insertion or other methods prior to recombination. Polynucleotides, polypeptides, proteins, or enzymes of the present disclosure may be produced by DNA shuffling, gene-shuffling, motif-shuffling, exon-shuffling, and/or codon-shuffling (collectively referred to as "DNA shuffling"). DNA shuffling involves the assembly of two or more DNA segments by homologous or site-specific recombination to generate variation in the polynucleotide sequence. DNA shuffling may be employed to modulate the activities of polynucleotides, polypeptides, proteins, or enzymes of the present disclosure, such methods can be used to generate polypeptides with altered activity. See, generally, U.S. Pat. Nos. 5,605,793; 5,811,238; 5,830,721; 5,834,252; 5,837,458; and 6,444,468; and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998). Polynucleotides, polypeptides, proteins, or enzymes of the present disclosure may contain one or more components, motifs, sections, parts, domains, fragments, etc., of a polynucleotide, polypeptide, protein, or enzyme of the present disclosure. In some instances, kits for use in mutagenic PCR, such as, for example, the Diversify PCR Random Mutagenesis Kit (Clontech) or the GeneMorph Random Mutagenesis Kit (Stratagene) may be used.

In some instances, variant proteins differ from a parent protein or modified enzymes differ from a wild-type or unmodified enzyme and one another by a small number of amino acid residues. The number of differing amino acid residues may be one or more, preferably about 1, 2, 3, 4, 5, 10, 15, 20, 30, 40, 50, 60, 70, 80, 90, 100 or more amino acid residues. In some instances, the number of different amino acids between variants is between about 1 and about 10. In some instances, related proteins and particularly variant proteins comprise at least about 35%, 40%, 45%, 50%, 55%, 60%, 65%, 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some instances, variant proteins have about 1, 2, 3, 4, 5, 6, 7, 8, 9, or 10 corresponding prominent regions that differ from the parent protein.

In some instances, screening methods can include conventional screening methods such as liquid phase, or microtiter plate based assays. The format for liquid phase assays is often robotically manipulated 96, 384, or 1536-well microtiter plates. Other screening methods include growth selection (Snustad et al., 1988; Lundberg et al., 1993; Yano et al., 1998), colorimetric screening of bacterial colonies or phage plaques (Kuritz, 1999), in vitro expression cloning (King et al., 1997) and cell surface or phage display (Benhar, 2001). In some instances, screening approaches may be a method selected from yeast-2-hybrid, n-hybrid, reverse-2-hybrid, reverse n-hybrid, split two hybrid, bacterial display, phage display, retroviral display, ribosome display, covalent display, in vitro display, or any other display method. In some instances, the library is screened using a phage display method.

Analysis of the sequences derived from template jumps: the band corresponding to the template jump product may be excised from a polyacrylamide gel, eluted with sodium acetate (e.g. 0.3 M sodium acetate, pH 5.2), SDS (e.g. 0.03%) for several hours at room temperature, phenol/chloroform extracted and ethanol precipitated. The isolated cDNA may then be used as a template for PCR amplification using one or more primer(s). The PCR products may then be directly cloned into a vector (Burke et al., "R4, a non-LTR Retrotransposon Specific to the Large Subunit rRNA Gene of Nematodes," Nucleic Acids Res. 23: 4628-4634 (1995)) and individual clones sequenced.

In some instances, the variants or modified enzymes or non-naturally occurring enzymes or modified polypeptides have/has improved enzyme property compared to the unmodified, wild type or naturally occurring enzyme or polypeptide. In some instances, the improved enzyme property is selected from at least one of the following: increased stability (e.g., increased thermostability), increased specific activity, increased protein expression, improved purification, improved processivity, improved strand displacement, increased template jumping, improved ssDNA priming, and improved fidelity. In some instances, the term stability may include, but it is not limited to, thermal stability, storage stability, and pH stability. In some instances, specific activity is a measurement of the enzymatic activity (in units) of the protein or enzyme relative to the total amount of protein or enzyme used in a reaction. In some instances, specific activity is measured based on the ability of the enzyme to produce cDNA molecule. In some instances, the specific activity is measured in U/mg protein determined based on a primer extension reaction. In some instances, the altered or improved property may be characterized by a Performance Index (PI), where the PI is a ratio of performance of the variant, the modified enzyme, or the non-naturally occurring enzyme compared to the wild-type or compared to a naturally occurring enzyme or protein. The term "performance index (PI)" may refer to the ratio of performance of a variant polypeptide to a parent polypeptide or of a modified enzyme to an unmodified enzyme (e.g., reverse transcriptase) or of a non-naturally occurring enzyme to a naturally-occurring enzyme for a specified performance characteristic. In some instances, the specified performance or enzyme property characteristic may include, but is not limited to, stability (e.g., thermostability), specific activity, protein expression, purification, processivity, strand displacement, end-to-end template jumping, improved ssDNA priming, and/or fidelity. In some instances, the PI is greater than about 0.5, while in other instances, the PI is about 1 or is greater than about 1. In some instances, the variant polypeptide, modified enzyme (e.g., modified reverse transcriptase), or the non-naturally occurring enzyme comprises a modification at one or more amino acid positions. In some instances, the modified enzyme or the non-naturally occurring enzyme has a performance index (PI) that is equal to or greater than about 0.1, equal to or greater than about 0.2, equal to or greater than about 0.3, equal to or greater than about 0.4, equal to or greater than about 0.5, equal to or greater than about 0.6, equal to or greater than about 0.7, equal to or greater than about 0.8, equal to or greater than about 0.9, equal to or greater than about 1, equal to or greater than about 1.2, equal to or greater than about 1.5, equal to or greater than about 2, equal to or greater than about 2.5, equal to or greater than about 3, equal to or greater than about 3.5, equal to or greater than about 4, equal to or greater than about 4.5, equal to or greater than about 5, equal to or greater than about 5.5, equal to or greater than about 6, equal to or greater than about 6.5, equal to or greater than about 7, equal to or greater than about 8, equal to or greater than about 9, equal to or greater than about 10, equal to or greater than about 50, equal to or greater than about 75, equal to or greater than about 100, equal to or greater than about 500, equal to or greater than about 1000. In some instances, the variant or modified enzyme has a performance index (PI) from about 0.1 to about 1, from about 0.5 to about 1, from about 0.1 to about 2, from about 1 to about 2, from about 0.5 to about 2, from about 0.5 to about 10, from about 1 to about 10, from about 0.1 to about 10, from about 1 to about 5, from about 0.5 to about 5, from about 0.5 to about 20, from about 0.3 to about 20, from about 5 to about 10, from about 1.5 to about 10, from about 1.5 to about 50, from about 1 to about 50, from about 1.5 to about 100, from about 1.5 to about 75, from about 4 to about 10, from 3 to about 10, from about 3 to about 25, from about 3 to about 50, from about 2 to about 20, from about 2 to about 100, from about 2 to about 1000, from about 1 to about 1000. In some instances, the performance index is determined for protein expression. In some instances, the performance index is determined for at least one characteristic that improves enzyme property. In some instances, the performance index is determined for purification. In some instances, the performance index is determined for stability (e.g., thermostability). In some instances, the performance index is determined for specific activity. In some instances, the performance index is determined for processivity. In some instances, the performance index is determined for strand displacement. In some instances, the performance index is determined for template jumping. In some instances, the performance index is determined for fidelity. In some instances, the characteristic that improves enzyme property is selected from the group consisting of increased thermal stability, increased specific activity, and increased protein expression. In some instances, the performance index is performed at 30° C. In some instances, the enzyme property is analyzed at 30° C. In some instances, the enzyme property, stability (e.g., thermostability), specific activity, protein expression, purification, processivity, strand displacement, template jumping, and/or fidelity is performed at 30° C. In some instances, the performance index for measuring enzyme property, is performed at a specific temperature. In some instances, the temperature is from about 25° C. to about 42° C. In some instances, the temperature is from about 8° C. to about 50° C. In some instances, the performance index for measuring enzyme property may be carried out at a temperature ranging from about from about 8° C. to about 50° C., from about 12° C. to about 42° C., 25° C. to about 42° C., from about 25° C. to about 40° C., from about 28° C. to about 38° C., from about 30° C. to about 38° C., from about 35° C. to about 37° C., from about 27° C. to about 38° C., from about 27° C. to about 37° C., from about 26° C. to about 42° C., from about 25° C. to about 38° C., from about 27° C. to about 38° C., from about 29° C. to about 38° C., from about 29° C. to about 32° C. In some instances, the performance index for measuring enzyme property may be carried out at a temperature that is equal to or lower than about 8° C., equal to or lower than about 12° C., equal to or lower than about 20° C., equal to or lower than about 4° C., equal to or lower than about 55° C., equal to or lower than about 37° C., equal to or lower than about 25° C., equal to or lower than about 28° C., equal to or lower than about 30° C., equal to or lower than about 32° C., equal to or lower than about 34° C., equal to or lower than about 35° C., equal to or lower than about 36° C., equal to or lower than about 33° C., equal to or lower than about 31° C., equal to or lower than about 60° C., equal to or lower than about 38° C., equal to or lower than about 39° C., equal to or lower than about 40° C., equal to or lower than about 41° C., equal to or lower than about 42° C., equal to or lower than about 50° C. In some instances, the temperature may range from about 25° C. to about 80° C.

In some instances, the specific activity of the modified enzyme is from about 5 units/mg to about 140,000 units/mg, from about 5 units/mg to about 125,000 units/mg, from about 50 units/mg to about 100,000 units/mg, from about 100 units/mg to about 100,000 units/mg, from about 250 units/mg to about 100,000 units/mg, from about 500 units/mg to about 100,000 units/mg, from about 1000 units/mg to about 100,000 units/mg, from about 5000 units/mg to about 100,000 units/mg, from about 10,000 units/mg to about 100,000 units/mg, from about 25,000 units/mg to about 75,000 units/mg. In some instances, the ranges of specific activities include a specific activity of from about 20,000 units/mg to about 140,000 units/mg, a specific activity from about 20,000 units/mg to about 130,000 units/mg, a specific activity from about 20,000 units/mg to about 120,000 units/mg, a specific activity from about 20,000 units/mg to about 110,000 units/mg, a specific activity from about 20,000 units/mg to about 100,000 units/mg, a specific activity from about 20,000 units/mg to about 90,000 units/mg, a specific activity from about 25,000 units/mg to about 140,000 units/mg, a specific activity from about 25,000 units/mg to about 130,000 units/mg, a specific activity from about 25,000 units/mg to about 120,000 units/mg, a specific activity from about 25,000 units/mg to about 110,000 units/mg, a specific activity from about 25,000 units/mg to about 100,000 units/mg, and a specific activity from about 25,000 units/mg to about 90,000 units/mg. In some instances, the lower end of the specific activity range may vary from 30,000, 35,000, 40,000, 45,000, 50,000, 55,000, 60,000, 65,000, 70,000, 75,000, and 80,000 units/mg. In some instances, the upper end of the range may vary from 150,000, 140,000, 130,000, 120,000, 110,000, 100,000, and 90,000 units/mg.

Kits

Any of the compositions described herein may be comprised in a kit. In a non-limiting example, the kit, in a suitable container, comprises one or more primer(s). The kit can also comprise reaction components for primer extension and amplification (e.g., dNTPs, polymerase, buffers). The kit can include reagents for library formation (e.g., primers (probes), dNTPs, polymerase, and enzymes). The kit may also comprise approaches for purification, such as a bead suspension. The kit can include reagents for sequencing, e.g., fluorescently labelled dNTPs, sequencing primers, etc.

In some instances, some of the components of the kit may be packaged either in aqueous media or in lyophilized form. The containers of the kits can include at least one vial, test tube, or other containers, into which a component may be placed and suitably aliquoted. Where there is more than one component in the kit, the kit also can contain a second, third or other additional container into which the additional components may be separately placed. When the components of the kit are provided in one or more liquid solutions, the liquid solution can be an aqueous solution. The components of the kit may be provided as dried powder(s). When reagents and/or components are provided as a dry powder, the powder can be reconstituted by the addition of a suitable solvent.

A kit can include instructions for employing the kit components as well the use of any other reagent not included in the kit. Instructions may include variations that can be implemented.

In some instances, a kit may be used for the preparation of cDNA from a template (e.g. RNA template). Such a kit may include a carrier device compartmentalized to receive one or more containers, such as vials, tubes, and the like, each of which includes one of the separate elements used to prepare cDNA from RNA. For example, there may be provided a first container, the contents of which include a reverse transcriptase (e.g. non-retroviral reverse transcriptase, non-LTR retrotransposon, R2 reverse transcriptase) or variants thereof, in a liquid solution, powder form, or lyophilized form. Further, any number of additional containers can be provided, the contents of which independently include suitable buffers, substrates for nucleotide synthesis such as the deoxynucleotide triphosphates (e. g., dATP, dCTP, dGTP, and dTTP) either individually or collectively in a suitable solution, a template (e.g. template RNA), one or more primer(s), and acceptor nucleic acid molecule (e.g. acceptor RNA), and optionally a terminal transferase in solution. In some instances, a kit may comprise a fragment or degraded nucleic acid, DNA, RNA, or a combination thereof, one of more primer(s), an acceptor nucleic acid molecule (e.g., an acceptor nucleic acid molecule comprising a modified nucleotide), a reverse transcriptase (e.g., non-retroviral reverse transcriptase, non-LTR retrotransposon, R2 reverse transcriptase) or variants thereof, suitable buffers, substrates for nucleotide synthesis such as the deoxynucleotide triphosphates (e. g., dATP, dCTP, dGTP, and dTTP). Any combinations of the above components can be provided. Any of the above components may be excluded from the kit. In some instances, the one or more primer(s) may be one or more random primer(s). In some instances, any of the components may be individually packed.

The present disclosure relates to a kit of producing a nucleic acid molecule (e.g., cDNA molecule) comprising: one or more primer(s), nucleotides, at least one modified reverse transcriptase, a template, and instructions for performing any of the methods disclosed in the present disclosure. In some instances, a kit can be used for detecting nucleic acid comprising a nucleic acid template (e.g., a DNA template), at least one modified reverse transcriptase, nucleotides, and instructions for performing any of the methods disclosed in the present disclosure. In some instances, the modified reverse transcriptase present in the kit or to be used with the kit has activity and/or is capable of template jumping at a temperature equal to or less than about or more than about 4° C., 8° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 45° C., 46° C., 47° C., 48° C., 49° C., 50° C., 52° C., 55° C., or 60° C. In some instances, the nucleic acid and/or the template (e.g., nucleic acid template, DNA, or RNA) is present at a concentration as low as about 50 femtomolar, as low as about 60 femtomolar, as low as about 70 femtomolar, as low as about 75 femtomolar, as low as about 80 femtomolar, as low as about 90 femtomolar, as low as about 100 femtomolar, as low as about 120 femtomolar, as low as about 150 femtomolar, as low as about 200 femtomolar, as low as about 250 femtomolar, as low as about 300 femtomolar, as low as about 350 femtomolar, as low as about 400 femtomolar, as low as about 500 femtomolar, as low as about 550 femtomolar, as low as about 600 femtomolar, as low as about 700 femtomolar, or as low as about 800 femtomolar. In some instances, the nucleic acid and/or the template (e.g., nucleic acid template, DNA, or RNA) is present at a concentration as high as 1 micromolar. In some instances, a kit may comprise one or more primer(s), and/or a template annealed to a primer. The present disclosure also relates to a kit of producing modified enzymes, modified reverse transcriptases, or modified polypeptides. In some instances, the kit includes a PCR step and/or components to use for PCR.

In some instances, the present disclosure relates to a kit for detecting nucleic acid comprising a template, at least one modified reverse transcriptase, nucleotides, and instructions to perform the method of the present disclosure. In some instances, the nucleic acid is present at a concentration of at least about 50 femtomolar, at least about 20 femtomolar, at least about 100 femtomolar, or greater than about 1000 femtomolar.

Sequencing

In some instances, determining the number of different labeled nucleic acids may comprise determining the sequence of the labeled nucleic acid or any product thereof (e.g., labeled-amplicons, labeled-cDNA molecules). In some instances, an amplified target nucleic acid may be subjected to sequencing. Determining the sequence of the labeled nucleic acid or any product thereof may comprise conducting a sequencing reaction to determine the sequence of at least a portion of the sample tag, molecular identifier label, at least a portion of the labeled nucleic acid, a complement thereof, a reverse complement thereof, or any combination thereof. In some instances, only the sample tag or a portion of the sample tag is sequenced. In some instances, only the molecular identifier label or a portion of the molecular identifier label is sequenced.

Determining the sequence of the labeled nucleic acid or any product thereof may be performed by sequencing methods such as Helioscope (Registered Trademark) single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent, Ion semiconductor sequencing, Single Molecule SMRT (Registered Trademark) sequencing, Polony sequencing, DNA nanoball sequencing, and VisiGen Biotechnologies approach. Alternatively, determining the sequence of the labeled nucleic acid or any product thereof may use sequencing platforms, including, but not limited to, Genome Analyzer IIx, HiSeq, and MiSeq offered by Illumina, Single Molecule Real Time (SMRT (Registered Trademark)) technology, such as the PacBio RS system offered by Pacific Biosciences (California) and the Solexa Sequencer, True Single Molecule Sequencing (tSMS (Registered Trademark)) technology such as the HeliScope (Registered Trademark) Sequencer offered by Helicos Inc. (Cambridge, Mass.). In some instances, the sequencing reaction can occur on a solid or semi-solid support, in a gel, in an emulsion, on a surface, on a bead, in a drop, in a continuous follow, in a dilution, or in one or more physically separate volumes.

Sequencing may comprise sequencing at least about 10, 20, 30, 40, 50, 60, 70, 80, 90, 100 or more nucleotides or base pairs of the labeled nucleic acid. In some instances, sequencing comprises sequencing at least about 200, 300, 400, 500, 600, 700, 800, 900, 1000 or more nucleotides or base pairs of the labeled nucleic acid. In other instances, sequencing comprises sequencing at least about 1500; 2,000; 3,000; 4,000; 5,000; 6,000; 7,000; 8,000; 9,000; or 10,000 or more nucleotides or base pairs of the labeled nucleic acid.

Sequencing may comprise at least about 200, 300, 400, 500, 600, 700, 800, 900, 1000 or more sequencing reads per run. In some instances, sequencing comprises sequencing at least about 1500; 2,000; 3,000; 4,000; 5,000; 6,000; 7,000; 8,000; 9,000; or 10,000 or more sequencing reads per run. Sequencing may comprise less than or equal to about 1,600,000,000 sequencing reads per run. Sequencing may comprise less than or equal to about 200,000,000 reads per run.

Cells

The cell as described in the present disclosure may be a cell from an animal (e.g., human, rat, pig, horse, cow, dog, mouse). In some instances, the cell may be a single cell. In some instances, the cell is a human cell. The cell may be a fetal human cell. The fetal human cell may be obtained from a mother pregnant with the fetus. The cell may be a cell from a pregnant mother. The cell may be a cell from a vertebrate, invertebrate, fungi, archaea, or bacteria. The cell may be from a multicellular tissue (e.g., an organ (e.g., brain, liver, lung, kidney, prostate, ovary, spleen, lymph node, thyroid, pancreas, heart, skeletal muscle, intestine, larynx, esophagus, and stomach), a blastocyst). The cell may be a cell from a cell culture. The cell may be a HeLa cell, a K562 cell, a Ramos cell, a hybridoma, a stem cell, an undifferentiated cell, a differentiated cell, a circulating cell, a CHO cell, a 3T3 cell, and the like.

Circulating diseased cells that can be used in the methods of the present disclosure include all types of circulating cells that may be affected by a disease or condition or infected by an infectious agent. A circulating cell refers to a cell present in the bodily fluid. A circulating cell may not necessarily circulate throughout the entire body or in the circulatory system. For example, a circulating cell may be present locally, such as in synovial fluid, or cerebrospinal fluid, or lymph fluid. A circulating diseased cell may also be detached from a tissue or organ that has been affected by a disease or condition or infected by an infectious agent. In other instances, the circulating diseased cells can be a mixture of different types of circulating diseased cells.

In some instances, the cell is a cancerous cell. Non-limiting examples of cancer cells may include a prostate cancer cell, a breast cancer cell, a colon cancer cell, a lung cancer cell, a brain cancer cell, and an ovarian cancer cell. In some instances, the cell is from a cancer (e.g., a circulating tumor cell). Non-limiting examples of cancers may include, adenoma, adenocarcinoma, squamous cell carcinoma, basal cell carcinoma, small cell carcinoma, large cell undifferentiated carcinoma, chondrosarcoma, and fibrosarcoma.

In some instances, the cell is a rare cell. A rare cell can be a circulating tumor cell (CTC), circulating epithelial cell (CEC), circulating stem cell (CSC), stem cells, undifferentiated stem cells, cancer stem cells, bone marrow cells, progenitor cells, foam cells, fetal cells, mesenchymal cells, circulating endothelial cells, circulating endometrial cells, trophoblasts, immune system cells (host or graft), connective tissue cells, bacteria, fungi, or pathogens (for example, bacterial or protozoa), microparticles, cellular fragments, proteins and nucleic acids, cellular organelles, other cellular components (for example, mitochondria and nuclei), and viruses.

In some instances, the cell is from a tumor. In some instances, the tumor is benign or malignant. The tumor cell may comprise a metastatic cell. In some instances, the cell is from a solid tissue that comprises a plurality of different cell types (e.g., different genotypes).

Samples

In some instances, the sample that includes the template nucleic acid, e.g. DNA and/or RNA, may be combined into the reaction mixture in an amount sufficient for producing a product. In some instances, the sample is combined into the reaction mixture such that the final concentration of DNA and/or RNA in the reaction mixture is from about 1 fg/µL to about 10 µg/µL, from about 1 µg/µL to about 5 µg/µL, from about 0.001 µg/µL to about 2.5 µg/µL, from about 0.005 µg/µL to about 1 µg/µL, from about 0.01 µg/µL to about 0.5 µg/µL, from about 0.1 µg/µL to about 0.25 µg/µL. In some instances, the sample that includes the template is isolated from a single cell. In some instances, the sample that includes the template is isolated from about 2, 3, 4, 5, 6, 7, 8, 9, 10, 20, 50, 100, 500 or more cells.

In some instances, the template is DNA, RNA, or a combination of DNA and RNA. In some instances, the template is a fragment or degraded DNA, a fragment or degraded RNA, or a combination of fragment or degraded DNA and fragment or degraded RNA. In some instances, the total amount of template is the total amount of template in a sample. In some instances, the total amount of template is the total amount of template in a reaction mixture. In some instances, the total amount of template is the total amount of template in one pot or a single vessel. In some instances, the total amount of template is the total amount of template in one pot or a single vessel reaction. In some instances, the total amount of the template is from about 1 femtomolar (fM) to about 100 micromolar, from about 0.0001 micromolar to about 0.01 micromolar, from about 0.0001 micromolar to about 0.1 micromolar, from about 40 femtomolar to about 0.01 micromolar, from about 50 femtomolar to about 500 femtomolar, from about 50 femtomolar to about 0.01 micromolar, from about 50 femtomolar to about 0.1 micromolar, from about 50 femtomolar to about 500 picomolar, from about 50 femtomolar to about 500 nanomolar, from about 50 femtomolar to about 500 micromolar, from about 50 femtomolar to about 1 picomolar, from about 40 femtomolar to about 1 nanomolar, from about 1 femtomolar to about 1 picolomar. In some instances, the total amount of template is equal to or at least about or lower than about 1000 micromolar, equal to or at least about or lower than about 500 micromolar, equal to or at least about or lower than about 250 micromolar, equal to or at least about or lower than about 100 micromolar, equal to or at least about or lower than about 50 micromolar, equal to or at least about or lower than about 25 micromolar, equal to or at least about or lower than about 10 micromolar, equal to or at least about or lower than about 1 micromolar, equal to or at least about or lower than about 0.1 micromolar, equal to or at least about or lower than about 0.01 micromolar, equal to or at least about or lower than about 0.001 micromolar, equal to or at least about or lower than about 0.0001 micromolar, equal to or at least about or lower than about 2000 nanomolar, equal to or at least about or lower than about 500 nanomolar, equal to or at least about or lower than about 250 nanomolar, equal to or at least about or lower than about 200 nanomolar, equal to or at least about or lower than about 50 nanomolar, equal to or at least about or lower than about 25 nanomolar, equal to or at least about or lower than about 20 nanomolar, equal to or at least about or lower than about 2 nanomolar, equal to or at least about or lower than about 0.2 nanomolar, equal to or at least about or lower than about 0.01 nanomolar, equal to or at least about or lower than about 0.001 nanomolar, equal to or at least about or lower than about 0.0001 nanomolar, equal to or at least about or lower than about 3000 picomolar, equal to or at least about or lower than about 500 picomolar, equal to or at least about or lower than about 250 picomolar, equal to or at least about or lower than about 300 picomolar, equal to or at least about or lower than about 50 picomolar, equal to or at least about or lower than about 25 picomolar, equal to or at least about or lower than about 30 picomolar, equal to or at least about or lower than about 3 picomolar, equal to or at least about or lower than about 0.3 picomolar, equal to or at least about or lower than about 0.01 picomolar, equal to or at least about or lower than about 0.001 picomolar, equal to or at least about or lower than about 0.0001 picomolar, equal to or at least about or lower than about 5000 femtomolar, equal to or at least about or lower than about 500 femtomolar, equal to or at least about or lower than about 250 femtomolar, equal to or at least about or lower than about 50 femtomolar, equal to or at least about or lower than about 25 femtomolar, equal to or at least about or lower than about 10 femtomolar, equal to or at least about or lower than about 1 femtomolar, equal to or at least about or lower than about 0.1 femtomolar, equal to or at least about or lower than about 0.01 femtomolar, equal to or at least about or lower than about 0.001 femtomolar, equal to or at least about or lower than about 0.0001 femtomolar.

In some instances, the sample may be obtained from a biological sample obtained from a subject. In some instances, a sample comprises circulating tumor DNA sample and/or a tissue sample. In some instances, the biological sample comprises a cell-free biological sample. In some instances, the biological sample comprises a circulating tumor DNA sample. In some instances, the biological sample comprises a biopsy sample. In some instances, the biological sample comprises a tissue sample. In some instances, the biological sample comprises liquid biopsy. In some instances, the biological sample comprises cell-free DNA. In some instances, the biological sample can be a solid biological sample, e.g., a tumor sample. In some instances, a sample from a subject can comprise at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or at least about 100% tumor cells or nucleic acid from a tumor. The solid biological sample can be processed by fixation in a formalin solution, followed by embedding in paraffin (e.g., a FFPE sample). The solid biological sample can be processed by freezing. Alternatively, the biological sample can be neither fixed nor frozen. The unfixed, unfrozen sample can be stored in a solution configured for the preservation of nucleic acid. The solid biological sample can optionally be subjected to homogenization, sonication, French press, dounce, freeze/thaw, which can be followed by centrifugation.

In some instances, the sample can be a liquid biological sample. In some instances, the liquid biological sample can be a blood sample (e.g., whole blood, plasma, or serum). A whole blood sample can be subjected to separation of cellular components (e.g., plasma, serum) and cellular components by use of a Ficoll reagent. In some instances, the liquid biological sample can be a urine sample. In some instances, the liquid biological sample can be a perilymph sample. In some instances, the liquid biological sample can be a fecal sample. In some instances, the liquid biological sample can be saliva. In some instances, the liquid biological sample can be semen. In some instances, the liquid biological sample can be amniotic fluid. In some instances, the liquid biological sample can be cerebrospinal fluid. In some instances, the liquid biological sample can be bile. In some instances, the liquid biological sample can be sweat. In some instances, the liquid biological sample can be tears. In some instances, the liquid biological sample can be sputum. In some instances, the liquid biological sample can be synovial fluid. In some instances, the liquid biological sample can be vomit. In some instances, the liquid biological sample can be a cell-free sample. In some specific instances, the cell-free sample can be a cell-free plasma sample.

Polynucleotides in a sample (which can be referred to as input nucleic acid or input) can comprise DNA. The input nucleic acid can be complex DNA, such as double-stranded DNA, genomic DNA or mixed nucleic acids from more than one organism. Polynucleotides in the sample can comprise RNA. The RNA can be obtained and purified. RNA can include RNAs in purified or unpurified form, which include, but are not limited to, mRNAs, tRNAs, snRNAs, rRNAs, retroviruses, small non-coding RNAs, microRNAs, polysomal RNAs, pre-mRNAs, intronic RNA, viral RNA, cell-free RNA and fragments thereof. The non-coding RNA, or ncRNA may include snoRNAs, microRNAs, siRNAs, piRNAs and long nc RNAs. Polynucleotides in the sample can comprise cDNA. The cDNA can be generated from RNA, e.g., mRNA. The cDNA can be single or double stranded. The input DNA can be mitochondrial DNA. The input DNA can be cell-free DNA. The cell-free DNA can be obtained from, e.g., a serum or plasma sample. The input DNA can be from more than one individual or organism. The input DNA can be double stranded or single stranded.

In some instances, samples can be collected over a period of time. Samples can be collected over regular time intervals, or can be collected intermittently over irregular time intervals. Nucleic acids from different samples can be compared, e.g., to monitor progression or recurrence of a condition or disease.

In some instances, a sample can be collected by core biopsy. In some instances, a sample can be collected as a purified nucleic acid. Examples of such purified samples can include precipitated nucleic acid affixed to filter paper, phenol-chloroform extractions, nucleic acid purified by kit purification (e.g. Quigen Miniprep (Registered Trademark) and the like), or gel purified nucleic acid as exemplary examples.

The sample of the disclosure may be a sample from an animal (e.g., human, rat, pig, horse, cow, dog, mouse). In some instances, the sample is a human sample. The sample may be a fetal human sample. The sample may be from a multicellular tissue (e.g., an organ (e.g., brain, liver, lung, kidney, prostate, ovary, spleen, lymph node, thyroid, pancreas, heart, skeletal muscle, intestine, larynx, esophagus, and stomach), a blastocyst). The sample may be a cell from a cell culture.

The sample may comprise a plurality of cells. The sample may comprise a plurality of the same type of cell. The sample may comprise a plurality of different types of cells. The sample may comprise a plurality of cells at the same point in the cell cycle and/or differentiation pathway. The sample may comprise a plurality of cells at different points in the cell cycle and/or differentiation pathway. A sample may comprise a plurality of samples.

The plurality of samples may comprise one or more malignant cell. The one or more malignant cells may be derived from a tumor, sarcoma or leukemia.

The plurality of samples may comprise at least one bodily fluid. The bodily fluid may comprise blood, urine, lymphatic fluid, saliva. The plurality of samples may comprise at least one blood sample.

The plurality of samples may comprise at least one cell from one or more biological tissues. The one or more biological tissues may be a bone, heart, thymus, artery, blood vessel, lung, muscle, stomach, intestine, liver, pancreas, spleen, kidney, gall bladder, thyroid gland, adrenal gland, mammary gland, ovary, prostate gland, testicle, skin, adipose, eye or brain.

The biological tissue may comprise an infected tissue, diseased tissue, malignant tissue, calcified tissue or healthy tissue.

In some instances, the characteristic that improves enzyme property is selected from the group consisting of increased stability (e.g., increased thermostability), increased specific activity, increased protein expression, increased processivity, increased strand displacement, increased end-to-end template jumping, and increased fidelity.

EXAMPLES

The following specific examples are illustrative and non-limiting. The examples described herein reference and provide non-limiting support to the various embodiments described in the preceding sections.

Example 1: Expression and Purification

Small and medium scale: Expression vector pET-45b caring modified R2 non-long terminal repeat (LTR) retrotransposon or one of the modified R2 reverse transcriptases of SEQ ID Nos: 1-20 was transformed into *E. coli* BL21 (DE3). TABLE 1 below shows examples of non-naturally occurring R2 enzyme variants of the present disclosure. For expression, pre-culture can be setup in 2 ml LB with 100 µM Corbenicillin and grown overnight for about 8 to 12 hours at room temperature. After about 8 h to 12 h, 200 µL of the pre-culture can be transferred to 25 mL of an auto-induction expression media, Overnight Express TB (Novagen), and shaker-incubated at room temperature for 36 hours to 48 hours. Cells were harvested by centrifugation at 8000×g for 10 min at 4-8° C. The biomass-pellet was frozen at −20° C. for a minimum of 1 h.

Purification: pellet can be re-suspended in 0.5 mL lysis buffer (0.5 mL lysis buffer per ⅙ of the biomass) and incubated for 30 minutes at room temperature. Lysis buffer composition: 1× BugBuster, 100 mM Sodium Phosphate, 0.1% Tween, 2.5 mM TCEP, 3 µL Protease inhibitor mix (Roche), 50 µg lysozyme, 0.5 µL DNaseI (2,000 units/ml, from NEB). After incubation, the lysate can be mixed with equal volume (0.5 mL) of His-binding buffer (50 mM Sodium Phosphate pH 7.7, 1.5M Sodium Chloride, 2.5 mM TCEP, 0.1% Tween, 0.03% Triton X-100, and 10 mM Imidazole) and incubated at room temperature for about 10-15 minutes. After incubation, the lysate can be centrifuged at 10000×g for about 15 min at a temperature from about 4° C. to about 8° C. Pellet can then mixed with 250 µL of His-Affinity Gel (His-Spin Protein Miniprep by Zymo Research) according to manufacturer's protocol. After the binding step, the His-Affinity Gel was washed three times with Washing buffer (50 mM Sodium Phosphate pH 7.7, 750 mM Sodium Chloride, 0.1% Tween, 0.03% Triton X-100, 2.5 mM TCEP, and 50 mM Imidazole). The R2 reverse transcriptase (RT) (e.g., non-naturally occurring enzyme) can be eluted with 150 µL of elution buffer (50 mM Sodium Phosphate pH 7.7, 300 mM Sodium Chloride, 2.5 mM TCEP, 0.1% Tween, and 250 mM Imidazole) and either used directly or frozen in 30% glycerol. This protocol can be adjusted for expression and purification of mutagenesis and for screening. For example, a similar protocol can be adjusted to a plate format, such as 2 mL of the Overnight Express TB (Novagen) instead of 25 mL can be used, and the purification step can comprise 96 well spin plates with nickel-immobilized resin.

Result: After purification, samples can be analyzed using sodium dodecyl sulfate polyacrylamide gel electrophoresis (SDS-PAGE), 4-12% polyacrylamide, Bis-Tris.

Example 2: Surrogate/Diagnostic Assays

Example of reverse transcriptase (RT) activity assay: activity assay can be used to compare enzyme activity, active fraction, stability (e.g., thermostability), and robustness of the non-naturally occurring enzymes. RT activity and active fraction(s) can be estimated based on primer extension assay by comparing fraction(s) of extended to non-extended DNA primer using various template/primer and enzyme concentrations. Extension assays can be conducted with and without the addition of a DNA trap.

Example protocol: annealed 0.2 µM template/primer with fluorescently labeled primer can be pre-incubated with various concentrations of R2 RT (relative to template/primer 0.1 to 4-fold) at room temperature for 20 minutes. Pre-incubation conditions can include 40 mM Tris pH 7.5, 200 mM NaCl, 5 mM TCEP, and 0.1% Tween. Extension can start with the addition of $MgCl_2$ (5 mM, final) and dNTPs (25 µM of each, final) and optionally a DNA trap (unlabeled DNA oligo duplex at 3 µM, final, or heparin). The addition of trap DNA helps to estimate RT active fraction(s). The reaction can then incubated for 10 minutes and stopped with EDTA (50 mM, final) or formamide (50%, final). The product of the reaction can then be analyzed with 15% PAGE-Urea. An example of a template sequence used is rCrArG rUrCrA rGrUrC rArGrU rCrArG rUrCrA rGrUrG rCrCrA rArArU rGrCrC rUrCrG rUrCrA rUrC and of a primer is /56-FAM/ TGATGACGAGGCATTTGGC.

Example of end-to-end template jumping assay: Primer extension assay with two templates where one template is annealed to a fluorescently labeled primer (donor template) and the other is primer-free (acceptor nucleic acid).

Example protocol: annealed 0.1 µM template/primer with fluorescently labeled primer (alternatively the product of the reaction can be stained with Syber Gold) can be pre-incubated with various concentrations of R2 RT (relative to template/primer 0.1 to 4-fold) at room temperature for 20 minutes. Pre-incubation conditions can include 40 mM Tris pH 7.5, 200 mM NaCl, 5 mM TCEP, and 0.1% Tween. Extension can start with the addition of $MgCl_2$ (5 mM, final), dNTPs (50 µM of each, final) and the acceptor nucleic acid at various concentrations (range from about 0.01 µM to about 5 µM). The reaction can then be incubated for 30 min-1 h and stopped with EDTA (50 mM, final) or formamide (50%, final). The product of the reaction can be analyzed with 15% PAGE-Urea.

Templates: the templates can be generated by in vitro RNA synthesis with T7 RNA polymerase based on the DNA template generated in a PCR reaction with two primers, one of which included a T7 promoter sequence (i.e., a first primer). The second primer can also be used as a DNA primer in the donor template/primer protocol. The product of the reaction can then be analyzed with 15% PAGE-Urea. Example of materials used: template for PCR amplification pUC18 with T7 primer CTGCAGTAATACGACTCAC-TATAGGATCCTCTAGAGTCGACCTGC (SEQ ID NO: 24); donor primer GCCATTCGCCATTCAGGCTGC (SEQ ID NO: 102)(used for both PCR amplification and priming at the donor RNA template); RNA template (~190 nucleotides); acceptor nucleic acid—G-block PCR template ACGGCCAGTGAATTGTAATACGACTCAC-TATAGGGCGAATTGGGTACCGCCTCGAG GTCGACGGTATCGATAAGCTTGATATCGAAT-TCCTGCAGCGGATCCACTAGTTCTAG AGCGGCCGCCACCGCGGTG-GAGCTCCAGCTTTTGTTCCCTTTAGTGAGGGT-TAATTT CGAGCTTGGCGTAATCATGGTCAT-AGCTGTTTCC (SEQ ID NO: 103); two primers for PCR amplification (a T7 primer ACGGCCAGTGAAT-TGTAATACGAC (SEQ ID NO: 104) and a second primer GGAAACAGCTATGACCATG (SEQ ID NO: 105)).

Example of processivity assay: processivity of each non-naturally occurring enzyme can be analyzed based on primer extension and product formation using a 15% PAGE-Urea, or a 1.2% agarose gel, or a 2% agarose gel. Product length distribution can be analyzed with densitometry.

Example protocol: annealed 0.05-0.1 µM template/primer with fluorescently labeled primer (alternatively product of the reaction can be stained with Syber Gold) can be pre-incubated with various concentration of R2 RT (0.1 to 4-fold relative to template/primer) for 20 minutes at room temperature. Pre-incubation conditions: 40 mM Tris pH 7.5, 200 mM NaCl, 5 mM TCEP, and 0.1% Tween. Extension can start with addition of $MgCl_2$ (5 mM, final), dNTPs (50 µM of each, final), and optionally a DNA trap (unlabeled DNA oligo duplex at 3 µM, final). The reaction can then be incubated for 30 min-1 h and stopped with EDTA (50 mM, final) or formamide (50%, final).

Templates: the templates can be generated by in vitro RNA synthesis with T7 RNA polymerase based on the DNA template generated in a PCR reaction with two primers, one of which included a T7 promoter sequence. The second primer can also be used as a DNA primer in the donor template/primer protocol. The product of the reaction was analyzed with a 15% PAGE-Urea, or a 1.2% agarose gel, or a 2% agarose gel. Materials included: template for PCR amplification pUC18 with T7 primer CTGCAGTAATACGACTCACTATAG-GATCCTCTAGAGTCGACCTGC, RT primer CAGGGTT-ATTGTCTCATGAGCG (SEQ ID NO: 101)(used for both PCR amplification and priming at the donor RNA template), and RNA template (~600 nucleotides).

Example of Random priming: Longer RNA template(s) with several primers with adapters or random primers with adapters; product analysis is performed after PCR amplification to compare product's length distribution (one primer is specific to the 5'-end of the template and the second primer is complementary to the adapter sequence).

Example 3: Activity and Template Jumping Experiment Using Synthetic RNA

Non-naturally occurring R2 enzymes can have template jumping properties.

Example protocol: reactions containing 0.25 mM of dNTPs, R2 buffer, 0.4 µM template/primer, acceptor nucleic acid (0 to 1 µM), non-naturally occurring R2, and $H_2O$ can be used to detect template jumping. The reactions containing the R2 enzyme or the R2 buffer can be incubated at 30° C. for 1 hour. Products can be analyzed using 15% PAGE-Urea gel. Sequences of templates, primers, and acceptors that can be used to test template jumping are shown below:

| | |
|---|---|
| P173 (RNA template) | CAGUCAGUCAGUCAGUCAGUGCCAAAUGCCUCGUCA UC (SEQ ID NO: 98) |
| P174 (fluorescently labeled primer) | /56-FAM/TGATGACGAGGCATTTGGC (SEQ ID NO: 99) |
| P181 (acceptor nucleic acid) | GTTAATAACGAAATGAGCAGCCrGrGrG (SEQ ID NO: 100) |

Example 4: DNA Fragments can be Captured and Tagged with Non-Naturally Occurring R2 Enzyme This experiment can be used to show that a 200 bp DNA fragment (typical size for cfDNA) can be captured and tagged in a 1-pot (single vessel) reaction using the methods of the present disclosure. Some facts of this experiment: no prior knowledge of the sequence is required and the data provided by this experiment may meet the sensitivity requirement (a typical liquid biopsy sample has between about 10-30 ng of DNA, a required sensitivity of 0.1% (~10-30 μg)).

This experiment can be used to show that 1-pot (single vessel) reaction containing DNA fragments (200 bp PCR product prepared by heat denaturation and quick cooling of PCR product) can be captured and tagged using a non-naturally occurring R2 enzyme (P8 variant R2 enzyme). In brief, this experiment can include two approaches: 1) capture of DNA fragment with RNA priming; and 2) capture of DNA fragment using RNA donor. Briefly, the reactions per the first approach (RNA priming) can include H$_2$O, 5×R2 buffer, 0.25 mM dNTPs, 200 bp DNA fragment (0 ng (no DNA template control (NTC)), 160 μg, 32 μg, or 6 μg of DNA template), enzyme (e.g., 0.023 μg/μL P8 variant R2 enzyme), and 0.5 μM of P173. The reactions per the second approach (RNA donor) can include H$_2$O, 5×R2 buffer, 0.25 mM dNTPs, 200 bp DNA fragment (0 ng (no DNA template control (NTC)), 160 pg, 32 pg, or 6 pg), enzyme (e.g., 0.023 μg/μL P8 variant R2 enzyme), and 0.2 μM RNA donor (P173+P174). The reactions can then be incubated at 30° C. for about 1 hour. The reactions can then be diluted 1:10 and supplemented with PCR reagents including amplification primers and hot-start polymerase. The PCR amplification reactions for the first approach (RNA priming) can include H$_2$O, 1× taq master mix with 1×SYBR Green, 0.5 μM of P169, 0.5 μM of P186, and 1× template (10 μL RT reaction in 100 μL total volume for PCR). The PCR amplification reactions for the second approach (RNA donor) can include H$_2$O, 1× Taq Mastermix with 1× sybr green, 0.5 μM of P169, 0.5 μM of P186, and 1× template (10 μL RT reaction in 100 μL total volume for PCR). The PCR conditions for the reactions were 95° C. for 3 minutes and 30 cycles of 95° C. for 3 seconds, 54° C. for 10 seconds, and 64° C. for 10 seconds. The reactions can then be increased to 68° C. for 2'. The length of the PCR products can be confirmed on an acrylamide gel. The results can be used to show that the DNA fragment (~200 bp) can be captured using either the RNA priming or the donor RNA mechanism without prior knowledge of the DNA sequence.

Sequences:

| | |
|---|---|
| 200 bp DNA fragment (PCR product) | CTGCAGTAATACGACTCACTATAGGATCCTCTAGAGTCGACCTG CAGGCATGCAAGCTTGGCACTGGCCGTCGTTTTACAACGTCGTG ACTGGGAAAACCCTGGCGTTACCCAACTTAATCGCCTTGCAGCA CATCCCCCTTTCGCCAGCTGGCGTAATAGCGAAGAGGCCCGCAC CGATCGCCCTTCCCAACAGTTGCGCAGCCTGAATGGCGAATGGC (SEQ ID NO: 23) |
| P169 | CTGCAGTAATACGACTCACTATAGGATCCTCTAGAGTCGACCTG C (SEQ ID NO: 24) |
| P186 | CAGTCAGTCAGTCAGTCAGTGCCA (SEQ ID NO: 25) |
| P173 (RNA template) | CAGUCAGUCAGUCAGUCAGUGCCAAAUGCCUCGUCAUC (SEQ ID NO: 26) |
| P174 | TGATGACGAGGCATTTGGC (SEQ ID NO: 27) |

Example 5: Template Concatemerization

This experiment was designed to demonstrate a method for converting short DNA fragments into a concatemer. Concatemers may contain about 2, 3, 4, 5, 6, 7, 8, 9, 10, 20, 30, 40, 50, 60, 70, 80, 90, 100, 500, 1000, or more copies of the starting nucleic acid. In brief, the initial PCR protocol for template preparation can include H$_2$O, 2×Q5 master mix, P316 (0.5 μM), P317 (0.5 μM), and pUC18 (0.05 ng/μL). The PCR condition can be 98° C. for 30 seconds followed by 30 cycles of: 98° C. for 10 seconds, 66° C. for 15 seconds, and 72° C. for 10 seconds. At the end of the 30 cycles, the reaction can be kept at 72° C. for 2 minutes and then, it can be reduced to 4° C. The adaptor annealing reaction can include H$_2$O, Tris pH 8.0 (20 mM), NaCl (100 mM), and two primers (25 μM each; (P312+P313) or (P314+P315) or (P320+P321)). The reaction can be incubated at 90° C. for 1 minute, followed by 0.1° C./second ramp to 25° C. (20 seconds) and then, it can be reduced and kept at 4° C. The first adaptor ligation reaction can include H$_2$O (30 μL), fragmented DNA (20 μL), end repair and T-tailing buffer (7

µL), and end repair and T-tailing enzyme mix (3 µL). The reaction can be incubated at 20° C. for 30 minutes and then increased to 65° C. for 30 minutes. H₂O (5 µL) can then added to the reaction (50 µL) along with 2.5 µL of 20 µM adaptor (P312+P313), 2.5 µL of 20 µM adaptor (P314+ P315), ligation buffer (30 µL), and DNA ligase (10 µL). The reaction can then be incubated at room temperature for 15 minutes, followed by a reaction clean-up. SPRI beads can then be added and the reaction can be eluted. The adaptor ligated library (10 µL) can be incubated with H₂O (40 µL) and 2× Kappa HiFi master mix (50 µL) and it can be subjected to PCR (98° C. for 45 seconds; 5 cycles of 98° C. for 15 seconds, 60° C. for 30 seconds, and 72° C. for 30 seconds; 72° C. for 1 minute; and kept at 4° C.). This protocol can then be modified in order to increase the number of cycles (e.g., from 5 cycles to 25 cycles). The second adaptor ligation reaction comprises of a similar protocol as the one described for the first adaptor ligation reaction; the difference being that 5 µL of 20 µM adaptor (P320+P321) can be used instead of 2.5 µL of 20 µM adaptor (P312+P313) and 2.5 µL of 20 µM adaptor (P314+P315).
Sequences:

RNA sample. For example, 3'-OH is required for RNA poly(A) tailing with a polymerase (e.g., poly-A polymerase), and/or for DNA poly-tailing with terminal deoxynucleotidyl transferase (TdT), and/or for ligation. Endogenous RNA usually contains a 3'-hydroxyl or a 2',3'-cyclic phosphate or a 3'-phosphate. The 3'-hydroxyl can be a product of transcription, poly(A) tail synthesis, or enzymatic cleavage (enzymes with catalytic mechanism similar to RNase H). The 2',3'-cyclic phosphate can be a product of enzymatic cleavage (enzymes like RNase A) or spontaneous hydrolysis (non-enzymatic intramolecular transphosphorylation). For example, RNA can be cleaved by intramolecular transesterification.

The 2',3'-cyclic phosphate is very common due to natural RNA phosphodiester bond instability and can occur naturally (cell free RNA degradation) or as a result of sample treatment or storage. RNA samples bearing 2',3'-cyclic phosphate or 3'-phosphate cannot be subsequently poly-tailed or ligated because the presence of a free 3'-hydroxyl group is required for both. For this reason, RNA samples with

| P312 | ACACTCTTTCCCTACACGACGCT (SEQ ID NO: 28) | Right adaptor |
| P313 | /5Phos/GCGTCGTGTAGGGAAAGAGTGT (SEQ ID NO: 29) | Right adaptor |
| P314 | /5Phos/CACTCTTTCCCTACACGACGCT (SEQ ID NO: 30) | Left adaptor |
| P315 | AGCGTCGTGTAGGGAAAGAGTGT CACTCTTTCCCTACACGACGCT (SEQ ID NO: 31) | Left adaptor |
| P316 | ACACTTTATGCTTCCGGCTC CACTCTTTCCCTACACGACGCT (SEQ ID NO: 32) | Amp pUC18 for 200 bp frag with KpnI in middle |
| P317 | TAAGTTGGGTAACGCCAGG CACTCTTTCCCTACACGACGCT (SEQ ID NO: 33) | Amp pUC18 for 200 bp frag with KpnI in middle |
| P318 | ACACTCTTTCC CACTCTTTCCCTACACGACGCT (SEQ ID NO: 34) | Invasion primers |
| P319 | AGCGTCGTG CACTCTTTCCCTACACGACGCT (SEQ ID NO: 35) | Invasion primers |
| P320 | TTCCAATGATACGGCGACCACCGAUACUGUCA UAGCTAGCTCCTCACTCTTTCCCTACACGACGC T (SEQ ID NO: 36) | Outside adaptor-can use P5 primer USER compatible |
| P321 | /5Phos/GGAGCTAGCTATGACAGTATCGGTGGTC GCCGTATCATTACTT CACTCTTTCCCTACACGACGCT (SEQ ID NO: 37) | Outside adaptor-can use P5 primer |

Example 5: Improved Conversion Efficiency (RNA Sample to Next-Generation Sequence (NGS) Library) after 3'-Phosphate, 2'-Phosphate and 2',3'-Cyclic Phosphate Removal Some of the proposed or demonstrated techniques of the present disclosure require free 3'-hydroxyl at the 3'-end of an 2',3'-cyclic phosphate or 3'-phosphate can be treated with a phosphatase (e.g., T4 polynucleotide kinase (PNK) enzyme) to generate a 3'-hydroxyl group. Other examples of phosphatases are disclosed in TABLE 1 below (Ushati Das and Stewart Shuman, Mechanism of RNA 2',3'-cyclic phosphate endhealing by T4 polynucleotide kinase-phosphatase, Nucleic Acids Research, 2013, vol. 41, No. 1, 355-365).

TABLE 1

Comparison of RNA repair enzymes that heal 2',3'-cyclic phosphate ends

| Enzyme | Family | Metal | End-product | CPDase product | 3'-Pase | 2'-Pase |
|---|---|---|---|---|---|---|
| T4 Pnkp | Acylphosphotase | $Mg^{2+}$ | 3'-OH, 2'-OH | 3'-$PO_4$, 2'-OH | Yes | Yes |
| CdPnkp | Binuclear metallophosphoesterase | $Mn^{2+}$ $Ni^{2+}$ | 3'-OH, 2'-OH | 3'-OH, 2'-$PO_4$ | Yes | Yes |
| Yeast and plant tRNA ligase | 211 phosphoesterase | None | 3'-OH, 2'-$PO_4$ | 3'-OH, 2'-$PO_4$ | No | No |
| RtcB | RtcB | $Mn^{2+}$ | 3'-$PO_4$, 2'-OH | 3'-$PO_4$, 2'-OH | No | ? |

T4 polynucleotide kinase (PNK) enzyme includes both kinase and phosphatase enzymatic activities. Thus, to optimize the T4 PNK, the kinase enzymatic activity can be removed by substituting at least one of the catalytically essential amino acids. This results in the phosphatase being the only enzymatic activity present. Removing the kinase activity helps with subsequent reactions such as poly-A tailing using ATP for example, because ATP is also a kinase substrate. Examples of cell free RNA NGS library preparation protocols including de-phosphorylation are disclosed herein. Also disclosed herein are comparison reactions (e.g., reactions not treated with T4 PNK).

Additional potential benefits: the unique properties of the 3'end of RNA particles depending on the type of process used to generate the RNA particles, allow one to focus and/or manipulate the sequencing library. For example, if one does not wish to sequence RNA fragments generated due to process degradation (e.g., incomplete RNA fragments bearing 2',3'-cyclic phosphate), one can avoid treating the sample with T4 PNK. In this way, the library will include full mRNAs and miRNAs (3'-hydroxyl).

Example 7: RNA Sample Fragmentation is Part of the NGS Library Preparation Workflow; Enzymatic and Nonenzymatic Methods Major DNA sequencing technologies, such as illumina or ion torrent, are limited in regards to sequencing read-length (meaning that a limited number of bases can be sequenced in each individual read). Both technologies have a read range of up to about 100 bp-500 bp, making it impractical to use a library that significantly exceeds this range. Cell free RNA usually ranges from about 20 to 2000 bases, formalin-fixed paraffin-embedded (FFPE) RNA ranges from about 20 to 500 bases and mRNA is usually around 2000 bases. For practical reasons, samples are usually fragmented, so effective library size is no more than 400 bp. Sample loading library fragments longer than 1000 bp is very inefficient compared to shorter fragments. Disclosed herein are two general methods of RNA sample fragmentation; enzymatic and non-enzymatic. The enzymatic method can use enzymes with RNase activity (e.g., RNase A, RNase P, RNase H, RNase III, RNase T1, RNase T2, RNase U2, RNase V1, RNase I, RNase L, RNase PhyM, RNase V, dicer, or argonaute). The non-enzymatic method disclosed herein takes advantage of the natural chemical instability of RNAs. RNA can undergo spontaneous non-enzymatic fragmentation as a result of internal transphosphorylation. Breaking of phosphodiester bonds of RNA can be brought about by various conditions (e.g., metals, such as Mg, Mn, Pb, or polyamines, or cofactors, such as PVP or PEG). An increase in the transphosphorylation rate can be achieved, for example, with high pH or with high(er) temperature. Non-enzymatic hydrolysis preferentially happens in single stranded portions of RNA particles, preferentially between bases UA or CA. The advantages of using a non-enzymatic method includes: simplicity and reliability (independent of enzyme activity or shelf life), and the fact that the reaction can be conducted in conditions compatible with the majority of the subsequent steps. TABLE 2 below shows a workflow of both a fragmentation protocol and a no-fragmentation protocol. The libraries were prepared using cell free RNA sample.

TABLE 2

Workflow

| Work flow: | No Fragmentation | | With Fragmentation |
|---|---|---|---|
| STEP_1 | PNK Treatment | STEP_1 | RNA fragmentation by heat treatment |
| STEP_2 | Poly Adenylation using Poly-A Polymerase | STEP_2 | PNK Treatment |
| | | STEP_3 | Poly Adenylation using Poly-A Polymerase |
| STEP_3 | Poly T Primer annealing | STEP_4 | Poly T Primer annealing |
| STEP_4 | 2D-RT & Tagging reaction | STEP_5 | 2D-RT & Tagging reaction |
| STEP_5 | primer-adapter excess and non-specific priming product cleaning with Magnetic beads with immobilized oligoA | STEP_6 | primer-adapter excess and non-specific priming product cleaning with Magnetic beads with immobilized oligoA |
| STEP_6 | SPRI cleanup | STEP_7 | SPRI cleanup |
| STEP_7 | Sample Index PCR | STEP_8 | Sample Index PCR |
| STEP_8 | SPRI cleanup | STEP_9 | SPRI cleanup |

In short, the no-fragmentation protocol can include 6.5 µL of $H_2O$, 2 µL of 10×T4 PNK buffer, 0.5 µL of 10×RNase inhibitor, 1 µL of 10 U/µL T4 PNK enzyme, and 10 µL sample (e.g., cell free RNA sample). The reaction can then be incubated at 37° C. for 20 minutes, 70° C. for 4 minutes, and then placed on ice. 3.25 µL of $H_2O$, 10 µL of 5×2D PNK buffer, 1.25 µL of 10×RNase inhibitor, 7.5 µL of 10 mM ATP, and 1.25 µL of 5 U/µL *E. coli* PolyA Pol can then be added to the reaction. The reaction can be incubated at 16° C. for 5 minutes and can then be placed on ice. 0.5 µL of 100× dNTPs, 1 µL of 10 µM P334 Primer, 0.25 µL of 100 µM P423 DNA ter acc can then be added to the reaction. The reaction can be incubated at 70° C. for 2 minutes, and can then be placed on ice for 2 minutes. 1.25 µL of 10×RNase inhibitor, 3.75 µL of P2 (e.g., R2 variant at 1 µg/µL can be added to the reaction (for a total of 50 µL reaction). The reaction can be incubated at 34° C. for 1 hour, pulled down, spri 1.6×, then eluted in 50 µL. In some instances, a reverse transcriptase or a modified reverse transcriptase, or an enzyme that has similar function to a reverse transcriptase can be used instead of P2.

In short, the fragmentation protocol can include 1 µL of 10× buffer A and 9 µL of sample (e.g., cell free RNA sample). The reaction can be incubated at 94° C. for 4 minutes and can then be placed on ice. 14.75 µL of H$_2$O, 3 µL of 10× buffer B, 0.75 µL of 10×RNase inhibitor, and 1.5 µL of 10 U/µL T4 PNK enzyme can be added to the reaction. The reaction can be incubated at 37° C. for 30 minutes, at 72° C. for 3 minutes and can then be placed on ice. 5 µL of 10× buffer C, 1.25 µL of 10×RNase inhibitor, 7.5 µL of 10 mM ATP, and 1.25 µL of 5 U/µL *E. coli* PolyA Pol can then be added to the reaction. The reaction can be incubated at 16° C. for 5 minutes and can then be placed on ice. 0.5 µL of 100×dNTPs, 1 µL of 10 µM P334 Primer, 0.25 µL of 100 µM P423 DNA ter acc can then be added to the reaction. The reaction can be incubated at 70° C. for 2 minutes, and can then be placed on ice for 2 minutes. 1.25 µL of 10×RNase inhibitor and 3.75 µL of P2 (e.g., R2 variant at 1 µg/µL (e.g., an R2 RT N-truncation, such as SEQ ID NO: 50)) (can be added to the reaction (for a total of 50 µL reaction). The reaction can be incubated at 34° C. for 1 hour, pulled down, spri 1.6×, then eluted in 50 µL. In some instances, a reverse transcriptase or a modified reverse transcriptase, or an enzyme that has similar function to a reverse transcriptase can be used instead of P2.

In short, the 5×2D PNK buffer can include 645 µL of H$_2$O, 10 µL of 1000 mM Tris-HCl pH 7.5, 300 µL of 5000 mM NaCl$_2$, 5 µL of 1000 mM MgCl$_2$, 25 µL of 10% tween, and 15 µL of 1000 mM DTT. The buffer A stock can include 60 µL of H$_2$O, 10 µL of 1000 mM Tris-HCl pH 8.3, and 30 µL of 1000 mM MgCl$_2$. The buffer B stock can include 45 µL of H$_2$O, 50 µL of 1000 mM Tris-HCl pH 7.5, and 5 µL of 1000 mM DTT. The buffer C stock can include 36 µL of H$_2$, 60 µL of 5000 mM NaC$_2$, 2.5 µL of 10% tween, and 1.5 µL of 1000 mM DTT. The 10×PNK buffer can include 150 µL of H$_2$O, 700 µL of 1000 mM Tris-HCl pH 7.5, 100 µL of MgCl$_2$, and 50 µL of 1000 mM DTT. The 100× balanced dNTPs can include 100 µL of H$_2$O, 75 µL of 100 mM dATP, 75 µL of 100 mM of dTTP, 375 µL of 100 mM dGTP, and 375 µL of 100 mM dCTP. The 5×R2 buffer+dNTPs can include 430 µL of H$_2$O, 150 µL of 1000 mM Tris-HCl pH 7.5, 300 µL of 5000 mM NaCl$_2$, 25 µL of 1000 mM MgC$_2$, 25 µL of 10% tween, 25 µL of 1000 mM DTT, 3.75 µL of 100 mM dATP, 3.75 µL of 100 mM of dTTP, 18.75 µL of 100 mM dGTP, and 18.75 µL of 100 mM dCTP. The streptavidin magnetic beads can include 160 µL of streptavidin magnetic beads (NEB) saturated with biotinylated oligo AAAAAAAAAAAAAAAAAAAAAAAAAAAAAAAAAA AA/3BioTEG/; beads can be resuspended in 10 mM Tris pH7.5, 300 mM NaCl$_2$. The primer sequences used can be: P334 (A/iSp9/CCGTGACTGGAGTTCA-GACGTGTGCTCTTCCGATCT NNNNNNNN TTTTTTTTTTTTTTTTT) (SEQ ID NO: 93); P423 (AA/iSp9/ACACTCTTTCCCTACACGACGCTCTTCC-GATCT/3ddC/) (SEQ ID NO: 94); P399 (AATGA-TACGGCGACCACCGAGATCTACACGTACTGACACA CTCTTTCCCTACACGA CGC) (SEQ ID NO: 95); P400 (CAAGCAGAAGACGGCATACGAGATAT-TACTCGGTGACTGGAGTTCAGACGTGT)(SEQ ID NO: 96)

Example 9: Robust Mechanism of R2 RT Jumping

R2 RT jumping is a very efficient mechanism. It is much less sensitive to the acceptor-adapter sequences compared to template switching mechanisms (e.g., methods that use MMLV). This low sensitivity allows for optimal utilization of sequencing adapters in the Illumina sequencing for example. In this experiment, a variety of acceptors can be tested. This experiment can be used to show efficiency similarities between RNA and DNA acceptors. The use of DNA acceptors allow for cheaper and more reliable and/or stable technology. This experiment can be used to show that the conversion efficiency is not sensitive to the 3'-end of the acceptor sequences. Thus, this mechanism allows for flexibility regarding acceptor sequences and it is relevant for both RNA and DNA samples. Examples of acceptors used: 1) AA/iSp9/ACACTCTTTCCCTACACGACGCTCTTCC-GATCTAGGG/3ddC/ (SEQ ID NO: 80); 2) AA/iSp9/ACACTCTTTCCCTACACGACGCTCTTCC-GATCTCAGGG/3ddC/ (SEQ ID NO: 81); 3) AA/iSp9/ACACTCTTTCCCTACACGACGCTCTTCCGATCTTCT GGG/3ddC/ (SEQ ID NO: 82); 4) AA/iSp9/ACACTCTTTCCCTACACGACGCTCTTCCGATCTG/ 3ddC/ (SEQ ID NO: 83); 5) AA/iSp9/ACACTCTTTCCC-TACACGACGCTCTTCCGATCT/3ddC/ (SEQ ID NO: 84); 6) AA/iSp9/ACACTCTTTCCCTACACGACGCTCTTCC-GATCTrGrGrG/3ddC/ (SEQ ID NO: 85); 7) AAAA/iSp9/ACACTCTTTCCCTACACGACGCTCTTCCGATCTrGr-GrG (SEQ ID NO: 86); 8) AA/iSp9/ACACTCTTTCCCTACACGACGCTCTTCCGATCTN/ 3ddC/ (SEQ ID NO: 87); 9) AA/iSp9/ACACTCTTTCCCTACACGACGCTCTTCCGATCTNN/ 3ddC/ (SEQ ID NO: 88); 10) AA/iSp9/ACACTCTTTCCCTACACGACGCTCTTCCGATCT*/ 3ddC/ (SEQ ID NO: 89); 11) AA/iSp9/ACACTCTTTCCCTACACGACGCTCTTCCGATCTN/ ideoxyI//3ddC/ (SEQ ID NO: 90); 12) AA/iSp9/ACACTCTTTCCCTACACGACGCTCTTCCGATC/ iSuper-dT//3ddC/ (SEQ ID NO: 91); and 13) A/iSp9/CCGTGACTGGAGTTCAGACGTGTGCTCTTCCGAT CT/3ddC/ (SEQ ID NO: 92).

Example 10: Poly-A Tail Length Control, Method with Non-Extendable Nucleotide

PolyA polymerase is an RNA polymerase used frequently to generate a poly-A tail on the 3' end of an RNA (e.g., poly-A polymerase form *E. coli* or yeast). Poly-A polymerase has enzymatic activity that allows for the generation of an RNA chain (i.e., extension of the 3'end of an RNA) without an RNA or DNA template. Although, poly-A polymerase preferably synthesizes a poly-A tail, poly-A polymerase also has activity with other ribonucleotides (e.g., CTP, GTP and UTP). Controlling the poly-A tail length is important for sequencing quality and yield. Typically, ATP concentration and reaction time and/or temperature are used to control the poly-A tail length. Alternative methods can be used, such as using a blocking (un-extendable) nucleotide (e.g., 3'-Deoxyadenosine-5'-Triphosphate (an ATP analog)). Once a blocking nucleotide, 3'-Deoxyadenosine-5'-Triphosphate, is incorporated to an RNA chain analog, it cannot be further extended due to a lack of a 3' hydroxyl group. Various concentrations of ATP and 3'-Deoxyadenosine-5'-Triphosphate can be used. Poly-A tail length can be controlled based on the concentration/ratio of ATP and 3'-Deoxyadenosine-5'-Triphosphate, which is independent of reaction time and/or enzyme concentration. This method provides for significant protocol advantage when applied to high throughput or automated processes.

Example 11: Library Preparation, Depletion of Ribosomal RNA (rRNA) and Transfer RNA (tRNA) to Maximize Sequencing Throughput Approximately 80% of the total RNA in cells is rRNA and 15% is tRNA. Ribosomal RNA rarely serves as a diagnostic target. Therefore, because of that, the practice is to remove/deplete rRNA and tRNA from sequencing libraries. The amount of rRNA and tRNA in sequencing libraries can be controlled at various stages of library preparation. For example, depletion of rRNA and tRNA can occur during the early stages, e.g., after total RNA isolation (RNA level), or after PCR amplification (dsDNA level). Two general methods to remove rRNA and tRNA is described herein: 1) pulling rRNA/tRNA or PCR products using complementary oligonucleotide attached to magnetic beads or solid support; and 2) oligonucleotide-guided degradation of the rRNA/tRNA or PCR products.

Method 1: In this method, amplified dsDNA can be denatured and hybridized to a pool of strategically designed oligonucleotides. Oligonucleotides are complementary to one or both DNA strands with rDNA sequence. For Illumina library, only one strand may be depleted as only one polarity is used in bridge amplification. Each oligonucleotide includes biotin modification. Ribosomal sequences (including DNA fragments) can be depleted/removed using straptvidin-immobilized magnetic beads or solid support. In some cases, depletion can be performed after PCR library amplification in order to mitigate losses of rare and low represented sequences. Depletion can also be performed during the early stages of library preparation (e.g., RNA level).

Example 12: A Method to Express the R2 Retrotransposon

Described herein are two methods of expressing the R2 retrotransposon enzyme: the first, involves the removal of the N-terminal domain, and the second, involves tag-fusion stabilization.

Method 1: N-terminal domain removal. This method can be used to transform the R2 retrotransposon, while increasing its protection, leading to increase expression in E. Coli and improved stability. It is important to note, however, that due to its eukaryotic origin as well as the structure and complexity of its R2 retroelements, a high level of expression, and thus, production is difficult to achieve. These R2 retroelements are multi-domain elements with a molecular mass that is usually over 100 kD. These elements are composed of three major domains (see, FIG. 1C): (1) the N-terminal domain, which usually includes DNA binding motifs zinc-finger and c-myb (see, FIG. 1A and FIG. 1B). This domain contributes to the ability of the R2 retrotransposon to have specific recognition and to bind to target DNA through the target primed reverse transcription mechanism (TPRT); (2) reverse transcriptase, which is responsible for copying the R2 RNA template; and (3) the endonuclease domain, which is responsible for the specific cleavage of target DNA.

This method, based on the underlying principle that the presence of the N-terminal domain interferes with the expression and stability of the R2 retroelement, focuses on the full or partial removal of the N-terminal domain. The removal method can be focused on either the full N-terminal domain, only a part of it, thus, a partial N-terminal domain removal. This method improves the expression and stability of the R2 protein without negatively affecting the enzyme's performance in the downstream process of library preparation (see, FIGS. 1A, B, and C).

Method 2: Tag-fusion stabilization. This method involves the extension of Method 1, whereby the N-terminal domain is removed, in combination with fusion-tags. These tags include: Fh8, MBP, NusA, Trx, SUMO, GST, SET, GB1, ZZ, HaloTag, SNUT, Skp, T7PK, EspA, Mocr, Ecotin, CaBP, ArsC, IF2-domain I, an expressivity tag, an expressivity tag that is part of IF2-domain I, RpoA, SlyD, Tsf, RpoS, PotD, Crr, msyB, yjgD, rpoD, His6, His-tag, His6-tag, Calmodulin-tag, CBP, CYD (covalent yet dissociable NorpD peptide), Strep II, FLAG-tag, HA-tag, Myc-tag, S-tag, SBP-tag, Softag-1, Softag-3, V5-tag, Xpress-tag, Isopeptag, SpyTag, B, HPC (heavy chain of protein C) peptide tags, GST, MBP, biotin, biotin carboxyl carrier protein, glutathione-S-transferase-tag, green fluorescent protein-tag, maltose binding protein-tag, Nus-tag, Strep-tag, and thioredoxin-tag.

Example 13: Mutagenesis of R2 Retrotransposon Motif-1, Motif 0, and Thumb Domain Mutagenesis of motif-1 and motif 0. The reverse transcriptases (RTs) that are the most studied and best described in the literature are those of retroviral and long terminal repeats (LTR)-retrotransposon origin. This family of reverse transcriptases shares seven highly conservative amino acid sequence motifs. RTs encoded by non-LTR retroelements as well as those encoded by telomerases include additional conservative motifs located at the N-terminal of the RT. These are referred to in the literature as motif-1 and motif-0. It was hypothesized that the non-LTR retroelement motifs-1 and 0 retain functional similarity to telomerase motif CP and T (part of RNA-Binding Domain (TRBD), see FIG. 3). Some reports also demonstrate the involvement of motif-1 and motif 0 in interactions with specific R2 RNA templates as well as other templates, contributing to the R2 jumping mechanism. This method focuses on the mutagenesis of motif-1 and motif 0 (see, FIG. 2). This mutagenesis results in an increase in jumping efficiency, single-stranded priming efficiency and processivity, as well as a significant reduction in bias toward RNA with similar sequences.

Mutagenesis of thumb domain. The thumb domain is mostly responsible for holding and/or interacting with the primer or the primer/template. R2 RTs possess a unique capability to use a single-stranded primer compared to other retroviral enzymes. More specifically, using defined sequences of single-stranded DNA primer, R2 RTs can prime the reverse transcription at the 3'-end of random RNA templates. This reaction does not require base pairing with the RNA template (see, FIG. 10). This property of R2 is perhaps linked to Target Primed Reverse Transcription (TPRT). In this mechanism, the R2 retrotransposon recognizes a specific double stranded DNA (dsDNA) sequence than endonuclease domain of R2 and cleaves one of the strands. The cleaved strand can then be transferred to the RT catalytic center and the 3'-end of the strand can be used as a primer. In this method, the R2 thumb domain can be mutagenized to improve single-stranded priming efficiency and processivity (see, FIG. 4).

Example 14: Method to Prepare RNA Library for Single Cell and Low Input Samples

Methods for single cell library preparation include, but are not limited to, confinement techniques focused on emulsion and nanofabrication. Other methods include cell sorting and serial dilution. Library preparation involving single cells and/or low RNA sample inputs (5-50 µg) have many challenges, and as such, limitations. Due to the small sample size, the possible presence of artifacts, and the presence of excess reaction reagents like oligo adapters and primers (in this case, outnumbering the RNA sample), one of the many challenges is the risk of artifact amplification. To ensure high quality library preparation, two major conditions must be met: the first being high conversion efficiency, thus, input RNA to DNA library, and the second, is a low oligo adapter-adapter product. The enzymatic platform of the present disclosure provides the possibility to use a simple technique that results in the necessary high RNA-sample-library conversion efficiency while ensuring relatively small sample loss. This small sample loss is mainly due to the shorter protocol, hence, less number of total steps in the method. Unlike current methods, which are limited to target Poly-adenylated RNA from the cells, the method described in the present disclosure can also capture non-polyadenylated RNA, like miRNA, and ncRNA lincRNA.

Example 15: Method to Anneal rRNA Fragments Using DNA-Sponge

A large majority of the RNA in cells consists of ribosomal RNA (rRNA), whereby 80% of the cell's RNA is rRNA. Another 15% consists of transfer RNA (tRNA) and other translational RNA machinery. Various methods have been developed to deplete rRNA and tRNA. These methods are based on two general ideas: the first, pulling rRNA using specific oligonucleotide probes attached to solid support, and the second, a specific probe guided degradation of the rRNA sequences, which is usually enzymatic. This depletion can be executed before library preparation, at the RNA level, or after library preparation, at the dsDNA level. In most current approaches, however, rRNA sequence depletion is an entirely separate and distinct protocol, thus, adding to the process of sample preparation.

In this method, rRNA sequence depletion can be integrated into the process of sample preparation. Briefly, during or right after RNA sample fragmentation ssDNA that is complementary to rRNA, referred to as the DNA-sponge, can be included in the library preparation reaction. The DNA-sponge consists of complete or large DNA fragments covering sequences of rRNA subunits. The length of the DNA-sponge is a multiplex of the length of average RNA sample after the fragmentation and can have a linear form with blocked 3'end, or a circular form, or it can be concatemerized. The main function of the DNA-sponge is to anneal to rRNA fragments. The annealing of the rRNA fragments to large complementary ssDNA make the 3'-end of the rRNA fragment not available to poly A polymerase (in a method with polyA tailing) or to 3'-priming by R2 enzyme (method with random 3'-end priming with ssDNA adapter). As such, rRNA fragments with no available 3'-end are not converted to the sequencing library (see, FIG. 5 and FIG. 6).

Example 16: Direct RNA and ssDNA Sequencing with R2 Enzyme

The non-naturally occurring R2 reverse transcriptase (RT) of the present disclosure can be used directly for RNA or ssDNA sequencing focused on single-molecule sequencing technology whereby confinement methods can be optic, microscopy-based, nanopore-based or field-effect transistors-based.

In this method, the R2 enzyme can be used as a tool for direct RNA sequencing using single-molecule technology, which as described above can be optic, microscopy-based, nanopore-based or field-effect transistors-based. These single-molecule sequencing methods require a processive enzyme since the essential property of these techniques is the enzyme/protein processivity. Direct RNA sequencing can be conducted with either Reverse transcriptase (RT) or RNA-directed-RNA polymerase. RTs of retroviral origin may be low processivity polymerases with polymerase-template complex lifetime of ~30 s. The R2-template complex, on the other hand, has a lifetime that is in the range of ~30 min. In this method, this enzyme can be used for direct RNA sequencing. The direct sequencing has a main advantage, which is that there is no need for conversion to DNA and the additional possibilities to detect RNA modifications, such as methylation.

Example 17: R2 Based Method for In Situ RNAseq

RNA-sequencing profiles gene expression over the whole transcriptome, but it lacks spatial context. In situ RNAseq allowed genome-wide profiling of gene expression in situ in fixed cells and tissues (see, FIG. 6). These cells and tissues can be from any animal which may benefit from the methods of the disclosure, including, e.g., humans and non-human mammals, such as primates, rodents, horses, dogs and cats. Subjects include without limitation a eukaryotic organism, a mammal such as a primate, e.g., chimpanzee or human, cow; dog; cat; a rodent, e.g., guinea pig, rat, mouse; rabbit; or a bird; reptile; or fish. Subjects specifically intended for treatment using the methods described herein include humans. A subject may be an individual or a patient.

In this method, RNA from fixed cells and/or tissues can be converted into cDNA and directly sequenced using single-molecule methods or by tagging the with barcode information including spatial-information. This cDNA can then be converted to sequencing library. One of the methods of spatial-specific barcoding can be by using a glass plate with printed in spatial-specific manner oligonucleotide primer (FIG. 6). The cDNA is generated using a slice of tissue.

In the methods of the present disclosure, the non-naturally occurring R2 enzyme and the jumping method can be used for spatial specific library generation. The primer can be specifically barcoded with poly T oligonucleotides (see, FIG. 6) and applied modification of the poly A based library preparation protocol. This method is highly efficient and the high conversion efficiency is critical for this application. Due to the nature of the samples (single cells, small tissue, etc), this method needs to be very sensitive and thus, operate with very low sample input. For this method, either a specific primer or a random primer can be used.

Example 18: RNA-Sequencing Library Preparation: A Poly-A-Based Method for Total-RNA, mRNA, miRNA, and cfRNA The methods described below require a poly A tail at the 3'-end of the RNA sample. A natural poly A can be used for the mRNA protocol. For the protocols for total-RNA, miRNA, and cfRNA, the poly A that is used can be synthesized with poly A polymerase or alternatively, poly U polymerase. Depending on which sequencing technology is used after sample preparation (either a long-read or short-read); RNA sample fragmentation can also be applied.

Figure 7:
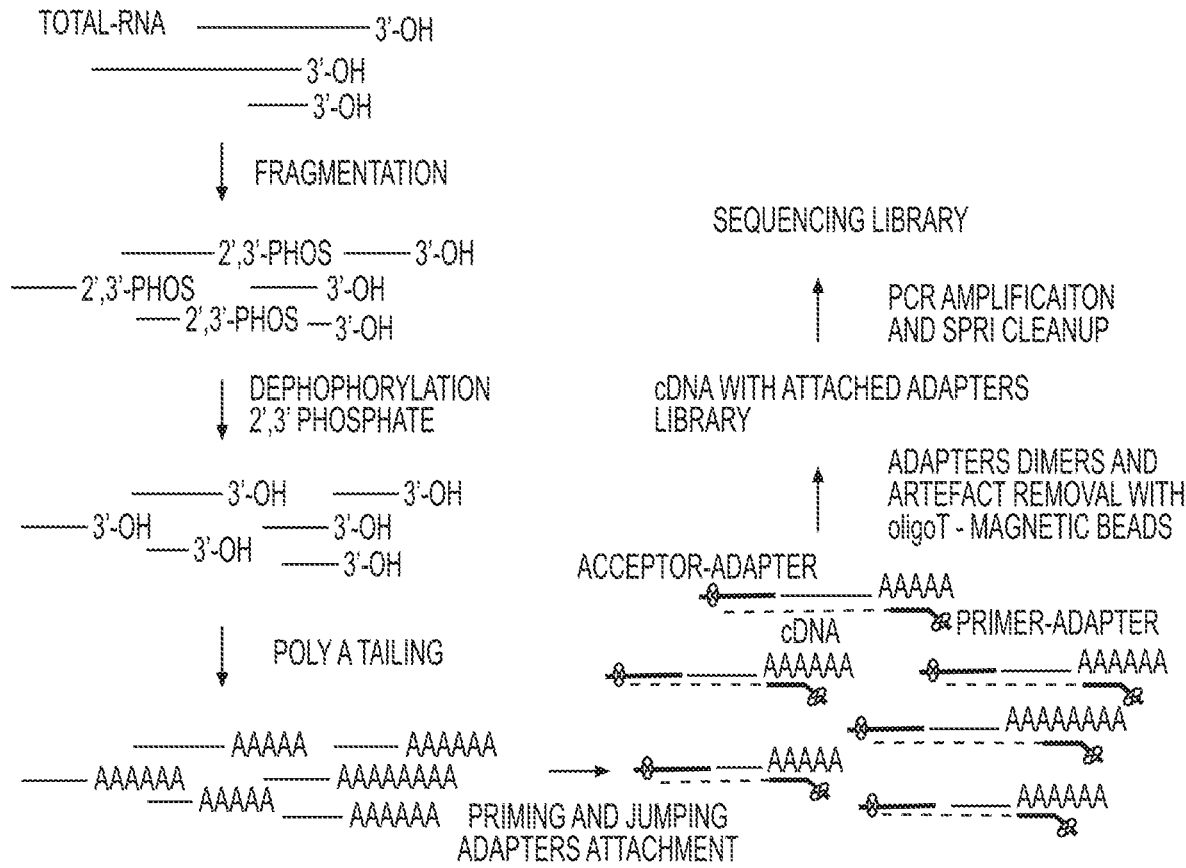
FIG. 7 illustrates the general Poly A based method of RNA-sequencing library prep. This figure illustrates the different steps starting with RNA fragmentation. The methods for fragmentation include spontaneous RNA magnesium induced degradation or enzymatic cleavage. This figure illustrates that depending on which method is used, the cleavage may result in 3'-OH or cyclic 2', 3'-phosphate at the 3'-end of the RNA fragment.
Figure 8:
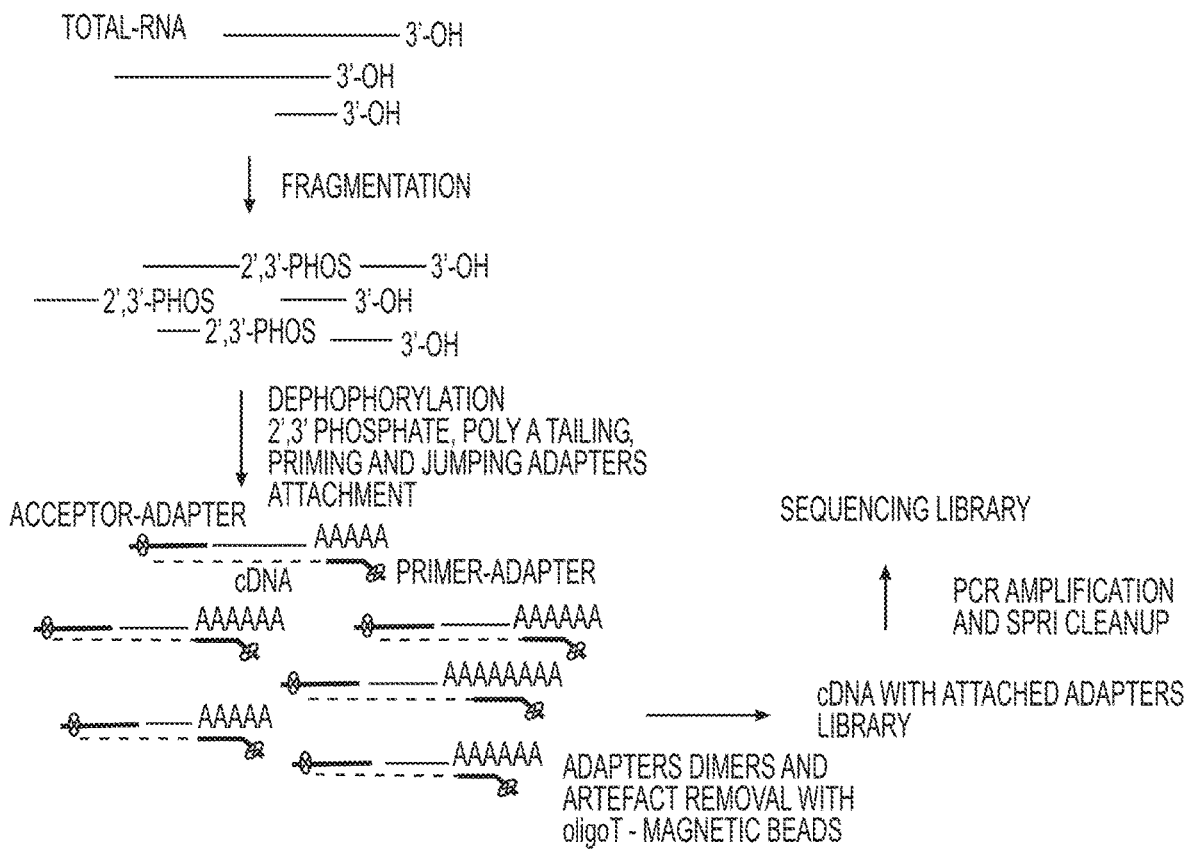
FIG. 8 illustrates a shorter version of the Poly A based method of RNA sequence library prep described in FIG. 7. This figure illustrates a method whereby engineered T4 PNK is used, thus, allowing the simultaneous use of both enzyme T4 PNK and Poly A polymerase without breaking the protocol into two steps as in FIG. 7.

General Poly-A based method. In a first step, the RNA sample can be fragmented. Several methods for fragmentation can be used, including but not limited to spontaneous RNA-magnesium-induced degradation or enzymatic cleavage (see, FIG. 7). Depending on the fragmentation method that is used, the cleavage may generate 3'-OH or cyclic 2',3'-phosphate at the 3'-end of the RNA fragment. For example, the method with spontaneous magnesium-catalyzed hydrolysis can produce 2', 3'-phosphate, which needs to be removed in order to generate 3' poly A tail with poly A polymerase. To remove the phosphate from the 3'-end, an enzymatic reaction where T4 polynucleotide kinase (PNK) is applied. It is important to note that T4 PNK includes two enzymatic activities: 5' kinase and cyclic 2',3'-phosphatase. After de-phosphorylation, the PNK can be temperature inactivated and RNA 3'-end can be poly A tailed with poly-A polymerase or alternatively, poly-U polymerase. Following the poly A polymerase temperature inactivation, poly A tailed RNA can be mixed with primer-adapter, including oligo-T sequences, acceptor-adapter, and R2 enzyme. Annealed to RNA poly-A tail oligo-T adapter can be used as a primer in an extension reaction catalyzed by R2 enzyme (reverse transcription). After reaching the 5'end of the RNA template, the R2 extension complex jumps to the 3'-end of the acceptor-adapter, and continues the extension. Extension can then be paused on the nucleotide analog, also referred to as the blocker, which is strategically incorporated in the adapter toward the 5'-end of the adapter. Blocking the analog prevent the R2 extension complex from second jumping (both primer-adapter and acceptor-adapter includes blocker nucleotide, blocker nucleotide analog here is Spacer 9). During the reaction, artifacts can be generated including primer-adapter-acceptor-adapter dimers or homogenous dimers (see, FIG. 9). The adapter dimers artifacts including acceptor extension are prevented by 3'-dideoxy nucleotide at the acceptor-adapter 3'-end. Alternatively, different extension blockers can be applied, such as 3'phospho-dNTP, 3'amino-dNTP. The artifacts primed by primer-adapter, including poly-T sequence, can be removed from the reaction with oligo-A attached to magnetic beads. The artifacts can be primed without annealing (template primer duplex formation) so the primer sequence remains single-stranded (see, FIG. 9). After pulling with oligo-A immobilized magnetic beads, additional cleanup with solid phase reverse immobilization (SPRI) can be conducted. The last step is polymerase chain reaction (PCR) amplification using primers that are complementary to both the primer- and the acceptor-adapter. The primers may include additional sequences for additional applications, such as barcodes, or adapter sequences that are compatible with/recommended by major sequencing technologies, such as Illumina, Ion Torrent, and PacBio, and Roche 454.

Shorter poly-A based method. In this method, engineered T4 PNK can be used. The modified enzyme retains only one enzymatic activity cyclic 2',3'-phosphatase and kinase activity can be removed. This change can allow the simultaneous use of both enzymes T4 PNK and poly-A polymerase without breaking the protocol into two separate steps. Both enzymes use the same substrate, ATP. As such, PNK mutation can be used to prevent the depletion of ATP and the 5'-end phosphorylation of the sample.

Ina first step, the RNA sample can be fragmented (for long read sequencing; miRNA application fragmentation is not required). Depending on the method that is used, cleavage may generate 3'-OH or cyclic 2',3'-phosphate at the 3'-end of the RNA fragment. To remove phosphate from 3'-end, enzymatic de-phosphorylation with T4 polynucleotide kinase can be applied (engineered T4 PNK—only cyclic 2',3'-phasphatase activity). De-phosphorylation can be conducted simultaneously with sample RNA 3'-end poly-A tailing with poly-A polymerase, or alternatively poly-U polymerase. After a short incubation, the reaction can be stopped by temperature inactivation. All subsequent steps are the same as the ones for the general poly-A based method described above.

TABLE 3

Protocol for Total RNA

Library Prep: Total RNA

| | [stock] | Reagent | vol | [final] |
|---|---|---|---|---|
| PNK MM | | H2O | 0 | |
| | 10 | X T4 PNK buffer | 2 | 1 |
| | 10 | X Rnase Inhibitor | 0.5 | 0.25 |
| | 10 | U/ul T4 PNK enz | 1 | 0.5 |
| | | Sample | 16.5 | 0 |
| | | Total | 20 | |
| | | 37 C., 20' -> 70 C., 4' -> on Ice | | |
| Poly A | | H2O | 8.5 | |
| Pol MM | 5 | X 2D PNK buffer | 10 | 1 |
| | 10 | X Rnase Inhibitor | 1.25 | 0.25 |
| | 10 | mM ATP | 2 | 0.4 |
| | 5 | U/uL Ecoli PolyA Pol | 1.25 | 0.125 |

TABLE 3-continued

Protocol for Total RNA

16 C. for 5 mins and then move to ice

| | | | | | | |
|---|---|---|---|---|---|---|
| P/A MM | | H2O | 1.15 | | | |
| | 100 | X dNTPs | 0.5 | 1 | | |
| | 100 | uM P334 Primer | 0.1 | 0.2 | | |
| | 100 | uM P423 DNA ter acc | 0.25 | 0.5 | | |
| | | Incubate at 70 C., 2 mins -> On ice for 2' | | | | |
| Enz MM | 10 | X Rnase Inhibitor | 1.25 | 0.25 | | |
| | 40 | P2 enzyme (1 mg/mL) | 3.75 | 3 | | |
| | | Total | 50 | | | |
| | | 34 C., 1 1 hr -> Pull down -> spri 1.6x -> Elute in 50 uL | | | | |
| | Pull down with pre-prepared beads | | 30 mins | | | |
| Before PCR | | SPRI | 80 ul | | | |
| cleanup | | Elution | 25 uL | | | |

| 2D | [stock] | Reagent | vol | [final] | Thermocycling | |
|---|---|---|---|---|---|---|
| Library | | H2O | 0 | 0 | 95 C.-3 min | |
| amp PCR | 2 | x Kapa Hifi MM | 25 | 1 | 98 C.-20 sec | 14 cycles |
| | 10 | uM SI primer P5 + P7 | 1.25 | 0.25 | 61 C.-15 sec | |
| | | Template | 23.75 | 0 | 72 C.-20 sec | |
| | | Total | 50 | | 72 C.-1 min | |
| | | | | | 4-forever | |
| Post PCR cleanup | | SPRI | 60 ul | | | |
| | | Elution | 25 uL | | | |

TABLE 4

Protocol for miRNA

Library Prep: miRNA

| | | | Template | |
|---|---|---|---|---|
| | [stock] | Reagent | vol | [final] |
| PolyA rxn | | H2O | 0.00 | |
| | | H2O | 11.2 | |
| | 10 | X Poly(A) Pol Rxn Buffer | 2 | 1 |
| | 10 | X Rnase Inhibitor | 0.5 | 0.25 |
| | 10 | mM ATP | 0.8 | 0.4 |
| | 5 | U/uL Ecoli PolyA Pol | 0.5 | 0.125 |
| | | Sample | 5 | |
| | | Total | 20 | |
| | 32 C. for 20 mins and then move to ice | | | |
| dNTP/P/A | 5 | X 2D miRNA buffer | 4 | 0.4 |
| | | dNTP/Accep/Primer Mix | 2 | |
| | Incubate at 70 C., 2 mins -> On ice for 2' | | | |
| Enz | 10 | X Rnase Inhibitor | 1.25 | 0.25 |
| | 40 | P2 enzyme (1 mg/mL) | 3.75 | 3 |
| | | Total | 50 | |
| | 34 C., 1 hr -> Pull down | | | |
| Pull down with pre-prepared beads | | | 30 mins | |
| Before PCR | SPRI | 80 ul | | |
| cleanup | Elution | 25 uL | | |

TABLE 4-continued

Protocol for miRNA

| 2D | [stock] | Reagent | vol | [final] | 12 cycles |
|---|---|---|---|---|---|
| Library amp PCR | 2 | H2O | 0 | 0 | |
| | 10 | x Kapa Hifi MM | 25 | 1 | |
| | | uM SI primer P5 + P7 | 1.25 | 0.25 | |
| | | Template | 23.75 | 0 | |
| | | Total | 50 | | |
| Post PCR cleanup | SPRI Elution | 60 ul 25 uL | | | |

| [stock] | [final] | 5X miRNA Buffer | Vol (uL) |
|---|---|---|---|
| | | H2O | 695 |
| 1000 | 50 | mM Tris-HCl pH7.5 | 50 |
| 5000 | 1000 | mM NaC12 | 200 |
| 1000 | 5 | mM MgC12 | 5 |
| 10 | 0.25 | % Tween | 25 |
| 1000 | 25 | mM DTT | 25 |
| | | Total | 1000 | dNTP/Accep/Primer Mix

| [stock] | | vol (uL) | [final] |
|---|---|---|---|
| | H2O | 1.15 | |
| 100 | X dNTPs | 0.5 | 1 |
| 100 | uM P334 Primer | 0.1 | 0.2 |
| 100 | uM P423 DNA ter acc | 0.25 | 0.5 |
| | Total | 2 uL/rxn | |

TABLE 5

Protocol for mRNA

| | temp ng | 10 |
|---|---|---|
| | | 1 |

| [stock] | Reagent | Vol | [final] |
|---|---|---|---|
| | H2O | 15.25 | |
| 5 | X 2D buffer + dNTPs | 10 | 1 |
| 10 | X Rnase Inhibitor | 1.25 | 0.25 |
| 10 | uM P334 Primer | 1 | 0.2 |
| 10 | uM P423 terminated acceptor | 2.5 | 0.5 |
| 5 | ng/uL | 15 | |

Total Human Brain RNA + ERCC
Incubate at Temperature, varying mins -> On ice for 2'

| 10 | X Rnase Inhibitor | 1.25 | 0.25 |
| 40 | P2 enzyme (1 mg/mL) | 3.75 | 3 |
| | Total | 50 | |

34 C., 30 min -> spri 0.8 x

TABLE 6

Protocol for 2D library amplification PCR

Library amp PCR

| | | | | Thermocycling | |
|---|---|---|---|---|---|
| [stock] | Reagent | Vol | [final] | 95 C.-3 min | 15 |
| | H2O | 0 | 0 | 98 C.-20 sec | cycles |
| 2 | x Kapa Hifi MM | 50 | 1 | 61 C.-15 sec | |
| 10 | uM SI primer P5 + P7 | 2.5 | 0.25 | 72 C.-20 sec | |
| | Template | 47.5 | 0 | 72 C.-1 min | |
| | Total | 100 | | 4-forever | |
| Cleanup SPRI 1.2X | | | | | |

5X R2

| [stock] | [final] | Buffer + dNTPs | vol (uL) |
|---|---|---|---|
| | | H2O | 430 |
| 1000 | 150 | mM Tris-HCl pH 7.5 | 150 |
| 5000 | 1500 | mM NaC 12 | 300 |
| 1000 | 25 | mM MgC 12 | 25 |
| 10 | 0.25 | % Tween | 25 |
| 100 | 0.375 | mM dATP | 3.75 |
| 100 | 0.375 | mM dTTP | 3.75 |
| 100 | 1.875 | mM dGTP | 18.75 |
| 100 | 1.875 | mM dCTP | 18.75 |
| 1000 | 25 | mM DTT | 25 |
| | | Total | 1000 |

Example 19: RNA-Sequencing Library Preparation: A Method Using Random Fragmentation for Total-RNA, mRNA, miRNA, and cfRNA This method focuses on random priming using the random fragmentation of the RNA samples in combination with the unique properties of the R2 enzyme. Here, the R2 enzyme is capable of priming the extension reaction without template-primer annealing. In this mechanism, extension can be primed on the 3'-end of the template by a ssDNA primer without a complementary sequence annealing to the template strand (R2 3'-end priming, see, FIG. 10). In contrast to random priming with a random oligonucleotide primer, the R2 3'-end priming efficiency is less template-length dependent and as such, library products are a full length copy of the template strand.

In a first step, the RNA sample can be fragmented. Here, several fragmentation methods can be used for this first step, including but not limited to spontaneous RNA hydrolysis with magnesium, or enzymatic cleavage (see, FIG. 11). After this first fragmentation step, the RNA sample can be mixed with primer-adapter (ssDNA), R2 enzyme, and acceptor-adapter (ssDNA or RNA). With dNTP present, the R2 enzyme can prime the extension at the template RNA 3'-end using ssDNA primer-adapter. Once the extension reaches the 5'end of the RNA template, the R2 enzyme can jump to the acceptor-adapter and can continue the reaction, pausing on the nucleotide analog, or blocker, which is strategically incorporated to the adapter toward the 5'-end of the adapter. The blocker nucleotide analog here is Spacer 9. The blocking of the analog prevents the R2 extension complex from a second jumping mechanism (both primer-adapter and acceptor-adapter include blocker nucleotide). In the next step, the reaction can be cleaned with solid phase reverse immobilization (SPRI). Similarly, size selection can be used to remove some adapter-adapter dimer artifacts. The last step is polymerase chain reaction (PCR) amplification whereby primers complementary to both the primer- and the acceptor-adapter can be used. These primers may include additional sequences for applications such as barcoding and/or adapter sequences that are compatible with/recommended by major sequencing technologies, such as Illumina, Ion Torrent, PacBio, and Roche 454.

TABLE 7

Protocol for miRNA

Random libraries

| [stock] | Reagent | vol | [final] |
|---|---|---|---|
|  | H2O | 14.7 |  |
| 5 | X 2D nmer frag buffer | 4 | 1 |
| 100 | uM nMer Primer P591 | 0.1 | 0.5 |
| 100 | ng/ul Total Human Brain RNA | 1.25 |  |
|  | Total | 20 |  |
|  | Incubate at 94 C., 3 mins -> On ice for 2' | | |
|  | H2O | 12 |  |
| 5 | X 2d nmer buff2 | 10 | 1 |
| 10 | X Rnase Inhibitor | 1.25 | 0.25 |
| 40 | P2 enzyme (1 mg/mL) | 3.75 | 3 |
|  | Incubate at RT, 5 mins | | |
| 100 | X dNTPs | 0.5 | 1 |
| 10 | uM P423 DNA ter acc | 2.5 | 0.5 |
|  | Total | 50 |  |
|  | 30 C., 60 mins -> spri 0.7 x (x2) -> Elute in 50 uL | | |

| [stock] | Reagent | Vol | [final] | Thermocycling | |
|---|---|---|---|---|---|
|  | H2O | 0 | 1 | 95 C.-3 min | |
| 2 | x Kapa Hifi MM | 25 | 1 | 98 C.-20 sec | 15 |
| 10 | uM SI primer P5 + P7 | 2.5 | 0.5 | 61 C.-15 sec | cycles |
|  | Template | 22.5 | 0 | 72 C.-20 sec | |
|  | Total | 50 |  | 72 C.-1 min | |
|  |  |  |  | 4-forever | |

TABLE 7-continued

Protocol for miRNA

Random libraries

| [stock] | [final] | 5X 2D nmer frag buffer | vol (uL) |
|---|---|---|---|
|  |  | H2O | 875 |
| 1000 | 100 | mM Tris-HCl pH 8.5 | 100 |
| 5000 | 0 | mM NaCl2 | 0 |
| 1000 | 25 | mM MgCl2 | 25 |
| 10 | 0 | % Tween | 0 |
| 1000 | 0 | mM DTT | 0 |
|  |  | Total | 1000 |

| [stock] | [final] | 5X 2d nmer buff2 | vol (uL) |
|---|---|---|---|
|  |  | H2O | 765 |
| 1000 | 110 | mM Tris-HCl pH 7.5 | 110 |
| 5000 | 300 | mM NaCl2 | 60 |
| 1000 | 15 | mM MgCl2 | 15 |
| 10 | 0.25 | % Tween | 25 |
| 1000 | 25 | mM DTT | 25 |
|  |  | Total | 1000 |

Example 20: Method for Abundant RNA Depletion from Full Length and Fragmented Sample Using Streptavidin-Magnetic-Beads to Remove RNA Comprising Biotin-Labeled Primers About 80% of the total RNA in cell is composed of ribosomal RNA (rRNA), another 15% is a transfer RNA (tRNA) and other translation RNA machinery. This example describes a method for depletion of abundant ribosomal sequent subsequent to cDNA synthesis and incorporation of both 3'- and 5' sequencing adapters.

In this method, cDNA comprising sequencing adapters is first pre-amplified with few PCR cycles, such as 1 single PCR cycle, but in some instances less than 10 or less than 5 PCR cycles using primers complementary to the adapter sequence. After the aforementioned pre-amplification step, the sample is mixed with strategically designed probes complementary to ribosomal sequence (both PCR product polarity) and subjected to single cycle PCR.

Figure 21:
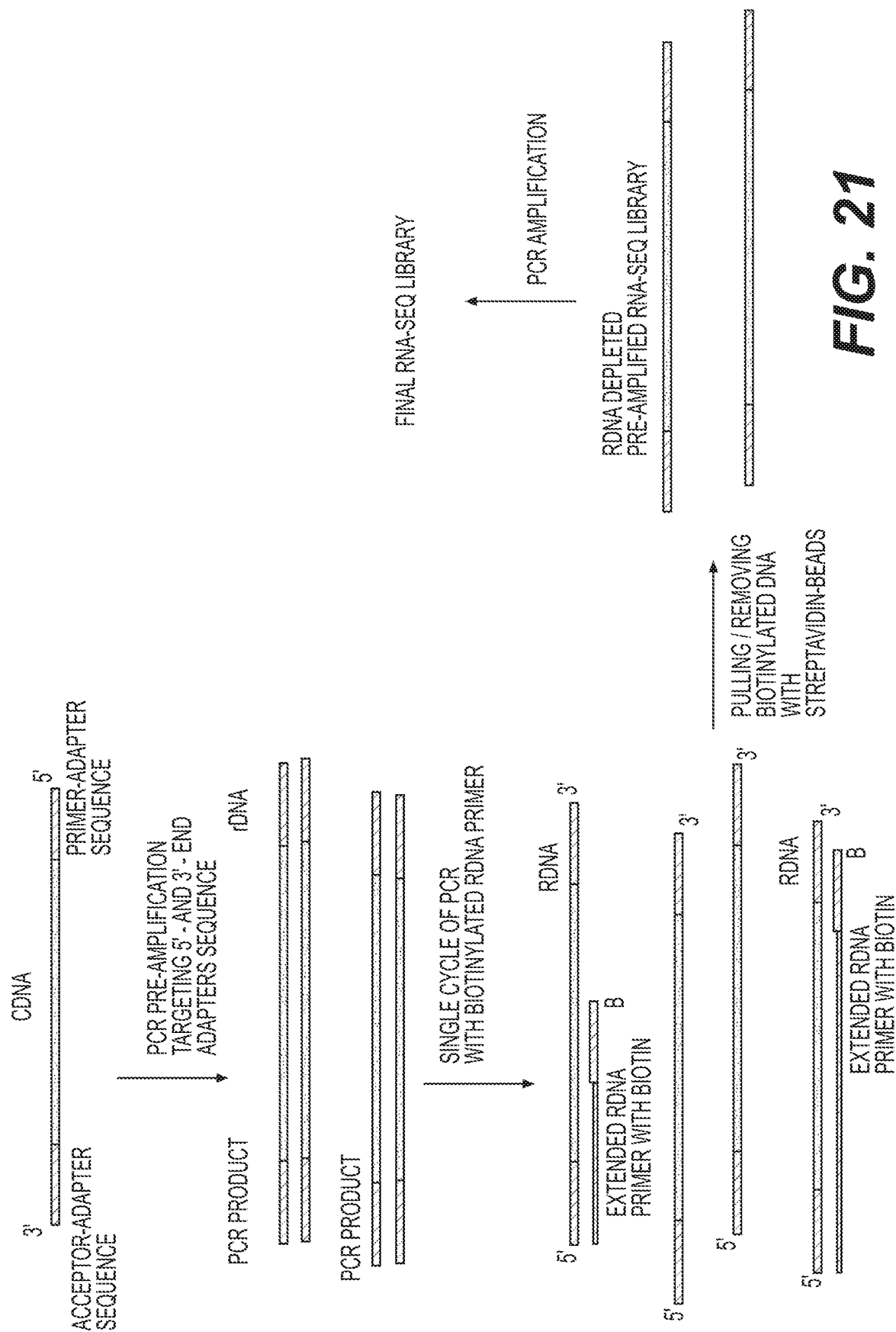
FIG. 21 illustrates the steps of a method for abundant (rRNA) sequence depletion with PCR extension and biotinylated oligo-primers.

The primers include nucleotide modification that allow for the binding/immobilization to a solid support, such as a primer comprising a biotin modification that allows for the binding to a streptavidin solid support. After the aforementioned PCR cycles the cDNA product that incorporated the primer is allowed to bind to the solid support and is thus removed from the liquid phase of the reaction. This product is subsequently removed from the reaction using magnetic beads coated with streptavidin. See FIG. 21.

Example 21: Method for Abundant RNA Depletion from Full Length and Fragmented Sample Using 5'-End Protected Oligo (PCR Primer)

Figure 22:
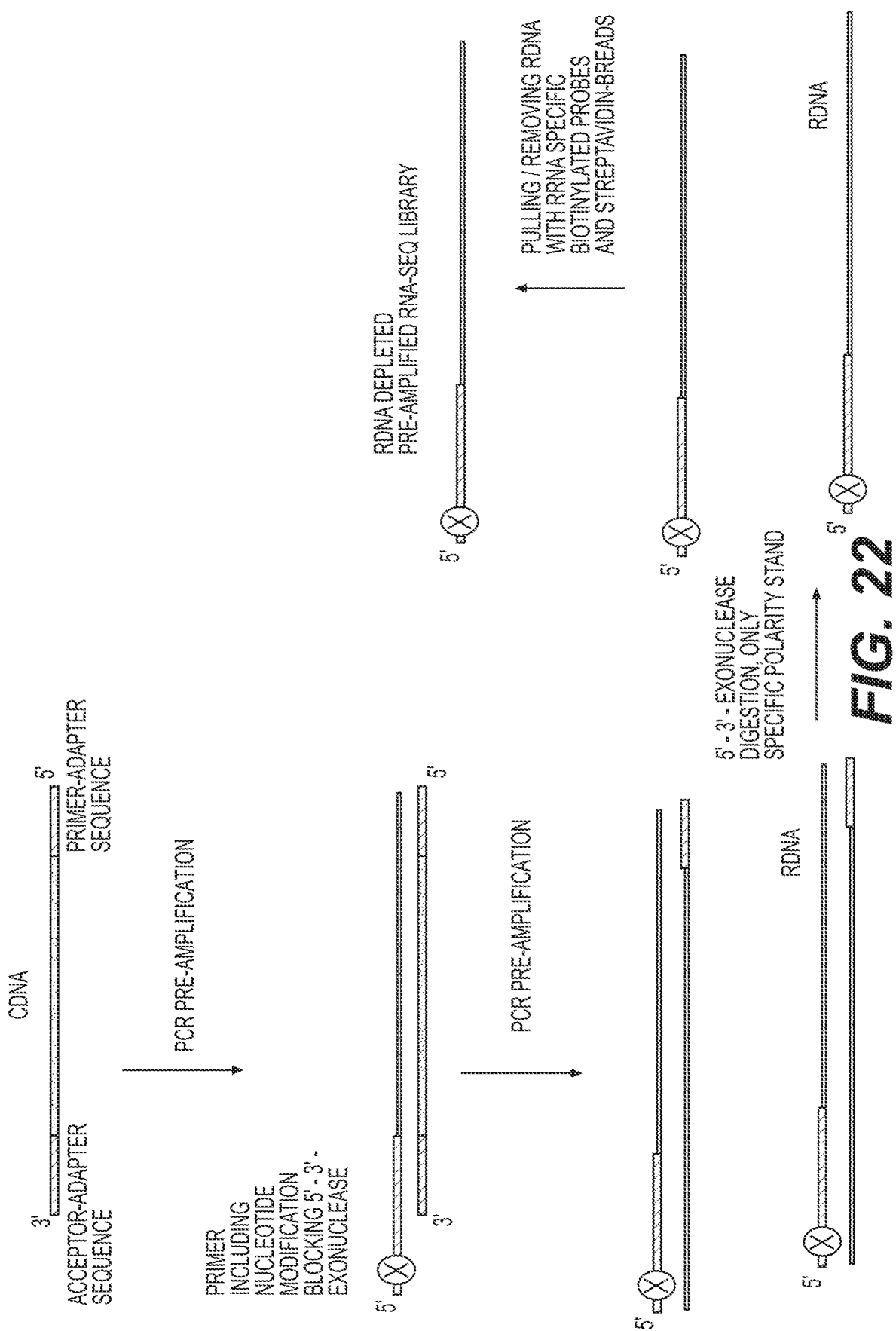
FIG. 22 illustrates the steps of a method for abundant (rRNA) sequence depletion with 5'-end protected oligos (PCR primer).

About 80% of the total RNA in cell is composed of ribosomal RNA (rRNA), another 15% is a transfer RNA (tRNA) and other translation RNA machinery. This example describes a method for the depletion of abundant ribosomal sequent after cDNA synthesis and incorporation of both 3'- and 5' modified sequencing adapters (See FIG. 22). These modified adapters have a modification at their 5'-end that prevents enzymatic degradation by an 5'- to 3'-exonuclease.

In this method a cDNA product including 3'- and 5' partial sequence adapters is subjected to PCR amplification using oligo primers where one of the primers include nucleotide modification(s) at the 5'-end preventing enzymatic degradation by 5'- to 3'-exonuclease, such as lambda exonuclease. These modified primers may be selected to have the same polarity as the RNA strands that they are designed to hybridize. Alternatively, the primers may be designed to have the opposite polarity.

After amplification the PCR product is digested with 5'-to-3'-exonuclease. During enzymatic digestion, the unprotected strand(s) is/are removed from the PCR product, and only ssDNA PCR product with one particular polarity is retained. Subsequently, rRNA depletion can be used by using, for instance, a commercial kit such as LexoGen RiboCop.

Figure 23:
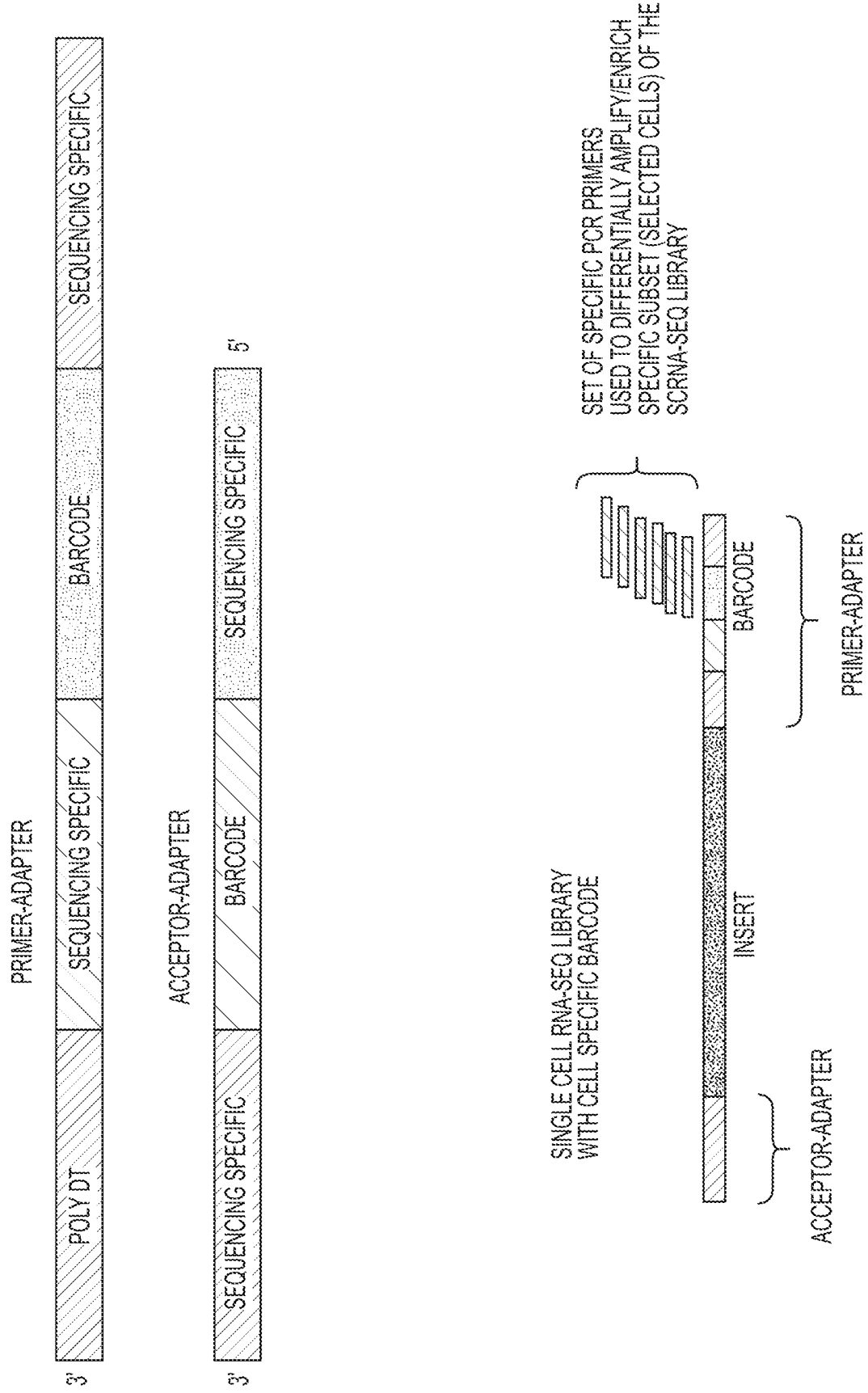
FIG. 23 illustrates the steps of a method for sequencing a pool of single cells where each single cell is labeled with a unique barcode as a selective target for PCR amplification.

Example 22: Method for Enrichment and Deep Sequencing of the Selected Single Cell Libraries Using a Barcode as a Selective Target for PCR Amplification This example describes the preparation of RNA-seq library(ies) from a multiplicity of single cells (single cell library) where each unique single cell is individually barcoded. Each unique barcode is configured to serve as a template for a specific PCR primer. The barcode design is to optimize for PCR specificity with individual specific primers. (See FIG. 23).

This library can be subsequently sequenced with moderate or low sequencing deepness (number of reads per cell). Based on complete or partial results from the sequencing, a single cell of interest may be selected from the single cell library. The barcode associated with such single cells can be identified. These barcodes may then be used to enrich and amplify a pool of nucleic acids derived from a selected single cell.

Example 23: Method for Direct RNA-Seq Library Preparation from Tissue/Cells Biomass without RNA Purification Step This example describes the preparation of nucleic acid libraries from tissue/cell biomass without RNA purification. Briefly, natural tissue is homogenized in a master mix that is insensitive to cell components inhibition. The mix includes collagenasis, estalases and other enzymes/protein promoting cell/tissue lysis, also a component library prep and reagents for converting RNA to RNA-seq library, including one or more enzymes described herein. Because the R2 derived enzymes described herein are resistant to the homogenizing reagents, the RNA-seq library preparation can proceed without RNA purification step. The cell dissociation and lysis reagents may include enzymes from a group of Collagenase, Hyaluronidase, DNase, Elastase, Papain, protease Type XIV, Trypsin, Lipase, alpha-hemolysin, and detergents.

Figure 24:
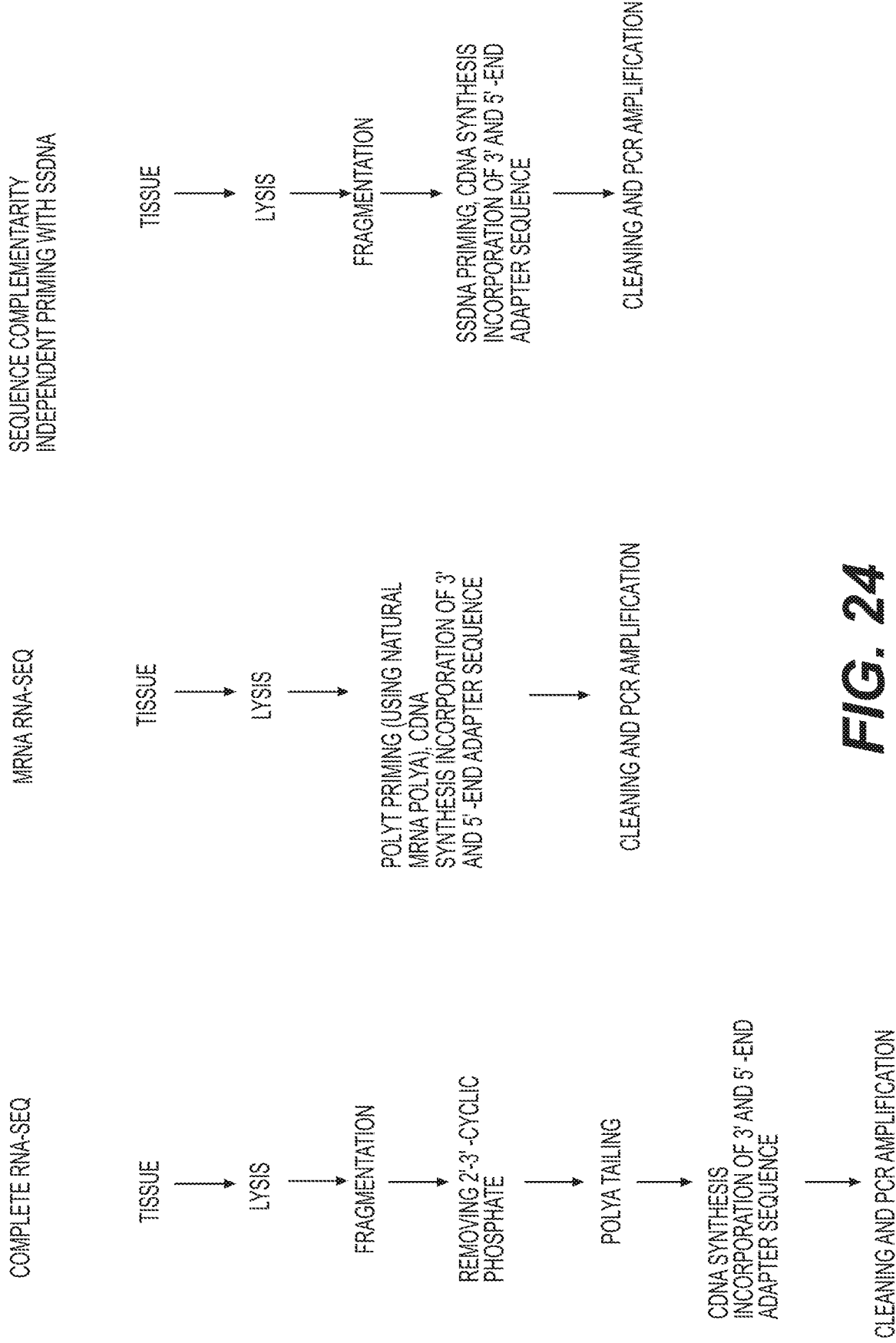
FIG. 24 illustrates the steps of a method for direct RNA-seq library preparation from tissue/cell biomass without RNA purification.

After lysis anyone of the protocols described above can be used for cDNA synthesis. (See FIG. 24).

Example 24: Method for Direct RNA-Seq Library Preparation from Tissue/Cells Biomass without RNA Purification Step This example describes the preparation of nucleic acid libraries from tissue/cell biomass without RNA purification by selecting a small of the tissue with a selected morphology or a different sub-substructure of the tissue. The selected tissue may be then collected separately or it may be collected together with a larger biopsy fragment. In this example, the selected tissue is labeled with a unique barcode on the adapter that may be used to retain the spatial information of the nucleic acids being analyzed, alternatively post library lysis/library prep mix can be collected by allowing the tissue slice to interact with surface (solid support) with immobilized oligonucleotide primer/adapter, where this primer-adapter is labeled to preserve the spatial information.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Example 25: Total RNA

Library preparation was performed by bringing sample volume up to 18 uL, adding 2 μl of nA (see Table 8) and mixing. The sample was fragmented, incubated at 94° C. for 6 minutes and placed on ice for 2 minutes. 25 μL of nB (see Table 8) was added and mixed followed by 5 μL of nC (see Table 8) with mixing. The sample was incubated at 30° C. for 1 hour and stored at 4° C.

A 0.7×SPRI cleanup standard protocol was performed. A double SPRI cleanup can be performed in cases of low sample input. The sample was eluted in 24 μL EB and transferred to new PCR tubes (22.5 μL).

A sample index PCR was performed (see Table 10) by adding 25 μL of 'Amp' mix to the cleaned sample. 2.5 μL of SI primer mix was added and mixed well. A PCR thermocycler program was run with the following protocol: 95° C. for 3 minutes; followed by n-cycles (dependent on input amount) of 98° C. for 20 seconds, 61° C. for 15 seconds, and 72° C. for 20 seconds; followed by 72° C. for 1 minute.

Another 0.7×SPRI cleanup was performed using standard protocols. The sample was then eluted in 20 μL EB and 18.5 μL transferred into new PCR tubes.

Library QC and sequencing were performed.

TABLE 8

Materials and Reaction Compositions 1

| [stock] | Reagent | vol | |
|---|---|---|---|
| | Template | 18 | |
| 10 | X Fragmentation Buffer | 2 | Tube nA |
| | Total | 20 | |
| | Incubate at 94 C., 4 mins -> On ice, 2' | | |
| | H2O | 14.15 | Tube nB |
| 5 | X 2d nmer buff2 | 10 | |
| 100 | uM nMer Primer P591 | 0.1 | |
| 100 | X dNTPs | 0.5 | |
| 100 | uM P423 DNA ter acc X | 0.25 | |
| 10 | X Rnase Inhibitor | 1.25 | Tube nC |
| 40 | R2 Enzyme (R2 Reverse transcriptase) | 3.75 | |
| | Total | 50 | |
| | Incubate at 30 C. for 60 mins -> spri 0.7x -> Elute in 24 uL | | |

TABLE 9

Materials and Reaction Compositions 2

| [stock] | 5X 2d nmer buff2 | vol (uL) |
|---|---|---|
| | H2O | 885 |
| 1000 | mM Tris-HCl pH 7.5 | 10 |
| 5000 | mM NaC12 | 60 |
| 1000 | mM MgC12 | 5 |
| 10 | % Tween | 25 |
| 1000 | mM DTT | 15 |
| | Total | 1000 |

The 10× Fragmentation Buffer was made up of 700 mM Tris-HC, 100 mM $MgC_2$, and 50 mM DTT at a pH of 7.6.

TABLE 10

Sample Index PCR

| [stock] | Reagent | vol | | |
|---|---|---|---|---|
| | H2O | 0 | | 95 C.-3 min |
| 2 | x Kapa Hifi MM | 25 | Tube Amp | 98 C.-20 sec cycle |
| 10 | uM SI primer P5 + P7 | 2.5 | | 61 C.-15 sec |
| | Template | 22.5 | | 72 C.-20 sec |
| | | | | 72 C.-1 min |
| | Total | 50 | | 4-forever |

The oligo primers used in the PCR were:
P423   AA/iSp9/ACACTCTTTCCCTA-CACGACGCTCTTCCGATCT/3ddC/(SEQ ID NO: 76)
P591/5Sp9/GTGACTGGAGTTCA-GACGTGTGCTCTTCCGATCT (SEQ ID NO: 77)

Sample Index P5 Primers:
P551   AATGATACGGCGACCACCGAGATCTA-CACTAATCTTAACACTCTTTCCCTACA CGA (SEQ ID NO: 78)

Sample Index P7 Primers:
P559   CAAGCAGAAGACGGCATACGAGATAT-TACTCGGTGACTGGAGTTCAGACG (SEQ ID NO: 79)

Figure 25:
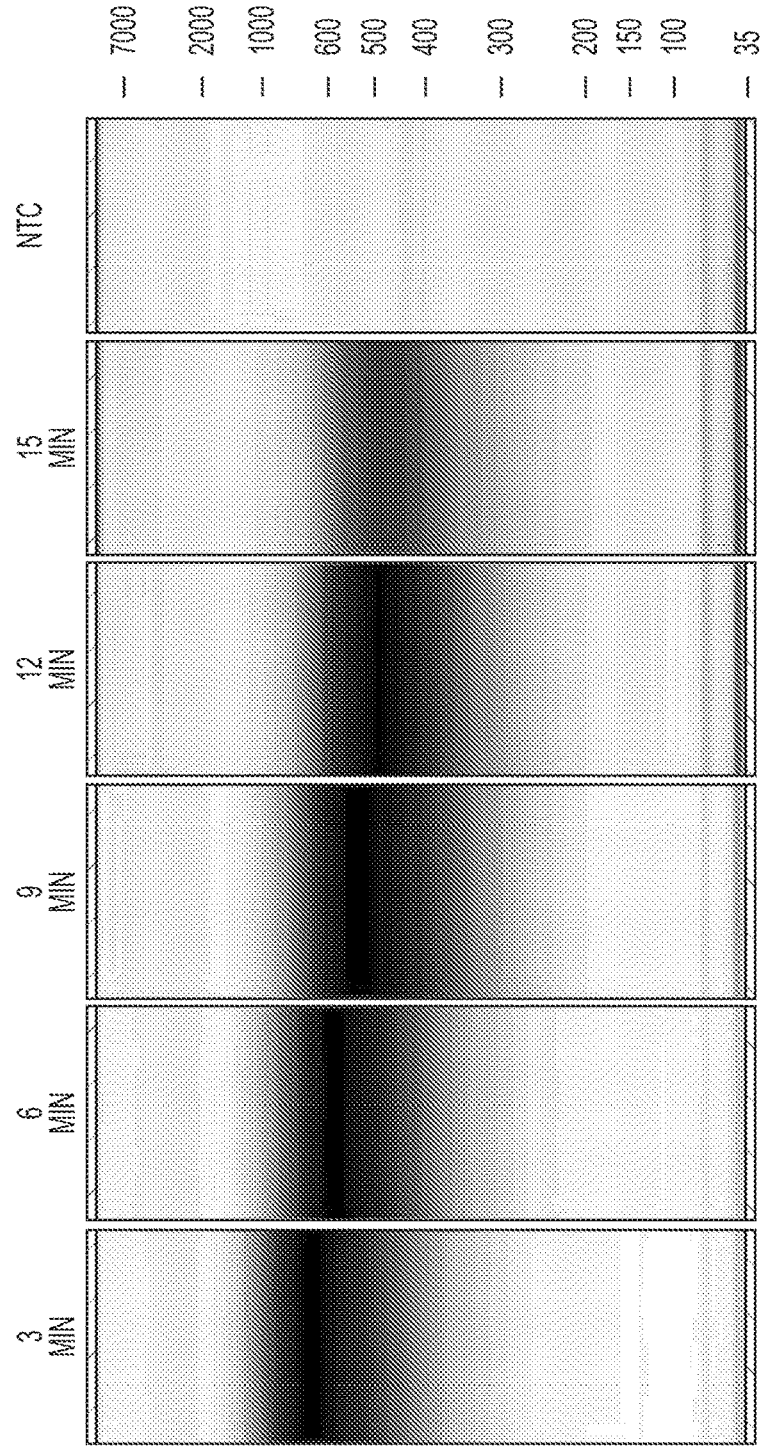
FIG. 25 illustrates bioanalyzer traces in Example 25.
Figure 26:
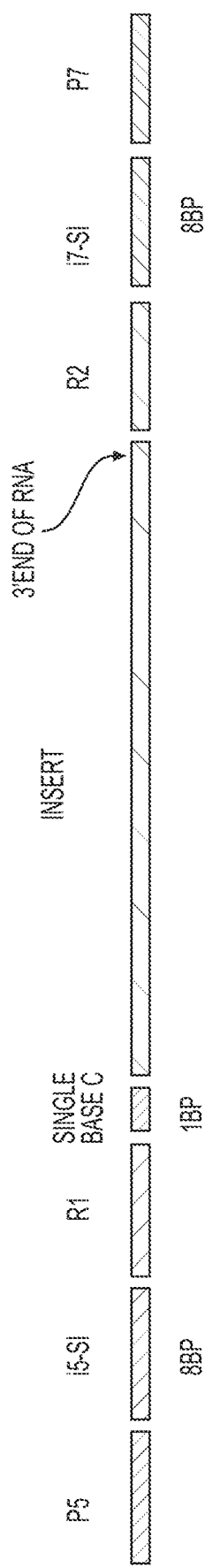
FIG. 26 illustrates library molecule structure in Example 25.

Bioanalyzer traces of the fragmentation are shown in FIG. 25 and the library molecule structure is illustrated in FIG. 26.

The sequencing results, using Illumina hiseq, are shown in Table 11. In the experiment with rRNA depletion before sample preparation, the sample was rRNA depleted using NEB Next rRNA Depletion (accordingly to NEB protocol). The sequencing results showed good RNA-seq library quality including percentage of the aligned reads, number of genes and coverage CV as shown in Table 11.

TABLE 11

Sequencing Data

| RNA Template | Ribo Depletion | # of reads | RL | RNA input | % aligned | % abundant | % unaligned | % IG |
|---|---|---|---|---|---|---|---|---|
| Human Brain mRNA | None | 22056690 | 2 × 100 | 100 ng | 93 | 9 | 7 | 4 |
| Universal Human Reference | NEB Next rRNA Depletion | 27949188 | 2 × 100 | 200 ng | 92 | 9 | 8 | 4 |

| RNA Template | Ribo Depletion | # of genes (0.1 FPKM) | Coverage CV | % stranded | % Exons | % Intron |
|---|---|---|---|---|---|---|
| Human Brain mRNA | None | 22681 | 0.58 | 99 | 51 | 49 |
| Universal Human Reference | NEB Next rRNA Depletion | 23237 | 0.58 | 99.3 | 51 | 45 |

Example 26: Ribo Depletion

Exemplary Protocol:

A template was prepared by starting with 5 ng of library material, diluting the 5 ng of library material in a total of 10 µL of volume using 10 mM Tris pH 8.0. The diluted library material was transferred to a PCR tube for PCR.

A 1 cycle PCR was performed for pull down. To the 10 µL of library (5 ng), 1.5 µL of Ribo depletion Primer Mix (stock concentration of 25 uM) was added. To that, 13.5 uL of 2× Kapa Hifi Mastermix was added. The reaction was kept on ice during setup. The reaction was then placed on a thermocycler and the following thermocycling protocol was run: 98° C.—1 min→62° C.—2 mins→72° C.—2 mins→1 cycle→hold at 20° C.

Pull Down Bead Preparation:

During the above PCR protocol, the pull down beads were prepared in following way. Ribo depletion pull down beads were vortexed to uniformly suspend. 50 µl for each reaction was transferred into separate PCR tubes. The PCR tubes were spun down briefly and placed on a magnetic rack until the 1 cycle PCR was done. Once the PCR was done, the buffer was removed from the beads and discarded. 25 µL of the PCR reaction product was added to the beads and vortexed to mix and incubated at room temperate for 15 minutes with mixing every 5 minutes. After 15 minutes the tubes were transferred to the magnetic rack and the solution was allowed to clear. Once the solution was clear, 23 µL of it was transferred to a fresh PCR tube and the amplification reaction was set up.

Sample index PCR was performed using the following protocol: The reaction was placed on a thermocycler and the following thermocycling protocol was run:

Step 1: 98° C.—1 min

Step 2: 98° C.—20 sec

Step 3: 61° C.—15 sec

Step 4: 72° C.—20 sec

Step 5: Repeat Step 2-Step 4 for 6 cycles

Step 6: 72° C.—2 min

Step 7: 4° C.—HOLD

PCR cleanup was then performed (0.8×SPRI cleanup using Ampure beads). The library was eluted in 20 µL EB and 18 µL of the library was transferred for storage, QC, and sequencing. The exemplary RiboDepletion Protocol is also shown in Table 12 and the bead washing protocol used is shown in Table 13. The wash buffer and resuspension buffer compositions are shown in Tables 14 and 15 respectively.

TABLE 12

RiboDepletion Protocol
Set up Biotin (18S) PCR

| [stock] | reagent | vol (uL) | [final] |
|---|---|---|---|
| | H2O | 0 | |
| 2 | x KapaHifi MM | 13.5 | 1.08 |
| 25 | uM Primers Biotin Mix | 1.5 | 1.5 |
| | Template | 10 | |
| | Total | 25 | |

Do 1 PCR cycle
Pull down with step beads - 50 uL ready beads
Final PCR

TABLE 12-continued

RiboDepletion Protocol
Set up Biotin (18S) PCR

| [stock] | reagent | vol (uL) | [final] |
|---|---|---|---|
| | h2o | 32 | |
| 2 | x Kapa Hifi MM | 40 | 0.8 |
| 10 | uM P5-P7 | 5 | 0.5 |
| | Template | 23 | |
| | Total | 100 | |

Do 6 PCR cycle
0.8x SPRI cleanup -> 20 ul Elute

TABLE 13

Bead Washing Protocol

| Step | Bead washing protocol |
|---|---|
| 1 | NEB streptavedin beads |
| 2 | 1 ml, put them against the magnet |
| 3 | wait till solution is clear, discard the buffer |
| 4 | respend the beads with 1 mL of wash buffer |
| 5 | wait till solution is clear, discard the buffer |
| 6 | Repeat step 4 & 5 for 3 times |
| 7 | Resuspend beads in 0.5 ml of Final resuspension buffer Store it at 4 C. |

TABLE 14

Wash Buffer Composition
Wash buffer

| [stock] | [final] | reagent | volume |
|---|---|---|---|
| | | H2O | 93850 |
| 1000 | 10 | mM Tris pH 8.3 | 1000 |
| 1000 | 50 | mM KCl | 5000 |
| 1000 | 1.5 | mM MgC12 | 150 |
| 50 | 0 | % Glyceraol | 0 |
| | | Total | 100000 |

TABLE 15

Final Resuspension Buffer Composition
Final resuspension buffer

| [stock] | [final] | reagent | volume |
|---|---|---|---|
| | | H2O | 6770 |
| 1000 | 10 | mM Tris pH 8.3 | 200 |
| 1000 | 50 | mM KCl | 1000 |
| 1000 | 1.5 | mM MgC12 | 30 |
| 50 | 30 | % Glyceraol | 12000 |
| | | Total | 20000 |

The sequencing results (using a illumna sequencer) showed a 3.6-times reduction in a number of sequencing reads mapping to 18S rRNA sequence and are summarized in Table 16.

TABLE 16

Sequencing Results

|  | 18S rRNA no depletion | 18S rRNA depleted |
| --- | --- | --- |
| Number of input reads | 263367 | 263198 |
| Number of quality reads | 262927 | 262586 |
| Reads mapped to 18 S | 96692 | 27142 |
| All rRNA (%) | 36.8% | 10.3% |

The probe sequences used were as follows:
Name SEQ ID NO: Sequence
P600 38/5Biosg/TACCTGGTTGATCCTGCCAGTAGCATATG
18S_1 39/5Biosg/CCGTGCGTACTCAGACATGCATG
18S_2 40/5Biosg/CAGTTATGGTTCCTTTGGTCGCTCGC
18S_3 41/5Biosg/GCCCGTCGGCATGTATTAGCTCTAGAATTAC
18S_4 42/5Biosg/CGTGCATTTATCAGATCAAAACCAACCCG
18S_5 43/5Biosg/GCCCGAGGTTATCTAGAGTCACCAAAGC
18S_6 44/5Biosg/CGACCCATTCGAACGTCTGCC
18S_7 45/5Biosg/CGTGGTCACCATGGTAGGCAC
18S_8 46/5Biosg/CGGAGAGGGAGCCTGAGAAAC
18S_9 47/5Biosg/GGTCGGGAGTGGGTAATTTGCG
18S_10 48/5Biosg/CTCTTTCGAGGCCCTGTAATTGGAATGAG
18S_11 49/5Biosg/GCACCAGACTTGCCCTCCAATG
18S_12 50/5Biosg/GTTGCTGCAGTTAAAAAGCTCGTAGTTGGATC
18S_13 51/5Biosg/GGGACACTCAGCTAAGAGCATCGAG
18S_14 52/5Biosg/GAGTGTTCAAAGCAGGCCCGAG
18S_15 53/5Biosg/CCCTCTTAATCATGGCCTCAGTTCCG
18S_16 54/5Biosg/GAGGTGAAATTCTTGGACCGGCG
18S_17 55/5Biosg/CGTCTTCGAACCTCCGACTTTCGTTC
18S_18 56/5Biosg/ATGCGGCGGCGTTATTCCC
18S_19 57/5Biosg/CCCGGAACCCAAAGACTTTGGTTTC
18S_20 58/5Biosg/GAATTGACGGAAGGGCACCACC
18S_21 59/5Biosg/GAGCTATCAATCTGTCAATCCTGTCCGTGTC
18S_22 60/5Biosg/GTTCTTAGTTGGTGGAGCGATTTGTCTGG
18S_23 61/5Biosg/GTCGCGTAACTAGTTAGCATGCCAG
18S_24 62/5Biosg/CAGCCACCCGAGATTGAGCAATAACA
18S_25 63/5Biosg/AGTCAGTGTAGCGCGCGTG
18S_26 64/5Biosg/TCAGCGTGTGCCTACCCTACG
18S_27 65/5Biosg/GCACTTACTGGGAATTCCTCGTTCATGG
18S_28 66/5Biosg/GCTTGCGTTGATTAAGTCCCTGCC
18S_29 67/5Biosg/CGAGGGCCTCACTAAACCATCCAATC
18S_30 68/5Biosg/GCTGAGAAGACGGTCGAACTTGACTATC
P601 69/5Biosg/TAATGATCCTTCCGCAGGTTCACCTACG
RiboHill-1 70/5Biosg/GGGGATTGCAATTATTCCCCATGAACGAG
RiboHill-2 71/5Biosg/GCTTATGACCCGCACTTACTGGGA
RiboHill-3 72/5Biosg/TGCGTTGATTAAGTCCCTGCCCT
RiboHill-4 73/5Biosg/TAGCGACGGGCGGTGTGTAC
RiboHill-5 74/5Biosg/TGGATGGTTTAGTGAGGCCCTCG
RiboHill-6 75/5Biosg/CTTCTCAGCGCTCCGCCA

SEQUENCES

SEQ ID NO: 1
CEPKRHQSPPPPKKRTTEEPKNRRQKIRSKYAQMQSLFKRDPKRVAAHL

IKNQPLCNVSCPIDAAESALRQRLSQRPGVDAAPFTSKCPQYSKNILDP

IFPEEVTLHLQKIKIHTLEGPDGIKVSHLRSCDPDCRTTLIPKTDDPHP

DAEDYRPITVASCLYRLFSKVVTRRLEDSLSLHPRQKAFRSGTDGAFDN

TSTLMTVIREAHNCGEELNIVSIDLAKAFDNVNHTSITRALRMHGLDDD

SRTLITQMVTGSSTIIKDGGALSNRIEINQGVRQGDPISPLLFNAVMDE

LVERLQLTGEGFKLKGVEVTTLAFADDVTLISRSHRGIEKLLSITLDFL

NERGLKLNINKCKGIRLVRTPKTKSLVEDTSKPFTVPSYGEENQHIPMV

PPGDLIKFLGVDITLNGKPHFDLAPLECTLERIRKAPLKPTQKLATVRD

YLIPSLEYRLGVPGISRKILESVDGAIRSAVKRFLHLPTTGMNSMFLSM

PIKKGGLGLRPLTTQHMARVAVGANNMMTSMDCLSRVVADTTTLRKPLL

SALEHFAVPAATKSAIREGKQNLLREEIAQLSETYHGSCLPSFKKGSLV

NSWLRGTGGMRSRDYITGLKLRFGVIETRSQKWKGRTPQNPDALLCRHC

GHLSGHRETAAHISQKCPTTQATIIQRHNKIVNLVGDRAKREGFAVHVE

PAIKSGDAVYKPDLVLVKDDTAHILDVAAPWEKGTTMHEKHERKISKYT

VLTEDVKALFDVQTCTVGAIIIGASSSWCPSNNRSLKACGLHMPKKFKR

LLCRVALEGTCKIFQNFFTLT

SEQ ID NO: 2
CESKSHQPPPPRKKRTREEPKNRRQKIRSKYAQMQTLFKRDPKRVAAHL

IRNQPLCNVSCPIDAAESALRQRLSQRPGVDAAPITSKCPQNSKNILDP

IFPEEVTLHLQKMKIHTSAGPDGIKVSHLRSCDPVCLAKAFNLFLLARH

IPQQLKDCRTTLIPKTDDPRPDAEDYRPITVASCLYRLFSKIVTRRLED

SLSLHPRQKAFRSGTDGAFDNTSTLMTVIREAHNCGKELNIVSIDLAKA

FDTVNHTSITRALRMHGLDDESRTLITEMVTGSSTIIKGDGGALSNRIE

INQGVRQGDPISPLLFNAVMDELVERLERTGEGFKLKGVEVTTLAFADD

VTLISRSHRGMEKLLSITLDFLNERGLQLNINKCKGIRLVRTPKTKSLV

EDTSKPFRVPSFGEENQHIPMVLPGDLIKFLGIDITLNGKPHFDLAPLE

DTLERIRKAPLKPAQKLATVRDYLIPSLEYRLGVPGISRKLLESVDGAI

RLTVKRFLHLPLTGMNSMFLSMPVKEGGLGLRSLSTQHIARLAVGTNSM

SISTDTVSRVVADTTTLRKPLLSALEHFAVPTATKSAIREGKRNLLRAE

IAQLSETYQGSCLPSFKHGSLVNTWLRGTSGMRSRDYITGLKLRFGVIE

TRSQKWRGRTPQNPDALLCRHCGHSSGNRETAAHVSQKCLVTHALIVQR

-continued
HNKIVRLVGDRAKDEGFAVHVETAVKSGEEVYKPDLILIKADTAHIIDV
AVPWEKGTNMHEKHERKTNKYAQLVDDVKALFGVQNCTVGALVIGARSS
WCTSNDGSLKACGLHLPKKTDGEDLTTEADDSDAEPWQKPEHSPPHAKE
NTEDRNTEEQSEPYTTPQTLRTSENPEIQRRRRLHRTTTRRDCARRTDH
NWTPERGTTHPQKQGP SEQ ID NO: 3
NCDGRNPPAPTNRRKRLPPPARNRSERKRCNYASFQSLFKRDPKRIAAH
LIKNQPLRNVSCPIDVAESALRQRLSQRPGIDAAPFKFKRPPNSECILS
PISADEVTLHLKLMSAETSAGLDGVQVSHLRQCDPMCLAKAFNCFLLAR
YIPPQLKDCRTTLIPKTDNPRPDADDYRPITIASCIYRLFSKIVTRRLE
NCISLHPRQKAFRSGTDGAFDNITTLTTIVRDAHKSGKELNIVCVDLAK
AFDTVNHSSIDRALRMHGLDANSRALIAQMVTGSTTVIKGDGGVLSHKI
EINQGVRQGDPISPLLFNSVMDELIERLEQSGVGYKINNTEVVTLAFAD
DVTLVSSSHRGMEKLLSITHDFINERGLKLNIRKCKGIRFVRTPKTKSL
VQDTSKAFKVRGSGEESSCIPMAGPGEFIKILGVPIAPNGKPSFDIDTL
EGTLERIRKAPLKPAQKLAIVRDYLIPSLEYKLGVPGVGRRVLDEVDAS
IRQTVKRFLHLPHTGMNSMFLTMPIKDGGLGLRSLRTQHLARVAVGTNS
MMSSADPTSHTIASMPQHQKPLHAALQHFSVPAATKDALKKGKRQLLCA
EIAELTETYQGSCLPTFRKRPVGNSWLSGLNGMRSRDFITGLKLRFGVI
ETRSQKWRGRTPQNPAVLLCRHCGHSTGKRETAAHISQKCPQTKNLNIQ
RHNKIVHLVAEHARREGFTVHVEHALKSDGQVYKPDLILTKGNAAHVLD
VAVPWETGTDMHEHHERKVTKYCMISDDVKAHFGVDSCTVGAIVVGARS
SWCASNKTTLKACNTHFTKRFKRLLCRVALEGTCRPLLSALEHFAVPAA
TKSAIREDKQNLLREEIGQLSETYRSSCLPSFKKASLVNSWLRGTSGMR
SRDYIAGLKLRFGVIKTRSQKWRG SEQ ID NO: 4
GAMRPEEERGPKKGRKKKKPEPSVPLNSKQRKRMAYRKVQQAYHKDPKR
VVAHLFHSQPLENVSCPVESGEKALQARLGKRPPADRAPFLPKRAPLKN
HLLSPISAKEVSEHLKQMNLASASGPDGVKVSHLRDIGPQCLSKIFNTF
LLERHIPQVLKDCRTTLIPKVDNPRPDAEDFRPITIGSCIYRLFSKIVT
SRLSQLTPLNPRQKAFRSGTDGAFDNITTVASLLKLARKTGKEINLACI
DLAKAFDTVNHTSITRALHRHGVDSASIELVESMVGEATTVIINSDGTR
SNVIKFNRGVRQGDPISPLLFNLVLDELIDNLDQARCGFSITKEIQVSC
VAFADDITLVSGSREGMNNLLTITREFLGERGLGINHSKCKGIRFTKVP
KSKSLIIDTNPNCFLIRNQQGTPEPIPMAKPGEPLKTLGINLTLEGNPT
FNYPELTRILNTIKHAPLKPHQKVQIIRDHLIPLLQYKLGVPTFYRATL
NNIDKSIRLTVKEILHLPTTGLHNSYLYLPLKEGGLGLKRLATQYASRV
GLGLSNMATSDDAVSRAVAGLHLSLMDKAKNCLGLSEISKEAIKKAKEK
LVQAEIRTLLQCHLGRSHSSFTNDTISNSWMRYPTFLSARNYIMGIKLR -continued
AGIIETRAQKWRGRSPPHPTMLLCRHCGARSRTRETDIHVSQKCLHNKK
LILRRHNCVVSTLGRRATQQGFAVYYEPCIKHGETVLKPDLVIIKGDTA
TIIDVAVPWEQGTNLREHNSRKISKYQCLEREAAKYFNVKTVKTGSLVV
GARGKWSAGNDSTLKSCGLHCSKRLKKLLCTIALEGTCAVFKH SEQ ID NO: 5
LEPNRRRRGYAKATRIALNAPGKVRRRAEYAAMQRQWKTKRGLCAREAL
EGTWKIPARTVSLSDQEAFWRPLMESQSKNDLREPAKVGETLWGLLDPI
TPDEVRQILGSMSSKAPGPDGHRLSDLRSIPIDQICSHFNLWLLAGYQP
KALRMGESCLIPKVKDASRPQQFRPITLGSYVGRCLHKCLASRFERDLP
ISIRQKAFRCMDGVAENVMILRSVLDDHKKRLAELNLVFLDVSKAFDSV
SHRSILHAVKRLGVPPPLLKYVEELYADSETFLRGSGELSPSIKVRRGV
KQGEPLSPHLFNAVIDWALSSLDQSFGVTVGEARVNHLAFADDIVLLSS
SQPGLQRLIDQLTTHLGESGLRVNSTKSASIRIAVDGKNKRWVVDPRDS
VHVGGVRIPAVAVSGSYRYLGVNISAAGMRVDAADSLASKLANLSRAPL
KPQQRLYILCTHLLPSIYHQLVLSSTSKKFLKYLDRCVRVAVRRWLRLP
KDTPKAYFHAKCNDGGLGVPELQRVIPLQKAGRWLKMTRSQDPVVQAAV
GLEYFQKLLERWSTPELYQWGGGGITTSGHLAVAQARSLYSSVNGRGLR
QSGLVSTQFDWVRSGCSLLSGRNFIGAMQLRGNLLATKLRASRGRPRVD
ISCDCCRTPESSGHILQVCPRTSWGARIGRHDNVAKLVARESAKRHWKV
IREPAIPTPAGIRRPDLVFSKGDTAIVVDVTIVPDNAELSDAHSSKVSY
YDNGAIRGWVALNTGASHITFSSVNNNWSDCMAEESKRMLKLGLGLPNS
IRGTISAVVLEKGFHMYLCFKRGTFRASY SEQ ID NO: 6
NHERTTKQVPENNTPARRPFKRRLHRVERYKRFQRMYDLQRKRLAEEIL
DGREAVTCNLKKEEIKDHYDQVYGVSNDRVSLDDCPRPPGANNTDLLKP
FTPTEVMDSLQGMKNGAPGPDKITLPFLQKRLKNGIHVSLANVFNLWQF
SGRIPECMKSNRSVLIPKGKSNLRDVRNWRPITISSIVLRLYTRILARR
LERAVQINPRQRGFVPQAGCRDNIFLLQSAMRRAKRKGTLALGLLDLSK
AFDTVGHKHLLTSLERFAVHPHFVRIVEDMYSGCSTSFRVGSQSTRPIV
LMRGVKQGDPMSPILFNIALDPLLRQLEEESRGFMFREGQAPVSSLAYA
DDMALLAKDHASLQSMLGTVDKFCSGNGLGLNIAKSAGLLIRGANKTFT
VNDCPSWLVNGETLPMIGPEQTYRYLGASICPWTGINSGPVKPTLEKWI
ANITESPLKPHQRVDILCKYALPRLFYQLELGTLNFKELKELDSMVKQA
VKRWCHLPACTADGLLYSRHRDGGLAVVKLESLVPCLKIKTNLRLVHST
DPVISSLAESDGLVGAIEGIAQKAGLPIPTPDQRSGTYHSNWRDMERRS
WERLALHGQGVELFKGSRSANHWLPRPVGMKPHHWVKCLAMRANVYPTK
RGLSRGNLSKNKDSAKCRGCTSMRETLCHLSGQCPKLKSMRIRRHNKIC

```
                                                       SEQ ID NO: 9
SDLEVTGRKRVARGPRAIPVLSKRKARRIEYRRMQQLWRTNMTKAAHKV
LDGDAGSLPHPTLAAQLGFWKPVLEAESVDLAWPFAVGHPGVAVGDLWS
PITEGEVINIRLPRTSSPGLDGLTVHRWFTEVPAILRATILNIFMATGW
VPPRFRHSRTVLIPKSSDLMDPAYYRPISVSSVILRHFHKILARRVAAC
ELLDVRQRAFIAADGCAENVAVLSAILFDARTNRRQLHVITLDVRKAFD
TVSHNAIRYVLSKHGMPQIMVEYLSTLYRTAAVRLEVDGEFSDEILPGR
GVRQGDPLSPLLFNLIMNEILAEVPDQVGYCMMDRNVNALAFADDLVLI
GATRDGAQRSLERVMAALYRFGLELAPAKCAAFSLVPCGKTKRIKILTD
PQFVAGDRPIPQLGVLHTVRYLGVRFGETGPVIQGVELLPLLERITRAP
LKPQQRLKILRTYLIPRYTHNLVLGRVSYSMLRKLDKQTRAAVRRWLVL
PDDVPVAFFHCPIKQGGLGIQSFETAIPRLTLLRLNRLKDSQYEMARVV
GSSAWADRRMRWCRFARRRDEDWPSELHAKVDGFELREAGNVSVSTRWL
DDAMVHIPSSDWLQYVKVWINALPTRIRTTRGSRRLREDVNCRGGCGVQ
ETAAHVVQQCFRTHGGRIMRHDAVASALAGELQRGGYNVHRERVFRTRE
GVRKPDILAAKGTHGHVLDVQIISGARPLSDGHDRKRSYYANNADLLAR
ISALLQVPVRNLDVSTVTLSWRGVWARESAAVLTSLGVSKAVLRGITTR
VLKGSYMNFSRFNQTTATCRGRANLRMSGWGPP

SEQ ID NO: 10
NTAKCPKGPRFRKTATHSGTNKQQRQQRYARVQKLYKMNRKVAAKMVLE
ETDKIQIKLPDHDPMFKFWESEFKEGEGMPERMPKDLKESPDLKAIWDP
VTEEEVRKAKVANNTAAGPDGIQPKSWNRISLKYKTLIYNLLLYYEKVP
HKLKVSRTVFIPKKKDGSSDPGEFRPLTICSVVLRGFNKILVQRLVSLY
KYDERQTAYLPIDGVGTNIHVLAAILNDSNTKLSELHVALLDITKAFNR
LHHTSIIKSLVGKGFPYGFITFIRRMYTGLQTMMQFEGHCKMTQVNRGV
YQQGDPLSGPIFLLAIEKGLQALDKEVGYDIGDVRVNAGAYADDTDLVAG
TRLGLQDNINRFSSTIKQVGLEVNPRKSMTLSLVPSGKEKKMKVETGKP
FRANDVPLKELSINDFWRYLGISYTNEGPERLSLTIEQDLERLTKAPLK
PQQRIHMLNAYVIPKYQDKLVLSKTTAKGLKRTDRQIRQYVRRWLKLPH
DVPIAYLHAPVKSGGLNIPCLQYWIPLLRVNRVNKITESQRSVLAAVGK
DDTAHIVDVQVARCSKLNESHVRKRSKYDKKEIEVEVKSRYRVSKVMYE
ATALLTSTVYKCNQSLATLGGNPTMLAYRTYWEKELYAKVDGKDLQNAR
DDKASTRWNGMLHSDISGEDYLNYHKLRTNSVPTKVRTARGRPQKETSC
RGGCKSTETLQHVVQQCHRTHGGRTLRHDRIVGLLQHELRRDYNVLAKQ
ELKTGIGLRKPDLVLIKCTISYKGIWDKQSVMSMRRLGVSEYCLFKIVT
STLRGTWLCWKRFNMITSVRS

SEQ ID NO: 11
FWKPLTPNLARVSLPSKDKVSRRRLRRADYGRVQRAWKRNRNTCLRDLL
RDKRTESAPPEELXVPYWESVLRSGSSCTPGQRGRTAERTELWDPVSSK
EVEQALPPLGTAPGPDSFTPKDFRAVPSAVWACIFNIFMLCGRLPDYLL
```

ESRTTLIPKRDGACNPEDFRPITVSSVVVRCFHKVIANRMSRHIQLDPR
QKAFRSLDGCSEGVFLLDFILGHARRNHRPVHLASLDVAKAFDSVSHAA
ILDVLRSFGVPDQMVEYIASVYAGSRTRLQGDGWQSHAIHPTCGVKQGD
PLSPMIFNMVIDRLFTLFPRDTGVSVGDTVLNGMGYADDLVLFATTPVG
LQQLLDITAEYLSQCGLRVNAAKCFSVSLAIVPHEKKVVVATKHRFKCL
GQPIPALKRSDQWKYLGVPFSPEGRLKIDPLGRLKDELEKLRRAPLKPQ
QRLYALRTVVVPGLYHLLVLGGTTISSLNRLDIAVRSTVRKWLSLPHDV
PNAYIHADARDGGLSIPSYRWTVPRLRFHRLKALSVLCDGGGPDEMVAC
VGDEIKRASARLQDHGMNINTRNTYRVRFARLLHTSNDGAPLKGSKKVE
GQHRWVTDGSLMLSGRDYIACNWVRINSIPLRKRTARGRVRDTRCRAGC
DSTETLHHVLQQCHRTHDMRIKRHNACVKYLLDRQRSRGKTVFWEPHFH
TAGGLLKPDSVILHDASTAVVVDALVAGERSDLDREHDRKVSKYEPLVD
LVKDRYSVDKVIFSSLIISARGVWGGRSFRHLSKLRLLDISDAKVLSTR
VLLGGMGAVRVFNRRTAVSGRVNGW

SEQ ID NO: 12:
EVFPAPPPRRERRRKKTPNPAPMRKREARRCEYGAAQSLWKRDRRHCIT
NILNEMGPVNQPPRETMEPYWTRMMTTDGRTSPPSDKVPIKEDIWTPIT
GNDIKRSRIPRASAPGPDGISARLYRSIPTTVIIRLFNLLLWCERLPED
LLLSRTIFLPKKTNASEPGDFRPITIPPVLVRGLHKILAKRLETALDID
PRQRAFRSMDGCADNTLLLDTLLRYHRKQYKSLYMASIDVSKAFDAVTH
PTIESTLISLGVPPPMIRYLGQVYANSRTRIEGDGWTSKPVHPKRGVRQ
GDPLSPILFNAVTHRLLQRLPREVGARLGNIPINAAAYADDLLLFASTS
MGLQQMIDTMTDYLAECGMTINVEKSMTVAIRAAPHLKKTAVDASLSFS
CGGRQLPSLKRTNKWRYLGVVFTPEGRAQCRPAEVVAPLLGALTKAPLK
PQQRLYALRTVVIPKLYHQLALGAVTIGTLNKTDRLVRGALRKWLAPH
DTPNAYFHTSVRDGGLGIPAIRWTAPVQRRGRLLGVMKALGQQGLDRFI
QDELNTCKKRLTDHGVLLGTPEMVAKRWAQQLYGSIDGAGLKDSAKTPH
QHQWIADGSKFLTGKDFINCNRARIGALPTRSRTTRGRPQDRRCRGGCL
AQEETLNHVLQHCHRTHGQRIKRHDAVVKYIARNMPRSGYEVHQEPHYKT
ELGLRKPDLVAVLGQTAIIIDAQVVSEQTNLDDAHTRKVAYYNEPATIR
AIKAEHGVRTVKVTSATLSWKGVWSPRSAEELRKLGFIRAGDAKVVATR
VLIGNIAAFRTFNATTSVEHRAGIG

SEQ ID NO: 13
SKEPAAHPPLPFGARRPPDKKRARRRWEYAAVQRAFRKNAARCVNGLLD
GTLLHQPPSIPGLVEFWKDLFTAPCASSRPRSKEGLSPMLLASSQPVSF
RDLWAPITSEEAAAALPPRNSAAGPDALTPAQLRRLPHPVFLKILNLFL
LARSLPSRLLRARTTLLPKKTSPASPADFRPITVCSVLARAFHKVLAGR
LMRYCVLDGRQRAFIPQDGMLHNSFLLDLAMAHSRRTACSLYVASLDVS
KAFDSLDHGALSPVLRAHGLPVEFVEYVRGCYQASTTVICGGGSSSDLV

RPSKGVRQGDPLSPILFNLSIDLLLSRLPGYIGARIFSRRVNAAAFADD
ILLFAETKGGLQELLSTATSALGDLGLEVNPFKCFSLALVASGREKKVK
VDNSVIFRAGNKNIPALAMGDTFRYLGLQFSTSGLSQFHPRQEVQEQLD
IIKRAPLKPQQRLFALRSVILPGTYHGLALGRTRLGALKSLDVCVRAAV
RAWLRLPDDTPIGYFHAPVIYGGLGIPATRWLGPLLRRRRLASMEGLGV
IVDEPSQDILKREICRLDNYLKWDGDVIKTSYQLGRFWALRLHSSVDGA
ALRRSAQTPGQHSWVSNTRLMLSGRDFLACVRARISALPSRARLLRGRE
GDTRCRAGCNASETNNHVIQHCWRSHEARVERHDAVALYMVRGLRRRGY
DVHRELHLRTSQGLKKPDIVAVSGTTAFVIDAQVIGDHLDADRCHREKV
EVYDQQPVHTEIKRMFPEVQMITTTSATLNWRGVWSPASAKALIGIGFN
SNHLSTMATRALLGSIMAARRFDSMTAPRRRMMPRTGVG

SEQ ID NO: 14
NRNDRPSSATVPARRPRNRRISRRQQYARCIKSLLDGTDESALPNQSIM
EPYWRQVMTQPSPSLCSNTVPRKGNMQEGVWSPITSRDLQVHKVPLTSS
PGPDGITSQTARSIPIGIMLRIVNLILWCGDLPVPFRMARTIFIPKTVR
ANRPQDFRPISVPSIVVRQLNAILASRLTAAVSWDPRQRGFLPTDGCAD
NATIVDLVLRDHHKRYASCYIATLDVSKAFDSVAHDAVFNTVTAYGAPK
SFVDYVRRWYSGGGTYFNGGDWRSEEFVPARGVKQGDPLSPVLFNLIID
RLLRSLPKDIGVHVGNAKVNACAFADDLMLFASTPKGLQELLNTTVKFL
SSVGLTLNADKCFTISIKGQPKQKVTVVEQRTFCIGRARVQLKRSEEWK
YLGIHFTADGRARYNPSEDIGPKLERLMQSPLPKPQQKLFALRTVLVPQL
YHKLTLGSVALGVLRKCDKLVRSFARKLLGLPLDVSVAFYHAPHSCGGL
GIPSVRWIAPMLRTKRLAGINWPHLEQSEVASAFLSEELRRARDRAKAG
VNELLSQPKIDTYWADRLYTSVDGNGLREARRYAPQHGWVSQPTRLMSG
KAYRTGIQLRINALPTRSRTTRGRHEMNRQCRAGCDAPSHNHVLQRCHR
THGSRVSRHNGVVSYLKKGLETRGYTVYSEQSLHGQNRVYKPDIVAFRH
DSTIVVDAQVVTDGLDLDRAHQSKVEIYNRQDLLTTLRSVYRARENIEV
VSATLNWRGIWSFQSITRLRTLGILTAGDSNVISSRVVSGRVYSFKTFM
FHAGFHRGMA

SEQ ID NO: 15
SSGRKLPVKSRGARETVQKKMANPRVAKYKRFQRLFRSNRRKLASHIFD
KASLEQFGGSIDEASDHLEKFLSRPRLESDSYSVINGNKSIGVAHPILA
EEVELELKASRPTAVGPDGIALEDIKKLNSYDLASLFNLWLKAGDLPES
VKASRTIFLPKSDGTTDISNCRPITIASALYRLFSKIITRRLAARLELN
VRQKAFRPEMNGVFENSAILYALIKDAKARSKEICITTLDLAKAFDTVP
HSRIVRALRKNNVDPESVDLISKMLTGTTYAEIKGLQGKPITIRNGVRQ
GDPLSPLLFSLFIDEIIGRLQACGPAYDFHGEKICILAFADDLTLVADN
AAGMKILLKAACDFLEESGMSLNAEKCRTLCISRSPRSRKTFVNPAAKF
NISDWKTGISSEIPSLCATDTFRFLGHTFDGEGKIHIDMEEIRSMLKSV

RSAPLKPEQKVALIRSHLLPRLQFLFSTAEADSRKAWLIDSIIRGCVKE

ILHSVKAGMCTEIFYIPSRDGGLGLTSLGEFSLFSRQKALAKMAGSSDP

LSKRVAEFFMERWNIARDPKVTEAARRVYQKKRYQRFFQTYQSGGWNEF

SGNTIGNAWLTNGRARGRNYVMAVKFRSNTAATRAENLRGRPGMKECRF

CKSATETLAHICQKCPANHGLVIQRHNAVVSFLGEVARKEGYQVMIEPK

VSTPVGALKPDLLLIKADTAFIVDVGIAWEGGRPLKLVNKMKCDKYKIA

IPAILETFHVGHAETYGVILGSRGCWLKSNDKALASIGLNITRKMKEHL

SWLTFENTIRIYNSFMKN

SEQ ID NO: 16
TKWRPSKPRLPPTYRANTSRKHLRRLQYGHIQTLYNRCRRDAANTVLDG

RWRSPHTSSPFSIPEFETFWKTIFTTPSTPDNRPVVPVLPTCPALLDPI

TPDEITWALKDMRNSAPGVDRLSAQHFLNFDVPSLAGYLNMVLAFKFLP

TNLSISRVTFIPKGASPQQPNDFRPISIAPVITRCLHKILAKRWMPLFP

SSKLQFAFLQRDGCFEAINLLHSLLRHAHERHSGCSIALLDISRAFDSV

SHHSILRAAHRFGAPDGLCQYLQRVYNGSTSLFNTVDCAPSRGVKQGDP

LSPLLFIMSLDEALESIETVSPVIVDGLPISYIAYADDLVILAPNADLL

QKKLDKLASLLQRSGLIINTSKSMSIDLIAGGHSKLTALKPTVFKIDGN

QLQRLNVSDHFDFLGISFDYKGRSKMDHVETLSAYLLNLTQAPLKPQQR

MSILRENLEPRLLYPLTIGVVHKCTLRQMDCLIRSSVRKWLRLPSDTPT

SFFHSSISTGGLGIPHLSSIIPLHRRKRAAKLLLSPCPIIRWVSQSPSF

SNFLRICNLPINVHRDLIHSFDEARCSWSKQLHSTCDGRGLSMSSRNTV

SHLWLRYPEHIFPRLYINAIKLRGGLLSTKVRRSRGRQENADLLCRGRC

GHHESIQHILQHCSLTHDIRCRRHNDICRLVASRLRRNNIRFFQEPCIP

TPVSFCKPDFIIIRDSIAYVLDVSVCDDANVHLSRQLKINKYGCSTVVS

SIYNFLNATGLRISSVRQTPLIITYRGLIDPLSTTSLRRLSFSSRDISD

LCVASIQGSMRIYNTYMRGTSPQDP

SEQ ID NO: 17
QHALDCFPRLWAPSRPRPNHPQPRSYRALRKAQYASLQRILHTSPKDAA

THVLDGSWRLLHQNRALPPDLHSFWTNVFRIPSFSDNRPVSATQPELSL

ISPITCEEVKKAIAGMGGTAPGLDRLTPANLKSFGLKPLTGYLNLILCY

GCPASLAAARVTLIPKVPDATRPEQYRPLAVSSVIVRCLHKILAFRWAS

VLKLSSLQLAFMQRDGCLEATTILQGVFRDAHSRRRPIAMAFLDVSKAF

DTVLHDSVFRAAAMYGAPPLLLRYLRKLYSQGTVTLGDIDILPKRGVRQ

GDPLSPLLFILAMEEILMAANPNDGYQLPSSTISTLAYADDLVLFAHSP

GALGLKLERVAAALRLAGMEINAAKSITFTISANTHNKNLCLENIAYTL

DGVSIAAADTETRVKYLGLHFNWKGQISYKDTARLAGYCQELTSAPLKP

QQRIHILRQVALPKLHHQLVLSSIHRRTLKAMDISCRHYVRRWLKLPQD

TSTAFFHAKIGDGGLGLTSLATSIPLWRRTRLTKLITSEHPVVRDVSI

CLTKALAVANEPVFVMGTVVSDKDEAAMWKLAMYATLDCADLQTIHET

PESSNWVVRPLRMTPSLYIRGLQLRAGTLGTKSRQQRGRAQMDKLCRRG

CGQTETLPHILQSCPAAHAARCVRHNRVAKSIAVSLRRKGYRVYEEPII

RTGTTYCKPDIIACQDGLGFVIDVAVVSGHRLHESWDLKIAKYDTDFIN

TAIIDCLPEDVEILSLIHQPAIISFKGVWFPPSAKRLKTLGLSADCLAG

LGLVTIKGSLACFDMFMMGSNG

SEQ ID NO: 18
KENLKKRACKTLTRRIKPKKSKKHEYWKMQQMYHRDRAGLAKLILEGEA

RDICPIPLTRLTTAFKEKWEKEDRFVSLGQFKSSCKAVNDIFASPISPE

EVCKIRSKMKNKAATGLDGISKTCLMRGDPKGINLANLFTAILLNGYIP

RALKKNRTTLLPKTQDKRKLSDTSQWRPITIGSTIQRLLSGVINDRLKE

ACEIHPRQRGFISSPGCAENLMLLRELIALSKRELKPLAVIFIDFAKAF

DTVSHKHIKAVLQQRGVDKMIIDLISNSYEGRTTILKAKGSYSREIRLK

MGVKQGDPLSPLLFNLAIDPLLCKLDKVGEGAIVDGIEITSLAFADDIV

LLSNSWSGMRKNLKILEVFCELTGLTLNVMKCHGFFIDSMNRCLAINEC

PPWRLQQNDLHMIGSKEKEKYLGMEISPWLGIIEPNIQKMINIMLNNLT

ASLLKPSQKLELLRTYAVPKLTYMADNGMVTQTTLITTDRKIRMTIKKW

FHLNHATTDGLLYTGCKSGGMGLVKLARVIPRIQVNRILGLCNSEDSCT

RTMARKAHRPSEFRKIWKMGMGKGGETTIQGASDIRTPYWNTPKIHSDW

RINELDKWKKMKTQGEGIEVFENDKISNSWLRHPTLSNFSERDYILALK

LRTNTYPMKAILARGRMAKNKGTKCRLCGYIKKTTKHVLGSCIGTRPNR

MQRHNKICALLAKAARQLGWETLTEHHLKMDNGKTLVPDLIMMKDTRAI

VADVTICYETNQYSLRKAYEVKVKKYAPLELPIKERWPGIKDVRIHGFP

LGTRGKWPSLNWRLLEELDMDKSKRRKFASLLSKRSLLYTIDILKWFSK

N

SEQ ID NO: 19
TRSAPSSTSSGKSTRNAKRLEKLKKYGYYQHLYYNNKKKLVAEILDGET

SGAKPPPMNLVEDYYKNIWSRSTIDDSPVNNIKTVNSDSIFAPISRDEI

KLALSNTKKDSAAGPDSVTIKEAKAIIDNLYVAYNIWLGVQGIPEQLKL

NKTILIPKGNSDLSLLKNWRPITISSIILRVYNRLLAYRMNKVFKTNDK

QVGFKPVNGCGINISWLHSLLKHARLNKNPIYACLVDVSKAFDSVSHQS

IVRALTMNGAPSLLVKLIMDQYTNINTIITCSGSISNKINISSGVKQGD

PLSSLLFNMVIDELFDVIKDQYGYTIDNIGTTNARCFADDLTLISSSRM

GMNKLLELTTEFFKERGLNVNPSKCMSIGMSKGYKGKKSKIESEPLFSI

ADAQIPMLGYIDKTTRYLGVNFTSIGAIDAKRIKKDLHDTLDKLEHKL

KAQCKMDLLRTYMIPRFMFQLIHTELYPKLLIKMDILIRKLAKRILHLP

ISTSSEFFYLPFKEGGLQLTSLKEAVGLAKIKLHKKIMSSNDPMLCYLI

ESQRSRIIEHFMKDLKLGDSLTLNEMDNIKECFMKEKRISFAQKIHGVG

FEVFSSSPLTNQWINGEIKTMTTRTYINSIKLRTNTLETRVTTSRGLNI

IKTCRRCHVADESLMHVLQYCSSTKGLRYSRHHRICAKVANKLMKNGYG

-continued

VYREKSYPDPNNSGSYLRPDLIAVKDGHVIVLDVTVVYEVTGATFINAY

QTKVNKYNTIMVQIEQMFNCVSGVLHGLVIGSRGSIHHSQLHIWHQMGF

SSTELKYVAIGCMEDSLRIMSTFSKAIL

SEQ ID NO: 20

KSKSLPRLKRTGRAFHRREKYAICQKSLDKDFSGTISKILDGVEISEAE

VRPEMAKIEEVYQQRLGNTSGALPENTDTPVVEGLRFERKTAPFDAQEV

TRAIRESNKSTAAGPDRWFNGRCLKNLDCETVAALFNLWRFKQKIPSAL

RENRTILLPKGGDLTDANNWRPLTIGSLLLRLYAKSLTTRWSDAPICER

QKAFRPVDGCWENINLLLGALKSAHKKRRQINLISIDLAKAFDNIQHGA

IFNAMRRFGFSPSEISVVKDLYTNVWTKISIGNEISGPINISRGVKQGC

-continued

PLSPPFLFNLVLDELINELQSSGYGYPVEGFKVPVLAYADDLILCGATDY

ETKRMVEITEKFFARQMLAVNLKKCKALRLLPVKGKRTLKVSSDPMLWK

GEQLPMVKSIDDFISYLGVKVSVTGKVIWSVDQLRLWLDRVMKAPLKPD

QKIKGIKEVLIGRLTYQLRLSEARVCELRRVTRMVRKACKQILHMQLGA

PNAWAHLPLRKCGLGLPDFELTIPLMRRAACEKMKSSPDPVVANISEKI

PIYESGLTRGLDVRAAKRAIQDKYEQAYLSTQRGKLMNARWISAVKPYW

LHGGTGVVKAGEYVSINKLVTRTIETRQFIHPGVTDFETLKCRRCGKAV

ETDLHVLNECPFTRLAQCRRHNFIADYLGKVLVDHGWEVWRERLVKKDL

ENFKPDLICRKGAEGAIIDVTVPYESNEAVLQSKERFKEAKYAGLKGQV

AELLNINGGVKVVGIAVGALGTILTSTLEKAKGLGLDPVKVGKSLQISA

LRGSGHVWKAFRS

What is claimed is:

1. A method for generating a modified R2 reverse transcriptase, the method comprising:
   a) expressing a heterologous nucleic acid sequence encoding said modified R2 reverse transcriptase in a host, wherein said modified R2 reverse transcriptase comprises a finger domain, thumb domain, palm domain, and endonuclease domain each derived from an R2 retrotransposon, and further wherein modified R2 reverse transcriptase has an amino acid sequence with at least 95% identity to an amino acid sequence selected from the group consisting of SEQ ID NOs: 2-20; and
   b) purifying said modified R2 reverse transcriptase.

2. The method of claim 1, wherein said modified R2 reverse transcriptase further comprises a fusion-tag molecule.

3. The method of claim 2, wherein said fusion tag-molecule stabilizes said modified R2 reverse transcriptase.

4. The method of claim 2, wherein said fusion-tag molecule is selected from the group consisting of: Fhb, MBP, NusA, Trx, SUMO, GST, SET, GB1, ZZ, HaloTag, SNUT, Skp, T7PK, EspA, Mocr, Ecotin, CaBP, ArsC, IF2-domain I, an IF2-domain I derived tag, RpoA, SlyD, Tsf, RpoS, PotD, Crr, msyB, yjgD, rpoD, and His6.

5. The method of claim 2, wherein said fusion-tag molecule is selected from the group consisting of: His-tag, His6-tag, Calmodulin-tag, CBP, CYD (covalent yet dissociable NorpD peptide), Strep II, FLAG-tag, HA-tag, Myc-tag, S-tag, SBP-tag, Softag-1, Softag-3, VS-tag, Xpresstag, Isopeptag, SpyTag, B, HPC (heavy chain of protein C) peptide tags, GST, MBP, biotin, biotin carboxyl carrier protein, glutathione-S-transferase-tag, green fluorescent protein-tag, maltose binding protein-tag, Nus-tag, Strep-tag, and thioredoxin-tag.

6. The method of claim 1, wherein said modified R2 reverse transcriptase comprises an amino acid sequence selected from the group consisting of SEQ ID NOs: 2-20.

7. The method of claim 1, wherein said host is selected from bacteria, yeast, algae, cyanobacteria, fungi, a plant cell, or any combination thereof.

8. The method of claim 1, wherein said host is *E. coli*.

9. The method of claim 1, wherein said modified R2 reverse transcriptase comprises a mutagenized motif-1 sequence.

10. The method of claim 9, wherein said mutagenized motif-1 sequence has an improved jumping activity as compared to a wild-type sequence.

11. The method of claim 1, wherein said modified R2 reverse transcriptase comprises a mutagenized motif 0 sequence.

12. The method of claim 11, wherein said mutagenized motif 0 sequence has an improved jumping activity as compared to a wild-type sequence.

13. The method of claim 1, wherein said modified R2 reverse transcriptase comprises a mutagenized thumb sequence.

14. The method of claim 13, wherein said mutagenized thumb sequence has an improved single-stranded priming efficiency.

15. The method of claim 13, wherein said mutagenized thumb sequence has an improved processivity.

* * * * *